United States Patent
Barouch

(10) Patent No.: US 10,376,583 B2
(45) Date of Patent: Aug. 13, 2019

(54) HUMAN IMMUNODEFICIENCY VIRUS THERAPIES UTILIZING N332-GLYCAN-DEPENDENT ANTIBODIES AND A RESERVOIR ACTIVATOR

(71) Applicant: Beth Israel Deaconess Medical Center, Inc., Boston, MA (US)

(72) Inventor: Dan H. Barouch, Newton, MA (US)

(73) Assignee: Beth Israel Deaconess Medical Center, Inc., Boston, MA (US)

(*) Notice: Subject to any disclaimer, the term of this patent is extended or adjusted under 35 U.S.C. 154(b) by 0 days.

(21) Appl. No.: 15/025,961

(22) PCT Filed: Sep. 30, 2014

(86) PCT No.: PCT/US2014/058383
§ 371 (c)(1),
(2) Date: Mar. 30, 2016

(87) PCT Pub. No.: WO2015/048770
PCT Pub. Date: Apr. 2, 2015

(65) Prior Publication Data
US 2016/0213779 A1    Jul. 28, 2016

Related U.S. Application Data

(60) Provisional application No. 61/884,414, filed on Sep. 30, 2013.

(51) Int. Cl.
| | |
|---|---|
| *A61K 39/42* | (2006.01) |
| *C07K 16/10* | (2006.01) |
| *A61K 39/395* | (2006.01) |
| *A61K 45/06* | (2006.01) |
| *A61K 39/00* | (2006.01) |

(52) U.S. Cl.
CPC .......... *A61K 39/42* (2013.01); *A61K 39/3955* (2013.01); *A61K 45/06* (2013.01); *C07K 16/1045* (2013.01); *C07K 16/1063* (2013.01); *A61K 2039/505* (2013.01); *A61K 2039/507* (2013.01); *C07K 2317/565* (2013.01); *C07K 2317/76* (2013.01); *C07K 2317/94* (2013.01)

(58) Field of Classification Search
CPC ............. A61K 39/42; A61K 2039/507; C07K 16/1063; C07K 2317/565; C07K 2317/76
See application file for complete search history.

(56) References Cited

U.S. PATENT DOCUMENTS

| 5,500,362 A | 3/1996 | Robinson et al. |
| 5,821,337 A | 10/1998 | Carter et al. |
| 6,737,056 B1 | 5/2004 | Presta |
| 9,017,691 B2 | 4/2015 | Barouch et al. |
| 9,464,131 B2 * | 10/2016 | Chan-Hui .......... C07K 16/1063 |
| 2005/0130125 A1 | 6/2005 | Zagyansky |
| 2007/0298051 A1 | 12/2007 | Barouch et al. |
| 2011/0295365 A1 | 12/2011 | Hyde et al. |
| 2012/0288502 A1 | 11/2012 | Diskin et al. |
| 2013/0071406 A1 | 3/2013 | Goldenberg et al. |
| 2013/0251726 A1 | 9/2013 | Mascola et al. |
| 2014/0302080 A1 | 10/2014 | Barouch et al. |
| 2014/0348791 A1 | 11/2014 | Barouch et al. |
| 2015/0291935 A1 | 10/2015 | Barouch et al. |
| 2016/0008374 A1 | 1/2016 | Geleziunas et al. |

FOREIGN PATENT DOCUMENTS

| WO | WO-038332 A1 | 1/2003 |
| WO | WO-2004/044155 A2 | 5/2004 |
| WO | WO-2007/104792 A2 | 9/2007 |
| WO | WO-2012/030904 A2 | 3/2012 |
| WO | WO-2014/047261 A1 | 3/2014 |
| WO | WO-2015/051270 A1 | 4/2015 |
| WO | WO-2016/014484 A1 | 1/2016 |

OTHER PUBLICATIONS

Bansal, G. P., 2007, A summary of the workshop on passive immunization using monoclonal antibodies for HIV/AIDS, held at the National Institute of Allergy and Infectious Diseases, Bethesda, Mar. 10, 2006, Biol. 35:367-371.*
Sadjadpour, R., et al., 2013, Emergence of gp120 V3 variants confers neutralization resistance in an R5 simian-human immunodeficiency virus-infected macaque elite neutralizer that targets the N332 glycan of the human immunodeficiency virus type 1 envelope glycoprotein, J. Virol. 87(15):8798-8804.*
Deshpande, S., et al., 2016, HIV-1 clade C escapes broadly neutralizing autologous antibodies with N332 glycan specificity by distinct mechanisms, Retrovirol. 13:48 (1-9).*
Van den Kerkhof, T.L.G.M., et al., 2016, HIV-1 escapes from N332-directed antibody neutralization in an elite neutralizer by envelope glycoprotein elongation and introduction of unusual disulfide bonds, Retrovirol. 13:48 (1-19).*
Chatellier, J., et al., 1996, Functional mapping of conserved residues located at the VL and VH domain interface of a Fab, J. Mol. Biol. 264:1-6.*
Chen, C., et al., 1992, Generation and analysis of random point mutations in an antibody CDR2 sequence: Many mutated antibodies lose their ability to bind antigen, J. Exp. Med. 176:855-866.*
Kala, M., et al., 2002, Phage displayed antibodies to heat stable alkaline phosphatase: framework region as a determinant of specificity, J. Biochem. 132:535-541.*
Liu, Z., et al., 1999, Fine mapping of the antigen-antibody interaction of scFv215, a recombinant antibody inhibiting RNA polymerase II from *Drosophila melanogaster*, J. Mol. Recog. 12:103-111.*

(Continued)

*Primary Examiner* — Jeffrey S Parkin
(74) *Attorney, Agent, or Firm* — Clark & Elbing LLP

(57) ABSTRACT

This invention relates to antibody therapies for human immunodeficiency virus (HIV). In particular, the invention provides methods of curing subjects infected with HIV and blocking HIV infections in subjects at risk of HIV transmission using a N332 glycan-dependent antibody (e.g., PGT121).

73 Claims, 23 Drawing Sheets

Specification includes a Sequence Listing.

(56) References Cited

OTHER PUBLICATIONS

Barouch, D. H., et al., Nov. 2013, Therapeutic efficacy of potent neutralizing HIV-1-specific monoclonal antibodies in SHIV-infected rhesus monkeys, Nature 503:224-229.*
Extended European Search Report for European Patent Application No. 14847004.0, dated Apr. 19, 2017 (9 pages).
Walker et al., "Broad neutralization coverage of HIV by multiple highly potent antibodies," Nature. 477(7365):466-470 (2011).
Barouch, et al., "Therapeutic efficacy of potent neutralizing HIV-1-specific monoclonal antibodies in SHIV-infected rhesus monkeys," available in PMC May 14, 2014, published in final edited form as: Nature. 503(7475):224-228 (2013) (24 pages).
Klein et al., "Antibodies in HIV-1 vaccine development and therapy," available in PMC Mar. 31, 2014, published in final edited form as: Science. 341(6151)1199-1204 (2013) (17 pages).
Zhou et al., "Structural basis for broad and potent neutralization of HIV-1 by antibody VRC01," available in PMC Aug. 13, 2011, published in final edited form as: Science. 329(5993):811-817 (2010) (19 pages).
Burton et al., "Efficient neutralization of primary isolates of HIV-1 by a recombinant human monoclonal antibody," Science. 266(5187):1024-7 (1994) (5 pages).
Pitcher et al., "Development and homeostasis of t cell memory in rhesus macaque," J Immunol. 168(1):29-43 (2002) (16 pages).
Stephenson et al., "Gag-specific cellular immunity determines in vitro viral inhibition and in vivo virologic control following simian immunodeficiency virus challenges of vaccinated rhesus monkeys," J Virol. 86(18):9583-9 (2012) (7 pages).
Horwitz et al., "HIV-1 suppression and durable control by combining single broadly neutralizing antibodies and antiretroviral drugs in humanized mice," Proc Natl Acad Sci U S A. 110(41):16538-43 (2013) (6 pages).
Jaworski et al., "Neutralizing polyclonal IgG present during acute infection prevents rapid disease onset in simian-human immunodeficiency virus SHIVSF162P3-infected infant rhesus macaques," J Virol. 87(19):10447-59 (2013) (13 pages).
Ng et al., "Passive neutralizing antibody controls SHIV viremia and enhances B cell responses in infant macaques," available in PMC Apr. 3, 2011, published in final edited form as: Nat Med. 16(10):1117-1119 (2010) (14 pages).
Jayaraman et al., "Evidence for persistent, occult infection in neonatal macaques following perinatal transmission of simian-human immunodeficiency virus SF162P3," J Virol. 81(2):822-34 (2007) (13 pages).
Kraft et al., "Macaques infected with a CCR5-tropic simian/human immunodeficiency virus (SHIV) develop broadly reactive anti-HIV neutralizing antibodies," J Virol. 81(12):6402-11 (2007) (10 pages).
Barouch et al., "Protective efficacy of a global HIV-1 mosaic vaccine against heterologous SHIV challenges in rhesus monkeys," available in PMC Oct. 24, 2014, published in final edited form as: Cell. 155(3):531-9 (2013) (16 pages).
Barouch et al., "Vaccine protection against acquisition of neutralization-resistant SIV challenges in rhesus monkeys," available in PMC Aug. 2, 2012, published in final edited form as: Nature. 482(7383):89-93 (2012) (17 pages).
Liu et al., "Immune control of an SIV challenge by a T-cell-based vaccine in rhesus monkeys," available in PMC Jul. 1, 2009, published in final edited form as: Nature. 457(7225):87-91 (2009) (17 pages).
Nishimura et al., "Generation of the pathogenic R5-tropic simian/human immunodeficiency virus SHIVAD8 by serial passaging in rhesus macaques," J Virol. 84(9):4769-81 (2010) (13 pages).
Gautam et al., "Pathogenicity and mucosal transmissibility of the R5-tropic simian/human immunodeficiency virus SHIV(AD8) in rhesus macaques: implications for use in vaccine studies," J Virol. 86(16):8516-26 (2012) (11 pages).
Pejchal et al., "A potent and broad neutralizing antibody recognizes and penetrates the HIV glycan shield," available in PMC Nov. 25, 2012, published in final edited form as: Science. 334(6059):1097-1103 (2011) (16 pages).

Burton et al., "Broadly neutralizing antibodies suggest new prospects to counter highly antigenically diverse viruses," available in PMC Jul. 13, 2013, published in final edited form as: Science. 337(6091):183-186 (2012) (13 pages).
McLellan et al., "Structure of HIV-1 gp120 V1/V2 domain with broadly neutralizing antibody PG9," available in PMC Dec. 15, 2012, published in final edited form as: Nature. 480(7377):336-343 (2011) (17 pages).
Althaus et al., "Dynamics of immune escape during HIV/SIV infection," PLoS Comput Biol. 4(7):e1000103 (2008).
Andrade et al., "Three distinct phases of HIV-1 RNA decay in treatment-naive patients receiving raltegravir-based antiretroviral therapy: ACTG A5248," J Infect Dis. 208(6):884-91 (2013).
De Boer et al., "Current estimates for HIV-1 production imply rapid viral clearance in lymphoid tissues," PLoS Comput Biol. 6(9):e1000906 (2010).
Diskin et al., "Increasing the potency and breadth of an HIV antibody by using structure-based rational design," Science. 334(6060):1289-93 (2011).
Diskin et al., "Restricting HIV-1 pathways for escape using rationally designed anti-HIV-1 antibodies," J Exp Med. 210(6):1235-49 (2013).
Hansen et al., "Profound early control of highly pathogenic SIV by an effector memory T-cell vaccine," Nature. 473(7348):523-7 (2011).
Hellerstein et al., "Directly measured kinetics of circulating T lymphocytes in normal and HIV-1-infected humans," Nat Med. 5(1):83-9 (1999).
Ho et al., "Rapid turnover of plasma virions and CD4 lymphocytes in HIV-1 infection," Nature. 373:123-126 (1995).
Huang et al., "Broad and potent neutralization of HIV-1 by a gp41-specific human antibody," Nature. 491(7427):406-12 (2012).
Igarashi et al., "Human immunodeficiency virus type 1 neutralizing antibodies accelerate clearance of cell-free virions from blood plasma," Nat Med. 5(2):211-6 (1999).
International Preliminary Report on Patentability for International Patent Application No. PCT/US2014/058383, dated Apr. 5, 2016 (7 pages).
International Search Report and Written Opinion for International Patent Application No. PCT/US2014/058383, dated Dec. 19, 2014 (12 pages).
Julien et al., "Broadly neutralizing antibody PGT121 allosterically modulates CD4 binding via recognition of the HIV-1 gp120 V3 base and multiple surrounding glycans," PLoS Pathog. 9(5):e1003342 (2013).
Kirschner et al., "Model of HIV-1 disease progression based on virus-induced lymph node homing and homing-induced apoptosis of CD4+ lymphocytes," J Acquir Immune Defic Syndr. 24(4):352-62 (2000).
Kirschner et al., "Role of the thymus in pediatric HIV-1 infection," J Acquir Immune Defic Syndr Hum Retrovirol. 18(2):95-109 (1998).
Klein et al., "HIV therapy by a combination of broadly neutralizing antibodies in humanized mice," Nature. 492(7427):118-22 (2012).
Kong et al., "Supersite of immune vulnerability on the glycosylated face of HIV-1 envelope glycoprotein gp120," Nat Struct Mol Biol. 20(7):796-803 (2013).
Letvin et al., "Immune and genetic correlates of vaccine protection against mucosal infection by SIV in monkeys," Sci Transl Med. 3(81)ra36 (2011).
Li et al., "Durable mucosal simian immunodeficiency virus-specific effector memory T lymphocyte responses elicited by recombinant adenovirus vectors in rhesus monkeys," J Virol. 85(21):11007-15 (2011).
Lim et al., "TRIM5alpha modulates immunodeficiency virus control in Rhesus monkeys," PLoS Pathog. 6(1):e1000738 (2010).
Liu et al., "Magnitude and phenotype of cellular immune responses elicited by recombinant adenovirus vectors and heterologous prime-boost regimens in rhesus monkeys," J Virol. 82(10):4844-52 (2008).
Loffredo et al., "Mamu-B*08-positive macaques control simian immunodeficiency virus replication," J Virol. 81(16):8827-32 (2007).
McLellan et al., "Structure of HIV-1 gp120 V1/V2 domain with broadly neutralizing antibody PG9," Nature. 480(7377):336-43 (2011).

(56) References Cited

OTHER PUBLICATIONS

Mehandru et al., "Adjunctive passive immunotherapy in human immunodeficiency virus type 1-infected individuals treated with antiviral therapy during acute and early infection," J Virol. 81(20):11016-31 (2007).

Mothe et al., "Expression of the major histocompatibility complex class I molecule Mamu-A*01 is associated with control of simian immunodeficiency virus SIVmac239 replication," J Virol. 77(4):2736-40 (2003).

Mouquet et al., "Complex-type N-glycan recognition by potent broadly neutralizing HIV antibodies," Proc Natl Acad Sci U.S.A. 109(47):E3268-77 (2012).

NCBI Blast fo Accesion No. NP_00607. Retrieved May 10, 2016 (4 pages).

Okoye et al.,"Progressive CD4+ central memory T cell decline results in CD4+ effector memory insufficiency and overt disease in chronic SIV infection," J Exp Med. 204(9):2171-85 (2007).

Perelson et al., "Dynamics of HIV infection of CD4+ T cells," Math Biosci. 114(1):81-125 (1993).

Perelson et al., "HIV-1 dynamics in vivo: virion clearance rate, infected cell life-span, and viral generation time," Science. 271(5255):1582-6 (1996).

Pitcher et al., "Development and homeostasis of T cell memory in rhesus macaque," J Immunol. 168(1):29-43 (2002).

Poignard et al.,"Neutralizing antibodies have limited effects on the control of established HIV-1 infection in vivo," Immunity. 10(4):431-8 (1999).

Roben et al., "Recognition properties of a panel of human recombinant Fab fragments to the CD4 binding site of gp120 that show differing abilities to neutralize human immunodeficiency virus type 1," J Virol. 68(8):4821-8 (1994).

Scheid et al., "Sequence and structural convergence of broad and potent HIV antibodies that mimic CD4 binding," Science. 333(6049):1633-7 (2011).

Trkola et al., "Delay of HIV-1 rebound after cessation of antiretroviral therapy through passive transfer of human neutralizing antibodies," Nat Med. 11(6):615-22 (2005).

Walker et al., "Broad and potent neutralizing antibodies from an African donor reveal a new HIV-1 vaccine target," Science. 326(5950):285-9 (2009).

Walker et al., "Broad neutralization coverage of HIV by multiple highly potent antibodies," Nature. 477(7365):466-70 (2011).

West et al., "Computational analysis of anti-HIV-1 antibody neutralization panel data to identify potential functional epitope residues," Proc Natl Acad Sci USA. 110(26)1 0598-603 (2013).

Whitney et al., "T-cell vaccination reduces simian immunodeficiency virus levels in semen," J Virol. 83(20):10840-3 (2009).

Wu et al., "Rational design of envelope identifies broadly neutralizing human monoclonal antibodies to HIV-1," Science. 329(5993):856-61 (2010).

Yant et al., "The high-frequency major histocompatibility complex class I allele Mamu-B*17 is associated with control of simian immunodeficiency virus SIVmac239 replication," J Virol. 80(10):5074-7 (2006).

Zhou et al., "Structural basis for broad and potent neutralization of HIV-1 by antibody VRC01," Science. 329(5993):811-7 (2010).

Scheid et al., "Broad diversity of neutralizing antibodies isolated from memory B cells in HIV-infected individuals," Nature. 458(7238):636-40 (2009).

Communication pursuant to Article 94(3) EPC for European Patent Application No. 14847004.0, dated Jan. 15, 2018 (8 pages).

Le Douce et al., "Achieving a cure for HIV infection: do we have reasons to be optimistic?" J Antimicrob Chemother. 67(5):1063-74 (2012).

Brooks et al., "Chapter 11: Clearance of Latent Reservoirs." *HIV Chemotherapy: A Critical Review*. Salvatore T. Butera, Calster Academic Press, 281-303 (2005) (24 pages).

Hatziioannou et al., "Animal models for HIV/AIDS research," author manuscript available in PubMed Central® Feb. 19, 2015, published in final edited form as: Nat Rev Microbiol. 10(12):852-867 (2012) (37 pages).

* cited by examiner

SEQUENCE LISTING

```
<160> NUMBER OF SEQ ID NOS: 322

<210> SEQ ID NO 1
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 1

Asp Ser Tyr Trp Ser
1               5

<210> SEQ ID NO 2
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 2

Tyr Val His Lys Ser Gly Asp Thr Asn Tyr Ser Pro Ser Leu Lys Ser
1               5                   10                  15

<210> SEQ ID NO 3
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 3

Thr Leu His Gly Arg Arg Ile Tyr Gly Ile Val Ala Phe Asn Glu Trp
```

```
1               5                   10                  15

Phe Thr Tyr Phe Tyr Met Asp Val
                20

<210> SEQ ID NO 4
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 4

Gly Glu Lys Ser Leu Gly Ser Arg Ala Val Gln
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 5

Asn Asn Gln Asp Arg Pro Ser
1               5

<210> SEQ ID NO 6
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 6

His Ile Trp Asp Ser Arg Val Pro Thr Lys Trp Val
1               5                   10

<210> SEQ ID NO 7
<211> LENGTH: 132
<212> TYPE: PRT
<213> ORGANISM: Artificial Sequence
<220> FEATURE:
<223> OTHER INFORMATION: Synthetic Peptide

<400> SEQUENCE: 7

Gln Met Gln Leu Gln Glu Ser Gly Pro Gly Leu Val Lys Pro Ser Glu
1               5                   10                  15

Thr Leu Ser Leu Thr Cys Ser Val Ser Gly Ala Ser Ile Ser Asp Ser
                20                  25                  30

Tyr Trp Ser Trp Ile Arg Arg Ser Pro Gly Lys Gly Leu Glu Trp Ile
            35                  40                  45

Gly Tyr Val His Lys Ser Gly Asp Thr Asn Tyr Ser Pro Ser Leu Lys
        50                  55                  60

Ser Arg Val Asn Leu Ser Leu Asp Thr Ser Lys Asn Gln Val Ser Leu
65                  70                  75                  80

Ser Leu Val Ala Ala Thr Ala Ala Asp Ser Gly Lys Tyr Tyr Cys Ala
                85                  90                  95

Arg Thr Leu His Gly Arg Ile Tyr Gly Ile Val Ala Phe Asn Glu
                100                 105                 110

Trp Phe Thr Tyr Phe Tyr Met Asp Val Trp Gly Asn Gly Thr Gln Val
            115                 120                 125

Thr Val Ser Ser
```

<210> SEQ ID NO 8
<211> LENGTH: 105
<212> TYPE: PRT
<213> ORGANISM: Artificial Sequence
<220> FEATURE:
<223> OTHER INFORMATION: Synthetic Peptide

<400> SEQUENCE: 8

```
Ser Asp Ile Ser Val Ala Pro Gly Glu Thr Ala Arg Ile Ser Cys Gly
1               5                   10                  15
Glu Lys Ser Leu Gly Ser Arg Ala Val Gln Trp Tyr Gln His Arg Ala
            20                  25                  30
Gly Gln Ala Pro Ser Leu Ile Ile Tyr Asn Asn Gln Asp Arg Pro Ser
        35                  40                  45
Gly Ile Pro Glu Arg Phe Ser Gly Ser Pro Asp Ser Pro Phe Gly Thr
    50                  55                  60
Thr Ala Thr Leu Thr Ile Thr Ser Val Glu Ala Gly Asp Glu Ala Asp
65                  70                  75                  80
Tyr Tyr Cys His Ile Trp Asp Ser Arg Val Pro Thr Lys Trp Val Phe
                85                  90                  95
Gly Gly Gly Thr Thr Leu Thr Val Leu
            100                 105
```

<210> SEQ ID NO 9
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 9

```
Asp Asn Tyr Trp Ser
1               5
```

<210> SEQ ID NO 10
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 10

```
Tyr Val His Asp Ser Gly Asp Thr Asn Tyr Asn Pro Ser Leu Lys Ser
1               5                   10                  15
```

<210> SEQ ID NO 11
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 11

```
Thr Lys His Gly Arg Arg Ile Tyr Gly Val Val Ala Phe Lys Glu Trp
1               5                   10                  15
Phe Thr Tyr Phe Tyr Met Asp Val
            20
```

<210> SEQ ID NO 12
<211> LENGTH: 11
<212> TYPE: PRT

```
<213> ORGANISM: Artificial Sequence
<220> FEATURE:
<223> OTHER INFORMATION: Synthetic Peptide

<400> SEQUENCE: 12

Gly Glu Glu Ser Leu Gly Ser Arg Ser Val Ile
1               5                   10

<210> SEQ ID NO 13
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 13

Asn Asn Asn Asp Arg Pro Ser
1               5

<210> SEQ ID NO 14
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 14

His Ile Trp Asp Ser Arg Arg Pro Thr Asn Trp Val
1               5                   10

<210> SEQ ID NO 15
<211> LENGTH: 116
<212> TYPE: PRT
<213> ORGANISM: Artificial Sequence
<220> FEATURE:
<223> OTHER INFORMATION: Synthetic Peptide

<400> SEQUENCE: 15

Thr Leu Ser Leu Thr Cys Asn Val Ser Gly Thr Leu Val Arg Asp Asn
1               5                   10                  15

Tyr Trp Ser Trp Ile Arg Gln Pro Leu Gly Lys Gln Pro Glu Trp Ile
            20                  25                  30

Gly Tyr Val His Asp Ser Gly Asp Thr Asn Tyr Asn Pro Ser Leu Lys
        35                  40                  45

Ser Arg Val His Leu Ser Leu Asp Lys Ser Lys Asn Leu Val Ser Leu
    50                  55                  60

Arg Leu Thr Gly Val Thr Ala Ala Asp Ser Ala Ile Tyr Tyr Cys Ala
65                  70                  75                  80

Thr Thr Lys His Gly Arg Arg Ile Tyr Gly Val Val Ala Phe Lys Glu
                85                  90                  95

Trp Phe Thr Tyr Phe Tyr Met Asp Val Trp Gly Lys Gly Thr Ser Val
            100                 105                 110

Thr Val Ser Ser
        115

<210> SEQ ID NO 16
<211> LENGTH: 105
<212> TYPE: PRT
<213> ORGANISM: Artificial Sequence
<220> FEATURE:
<223> OTHER INFORMATION: Synthetic Peptide

<400> SEQUENCE: 16
```

```
Thr Phe Val Ser Val Ala Pro Gly Gln Thr Ala Arg Ile Thr Cys Gly
1               5                   10                  15

Glu Glu Ser Leu Gly Ser Arg Ser Val Ile Trp Tyr Gln Gln Arg Pro
            20                  25                  30

Gly Gln Ala Pro Ser Leu Ile Ile Tyr Asn Asn Asn Asp Arg Pro Ser
        35                  40                  45

Gly Ile Pro Asp Arg Phe Ser Gly Ser Pro Gly Ser Thr Phe Gly Thr
    50                  55                  60

Thr Ala Thr Leu Thr Ile Thr Ser Val Glu Ala Gly Asp Glu Ala Asp
65                  70                  75                  80

Tyr Tyr Cys His Ile Trp Asp Ser Arg Arg Pro Thr Asn Trp Val Phe
                85                  90                  95

Gly Glu Gly Thr Thr Leu Ile Val Leu
            100                 105
```

<210> SEQ ID NO 17
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 17

```
Asp Ala Tyr Trp Ser
1               5
```

<210> SEQ ID NO 18
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 18

```
Tyr Val His His Ser Gly Asp Thr Asn Tyr Asn Pro Ser Leu Lys Arg
1               5                   10                  15
```

<210> SEQ ID NO 19
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 19

```
Ala Leu His Gly Lys Arg Ile Tyr Gly Ile Val Ala Leu Gly Glu Leu
1               5                   10                  15

Phe Thr Tyr Phe Tyr Met Asp Val
            20
```

<210> SEQ ID NO 20
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 20

```
Gly Lys Glu Ser Ile Gly Ser Arg Ala Val Gln
1               5                   10
```

<210> SEQ ID NO 21
<211> LENGTH: 7

```
<212> TYPE: PRT
<213> ORGANISM: Artificial Sequence
<220> FEATURE:
<223> OTHER INFORMATION: Synthetic Peptide

<400> SEQUENCE: 21

Asn Asn Gln Asp Arg Pro Ala
1               5

<210> SEQ ID NO 22
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 22

His Ile Tyr Asp Ala Arg Gly Gly Thr Asn Trp Val
1               5                   10

<210> SEQ ID NO 23
<211> LENGTH: 132
<212> TYPE: PRT
<213> ORGANISM: Artificial Sequence
<220> FEATURE:
<223> OTHER INFORMATION: Synthetic Peptide

<400> SEQUENCE: 23

Gln Leu His Leu Gln Glu Ser Gly Pro Gly Leu Val Lys Pro Pro Glu
1               5                   10                  15

Thr Leu Ser Leu Thr Cys Ser Val Ser Gly Ala Ser Ile Asn Asp Ala
            20                  25                  30

Tyr Trp Ser Trp Ile Arg Gln Ser Pro Gly Lys Arg Pro Glu Trp Val
        35                  40                  45

Gly Tyr Val His His Ser Gly Asp Thr Asn Tyr Asn Pro Ser Leu Lys
    50                  55                  60

Arg Arg Val Thr Phe Ser Leu Asp Thr Ala Lys Asn Glu Val Ser Leu
65                  70                  75                  80

Lys Leu Val Asp Leu Thr Ala Ala Asp Ser Ala Thr Tyr Phe Cys Ala
                85                  90                  95

Arg Ala Leu His Gly Lys Arg Ile Tyr Gly Ile Val Ala Leu Gly Glu
            100                 105                 110

Leu Phe Thr Tyr Phe Tyr Met Asp Val Trp Gly Lys Gly Thr Ala Val
        115                 120                 125

Thr Val Ser Ser
    130

<210> SEQ ID NO 24
<211> LENGTH: 105
<212> TYPE: PRT
<213> ORGANISM: Artificial Sequence
<220> FEATURE:
<223> OTHER INFORMATION: Synthetic Peptide

<400> SEQUENCE: 24

Ser Ser Met Ser Val Ser Pro Gly Glu Thr Ala Lys Ile Ser Cys Gly
1               5                   10                  15

Lys Glu Ser Ile Gly Ser Arg Ala Val Gln Trp Tyr Gln Gln Lys Pro
            20                  25                  30

Gly Gln Pro Pro Ser Leu Ile Ile Tyr Asn Asn Gln Asp Arg Pro Ala
        35                  40                  45
```

Gly Val Pro Glu Arg Phe Ser Ala Ser Pro Asp Phe Arg Pro Gly Thr
    50                       55                   60

Thr Ala Thr Leu Thr Ile Thr Asn Val Asp Ala Glu Asp Glu Ala Asp
 65                    70                 75                  80

Tyr Tyr Cys His Ile Tyr Asp Ala Arg Gly Gly Thr Asn Trp Val Phe
                  85                   90                  95

Asp Arg Gly Thr Thr Leu Thr Val Leu
           100               105

<210> SEQ ID NO 25
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 25

Ala Cys Thr Tyr Phe Trp Gly
1            5

<210> SEQ ID NO 26
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 26

Ser Leu Ser His Cys Gln Ser Phe Trp Gly Ser Gly Trp Thr Phe His
1            5                  10                15

Asn Pro Ser Leu Lys Ser
           20

<210> SEQ ID NO 27
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 27

Phe Asp Gly Glu Val Leu Val Tyr Asn His Trp Pro Lys Pro Ala Trp
1            5                  10                15

Val Asp Leu

<210> SEQ ID NO 28
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 28

Asn Gly Thr Ala Thr Asn Phe Val Ser
1            5

<210> SEQ ID NO 29
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 29

```
Gly Val Asp Lys Arg Pro Pro
1               5

<210> SEQ ID NO 30
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 30

Gly Ser Leu Val Gly Asn Trp Asp Val Ile
1               5                   10

<210> SEQ ID NO 31
<211> LENGTH: 135
<212> TYPE: PRT
<213> ORGANISM: Artificial Sequence
<220> FEATURE:
<223> OTHER INFORMATION: Synthetic Peptide

<400> SEQUENCE: 31

Gln Ser Gln Leu Gln Glu Ser Gly Pro Arg Leu Val Glu Ala Ser Glu
1               5                   10                  15

Thr Leu Ser Leu Thr Cys Asn Val Ser Gly Glu Ser Thr Gly Ala Cys
            20                  25                  30

Thr Tyr Phe Trp Gly Trp Val Arg Gln Ala Pro Gly Lys Gly Leu Glu
        35                  40                  45

Trp Ile Gly Ser Leu Ser His Cys Gln Ser Phe Trp Gly Ser Gly Trp
    50                  55                  60

Thr Phe His Asn Pro Ser Leu Lys Ser Arg Leu Thr Ile Ser Leu Asp
65                  70                  75                  80

Thr Pro Lys Asn Gln Val Phe Leu Lys Leu Thr Ser Leu Thr Ala Ala
                85                  90                  95

Asp Thr Ala Thr Tyr Tyr Cys Ala Arg Phe Asp Gly Glu Val Leu Val
            100                 105                 110

Tyr Asn His Trp Pro Lys Pro Ala Trp Val Asp Leu Trp Gly Arg Gly
        115                 120                 125

Ile Pro Val Thr Val Ser Ser
    130                 135

<210> SEQ ID NO 32
<211> LENGTH: 105
<212> TYPE: PRT
<213> ORGANISM: Artificial Sequence
<220> FEATURE:
<223> OTHER INFORMATION: Synthetic Peptide

<400> SEQUENCE: 32

Gln Ser Ala Leu Thr Gln Pro Pro Ser Ala Ser Gly Ser Pro Gly Gln
1               5                   10                  15

Ser Ile Thr Ile Ser Cys Asn Gly Thr Ala Thr Asn Phe Val Ser Trp
            20                  25                  30

Tyr Gln Gln Phe Pro Asp Lys Ala Pro Lys Leu Ile Ile Phe Gly Val
        35                  40                  45

Asp Lys Arg Pro Pro Gly Val Pro Asp Arg Phe Ser Gly Ser Arg Ser
    50                  55                  60

Gly Thr Thr Ala Ser Leu Thr Val Ser Arg Leu Gln Thr Asp Asp Glu
65                  70                  75                  80

Ala Val Tyr Tyr Cys Gly Ser Leu Val Gly Asn Trp Asp Val Ile Phe
```

Gly Gly Gly Thr Thr Leu Thr Val Leu
            100                 105

<210> SEQ ID NO 33
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 33

Ala Cys Asp Tyr Phe Trp Gly
1               5

<210> SEQ ID NO 34
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 34

Gly Leu Ser His Cys Ala Gly Tyr Tyr Asn Thr Gly Trp Thr Tyr His
1               5                   10                  15

Asn Pro Ser Leu Lys Ser
            20

<210> SEQ ID NO 35
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 35

Phe Asp Gly Glu Val Leu Val Tyr His Asp Trp Pro Lys Pro Ala Trp
1               5                   10                  15

Val Asp Leu

<210> SEQ ID NO 36
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 36

Thr Gly Thr Ser Asn Arg Phe Val Ser
1               5

<210> SEQ ID NO 37
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 37

Gly Val Asn Lys Arg Pro Ser
1               5

<210> SEQ ID NO 38
<211> LENGTH: 10
<212> TYPE: PRT

```
<213> ORGANISM: Artificial Sequence
<220> FEATURE:
<223> OTHER INFORMATION: Synthetic Peptide

<400> SEQUENCE: 38

Ser Ser Leu Val Gly Asn Trp Asp Val Ile
1               5                   10

<210> SEQ ID NO 39
<211> LENGTH: 135
<212> TYPE: PRT
<213> ORGANISM: Artificial Sequence
<220> FEATURE:
<223> OTHER INFORMATION: Synthetic Peptide

<400> SEQUENCE: 39

Gln Pro Gln Leu Gln Glu Ser Gly Pro Gly Leu Val Glu Ala Ser Glu
1               5                   10                  15

Thr Leu Ser Leu Thr Cys Thr Val Ser Gly Asp Ser Thr Ala Ala Cys
                20                  25                  30

Asp Tyr Phe Trp Gly Trp Val Arg Gln Pro Pro Gly Lys Gly Leu Glu
            35                  40                  45

Trp Ile Gly Gly Leu Ser His Cys Ala Gly Tyr Tyr Asn Thr Gly Trp
    50                  55                  60

Thr Tyr His Asn Pro Ser Leu Lys Ser Arg Leu Thr Ile Ser Leu Asp
65                  70                  75                  80

Thr Pro Lys Asn Gln Val Phe Leu Lys Leu Asn Ser Val Thr Ala Ala
                85                  90                  95

Asp Thr Ala Ile Tyr Tyr Cys Ala Arg Phe Asp Gly Glu Val Leu Val
            100                 105                 110

Tyr His Asp Trp Pro Lys Pro Ala Trp Val Asp Leu Trp Gly Arg Gly
        115                 120                 125

Thr Leu Val Thr Val Ser Ser
    130                 135

<210> SEQ ID NO 40
<211> LENGTH: 105
<212> TYPE: PRT
<213> ORGANISM: Artificial Sequence
<220> FEATURE:
<223> OTHER INFORMATION: Synthetic Peptide

<400> SEQUENCE: 40

Gln Ser Ala Leu Thr Gln Pro Pro Ser Ala Ser Gly Ser Pro Gly Gln
1               5                   10                  15

Ser Ile Ser Ile Ser Cys Thr Gly Thr Ser Asn Arg Phe Val Ser Trp
                20                  25                  30

Tyr Gln Gln His Pro Gly Lys Ala Pro Lys Leu Val Ile Tyr Gly Val
            35                  40                  45

Asn Lys Arg Pro Ser Gly Val Pro Asp Arg Phe Ser Gly Ser Lys Ser
        50                  55                  60

Gly Asn Thr Ala Ser Leu Thr Val Ser Gly Leu Gln Thr Asp Asp Glu
65                  70                  75                  80

Ala Val Tyr Tyr Cys Ser Ser Leu Val Gly Asn Trp Asp Val Ile Phe
                85                  90                  95

Gly Gly Gly Thr Lys Leu Thr Val Leu
            100                 105

<210> SEQ ID NO 41
```

```
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 41

Arg Cys Asn Tyr Phe Trp Gly
1               5

<210> SEQ ID NO 42
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 42

Ser Leu Ser His Cys Arg Ser Tyr Tyr Asn Thr Asp Trp Thr Tyr His
1               5                   10                  15

Asn Pro Ser Leu Lys Ser
            20

<210> SEQ ID NO 43
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 43

Phe Gly Gly Glu Val Leu Val Tyr Arg Asp Trp Pro Lys Pro Ala Trp
1               5                   10                  15

Val Asp Leu

<210> SEQ ID NO 44
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 44

Thr Gly Thr Ser Asn Asn Phe Val Ser
1               5

<210> SEQ ID NO 45
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 45

Glu Val Asn Lys Arg Pro Ser
1               5

<210> SEQ ID NO 46
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 46

Ser Ser Leu Val Gly Asn Trp Asp Val Ile
```

<210> SEQ ID NO 47
<211> LENGTH: 136
<212> TYPE: PRT
<213> ORGANISM: Artificial Sequence
<220> FEATURE:
<223> OTHER INFORMATION: Synthetic Peptide

<400> SEQUENCE: 47

```
Gln Pro Gln Leu Gln Glu Ser Gly Pro Gly Leu Val Glu Ala Ser Glu
1               5                   10                  15

Thr Leu Ser Leu Thr Cys Thr Val Ser Gly Asp Ser Thr Gly Arg Cys
            20                  25                  30

Asn Tyr Phe Trp Gly Trp Val Arg Gln Pro Pro Gly Lys Gly Leu Glu
        35                  40                  45

Trp Ile Gly Ser Leu Ser His Cys Arg Ser Tyr Tyr Asn Thr Asp Trp
    50                  55                  60

Thr Tyr His Asn Pro Ser Leu Lys Ser Arg Leu Thr Ile Ser Leu Asp
65                  70                  75                  80

Thr Pro Lys Asn Gln Val Phe Leu Arg Leu Thr Ser Val Thr Ala Ala
                85                  90                  95

Asp Thr Ala Thr Tyr Tyr Cys Ala Arg Phe Gly Gly Glu Val Leu Val
            100                 105                 110

Tyr Arg Asp Trp Pro Lys Pro Ala Trp Val Asp Leu Trp Gly Arg Gly
        115                 120                 125

Thr Leu Val Val Thr Val Ser Ser
    130                 135
```

<210> SEQ ID NO 48
<211> LENGTH: 105
<212> TYPE: PRT
<213> ORGANISM: Artificial Sequence
<220> FEATURE:
<223> OTHER INFORMATION: Synthetic Peptide

<400> SEQUENCE: 48

```
Gln Ser Ala Leu Thr Gln Pro Pro Ser Ala Ser Gly Ser Pro Gly Gln
1               5                   10                  15

Ser Ile Thr Ile Ser Cys Thr Gly Thr Ser Asn Asn Phe Val Ser Trp
            20                  25                  30

Tyr Gln Gln Tyr Pro Gly Lys Ala Pro Lys Leu Val Ile Tyr Glu Val
        35                  40                  45

Asn Lys Arg Pro Ser Gly Val Pro Asp Arg Phe Ser Gly Ser Lys Ser
    50                  55                  60

Gly Ser Thr Ala Ser Leu Thr Val Ser Gly Leu Gln Ala Asp Asp Glu
65                  70                  75                  80

Gly Val Tyr Tyr Cys Ser Ser Leu Val Gly Asn Trp Asp Val Ile Phe
                85                  90                  95

Gly Gly Gly Thr Lys Leu Thr Val Leu
            100                 105
```

<210> SEQ ID NO 49
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 49

```
Ala Cys Asn Ser Phe Trp Gly
1               5
```

<210> SEQ ID NO 50
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 50

```
Ser Leu Ser His Cys Ala Ser Tyr Trp Asn Arg Gly Trp Thr Tyr His
1               5                   10                  15

Asn Pro Ser Leu Lys Ser
            20
```

<210> SEQ ID NO 51
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 51

```
Phe Gly Gly Glu Val Leu Arg Tyr Thr Asp Trp Pro Lys Pro Ala Trp
1               5                   10                  15

Val Asp Leu
```

<210> SEQ ID NO 52
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 52

```
Thr Gly Thr Ser Asn Asn Phe Val Ser
1               5
```

<210> SEQ ID NO 53
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 53

```
Asp Val Asn Lys Arg Pro Ser
1               5
```

<210> SEQ ID NO 54
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 54

```
Gly Ser Leu Val Gly Asn Trp Asp Val Ile
1               5                   10
```

<210> SEQ ID NO 55
<211> LENGTH: 135
<212> TYPE: PRT
<213> ORGANISM: Artificial Sequence

```
<220> FEATURE:
<223> OTHER INFORMATION: Synthetic Peptide

<400> SEQUENCE: 55

Gln Pro Gln Leu Gln Glu Ser Gly Pro Thr Leu Val Glu Ala Ser Glu
1               5                   10                  15

Thr Leu Ser Leu Thr Cys Ala Val Ser Gly Asp Ser Thr Ala Ala Cys
            20                  25                  30

Asn Ser Phe Trp Gly Trp Val Arg Gln Pro Pro Gly Lys Gly Leu Glu
        35                  40                  45

Trp Val Gly Ser Leu Ser His Cys Ala Ser Tyr Trp Asn Arg Gly Trp
    50                  55                  60

Thr Tyr His Asn Pro Ser Leu Lys Ser Arg Leu Thr Leu Ala Leu Asp
65                  70                  75                  80

Thr Pro Lys Asn Leu Val Phe Leu Lys Leu Asn Ser Val Thr Ala Ala
                85                  90                  95

Asp Thr Ala Thr Tyr Tyr Cys Ala Arg Phe Gly Gly Glu Val Leu Arg
            100                 105                 110

Tyr Thr Asp Trp Pro Lys Pro Ala Trp Val Asp Leu Trp Gly Arg Gly
        115                 120                 125

Thr Leu Val Thr Val Ser Ser
    130                 135

<210> SEQ ID NO 56
<211> LENGTH: 105
<212> TYPE: PRT
<213> ORGANISM: Artificial Sequence
<220> FEATURE:
<223> OTHER INFORMATION: Synthetic Peptide

<400> SEQUENCE: 56

Gln Ser Ala Leu Thr Gln Pro Pro Ser Ala Ser Gly Ser Pro Gly Gln
1               5                   10                  15

Ser Ile Thr Ile Ser Cys Thr Gly Thr Ser Asn Asn Phe Val Ser Trp
            20                  25                  30

Tyr Gln Gln His Ala Gly Lys Ala Pro Lys Leu Val Ile Tyr Asp Val
        35                  40                  45

Asn Lys Arg Pro Ser Gly Val Pro Asp Arg Phe Ser Gly Ser Lys Ser
    50                  55                  60

Gly Asn Thr Ala Ser Leu Thr Val Ser Gly Leu Gln Thr Asp Asp Glu
65                  70                  75                  80

Ala Val Tyr Tyr Cys Gly Ser Leu Val Gly Asn Trp Asp Val Ile Phe
                85                  90                  95

Gly Gly Gly Thr Lys Leu Thr Val Leu
            100                 105

<210> SEQ ID NO 57
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 57

Thr Gly His Tyr Tyr Trp Gly
1               5

<210> SEQ ID NO 58
<211> LENGTH: 16
```

```
<212> TYPE: PRT
<213> ORGANISM: Artificial Sequence
<220> FEATURE:
<223> OTHER INFORMATION: Synthetic Peptide

<400> SEQUENCE: 58

His Ile His Tyr Thr Thr Ala Val Leu His Asn Pro Ser Leu Lys Ser
1               5                   10                  15

<210> SEQ ID NO 59
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 59

Ser Gly Gly Asp Ile Leu Tyr Tyr Tyr Glu Trp Gln Lys Pro His Trp
1               5                   10                  15

Phe Ser Pro

<210> SEQ ID NO 60
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 60

Asn Gly Thr Ser Ser Asp Ile Gly Gly Trp Asn Phe Val Ser
1               5                   10

<210> SEQ ID NO 61
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 61

Glu Val Asn Lys Arg Pro Ser
1               5

<210> SEQ ID NO 62
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 62

Ser Ser Leu Phe Gly Arg Trp Asp Val Val
1               5                   10

<210> SEQ ID NO 63
<211> LENGTH: 129
<212> TYPE: PRT
<213> ORGANISM: Artificial Sequence
<220> FEATURE:
<223> OTHER INFORMATION: Synthetic Peptide

<400> SEQUENCE: 63

Gln Val Gln Leu Gln Glu Ser Gly Pro Gly Leu Val Lys Pro Ala Glu
1               5                   10                  15

Thr Leu Ser Leu Thr Cys Ser Val Ser Gly Glu Ser Ile Asn Thr Gly
                20                  25                  30
```

His Tyr Tyr Trp Gly Trp Val Arg Gln Val Pro Gly Lys Gly Leu Glu
              35                  40                  45

Trp Ile Gly His Ile His Tyr Thr Thr Ala Val Leu His Asn Pro Ser
         50                  55                  60

Leu Lys Ser Arg Leu Thr Ile Lys Ile Tyr Thr Leu Arg Asn Gln Ile
65                  70                  75                  80

Thr Leu Arg Leu Ser Asn Val Thr Ala Ala Asp Thr Ala Val Tyr His
                 85                  90                  95

Cys Val Arg Ser Gly Gly Asp Ile Leu Tyr Tyr Glu Trp Gln Lys
                100                 105                 110

Pro His Trp Phe Ser Pro Trp Gly Pro Gly Ile His Val Thr Val Ser
             115                 120                 125

Ser

<210> SEQ ID NO 64
<211> LENGTH: 110
<212> TYPE: PRT
<213> ORGANISM: Artificial Sequence
<220> FEATURE:
<223> OTHER INFORMATION: Synthetic Peptide

<400> SEQUENCE: 64

Gln Ser Ala Leu Thr Gln Pro Pro Ser Ala Ser Gly Ser Leu Gly Gln
1               5                   10                  15

Ser Val Thr Ile Ser Cys Asn Gly Thr Ser Ser Asp Ile Gly Gly Trp
            20                  25                  30

Asn Phe Val Ser Trp Tyr Gln Gln Phe Pro Gly Arg Ala Pro Arg Leu
         35                  40                  45

Ile Ile Phe Glu Val Asn Lys Arg Pro Ser Gly Val Pro Gly Arg Phe
     50                  55                  60

Ser Gly Ser Lys Ser Gly Asn Ser Ala Ser Leu Thr Val Ser Gly Leu
65                  70                  75                  80

Gln Ser Asp Asp Glu Gly Gln Tyr Phe Cys Ser Ser Leu Phe Gly Arg
                 85                  90                  95

Trp Asp Val Val Phe Gly Gly Gly Thr Lys Leu Thr Val Leu
             100                 105                 110

<210> SEQ ID NO 65
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 65

Thr Gly His His Tyr Trp Gly
1               5

<210> SEQ ID NO 66
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 66

His Ile His Tyr Asn Thr Ala Val Leu His Asn Pro Ala Leu Lys Ser
1               5                   10                  15

```
<210> SEQ ID NO 67
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 67

Ser Gly Gly Asp Ile Leu Tyr Tyr Ile Glu Trp Gln Lys Pro His Trp
1               5                   10                  15

Phe Tyr Pro

<210> SEQ ID NO 68
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 68

Ser Gly Thr Gly Ser Asp Ile Gly Ser Trp Asn Phe Val Ser
1               5                   10

<210> SEQ ID NO 69
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 69

Glu Val Asn Arg Arg Arg Ser
1               5

<210> SEQ ID NO 70
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 70

Ser Ser Leu Ser Gly Arg Trp Asp Ile Val
1               5                   10

<210> SEQ ID NO 71
<211> LENGTH: 129
<212> TYPE: PRT
<213> ORGANISM: Artificial Sequence
<220> FEATURE:
<223> OTHER INFORMATION: Synthetic Peptide

<400> SEQUENCE: 71

Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Asn Thr Gly
                20                  25                  30

His His Tyr Trp Gly Trp Val Arg Gln Val Pro Gly Lys Gly Pro Glu
            35                  40                  45

Trp Ile Ala His Ile His Tyr Asn Thr Ala Val Leu His Asn Pro Ala
    50                  55                  60

Leu Lys Ser Arg Val Thr Ile Ser Ile Phe Thr Leu Lys Asn Leu Ile
65                  70                  75                  80

Thr Leu Ser Leu Ser Asn Val Thr Ala Ala Asp Thr Ala Val Tyr Phe
```

```
                85                  90                  95
Cys Val Arg Ser Gly Gly Asp Ile Leu Tyr Tyr Ile Glu Trp Gln Lys
            100                 105                 110
Pro His Trp Phe Tyr Pro Trp Gly Pro Gly Ile Leu Val Thr Val Ser
        115                 120                 125
Ser
```

<210> SEQ ID NO 72
<211> LENGTH: 110
<212> TYPE: PRT
<213> ORGANISM: Artificial Sequence
<220> FEATURE:
<223> OTHER INFORMATION: Synthetic Peptide

<400> SEQUENCE: 72

```
Gln Ser Ala Leu Thr Gln Pro Pro Ser Ala Ser Gly Ser Leu Gly Gln
1               5                   10                  15
Ser Leu Thr Ile Ser Cys Ser Gly Thr Gly Ser Asp Ile Gly Ser Trp
            20                  25                  30
Asn Phe Val Ser Trp Tyr Gln Gln Phe Pro Gly Arg Ala Pro Asn Leu
        35                  40                  45
Ile Ile Phe Glu Val Asn Arg Arg Ser Gly Val Pro Asp Arg Phe
    50                  55                  60
Ser Gly Ser Lys Ser Gly Asn Thr Ala Ser Leu Thr Val Ser Gly Leu
65                  70                  75                  80
Arg Ser Glu Asp Glu Ala Glu Tyr Phe Cys Ser Ser Leu Ser Gly Arg
                85                  90                  95
Trp Asp Ile Val Phe Gly Gly Gly Thr Lys Val Thr Val Leu
            100                 105                 110
```

<210> SEQ ID NO 73
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 73

```
Gly Gly Glu Trp Gly Asp Lys Asp Tyr His Trp Gly
1               5                   10
```

<210> SEQ ID NO 74
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 74

```
Ser Ile His Trp Arg Gly Thr Thr His Tyr Lys Glu Ser Leu Arg Arg
1               5                   10                  15
```

<210> SEQ ID NO 75
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 75

```
His Arg His His Asp Val Phe Met Leu Val Pro Ile Ala Gly Trp Phe
1               5                   10                  15
```

Asp Val

<210> SEQ ID NO 76
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 76

Arg Ala Ser Gln Asn Ile Asn Lys Asn Leu Ala
1               5                   10

<210> SEQ ID NO 77
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 77

Glu Thr Tyr Ser Lys Ile Ala
1               5

<210> SEQ ID NO 78
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 78

Gln Gln Tyr Glu Glu Trp Pro Arg Thr
1               5

<210> SEQ ID NO 79
<211> LENGTH: 133
<212> TYPE: PRT
<213> ORGANISM: Artificial Sequence
<220> FEATURE:
<223> OTHER INFORMATION: Synthetic Peptide

<400> SEQUENCE: 79

Gln Leu Gln Met Gln Glu Ser Gly Pro Gly Leu Val Lys Pro Ser Glu
1               5                   10                  15

Thr Leu Ser Leu Ser Cys Thr Val Ser Gly Asp Ser Ile Arg Gly Gly
            20                  25                  30

Glu Trp Gly Asp Lys Asp Tyr His Trp Gly Trp Val Arg His Ser Ala
        35                  40                  45

Gly Lys Gly Leu Glu Trp Ile Gly Ser Ile His Trp Arg Gly Thr Thr
    50                  55                  60

His Tyr Lys Glu Ser Leu Arg Arg Arg Val Ser Met Ser Ile Asp Thr
65                  70                  75                  80

Ser Arg Asn Trp Phe Ser Leu Arg Leu Ala Ser Val Thr Ala Ala Asp
                85                  90                  95

Thr Ala Val Tyr Phe Cys Ala Arg His Arg His His Asp Val Phe Met
            100                 105                 110

Leu Val Pro Ile Ala Gly Trp Phe Asp Val Trp Gly Pro Gly Val Gln
        115                 120                 125

Val Thr Val Ser Ser
        130

<210> SEQ ID NO 80
<211> LENGTH: 107
<212> TYPE: PRT
<213> ORGANISM: Artificial Sequence
<220> FEATURE:
<223> OTHER INFORMATION: Synthetic Peptide

<400> SEQUENCE: 80

```
Glu Ile Val Met Thr Gln Ser Pro Asp Thr Leu Ser Val Ser Pro Gly
1               5                   10                  15

Glu Thr Val Thr Leu Ser Cys Arg Ala Ser Gln Asn Ile Asn Lys Asn
            20                  25                  30

Leu Ala Trp Tyr Gln Tyr Lys Pro Gly Gln Ser Pro Arg Leu Val Ile
        35                  40                  45

Phe Glu Thr Tyr Ser Lys Ile Ala Ala Phe Pro Ala Arg Phe Val Ala
50                  55                  60

Ser Gly Ser Gly Thr Glu Phe Thr Leu Thr Ile Asn Asn Met Gln Ser
65                  70                  75                  80

Glu Asp Val Ala Val Tyr Tyr Cys Gln Gln Tyr Glu Glu Trp Pro Arg
                85                  90                  95

Thr Phe Gly Gln Gly Thr Lys Val Asp Ile Lys
            100                 105
```

<210> SEQ ID NO 81
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 81

```
Gly Thr Asp Trp Gly Glu Asn Asp Phe His Tyr Gly
1               5                   10
```

<210> SEQ ID NO 82
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 82

```
Ser Ile His Trp Arg Gly Arg Thr Thr His Tyr Lys Thr Ser Phe Arg
1               5                   10                  15

Ser
```

<210> SEQ ID NO 83
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 83

```
His Lys Tyr His Asp Ile Phe Arg Val Val Pro Val Ala Gly Trp Phe
1               5                   10                  15

Asp Pro
```

<210> SEQ ID NO 84
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 84

Arg Ala Ser Gln Asn Val Lys Asn Asn Leu Ala
1               5                   10

<210> SEQ ID NO 85
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 85

Asp Ala Ser Ser Arg Ala Gly
1               5

<210> SEQ ID NO 86
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 86

Gln Gln Tyr Glu Glu Trp Pro Arg Thr
1               5

<210> SEQ ID NO 87
<211> LENGTH: 134
<212> TYPE: PRT
<213> ORGANISM: Artificial Sequence
<220> FEATURE:
<223> OTHER INFORMATION: Synthetic Peptide

<400> SEQUENCE: 87

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Met Arg Gly Thr
            20                  25                  30

Asp Trp Gly Glu Asn Asp Phe His Tyr Gly Trp Ile Arg Gln Ser Ser
        35                  40                  45

Ala Lys Gly Leu Glu Trp Ile Gly Ser Ile His Trp Arg Gly Arg Thr
    50                  55                  60

Thr His Tyr Lys Thr Ser Phe Arg Ser Arg Ala Thr Leu Ser Ile Asp
65                  70                  75                  80

Thr Ser Asn Asn Arg Phe Ser Leu Thr Phe Ser Val Thr Ala Ala
                85                  90                  95

Asp Thr Ala Val Tyr Tyr Cys Ala Arg His Lys Tyr His Asp Ile Phe
                100                 105                 110

Arg Val Val Pro Val Ala Gly Trp Phe Asp Pro Trp Gly Gln Gly Leu
            115                 120                 125

Leu Val Thr Val Ser Ser
        130

<210> SEQ ID NO 88
<211> LENGTH: 107
<212> TYPE: PRT
<213> ORGANISM: Artificial Sequence
<220> FEATURE:
<223> OTHER INFORMATION: Synthetic Peptide -continued

```
<400> SEQUENCE: 88

Glu Ile Val Met Thr Gln Ser Pro Pro Thr Leu Ser Val Ser Pro Gly
1               5                   10                  15

Glu Thr Ala Thr Leu Ser Cys Arg Ala Ser Gln Asn Val Lys Asn Asn
            20                  25                  30

Leu Ala Trp Tyr Gln Leu Lys Pro Gly Gln Ala Pro Arg Leu Leu Ile
        35                  40                  45

Phe Asp Ala Ser Arg Ala Gly Gly Ile Pro Asp Arg Phe Ser Gly
    50                  55                  60

Ser Gly Tyr Gly Thr Asp Phe Thr Leu Thr Val Asn Ser Val Gln Ser
65                  70                  75                  80

Glu Asp Phe Gly Asp Tyr Phe Cys Gln Gln Tyr Glu Glu Trp Pro Arg
                85                  90                  95

Thr Phe Gly Gln Gly Thr Lys Val Asp Ile Lys
            100                 105

<210> SEQ ID NO 89
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 89

Lys Tyr Asp Val His
1               5

<210> SEQ ID NO 90
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 90

Trp Met Ser His Glu Gly Asp Lys Thr Glu Ser Ala Gln Arg Phe Lys
1               5                   10                  15

Gly

<210> SEQ ID NO 91
<211> LENGTH: 32
<212> TYPE: PRT
<213> ORGANISM: Artificial Sequence
<220> FEATURE:
<223> OTHER INFORMATION: Synthetic Peptide

<400> SEQUENCE: 91

Gly Ser Lys His Arg Leu Arg Asp Tyr Val Leu Tyr Asp Asp Tyr Gly
1               5                   10                  15

Leu Ile Asn Tyr Gln Glu Trp Asn Asp Tyr Leu Glu Phe Leu Asp Val
            20                  25                  30

<210> SEQ ID NO 92
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 92

Ser Ser Thr Gln Ser Leu Arg His Ser Asn Gly Ala Asn Tyr Leu Ala
1               5                   10                  15
```

<210> SEQ ID NO 93
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 93

Leu Gly Ser Gln Arg Ala Ser
1               5

<210> SEQ ID NO 94
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 94

Met Gln Gly Leu Asn Arg Pro Trp Thr
1               5

<210> SEQ ID NO 95
<211> LENGTH: 141
<212> TYPE: PRT
<213> ORGANISM: Artificial Sequence
<220> FEATURE:
<223> OTHER INFORMATION: Synthetic Peptide

<400> SEQUENCE: 95

Gln Val Gln Leu Val Gln Ser Gly Pro Glu Val Lys Lys Pro Gly Ser
1               5                   10                  15

Ser Val Lys Val Ser Cys Lys Ala Ser Gly Asn Thr Phe Ser Lys Tyr
            20                  25                  30

Asp Val His Trp Val Arg Gln Ala Thr Gly Gln Gly Leu Glu Trp Val
        35                  40                  45

Gly Trp Met Ser His Glu Gly Asp Lys Thr Glu Ser Ala Gln Arg Phe
    50                  55                  60

Lys Gly Arg Val Thr Phe Thr Arg Asp Thr Ser Ala Ser Thr Ala Tyr
65                  70                  75                  80

Met Glu Leu Arg Gly Leu Thr Ser Asp Asp Thr Ala Ile Tyr Tyr Cys
                85                  90                  95

Thr Arg Gly Ser Lys His Arg Leu Arg Asp Tyr Val Leu Tyr Asp Asp
            100                 105                 110

Tyr Gly Leu Ile Asn Tyr Gln Glu Trp Asn Asp Tyr Leu Glu Phe Leu
        115                 120                 125

Asp Val Trp Gly His Gly Thr Ala Val Thr Val Ser Ser
    130                 135                 140

<210> SEQ ID NO 96
<211> LENGTH: 112
<212> TYPE: PRT
<213> ORGANISM: Artificial Sequence
<220> FEATURE:
<223> OTHER INFORMATION: Synthetic Peptide

<400> SEQUENCE: 96

Asp Thr Val Val Thr Gln Ser Pro Leu Ser Leu Pro Val Thr Pro Gly
1               5                   10                  15

Glu Ala Ala Ser Met Ser Cys Ser Ser Thr Gln Ser Leu Arg His Ser
            20                  25                  30

Asn Gly Ala Asn Tyr Leu Ala Trp Tyr Gln His Lys Pro Gly Gln Ser
            35                  40                  45

Pro Arg Leu Leu Ile Arg Leu Gly Ser Gln Arg Ala Ser Gly Val Pro
     50                  55                  60

Asp Arg Phe Ser Gly Ser Gly Ser Gly Thr His Phe Thr Leu Lys Ile
 65                  70                  75                  80

Ser Arg Val Glu Ala Glu Asp Ala Ala Ile Tyr Tyr Cys Met Gln Gly
                 85                  90                  95

Leu Asn Arg Pro Trp Thr Phe Gly Lys Gly Thr Lys Leu Glu Ile Lys
            100                 105                 110

<210> SEQ ID NO 97
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 97

Gly Gly Glu Trp Gly Asp Ser Asp Tyr His Trp Gly
1               5                   10

<210> SEQ ID NO 98
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 98

Ser Ile His Trp Arg Gly Thr Thr His Tyr Asn Ala Pro Phe Arg Gly
1               5                   10                  15

<210> SEQ ID NO 99
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 99

His Lys Tyr His Asp Ile Val Met Val Val Pro Ile Ala Gly Trp Phe
1               5                   10                  15

Asp Pro

<210> SEQ ID NO 100
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 100

Arg Ala Ser Gln Ser Val Lys Asn Asn Leu Ala
1               5                   10

<210> SEQ ID NO 101
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 101

```
Asp Thr Ser Ser Arg Ala Ser
1               5

<210> SEQ ID NO 102
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 102

Gln Gln Tyr Glu Glu Trp Pro Arg Thr
1               5

<210> SEQ ID NO 103
<211> LENGTH: 133
<212> TYPE: PRT
<213> ORGANISM: Artificial Sequence
<220> FEATURE:
<223> OTHER INFORMATION: Synthetic Peptide

<400> SEQUENCE: 103

Glu Val His Leu Glu Glu Ser Gly Pro Gly Leu Val Arg Pro Ser Glu
1               5                   10                  15

Thr Leu Ser Leu Thr Cys Thr Ala Ser Gly Gly Ser Ile Arg Gly Gly
                20                  25                  30

Glu Trp Gly Asp Ser Asp Tyr His Trp Gly Trp Val Arg His Ser Pro
            35                  40                  45

Glu Lys Gly Leu Glu Trp Ile Gly Ser Ile His Trp Arg Gly Thr Thr
    50                  55                  60

His Tyr Asn Ala Pro Phe Arg Gly Arg Gly Arg Leu Ser Ile Asp Leu
65                  70                  75                  80

Ser Arg Asn Gln Phe Ser Leu Arg Leu Thr Ser Val Thr Ala Glu Asp
                85                  90                  95

Thr Ala Val Tyr Tyr Cys Val Lys His Lys Tyr His Asp Ile Val Met
            100                 105                 110

Val Val Pro Ile Ala Gly Trp Phe Asp Pro Trp Gly Gln Gly Leu Gln
        115                 120                 125

Val Thr Val Ser Ser
        130

<210> SEQ ID NO 104
<211> LENGTH: 107
<212> TYPE: PRT
<213> ORGANISM: Artificial Sequence
<220> FEATURE:
<223> OTHER INFORMATION: Synthetic Peptide

<400> SEQUENCE: 104

Glu Ile Met Met Thr Gln Ser Pro Ala Ile Leu Ser Val Ser Pro Gly
1               5                   10                  15

Asp Arg Ala Thr Leu Ser Cys Arg Ala Ser Gln Ser Val Lys Asn Asn
                20                  25                  30

Leu Ala Trp Tyr Gln Lys Arg Pro Gly Gln Ala Pro Arg Leu Leu Ile
            35                  40                  45

Phe Asp Thr Ser Ser Arg Ala Ser Gly Ile Pro Ala Arg Phe Ser Gly
        50                  55                  60

Gly Gly Ser Gly Thr Glu Phe Thr Leu Thr Val Asn Ser Met Gln Ser
65                  70                  75                  80
```

```
Glu Asp Phe Ala Thr Tyr Tyr Cys Gln Gln Tyr Glu Glu Trp Pro Arg
                85                  90                  95

Thr Phe Gly Gln Gly Thr Lys Val Glu Ile Lys
            100                 105

<210> SEQ ID NO 105
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 105

Lys Tyr Asp Val His
1               5

<210> SEQ ID NO 106
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 106

Trp Ile Ser His Glu Arg Asp Lys Thr Glu Ser Ala Gln Arg Phe Lys
1               5                   10                  15

Gly

<210> SEQ ID NO 107
<211> LENGTH: 32
<212> TYPE: PRT
<213> ORGANISM: Artificial Sequence
<220> FEATURE:
<223> OTHER INFORMATION: Synthetic Peptide

<400> SEQUENCE: 107

Gly Ser Lys His Arg Leu Arg Asp Tyr Val Leu Tyr Asp Asp Tyr Gly
1               5                   10                  15

Leu Ile Asn Tyr Gln Glu Trp Asn Asp Tyr Leu Glu Phe Leu Asp Val
            20                  25                  30

<210> SEQ ID NO 108
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 108

Ser Ser Thr Gln Ser Leu Arg His Ser Asn Gly Ala Asn Tyr Leu Ala
1               5                   10                  15

<210> SEQ ID NO 109
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 109

Leu Gly Ser Gln Arg Ala Ser
1               5

<210> SEQ ID NO 110
<211> LENGTH: 9
```

```
<212> TYPE: PRT
<213> ORGANISM: Artificial Sequence
<220> FEATURE:
<223> OTHER INFORMATION: Synthetic Peptide

<400> SEQUENCE: 110

Met Gln Gly Leu Asn Arg Pro Trp Thr
1               5

<210> SEQ ID NO 111
<211> LENGTH: 141
<212> TYPE: PRT
<213> ORGANISM: Artificial Sequence
<220> FEATURE:
<223> OTHER INFORMATION: Synthetic Peptide

<400> SEQUENCE: 111

Gln Val Gln Leu Val Gln Ser Gly Pro Glu Val Lys Lys Pro Gly Ser
1               5                   10                  15

Ser Val Lys Val Ser Cys Lys Ala Ser Gly Asn Thr Phe Ser Lys Tyr
            20                  25                  30

Asp Val His Trp Val Arg Gln Ala Thr Gly Gln Gly Leu Glu Trp Val
        35                  40                  45

Gly Trp Ile Ser His Glu Arg Asp Lys Thr Glu Ser Ala Gln Arg Phe
    50                  55                  60

Lys Gly Arg Val Thr Phe Thr Arg Asp Thr Ser Ala Thr Thr Ala Tyr
65                  70                  75                  80

Met Glu Leu Arg Gly Leu Thr Ser Asp Asp Thr Ala Ile Tyr Tyr Cys
                85                  90                  95

Thr Arg Gly Ser Lys His Arg Leu Arg Asp Tyr Val Leu Tyr Asp Asp
            100                 105                 110

Tyr Gly Leu Ile Asn Tyr Gln Glu Trp Asn Asp Tyr Leu Glu Phe Leu
        115                 120                 125

Asp Val Trp Gly His Gly Thr Ala Val Thr Val Ser Ser
    130                 135                 140

<210> SEQ ID NO 112
<211> LENGTH: 112
<212> TYPE: PRT
<213> ORGANISM: Artificial Sequence
<220> FEATURE:
<223> OTHER INFORMATION: Synthetic Peptide

<400> SEQUENCE: 112

Asp Thr Val Val Thr Gln Ser Pro Leu Ser Leu Pro Val Thr Pro Gly
1               5                   10                  15

Glu Ala Ala Ser Met Ser Cys Ser Ser Thr Gln Ser Leu Arg His Ser
            20                  25                  30

Asn Gly Ala Asn Tyr Leu Ala Trp Tyr Gln His Lys Pro Gly Gln Ser
        35                  40                  45

Pro Arg Leu Leu Ile Arg Leu Gly Ser Gln Arg Ala Ser Gly Val Pro
    50                  55                  60

Asp Arg Phe Ser Gly Ser Gly Ser Gly Thr His Phe Thr Leu Lys Ile
65                  70                  75                  80

Ser Arg Val Glu Ala Glu Asp Ala Ala Ile Tyr Tyr Cys Met Gln Gly
                85                  90                  95

Leu Asn Arg Pro Trp Thr Phe Gly Lys Gly Thr Lys Leu Glu Ile Lys
            100                 105                 110
```

```
<210> SEQ ID NO 113
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 113

Lys Tyr Asp Val His
1               5

<210> SEQ ID NO 114
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 114

Trp Met Ser His Glu Gly Asp Lys Thr Glu Ser Ala Gln Arg Phe Lys
1               5                   10                  15

Gly

<210> SEQ ID NO 115
<211> LENGTH: 32
<212> TYPE: PRT
<213> ORGANISM: Artificial Sequence
<220> FEATURE:
<223> OTHER INFORMATION: Synthetic Peptide

<400> SEQUENCE: 115

Gly Ser Lys His Arg Leu Arg Asp Tyr Val Leu Tyr Asp Asp Tyr Gly
1               5                   10                  15

Leu Ile Asn Tyr Gln Glu Trp Asn Asp Tyr Leu Glu Phe Leu Asp Val
            20                  25                  30

<210> SEQ ID NO 116
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 116

Thr Ser Thr Gln Ser Leu Arg His Ser Asn Gly Ala Asn Tyr Leu Ala
1               5                   10                  15

<210> SEQ ID NO 117
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 117

Leu Gly Ser Gln Arg Ala Ser
1               5

<210> SEQ ID NO 118
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 118
```

```
Met Gln Gly Leu Asn Arg Pro Trp Thr
1               5
```

<210> SEQ ID NO 119
<211> LENGTH: 141
<212> TYPE: PRT
<213> ORGANISM: Artificial Sequence
<220> FEATURE:
<223> OTHER INFORMATION: Synthetic Peptide

<400> SEQUENCE: 119

```
Gln Val Gln Leu Glu Gln Ser Gly Ala Glu Val Lys Pro Gly Ser
1               5                   10                  15

Ser Val Lys Val Ser Cys Lys Ala Ser Gly Asn Thr Phe Ser Lys Tyr
            20                  25                  30

Asp Val His Trp Val Arg Gln Ala Thr Gly Gln Gly Leu Glu Trp Val
        35                  40                  45

Gly Trp Met Ser His Glu Gly Asp Lys Thr Glu Ser Ala Gln Arg Phe
    50                  55                  60

Lys Gly Arg Val Thr Phe Thr Arg Asp Thr Ser Ala Ser Thr Ala Tyr
65                  70                  75                  80

Met Glu Leu Arg Gly Leu Thr Ser Asp Asp Thr Ala Ile Tyr Tyr Cys
                85                  90                  95

Thr Arg Gly Ser Lys His Arg Leu Arg Asp Tyr Val Leu Tyr Asp Asp
            100                 105                 110

Tyr Gly Leu Ile Asn Tyr Gln Glu Trp Asn Asp Tyr Leu Glu Phe Leu
        115                 120                 125

Asp Val Trp Gly His Gly Thr Ala Val Thr Val Ser Ser
    130                 135                 140
```

<210> SEQ ID NO 120
<211> LENGTH: 112
<212> TYPE: PRT
<213> ORGANISM: Artificial Sequence
<220> FEATURE:
<223> OTHER INFORMATION: Synthetic Peptide

<400> SEQUENCE: 120

```
Asp Thr Val Val Thr Gln Ser Pro Leu Ser Leu Pro Val Thr Pro Gly
1               5                   10                  15

Glu Ala Ala Ser Met Ser Cys Thr Ser Thr Gln Ser Leu Arg His Ser
            20                  25                  30

Asn Gly Ala Asn Tyr Leu Ala Trp Tyr Gln His Lys Pro Gly Gln Ser
        35                  40                  45

Pro Arg Leu Leu Ile Arg Leu Gly Ser Gln Arg Ala Ser Gly Val Pro
    50                  55                  60

Asp Arg Phe Ser Gly Ser Gly Ser Gly Thr His Phe Thr Leu Lys Ile
65                  70                  75                  80

Ser Arg Val Glu Pro Glu Asp Ala Ala Ile Tyr Tyr Cys Met Gln Gly
                85                  90                  95

Leu Asn Arg Pro Trp Thr Phe Gly Lys Gly Thr Lys Leu Glu Ile Lys
            100                 105                 110
```

<210> SEQ ID NO 121
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 121

Lys Tyr Asp Val His
1               5

<210> SEQ ID NO 122
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 122

Trp Met Ser His Glu Gly Asp Lys Thr Glu Ser Ala Gln Arg Phe Lys
1               5                   10                  15

Gly

<210> SEQ ID NO 123
<211> LENGTH: 32
<212> TYPE: PRT
<213> ORGANISM: Artificial Sequence
<220> FEATURE:
<223> OTHER INFORMATION: Synthetic Peptide

<400> SEQUENCE: 123

Gly Ser Lys His Arg Leu Arg Asp Tyr Val Leu Tyr Asp Asp Tyr Gly
1               5                   10                  15

Leu Ile Asn Gln Gln Glu Trp Asn Asp Tyr Leu Glu Phe Leu Asp Val
            20                  25                  30

<210> SEQ ID NO 124
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 124

Thr Ser Thr Gln Ser Leu Arg His Ser Asn Gly Ala Asn Tyr Leu Ala
1               5                   10                  15

<210> SEQ ID NO 125
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 125

Leu Gly Ser Gln Arg Ala Ser
1               5

<210> SEQ ID NO 126
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 126

Met Gln Gly Leu Asn Arg Pro Trp Thr
1               5

<210> SEQ ID NO 127
<211> LENGTH: 141
<212> TYPE: PRT

```
<213> ORGANISM: Artificial Sequence
<220> FEATURE:
<223> OTHER INFORMATION: Synthetic Peptide

<400> SEQUENCE: 127

Gln Val Gln Leu Val Gln Ser Gly Ala Glu Val Lys Lys Pro Gly Ser
1               5                   10                  15

Ser Val Lys Val Ser Cys Lys Ala Ser Gly Asn Thr Phe Arg Lys Tyr
                20                  25                  30

Asp Val His Trp Val Arg Gln Ala Thr Gly Gln Gly Leu Glu Trp Val
            35                  40                  45

Gly Trp Met Ser His Glu Gly Asp Lys Thr Glu Ser Ala Gln Arg Phe
    50                  55                  60

Lys Gly Arg Val Ser Phe Thr Arg Asp Asn Ser Ala Ser Thr Ala Tyr
65                  70                  75                  80

Ile Glu Leu Arg Gly Leu Thr Ser Asp Asp Thr Ala Ile Tyr Tyr Cys
                85                  90                  95

Thr Gly Gly Ser Lys His Arg Leu Arg Asp Tyr Val Leu Tyr Asp Asp
            100                 105                 110

Tyr Gly Leu Ile Asn Gln Gln Glu Trp Asn Asp Tyr Leu Glu Phe Leu
        115                 120                 125

Asp Val Trp Gly His Gly Thr Ala Val Thr Val Ser Ser
    130                 135                 140

<210> SEQ ID NO 128
<211> LENGTH: 112
<212> TYPE: PRT
<213> ORGANISM: Artificial Sequence
<220> FEATURE:
<223> OTHER INFORMATION: Synthetic Peptide

<400> SEQUENCE: 128

Asp Thr Val Val Thr Gln Ser Pro Leu Ser Leu Ser Val Thr Pro Gly
1               5                   10                  15

Glu Ala Ala Ser Met Ser Cys Thr Ser Thr Gln Ser Leu Arg His Ser
                20                  25                  30

Asn Gly Ala Asn Tyr Leu Ala Trp Tyr Gln His Lys Pro Gly Gln Ser
            35                  40                  45

Pro Arg Leu Leu Ile Arg Leu Gly Ser Gln Arg Ala Ser Gly Val Pro
    50                  55                  60

Asp Arg Phe Ser Gly Ser Gly Ser Gly Thr His Phe Thr Leu Lys Ile
65                  70                  75                  80

Ser Arg Val Glu Ala Asp Ala Ala Ile Tyr Tyr Cys Met Gln Gly
                85                  90                  95

Leu Asn Arg Pro Trp Thr Phe Gly Lys Gly Thr Lys Leu Glu Ile Lys
            100                 105                 110

<210> SEQ ID NO 129
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 129

Asn His Asp Val His
1               5

<210> SEQ ID NO 130
```

<211> LENGTH: 17
<212> TYPE: PRT
<213> ORGANISM: Artificial Sequence
<220> FEATURE:
<223> OTHER INFORMATION: Synthetic Peptide

<400> SEQUENCE: 130

Trp Met Ser His Glu Gly Asp Lys Thr Gly Leu Ala Gln Lys Phe Gln
1               5                   10                  15

Gly

<210> SEQ ID NO 131
<211> LENGTH: 31
<212> TYPE: PRT
<213> ORGANISM: Artificial Sequence
<220> FEATURE:
<223> OTHER INFORMATION: Synthetic Peptide

<400> SEQUENCE: 131

Gly Ser Lys His Arg Leu Arg Asp Tyr Phe Leu Tyr Asn Glu Tyr Gly
1               5                   10                  15

Pro Asn Tyr Glu Glu Trp Gly Asp Tyr Leu Ala Thr Leu Asp Val
            20                  25                  30

<210> SEQ ID NO 132
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 132

Lys Cys Ser His Ser Leu Gln His Ser Thr Gly Ala Asn Tyr Leu Ala
1               5                   10                  15

<210> SEQ ID NO 133
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 133

Leu Ala Thr His Arg Ala Ser
1               5

<210> SEQ ID NO 134
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 134

Met Gln Gly Leu His Ser Pro Trp Thr
1               5

<210> SEQ ID NO 135
<211> LENGTH: 140
<212> TYPE: PRT
<213> ORGANISM: Artificial Sequence
<220> FEATURE:
<223> OTHER INFORMATION: Synthetic Peptide

<400> SEQUENCE: 135

Gln Val Gln Leu Val Gln Ser Gly Ala Glu Val Lys Lys Pro Gly Ser

```
                1               5                  10                  15
            Ser Val Lys Val Ser Cys Lys Ala Ser Gly Asn Ser Phe Ser Asn His
                                20                  25                  30

Asp Val His Trp Val Arg Gln Ala Thr Gly Gln Gly Leu Glu Trp Met
                                35                  40                  45

Gly Trp Met Ser His Glu Gly Asp Lys Thr Gly Leu Ala Gln Lys Phe
                     50                  55                  60

Gln Gly Arg Val Thr Ile Thr Arg Asp Ser Gly Ala Ser Thr Val Tyr
            65                  70                  75                  80

Met Glu Leu Arg Gly Leu Thr Ala Asp Thr Ala Ile Tyr Tyr Cys
                                85                  90                  95

Leu Thr Gly Ser Lys His Arg Leu Arg Asp Tyr Phe Leu Tyr Asn Glu
                                100                 105                 110

Tyr Gly Pro Asn Tyr Glu Glu Trp Gly Asp Tyr Leu Ala Thr Leu Asp
                                115                 120                 125

Val Trp Gly His Gly Thr Ala Val Thr Val Ser Ser
                     130                 135                 140

<210> SEQ ID NO 136
<211> LENGTH: 112
<212> TYPE: PRT
<213> ORGANISM: Artificial Sequence
<220> FEATURE:
<223> OTHER INFORMATION: Synthetic Peptide

<400> SEQUENCE: 136

Glu Val Val Ile Thr Gln Ser Pro Leu Phe Leu Pro Val Thr Pro Gly
            1               5                   10                  15

Glu Ala Ala Ser Leu Ser Cys Lys Cys Ser His Ser Leu Gln His Ser
                                20                  25                  30

Thr Gly Ala Asn Tyr Leu Ala Trp Tyr Leu Gln Arg Pro Gly Gln Thr
                                35                  40                  45

Pro Arg Leu Leu Ile His Leu Ala Thr His Arg Ala Ser Gly Val Pro
                     50                  55                  60

Asp Arg Phe Ser Gly Ser Gly Ser Gly Thr Asp Phe Thr Leu Lys Ile
            65                  70                  75                  80

Ser Arg Val Glu Ser Asp Asp Val Gly Thr Tyr Tyr Cys Met Gln Gly
                                85                  90                  95

Leu His Ser Pro Trp Thr Phe Gly Gln Gly Thr Lys Val Glu Ile Lys
                                100                 105                 110

<210> SEQ ID NO 137
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 137

Asn Tyr Tyr Trp Thr
            1               5

<210> SEQ ID NO 138
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 138
```

```
Tyr Ile Ser Asp Arg Glu Thr Thr Thr Tyr Asn Pro Ser Leu Asn Ser
1               5                   10                  15
```

<210> SEQ ID NO 139
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 139

```
Ala Arg Arg Gly Gln Arg Ile Tyr Gly Val Val Ser Phe Gly Glu Phe
1               5                   10                  15

Phe Tyr Tyr Tyr Tyr Met Asp Val
            20
```

<210> SEQ ID NO 140
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 140

```
Gly Arg Gln Ala Leu Gly Ser Arg Ala Val Gln
1               5                   10
```

<210> SEQ ID NO 141
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 141

```
Asn Asn Gln Asp Arg Pro Ser
1               5
```

<210> SEQ ID NO 142
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 142

```
His Met Trp Asp Ser Arg Ser Gly Phe Ser Trp Ser
1               5                   10
```

<210> SEQ ID NO 143
<211> LENGTH: 132
<212> TYPE: PRT
<213> ORGANISM: Artificial Sequence
<220> FEATURE:
<223> OTHER INFORMATION: Synthetic Peptide

<400> SEQUENCE: 143

```
Gln Val Gln Leu Gln Glu Ser Gly Pro Gly Leu Val Arg Pro Ser Glu
1               5                   10                  15

Thr Leu Ser Val Thr Cys Ile Val Ser Gly Gly Ser Ile Ser Asn Tyr
            20                  25                  30

Tyr Trp Thr Trp Ile Arg Gln Ser Pro Gly Lys Gly Leu Glu Trp Ile
        35                  40                  45

Gly Tyr Ile Ser Asp Arg Glu Thr Thr Thr Tyr Asn Pro Ser Leu Asn
```

```
                    50                  55                  60
Ser Arg Ala Val Ile Ser Arg Asp Thr Ser Lys Asn Gln Leu Ser Leu
 65                  70                  75                  80

Gln Leu Arg Ser Val Thr Thr Ala Asp Thr Ala Ile Tyr Phe Cys Ala
                 85                  90                  95

Thr Ala Arg Arg Gly Gln Arg Ile Tyr Gly Val Val Ser Phe Gly Glu
            100                 105                 110

Phe Phe Tyr Tyr Tyr Tyr Met Asp Val Trp Gly Lys Gly Thr Ala Val
            115                 120                 125

Thr Val Ser Ser
        130

<210> SEQ ID NO 144
<211> LENGTH: 108
<212> TYPE: PRT
<213> ORGANISM: Artificial Sequence
<220> FEATURE:
<223> OTHER INFORMATION: Synthetic Peptide

<400> SEQUENCE: 144

Ser Tyr Val Ser Pro Leu Ser Val Ala Leu Gly Glu Thr Ala Arg Ile
 1               5                  10                  15

Ser Cys Gly Arg Gln Ala Leu Gly Ser Arg Ala Val Gln Trp Tyr Gln
                20                  25                  30

His Lys Pro Gly Gln Ala Pro Ile Leu Leu Ile Tyr Asn Asn Gln Asp
             35                  40                  45

Arg Pro Ser Gly Ile Pro Glu Arg Phe Ser Gly Thr Pro Asp Ile Asn
 50                  55                  60

Phe Gly Thr Thr Ala Thr Leu Thr Ile Ser Gly Val Glu Val Gly Asp
 65                  70                  75                  80

Glu Ala Asp Tyr Tyr Cys His Met Trp Asp Ser Arg Ser Gly Phe Ser
                 85                  90                  95

Trp Ser Phe Gly Gly Ala Thr Arg Leu Thr Val Leu
            100                 105

<210> SEQ ID NO 145
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 145

Gly Arg Phe Trp Ser
 1               5

<210> SEQ ID NO 146
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 146

Tyr Phe Ser Asp Thr Asp Arg Ser Glu Tyr Asn Pro Ser Leu Arg Ser
 1               5                  10                  15

<210> SEQ ID NO 147
<211> LENGTH: 24
<212> TYPE: PRT
<213> ORGANISM: Artificial Sequence
```

```
<220> FEATURE:
<223> OTHER INFORMATION: Synthetic Peptide

<400> SEQUENCE: 147

Ala Gln Gln Gly Lys Arg Ile Tyr Gly Ile Val Ser Phe Gly Glu Phe
1               5                   10                  15

Phe Tyr Tyr Tyr Tyr Met Asp Ala
            20

<210> SEQ ID NO 148
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 148

Gly Glu Arg Ser Arg Gly Ser Arg Ala Val Gln
1               5                   10

<210> SEQ ID NO 149
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 149

Asn Asn Gln Asp Arg Pro Ala
1               5

<210> SEQ ID NO 150
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 150

His Tyr Trp Asp Ser Arg Ser Pro Ile Ser Trp Ile
1               5                   10

<210> SEQ ID NO 151
<211> LENGTH: 132
<212> TYPE: PRT
<213> ORGANISM: Artificial Sequence
<220> FEATURE:
<223> OTHER INFORMATION: Synthetic Peptide

<400> SEQUENCE: 151

Gln Val His Leu Gln Glu Ser Gly Pro Gly Leu Val Thr Pro Ser Glu
1               5                   10                  15

Thr Leu Ser Leu Thr Cys Thr Val Ser Asn Gly Ser Val Ser Gly Arg
            20                  25                  30

Phe Trp Ser Trp Ile Arg Gln Ser Pro Gly Arg Gly Leu Glu Trp Ile
        35                  40                  45

Gly Tyr Phe Ser Asp Thr Asp Arg Ser Glu Tyr Asn Pro Ser Leu Arg
    50                  55                  60

Ser Arg Leu Thr Leu Ser Val Asp Arg Ser Lys Asn Gln Leu Ser Leu
65                  70                  75                  80

Arg Leu Lys Ser Val Thr Ala Ala Asp Ser Ala Thr Tyr Tyr Cys Ala
                85                  90                  95

Arg Ala Gln Gln Gly Lys Arg Ile Tyr Gly Ile Val Ser Phe Gly Glu
```

```
                    100                 105                 110
Phe Phe Tyr Tyr Tyr Tyr Met Asp Ala Trp Gly Lys Gly Thr Pro Val
        115                 120                 125

Thr Val Ser Ser
    130

<210> SEQ ID NO 152
<211> LENGTH: 107
<212> TYPE: PRT
<213> ORGANISM: Artificial Sequence
<220> FEATURE:
<223> OTHER INFORMATION: Synthetic Peptide

<400> SEQUENCE: 152

Ser Leu Asn Pro Leu Ser Leu Ala Pro Gly Ala Thr Ala Lys Ile Pro
1               5                   10                  15

Cys Gly Glu Arg Ser Arg Gly Ser Arg Ala Val Gln Trp Tyr Gln Gln
            20                  25                  30

Lys Pro Gly Gln Ala Pro Thr Leu Ile Ile Tyr Asn Asn Gln Asp Arg
        35                  40                  45

Pro Ala Gly Val Ser Glu Arg Phe Ser Gly Asn Pro Asp Val Ala Ile
    50                  55                  60

Gly Val Thr Ala Thr Leu Thr Ile Ser Arg Val Glu Val Gly Asp Glu
65                  70                  75                  80

Ala Asp Tyr Tyr Cys His Tyr Trp Asp Ser Arg Ser Pro Ile Ser Trp
                85                  90                  95

Ile Phe Gly Gly Gly Thr Gln Leu Thr Val Leu
            100                 105

<210> SEQ ID NO 153
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 153

Gly Arg Phe Trp Ser
1               5

<210> SEQ ID NO 154
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 154

Tyr Phe Ser Asp Thr Asp Arg Ser Glu Tyr Asn Pro Ser Leu Arg Ser
1               5                   10                  15

<210> SEQ ID NO 155
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 155

Ala Gln Gln Gly Lys Arg Ile Tyr Gly Ile Val Ser Phe Gly Glu Leu
1               5                   10                  15

Phe Tyr Tyr Tyr Tyr Met Asp Ala
```

```
<210> SEQ ID NO 156
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 156

Gly Glu Arg Ser Arg Gly Ser Arg Ala Val Gln
1               5                   10

<210> SEQ ID NO 157
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 157

Asn Asn Gln Asp Arg Pro Ala
1               5

<210> SEQ ID NO 158
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 158

His Tyr Trp Asp Ser Arg Ser Pro Ile Ser Trp Ile
1               5                   10

<210> SEQ ID NO 159
<211> LENGTH: 132
<212> TYPE: PRT
<213> ORGANISM: Artificial Sequence
<220> FEATURE:
<223> OTHER INFORMATION: Synthetic Peptide

<400> SEQUENCE: 159

Gln Val His Leu Gln Glu Ser Gly Pro Gly Leu Val Thr Pro Ser Glu
1               5                   10                  15

Thr Leu Ser Leu Thr Cys Thr Val Ser Asn Gly Ser Val Ser Gly Arg
            20                  25                  30

Phe Trp Ser Trp Ile Arg Gln Ser Pro Gly Arg Gly Leu Glu Trp Ile
        35                  40                  45

Gly Tyr Phe Ser Asp Thr Asp Arg Ser Glu Tyr Asn Pro Ser Leu Arg
    50                  55                  60

Ser Arg Leu Thr Leu Ser Val Asp Arg Ser Lys Asn Gln Leu Ser Leu
65                  70                  75                  80

Lys Leu Lys Ser Val Thr Ala Ala Asp Ser Ala Thr Tyr Tyr Cys Ala
                85                  90                  95

Arg Ala Gln Gln Gly Lys Arg Ile Tyr Gly Ile Val Ser Phe Gly Glu
            100                 105                 110

Leu Phe Tyr Tyr Tyr Tyr Met Asp Ala Trp Gly Lys Gly Thr Pro Val
        115                 120                 125

Thr Val Ser Ser
    130
```

```
<210> SEQ ID NO 160
<211> LENGTH: 107
<212> TYPE: PRT
<213> ORGANISM: Artificial Sequence
<220> FEATURE:
<223> OTHER INFORMATION: Synthetic Peptide

<400> SEQUENCE: 160

Ser Leu Asn Pro Leu Ser Leu Ala Pro Gly Ala Thr Ala Lys Ile Pro
1               5                   10                  15

Cys Gly Glu Arg Ser Arg Gly Ser Ala Val Gln Trp Tyr Gln Gln
            20                  25                  30

Lys Pro Gly Gln Ala Pro Thr Leu Ile Ile Tyr Asn Asn Gln Asp Arg
        35                  40                  45

Pro Ala Gly Val Ser Glu Arg Phe Ser Gly Asn Pro Asp Val Ala Ile
    50                  55                  60

Gly Val Thr Ala Thr Leu Thr Ile Ser Arg Val Glu Val Gly Asp Glu
65                  70                  75                  80

Gly Asp Tyr Tyr Cys His Tyr Trp Asp Ser Arg Ser Pro Ile Ser Trp
                85                  90                  95

Ile Phe Ala Gly Gly Thr Gln Leu Thr Val Leu
            100                 105

<210> SEQ ID NO 161
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 161

Thr Gly His His Tyr Trp Gly
1               5

<210> SEQ ID NO 162
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 162

His Ile His Tyr Asn Thr Ala Val Leu His Asn Pro Ala Leu Lys Ser
1               5                   10                  15

<210> SEQ ID NO 163
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 163

Ser Gly Gly Asp Ile Leu Tyr Tyr Asn Glu Trp Gln Lys Pro His Trp
1               5                   10                  15

Phe Tyr Pro

<210> SEQ ID NO 164
<211> LENGTH: 14
<212> TYPE: PRT
<213> ORGANISM: Artificial Sequence
<220> FEATURE:
<223> OTHER INFORMATION: Synthetic Peptide
```

<400> SEQUENCE: 164

Ser Gly Thr Ala Ser Asp Ile Gly Ser Trp Asn Phe Val Ser
1               5                   10

<210> SEQ ID NO 165
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 165

Glu Val Asn Arg Arg Ser
1               5

<210> SEQ ID NO 166
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 166

Ser Ser Leu Ser Gly Arg Trp Asp Ile Val
1               5                   10

<210> SEQ ID NO 167
<211> LENGTH: 129
<212> TYPE: PRT
<213> ORGANISM: Artificial Sequence
<220> FEATURE:
<223> OTHER INFORMATION: Synthetic Peptide

<400> SEQUENCE: 167

Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Asn Thr Gly
            20                  25                  30

His His Tyr Trp Gly Trp Val Arg Gln Val Pro Gly Lys Gly Pro Glu
        35                  40                  45

Trp Ile Ala His Ile His Tyr Asn Thr Ala Val Leu His Asn Pro Ala
    50                  55                  60

Leu Lys Ser Arg Val Thr Ile Ser Ile Phe Thr Leu Lys Asn Leu Ile
65                  70                  75                  80

Thr Leu Arg Leu Ser Asn Met Thr Ala Ala Asp Thr Ala Val Tyr Phe
                85                  90                  95

Cys Val Arg Ser Gly Gly Asp Ile Leu Tyr Tyr Asn Glu Trp Gln Lys
            100                 105                 110

Pro His Trp Phe Tyr Pro Trp Gly Pro Gly Ile Leu Val Thr Val Ser
        115                 120                 125

Ser

<210> SEQ ID NO 168
<211> LENGTH: 110
<212> TYPE: PRT
<213> ORGANISM: Artificial Sequence
<220> FEATURE:
<223> OTHER INFORMATION: Synthetic Peptide

<400> SEQUENCE: 168

Gln Ser Ala Leu Thr Gln Pro Pro Ser Ala Ser Gly Ser Leu Gly Gln
1               5                   10                  15

```
Ser Leu Thr Ile Ser Cys Ser Gly Thr Ala Ser Asp Ile Gly Ser Trp
            20                  25                  30

Asn Phe Val Ser Trp Tyr Gln Gln Phe Pro Gly Arg Ala Pro Asn Leu
            35                  40                  45

Ile Ile Phe Glu Val Asn Arg Arg Ser Gly Val Pro Asp Arg Phe
 50                  55                  60

Ser Gly Ser Lys Ser Gly Asn Thr Ala Ser Leu Thr Val Ser Gly Leu
 65                  70                  75                  80

Arg Ser Glu Asp Glu Ala Glu Tyr Phe Cys Ser Ser Leu Ser Gly Arg
                85                  90                  95

Trp Asp Ile Val Phe Gly Gly Gly Thr Lys Val Thr Val Leu
            100                 105                 110

<210> SEQ ID NO 169
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 169

Ala Cys Asp Tyr Phe Trp Gly
1               5

<210> SEQ ID NO 170
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 170

Ser Leu Ser His Cys Ala Gly Tyr Tyr Asn Ser Gly Trp Thr Tyr His
1               5                   10                  15

Asn Pro Ser Leu Lys Ser
            20

<210> SEQ ID NO 171
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 171

Phe Gly Gly Asp Val Leu Val Tyr His Asp Trp Pro Lys Pro Ala Trp
1               5                   10                  15

Val Asp Leu

<210> SEQ ID NO 172
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 172

Thr Gly Asn Ile Asn Asn Phe Val Ser
1               5

<210> SEQ ID NO 173
<211> LENGTH: 7
```

```
<212> TYPE: PRT
<213> ORGANISM: Artificial Sequence
<220> FEATURE:
<223> OTHER INFORMATION: Synthetic Peptide

<400> SEQUENCE: 173

Gly Val Asn Lys Arg Pro Ser
1               5

<210> SEQ ID NO 174
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 174

Gly Ser Leu Ala Gly Asn Trp Asp Val Val
1               5                   10

<210> SEQ ID NO 175
<211> LENGTH: 135
<212> TYPE: PRT
<213> ORGANISM: Artificial Sequence
<220> FEATURE:
<223> OTHER INFORMATION: Synthetic Peptide

<400> SEQUENCE: 175

Gln Pro Gln Leu Gln Glu Ser Gly Pro Gly Leu Val Glu Ala Ser Glu
1               5                   10                  15

Thr Leu Ser Leu Thr Cys Thr Val Ser Gly Asp Ser Thr Ala Ala Cys
            20                  25                  30

Asp Tyr Phe Trp Gly Trp Val Arg Gln Pro Pro Gly Lys Gly Leu Glu
        35                  40                  45

Trp Ile Gly Ser Leu Ser His Cys Ala Gly Tyr Tyr Asn Ser Gly Trp
    50                  55                  60

Thr Tyr His Asn Pro Ser Leu Lys Ser Arg Leu Thr Ile Ser Leu Asp
65                  70                  75                  80

Thr Pro Lys Asn Gln Val Phe Leu Lys Leu Asn Ser Val Thr Ala Ala
                85                  90                  95

Asp Thr Ala Ile Tyr Tyr Cys Ala Arg Phe Gly Gly Asp Val Leu Val
            100                 105                 110

Tyr His Asp Trp Pro Lys Pro Ala Trp Val Asp Leu Trp Gly Arg Gly
        115                 120                 125

Val Leu Val Thr Val Ser Ser
    130                 135

<210> SEQ ID NO 176
<211> LENGTH: 105
<212> TYPE: PRT
<213> ORGANISM: Artificial Sequence
<220> FEATURE:
<223> OTHER INFORMATION: Synthetic Peptide

<400> SEQUENCE: 176

Gln Ser Ala Leu Thr Gln Pro Pro Ser Ala Ser Gly Ser Pro Gly Gln
1               5                   10                  15

Ser Ile Thr Ile Ser Cys Thr Gly Asn Ile Asn Asn Phe Val Ser Trp
            20                  25                  30

Tyr Gln Gln His Pro Gly Lys Ala Pro Lys Leu Val Ile Tyr Gly Val
        35                  40                  45
```

```
Asn Lys Arg Pro Ser Gly Val Pro Asp Arg Phe Ser Gly Ser Lys Ser
 50                  55                  60
Gly Asn Ala Ala Ser Leu Thr Val Ser Gly Leu Gln Thr Asp Asp Glu
 65                  70                  75                  80
Ala Val Tyr Tyr Cys Gly Ser Leu Ala Gly Asn Trp Asp Val Val Phe
                 85                  90                  95
Gly Gly Gly Thr Lys Leu Thr Val Leu
            100                 105

<210> SEQ ID NO 177
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 177

Gly Cys Asp Tyr Phe Trp Gly
1               5

<210> SEQ ID NO 178
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 178

Gly Leu Ser His Cys Ala Gly Tyr Tyr Asn Thr Gly Trp Thr Tyr His
1               5                   10                  15
Asn Pro Ser Leu Lys Ser
            20

<210> SEQ ID NO 179
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 179

Phe Asp Gly Glu Val Leu Val Tyr Asn Asp Trp Pro Lys Pro Ala Trp
1               5                   10                  15
Val Asp Leu

<210> SEQ ID NO 180
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 180

Thr Gly Thr Ser Asn Asn Phe Val Ser
1               5

<210> SEQ ID NO 181
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 181
```

```
Gly Val Asn Lys Arg Pro Ser
1               5

<210> SEQ ID NO 182
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 182

Gly Ser Leu Val Gly Asn Trp Asp Val Ile
1               5                   10

<210> SEQ ID NO 183
<211> LENGTH: 135
<212> TYPE: PRT
<213> ORGANISM: Artificial Sequence
<220> FEATURE:
<223> OTHER INFORMATION: Synthetic Peptide

<400> SEQUENCE: 183

Gln Pro Gln Leu Gln Glu Ser Gly Pro Gly Leu Val Glu Ala Ser Glu
1               5                   10                  15

Thr Leu Ser Leu Thr Cys Thr Val Ser Gly Asp Ser Thr Ala Gly Cys
                20                  25                  30

Asp Tyr Phe Trp Gly Trp Val Arg Gln Pro Pro Gly Lys Gly Leu Glu
            35                  40                  45

Trp Ile Gly Gly Leu Ser His Cys Ala Gly Tyr Tyr Asn Thr Gly Trp
    50                  55                  60

Thr Tyr His Asn Pro Ser Leu Lys Ser Arg Leu Thr Ile Ser Leu Asp
65                  70                  75                  80

Thr Pro Lys Asn Gln Val Phe Leu Lys Leu Asn Ser Val Thr Ala Ala
                85                  90                  95

Asp Thr Ala Ile Tyr Tyr Cys Ala Arg Phe Asp Gly Glu Val Leu Val
            100                 105                 110

Tyr Asn Asp Trp Pro Lys Pro Ala Trp Val Asp Leu Trp Gly Arg Gly
        115                 120                 125

Thr Leu Val Thr Val Ser Ser
        130             135

<210> SEQ ID NO 184
<211> LENGTH: 105
<212> TYPE: PRT
<213> ORGANISM: Artificial Sequence
<220> FEATURE:
<223> OTHER INFORMATION: Synthetic Peptide

<400> SEQUENCE: 184

Gln Ser Ala Leu Thr Gln Pro Pro Ser Ala Ser Gly Ser Pro Gly Gln
1               5                   10                  15

Ser Ile Thr Ile Ser Cys Thr Gly Thr Ser Asn Asn Phe Val Ser Trp
                20                  25                  30

Tyr Gln Gln His Pro Ala Lys Ala Pro Lys Leu Val Ile Tyr Gly Val
            35                  40                  45

Asn Lys Arg Pro Ser Gly Val Pro Asp Arg Phe Ser Gly Ser Lys Ser
        50                  55                  60

Gly Asn Thr Ala Ser Leu Thr Val Ser Gly Leu Gln Thr Asp Asp Glu
65                  70                  75                  80

Ala Val Tyr Tyr Cys Gly Ser Leu Val Gly Asn Trp Asp Val Ile Phe
```

```
                85                  90                  95

Gly Gly Gly Thr Lys Leu Thr Val Leu
            100                 105

<210> SEQ ID NO 185
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 185

Lys Tyr Pro Met Tyr
1               5

<210> SEQ ID NO 186
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 186

Ala Ile Ser Gly Asp Ala Trp His Val Val Tyr Ser Asn Ser Val Gln
1               5                   10                  15

<210> SEQ ID NO 187
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 187

Met Phe Gln Glu Ser Gly Pro Pro Arg Leu Asp Arg Trp Ser Gly Arg
1               5                   10                  15

Asn Tyr Tyr Tyr Tyr Ser Gly Met Asp Val
            20                  25

<210> SEQ ID NO 188
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 188

Lys Ser Ser Glu Ser Leu Arg Gln Ser Asn Gly Lys Thr Ser Leu Tyr
1               5                   10                  15

<210> SEQ ID NO 189
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 189

Glu Val Ser Asn Arg Phe Ser
1               5

<210> SEQ ID NO 190
<211> LENGTH: 9
<212> TYPE: PRT
<213> ORGANISM: Artificial Sequence
<220> FEATURE:
```

<223> OTHER INFORMATION: Synthetic Peptide

<400> SEQUENCE: 190

Met Gln Ser Lys Asp Phe Pro Leu Thr
1               5

<210> SEQ ID NO 191
<211> LENGTH: 135
<212> TYPE: PRT
<213> ORGANISM: Artificial Sequence
<220> FEATURE:
<223> OTHER INFORMATION: Synthetic Peptide

<400> SEQUENCE: 191

Arg Val Gln Leu Val Glu Ser Gly Gly Gly Val Val Gln Pro Gly Lys
1               5                   10                  15

Ser Val Arg Leu Ser Cys Val Val Ser Asp Phe Pro Phe Ser Lys Tyr
            20                  25                  30

Pro Met Tyr Trp Val Arg Gln Ala Pro Gly Lys Gly Leu Glu Trp Val
        35                  40                  45

Ala Ala Ile Ser Gly Asp Ala Trp His Val Val Tyr Ser Asn Ser Val
    50                  55                  60

Gln Gly Arg Phe Leu Val Ser Arg Asp Asn Val Lys Asn Thr Leu Tyr
65                  70                  75                  80

Leu Glu Met Asn Ser Leu Lys Ile Glu Asp Thr Ala Val Tyr Arg Cys
                85                  90                  95

Ala Arg Met Phe Gln Glu Ser Gly Pro Pro Arg Leu Asp Arg Trp Ser
            100                 105                 110

Gly Arg Asn Tyr Tyr Tyr Ser Gly Met Asp Val Trp Gly Gln Gly
        115                 120                 125

Thr Thr Val Thr Val Ser Ser
    130                 135

<210> SEQ ID NO 192
<211> LENGTH: 112
<212> TYPE: PRT
<213> ORGANISM: Artificial Sequence
<220> FEATURE:
<223> OTHER INFORMATION: Synthetic Peptide

<400> SEQUENCE: 192

Asp Ile Val Met Thr Gln Thr Pro Leu Ser Leu Ser Val Thr Pro Gly
1               5                   10                  15

Gln Pro Ala Ser Ile Ser Cys Lys Ser Ser Glu Ser Leu Arg Gln Ser
            20                  25                  30

Asn Gly Lys Thr Ser Leu Tyr Trp Tyr Arg Gln Lys Pro Gly Gln Ser
        35                  40                  45

Pro Gln Leu Leu Val Phe Glu Val Ser Asn Arg Phe Ser Gly Val Ser
    50                  55                  60

Asp Arg Phe Val Gly Ser Gly Ser Gly Thr Asp Phe Thr Leu Arg Ile
65                  70                  75                  80

Ser Arg Val Glu Ala Glu Asp Val Gly Phe Tyr Tyr Cys Met Gln Ser
                85                  90                  95

Lys Asp Phe Pro Leu Thr Phe Gly Gly Gly Thr Lys Val Asp Leu Lys
            100                 105                 110

<210> SEQ ID NO 193
<211> LENGTH: 5
<212> TYPE: PRT

```
<213> ORGANISM: Artificial Sequence
<220> FEATURE:
<223> OTHER INFORMATION: Synthetic Peptide

<400> SEQUENCE: 193

Lys Tyr Pro Met Tyr
1               5

<210> SEQ ID NO 194
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 194

Ala Ile Ser Ala Asp Ala Trp His Val Val Tyr Ser Gly Ser Val Gln
1               5                   10                  15

Gly

<210> SEQ ID NO 195
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 195

Met Phe Gln Glu Ser Gly Pro Pro Arg Phe Asp Ser Trp Ser Gly Arg
1               5                   10                  15

Asn Tyr Tyr Tyr Tyr Ser Gly Met Asp Val
            20                  25

<210> SEQ ID NO 196
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 196

Lys Ser Ser Gln Ser Leu Arg Gln Ser Asn Gly Lys Thr Ser Leu Tyr
1               5                   10                  15

<210> SEQ ID NO 197
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 197

Glu Val Ser Asn Arg Phe Ser
1               5

<210> SEQ ID NO 198
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 198

Met Gln Ser Lys Asp Phe Pro Leu Thr
1               5
```

```
<210> SEQ ID NO 199
<211> LENGTH: 135
<212> TYPE: PRT
<213> ORGANISM: Artificial Sequence
<220> FEATURE:
<223> OTHER INFORMATION: Synthetic Peptide

<400> SEQUENCE: 199

Arg Val Gln Leu Val Glu Ser Gly Gly Gly Val Val Gln Pro Gly Lys
1               5                   10                  15

Ser Val Arg Leu Ser Cys Val Val Ser Asp Phe Pro Phe Ser Lys Tyr
            20                  25                  30

Pro Met Tyr Trp Val Arg Gln Ala Pro Gly Lys Gly Leu Glu Trp Val
        35                  40                  45

Ala Ala Ile Ser Ala Asp Ala Trp His Val Val Tyr Ser Gly Ser Val
    50                  55                  60

Gln Gly Arg Phe Leu Val Ser Arg Asp Asn Ser Lys Asn Ile Leu Tyr
65                  70                  75                  80

Leu Glu Met Asn Thr Leu Lys Ile Glu Asp Thr Ala Val Tyr Arg Cys
                85                  90                  95

Ala Arg Met Phe Gln Glu Ser Gly Pro Pro Arg Phe Asp Ser Trp Ser
            100                 105                 110

Gly Arg Asn Tyr Tyr Tyr Ser Gly Met Asp Val Trp Gly Gln Gly
        115                 120                 125

Thr Thr Val Thr Val Ser Ser
        130                 135

<210> SEQ ID NO 200
<211> LENGTH: 112
<212> TYPE: PRT
<213> ORGANISM: Artificial Sequence
<220> FEATURE:
<223> OTHER INFORMATION: Synthetic Peptide

<400> SEQUENCE: 200

Asp Ile Val Met Thr Gln Thr Pro Leu Ser Leu Ser Val Asp Pro Gly
1               5                   10                  15

Gln Pro Ala Ser Ile Ser Cys Lys Ser Ser Gln Ser Leu Arg Gln Ser
            20                  25                  30

Asn Gly Lys Thr Ser Leu Tyr Trp Tyr Gln Gln Lys Pro Gly Gln Ser
        35                  40                  45

Pro Gln Leu Leu Ile Phe Glu Val Ser Asn Arg Phe Ser Gly Val Ser
    50                  55                  60

Asp Arg Phe Val Gly Ser Gly Ser Gly Thr Asp Phe Thr Leu Arg Ile
65                  70                  75                  80

Ser Arg Val Glu Ala Glu Asp Val Gly Phe Tyr Tyr Cys Met Gln Ser
                85                  90                  95

Lys Asp Phe Pro Leu Thr Phe Gly Gly Gly Thr Lys Val Asp Leu Asn
            100                 105                 110

<210> SEQ ID NO 201
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 201

Lys Arg His Met His
```

```
<210> SEQ ID NO 202
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 202

Val Ile Ser Ser Asp Ala Ile His Val Asp Tyr Ala Ser Ser Val Arg
1               5                   10                  15

Gly

<210> SEQ ID NO 203
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 203

Asp Arg Asp Gly Tyr Gly Pro Pro Gln Ile Gln Thr Trp Ser Gly Arg
1               5                   10                  15

Tyr Leu His Leu Tyr Ser Gly Ile Asp Ala
            20                  25

<210> SEQ ID NO 204
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 204

Lys Ser Ser Gln Ser Leu Arg Gln Ser Asn Gly Lys Thr Tyr Leu Tyr
1               5                   10                  15

<210> SEQ ID NO 205
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 205

Glu Val Ser Ile Arg Phe Ser
1               5

<210> SEQ ID NO 206
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 206

Met Gln Ser Lys Asp Phe Pro Leu Thr
1               5

<210> SEQ ID NO 207
<211> LENGTH: 135
<212> TYPE: PRT
<213> ORGANISM: Artificial Sequence
<220> FEATURE:
<223> OTHER INFORMATION: Synthetic Peptide
```

<400> SEQUENCE: 207

Gln Val Gln Leu Val Glu Ser Gly Gly Gly Val Val Gln Pro Gly Lys
1               5                   10                  15

Ser Leu Arg Leu Ser Cys Val Val Ser Asn Phe Leu Phe Asn Lys Arg
            20                  25                  30

His Met His Trp Val Arg Gln Ala Pro Gly Lys Gly Leu Glu Trp Ile
        35                  40                  45

Ala Val Ile Ser Ser Asp Ala Ile His Val Asp Tyr Ala Ser Ser Val
    50                  55                  60

Arg Gly Arg Ser Leu Ile Ser Arg Asp Asn Ser Lys Asn Ser Leu Tyr
65                  70                  75                  80

Leu Asp Met Asn Asn Leu Lys Ile Glu Asp Thr Ala Thr Tyr Tyr Cys
                85                  90                  95

Ala Arg Asp Arg Asp Gly Tyr Gly Pro Pro Gln Ile Gln Thr Trp Ser
            100                 105                 110

Gly Arg Tyr Leu His Leu Tyr Ser Gly Ile Asp Ala Trp Gly Leu Gly
        115                 120                 125

Thr Thr Val Thr Val Ser Ser
    130                 135

<210> SEQ ID NO 208
<211> LENGTH: 112
<212> TYPE: PRT
<213> ORGANISM: Artificial Sequence
<220> FEATURE:
<223> OTHER INFORMATION: Synthetic Peptide

<400> SEQUENCE: 208

Asp Ile Val Leu Thr Gln Ser Pro Leu Phe Leu Ser Val Ser Pro Gly
1               5                   10                  15

Gln Pro Ala Ser Ile Ser Cys Lys Ser Ser Gln Ser Leu Arg Gln Ser
            20                  25                  30

Asn Gly Lys Thr Tyr Leu Tyr Trp Tyr Val Gln Lys Ser Gly Gln Ser
        35                  40                  45

Pro Gln Pro Leu Ile Gln Glu Val Ser Ile Arg Phe Ser Gly Val Pro
    50                  55                  60

Gly Arg Phe Ala Gly Ser Gly Ser Gly Thr Asp Phe Thr Leu Lys Ile
65                  70                  75                  80

Ser Arg Val Glu Ala Glu Asp Val Gly Val Tyr Phe Cys Met Gln Ser
                85                  90                  95

Lys Asp Phe Pro Leu Thr Phe Gly Gly Gly Thr Lys Val Asp Leu Asn
            100                 105                 110

<210> SEQ ID NO 209
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 209

Lys Tyr Pro Met Tyr
1               5

<210> SEQ ID NO 210
<211> LENGTH: 17
<212> TYPE: PRT
<213> ORGANISM: Artificial Sequence

```
<220> FEATURE:
<223> OTHER INFORMATION: Synthetic Peptide

<400> SEQUENCE: 210

Ala Ile Ser Ala Asp Ala Trp His Val Asp Tyr Ala Ala Ser Val Lys
1               5                   10                  15
Asp

<210> SEQ ID NO 211
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 211

Asn Ile Glu Glu Phe Ser Val Pro Gln Phe Asp Ser Trp Ser Gly Arg
1               5                   10                  15
Ser Tyr Tyr His Tyr Phe Gly Met Asp Val
            20                  25

<210> SEQ ID NO 212
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 212

Ser Ser Ser Glu Ser Leu Gly Arg Gly Asp Gly Arg Thr Tyr Leu His
1               5                   10                  15

<210> SEQ ID NO 213
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 213

Glu Val Ser Thr Arg Phe Ser
1               5

<210> SEQ ID NO 214
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 214

Met Gln Ser Arg Asp Phe Pro Ile Thr
1               5

<210> SEQ ID NO 215
<211> LENGTH: 135
<212> TYPE: PRT
<213> ORGANISM: Artificial Sequence
<220> FEATURE:
<223> OTHER INFORMATION: Synthetic Peptide

<400> SEQUENCE: 215

Gln Val Gln Leu Val Glu Ser Gly Gly Gly Val Val Gln Pro Gly Lys
1               5                   10                  15
Ser Leu Arg Leu Ser Cys Val Val Ser Asn Phe Ile Phe Asn Lys Tyr
```

```
                    20                  25                  30
Pro Met Tyr Trp Val Arg Gln Ala Pro Gly Lys Gly Leu Glu Trp Val
                35                  40                  45

Ala Ala Ile Ser Ala Asp Ala Trp His Val Asp Tyr Ala Ala Ser Val
            50                  55                  60

Lys Asp Arg Phe Leu Ile Ser Arg Asp Asn Ser Lys Asn Ala Leu Tyr
65                  70                  75                  80

Leu Glu Met Asn Thr Leu Arg Val Glu Asp Thr Gly Ile Tyr Tyr Cys
                85                  90                  95

Ala Arg Asn Ile Glu Glu Phe Ser Val Pro Gln Phe Asp Ser Trp Ser
                100                 105                 110

Gly Arg Ser Tyr Tyr His Tyr Phe Gly Met Asp Val Trp Gly Gln Gly
                115                 120                 125

Thr Thr Val Thr Val Ser Ser
                130                 135

<210> SEQ ID NO 216
<211> LENGTH: 112
<212> TYPE: PRT
<213> ORGANISM: Artificial Sequence
<220> FEATURE:
<223> OTHER INFORMATION: Synthetic Peptide

<400> SEQUENCE: 216

Asp Ile Val Met Thr Gln Thr Pro Val Ser Leu Ser Val Ser Leu Gly
1               5                   10                  15

Gln Ala Ala Ser Ile Ser Cys Ser Ser Ser Glu Ser Leu Gly Arg Gly
                20                  25                  30

Asp Gly Arg Thr Tyr Leu His Trp Tyr Arg Gln Lys Pro Gly Gln Thr
                35                  40                  45

Pro Gln Leu Leu Met Tyr Glu Val Ser Thr Arg Phe Ser Gly Val Ser
            50                  55                  60

Asp Arg Phe Ala Gly Ser Gly Ser Arg Thr Gln Phe Thr Leu Lys Ile
65                  70                  75                  80

Ser Arg Val Glu Ala Glu Asp Val Gly Val Tyr Tyr Cys Met Gln Ser
                85                  90                  95

Arg Asp Phe Pro Ile Thr Phe Gly Gly Gly Thr Arg Val Asp Leu Lys
                100                 105                 110

<210> SEQ ID NO 217
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 217

Glu Tyr Pro Met Tyr
1               5

<210> SEQ ID NO 218
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 218

Ala Ile Ser Ala Asp Ala Trp His Val Asp Tyr Ala Gly Ser Val Arg
1               5                   10                  15
```

Gly

<210> SEQ ID NO 219
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 219

Asp Gly Glu Glu His Lys Val Pro Gln Leu His Ser Trp Ser Gly Arg
1               5                   10                  15

Asn Leu Tyr His Tyr Thr Gly Phe Asp Val
            20                  25

<210> SEQ ID NO 220
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 220

Lys Ser Ser Gln Ser Val Arg Gln Ser Asp Gly Lys Thr Phe Leu Tyr
1               5                   10                  15

<210> SEQ ID NO 221
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 221

Glu Gly Ser Ser Arg Phe Ser
1               5

<210> SEQ ID NO 222
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 222

Leu Gln Thr Lys Asp Phe Pro Leu Thr
1               5

<210> SEQ ID NO 223
<211> LENGTH: 135
<212> TYPE: PRT
<213> ORGANISM: Artificial Sequence
<220> FEATURE:
<223> OTHER INFORMATION: Synthetic Peptide

<400> SEQUENCE: 223

Gln Val His Leu Val Glu Ser Gly Gly Gly Val Val Gln Pro Gly Lys
1               5                   10                  15

Ser Leu Arg Leu Ser Cys Glu Thr Ser Gly Phe Ile Phe Asn Glu Tyr
            20                  25                  30

Pro Met Tyr Trp Ile Arg Gln Ala Pro Gly Lys Gly Pro Glu Trp Val
        35                  40                  45

Ala Ala Ile Ser Ala Asp Ala Trp His Val Asp Tyr Ala Gly Ser Val
    50                  55                  60

```
Arg Gly Arg Phe Thr Val Ser Arg Asp Asn Ser Lys Asn Ser Leu Tyr
65                  70                  75                  80

Leu Asp Met Lys Ser Leu Lys Val Glu Asp Thr Ala Ile Tyr Phe Cys
                85                  90                  95

Ala Lys Asp Gly Glu Glu His Lys Val Pro Gln Leu His Ser Trp Ser
            100                 105                 110

Gly Arg Asn Leu Tyr His Tyr Thr Gly Phe Asp Val Trp Gly Pro Gly
        115                 120                 125

Thr Thr Val Thr Val Ser Ser
    130                 135
```

<210> SEQ ID NO 224
<211> LENGTH: 112
<212> TYPE: PRT
<213> ORGANISM: Artificial Sequence
<220> FEATURE:
<223> OTHER INFORMATION: Synthetic Peptide

<400> SEQUENCE: 224

```
Asp Ile Val Met Thr Gln Ser Pro Val Ser Leu Ser Val Thr Leu Gly
1               5                   10                  15

Gln Pro Ala Ser Met Ser Cys Lys Ser Ser Gln Ser Val Arg Gln Ser
                20                  25                  30

Asp Gly Lys Thr Phe Leu Tyr Trp Tyr Arg Gln Lys Pro Gly Gln Ser
            35                  40                  45

Pro Gln Leu Leu Ile Tyr Glu Gly Ser Ser Arg Phe Ser Gly Val Ser
        50                  55                  60

Asp Arg Ile Ser Gly Ser Gly Ser Gly Thr Asp Phe Thr Leu Arg Ile
65                  70                  75                  80

Ser Arg Val Glu Ala Glu Asp Ala Gly Val Tyr Phe Cys Leu Gln Thr
                85                  90                  95

Lys Asp Phe Pro Leu Thr Phe Gly Gly Gly Thr Arg Val Asp Leu Lys
            100                 105                 110
```

<210> SEQ ID NO 225
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 225

```
Gln Tyr Pro Met Tyr
1               5
```

<210> SEQ ID NO 226
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 226

```
Ala Ile Ser Ala Asp Ala Trp His Val Asp Tyr Pro Gly Ser Val Arg
1               5                   10                  15

Gly
```

<210> SEQ ID NO 227
<211> LENGTH: 26
<212> TYPE: PRT

```
<213> ORGANISM: Artificial Sequence
<220> FEATURE:
<223> OTHER INFORMATION: Synthetic Peptide

<400> SEQUENCE: 227

Asp Gly Glu Glu His Lys Val Pro Gln Leu His Ser Trp Ser Gly Arg
1               5                   10                  15

Asn Leu Tyr His Tyr Thr Gly Phe Asp Val
            20                  25

<210> SEQ ID NO 228
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 228

Lys Ser Ser Gln Thr Val Arg Gln Ser Asp Gly Lys Thr Phe Leu Tyr
1               5                   10                  15

<210> SEQ ID NO 229
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 229

Glu Gly Ser Asn Arg Phe Ser
1               5

<210> SEQ ID NO 230
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 230

Leu Gln Thr Lys Asp Phe Pro Leu Thr
1               5

<210> SEQ ID NO 231
<211> LENGTH: 135
<212> TYPE: PRT
<213> ORGANISM: Artificial Sequence
<220> FEATURE:
<223> OTHER INFORMATION: Synthetic Peptide

<400> SEQUENCE: 231

Gln Val His Leu Val Glu Ser Gly Gly Val Val Gln Pro Gly Lys
1               5                   10                  15

Ser Leu Arg Leu Ser Cys Glu Thr Ser Gly Phe Ile Phe Asn Gln Tyr
            20                  25                  30

Pro Met Tyr Trp Val Arg Gln Ala Pro Gly Lys Gly Pro Glu Trp Val
        35                  40                  45

Ala Ala Ile Ser Ala Asp Ala Trp His Val Asp Tyr Pro Gly Ser Val
    50                  55                  60

Arg Gly Arg Phe Thr Val Ser Arg Asp Asn Ser Lys Ser Ser Leu Tyr
65                  70                  75                  80

Leu Asp Met Lys Ser Leu Lys Val Glu Asp Thr Ala Ile Tyr Phe Cys
                85                  90                  95
```

Ala Lys Asp Gly Glu Glu His Lys Val Pro Gln Leu His Ser Trp Ser
            100                 105                 110

Gly Arg Asn Leu Tyr His Tyr Thr Gly Phe Asp Val Trp Gly Pro Gly
            115                 120                 125

Thr Thr Val Thr Val Ser Ser
            130                 135

<210> SEQ ID NO 232
<211> LENGTH: 112
<212> TYPE: PRT
<213> ORGANISM: Artificial Sequence
<220> FEATURE:
<223> OTHER INFORMATION: Synthetic Peptide

<400> SEQUENCE: 232

Asp Ile Val Met Thr Gln Ser Pro Val Ser Leu Ser Val Thr Leu Gly
1               5                   10                  15

Gln Pro Ala Ser Met Ser Cys Lys Ser Ser Gln Thr Val Arg Gln Ser
            20                  25                  30

Asp Gly Lys Thr Phe Leu Tyr Trp Tyr Arg Gln Lys Ala Gly Gln Ser
        35                  40                  45

Pro Gln Leu Leu Ile Tyr Glu Gly Ser Asn Arg Phe Ser Gly Val Ser
    50                  55                  60

Asp Arg Ile Ser Gly Ser Gly Ser Gly Thr Asp Phe Thr Leu Arg Ile
65                  70                  75                  80

Ser Arg Val Glu Ala Glu Asp Val Gly Val Tyr Phe Cys Leu Gln Thr
                85                  90                  95

Lys Asp Phe Pro Leu Thr Phe Gly Gly Gly Thr Arg Val Asp Ile Lys
            100                 105                 110

<210> SEQ ID NO 233
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 233

Gln Tyr Pro Met Tyr
1               5

<210> SEQ ID NO 234
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 234

Ala Ile Ser Ala Asp Ala Trp His Val Asp Tyr Ala Gly Ser Val Arg
1               5                   10                  15

Gly

<210> SEQ ID NO 235
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 235

Asp Gly Glu Glu His Glu Val Pro Gln Leu His Ser Trp Ser Gly Arg

```
                1               5                   10                  15
Asn Leu Tyr His Tyr Thr Gly Val Asp Ile
            20                  25
```

<210> SEQ ID NO 236
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 236

```
Lys Ser Ser Gln Ser Leu Arg Gln Ser Asp Gly Lys Thr Phe Leu Tyr
1               5                   10                  15
```

<210> SEQ ID NO 237
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 237

```
Glu Ala Ser Asn Arg Phe Ser
1               5
```

<210> SEQ ID NO 238
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 238

```
Met Gln Thr Lys Asp Phe Pro Leu Thr
1               5
```

<210> SEQ ID NO 239
<211> LENGTH: 135
<212> TYPE: PRT
<213> ORGANISM: Artificial Sequence
<220> FEATURE:
<223> OTHER INFORMATION: Synthetic Peptide

<400> SEQUENCE: 239

```
Glu Val His Leu Val Glu Ser Gly Gly Gly Val Val Gln Pro Gly Lys
1               5                   10                  15

Ser Leu Arg Leu Ser Cys Val Thr Ser Gly Phe Ile Phe Lys Gln Tyr
            20                  25                  30

Pro Met Tyr Trp Ile Arg Gln Ala Pro Gly Lys Gly Leu Glu Trp Val
        35                  40                  45

Ala Ala Ile Ser Ala Asp Ala Trp His Val Asp Tyr Ala Gly Ser Val
    50                  55                  60

Arg Gly Arg Phe Thr Val Ser Arg Asp Asn Ser Lys Asn Ser Leu Tyr
65                  70                  75                  80

Leu Asp Met Asn Ser Leu Thr Val Glu Asp Thr Ala Ile Tyr Phe Cys
                85                  90                  95

Ala Lys Asp Gly Glu His Glu Val Pro Gln Leu His Ser Trp Ser
            100                 105                 110

Gly Arg Asn Leu Tyr His Tyr Thr Gly Val Asp Ile Trp Gly Pro Gly
            115                 120                 125

Thr Thr Val Thr Val Ser Ser
```

```
            130                 135
```

<210> SEQ ID NO 240
<211> LENGTH: 112
<212> TYPE: PRT
<213> ORGANISM: Artificial Sequence
<220> FEATURE:
<223> OTHER INFORMATION: Synthetic Peptide

<400> SEQUENCE: 240

```
Asp Ile Val Met Thr Gln Thr Pro Val Ser Leu Ser Val Thr Leu Gly
1               5                   10                  15

Gln Pro Ala Ser Met Ser Cys Lys Ser Ser Gln Ser Leu Arg Gln Ser
            20                  25                  30

Asp Gly Lys Thr Phe Leu Tyr Trp Tyr Arg Gln Lys Ala Gly Gln Ser
        35                  40                  45

Pro Gln Leu Leu Ile Ser Glu Ala Ser Asn Arg Phe Ser Gly Val Ser
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Phe Cys Met Gln Thr
                85                  90                  95

Lys Asp Phe Pro Leu Thr Phe Gly Gly Gly Thr Lys Val Asp Leu Lys
            100                 105                 110
```

<210> SEQ ID NO 241
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 241

```
Lys Tyr Pro Met Tyr
1               5
```

<210> SEQ ID NO 242
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 242

```
Ala Ile Ser Ala Asp Ala Trp His Val Asp Tyr Pro Gly Ser Val Arg
1               5                   10                  15

Gly
```

<210> SEQ ID NO 243
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 243

```
Asp Gly Glu Glu His Glu Val Pro Gln Leu His Ser Trp Ser Gly Arg
1               5                   10                  15

Asn Leu Tyr His Tyr Thr Gly Val Asp Val
            20                  25
```

<210> SEQ ID NO 244

```
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 244

Lys Ser Ser Gln Ser Val Arg Gln Ser Asp Gly Lys Thr Phe Leu Tyr
1               5                   10                  15

<210> SEQ ID NO 245
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 245

Glu Ala Ser Lys Arg Phe Ser
1               5

<210> SEQ ID NO 246
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 246

Met Gln Thr Lys Asp Phe Pro Leu Thr
1               5

<210> SEQ ID NO 247
<211> LENGTH: 135
<212> TYPE: PRT
<213> ORGANISM: Artificial Sequence
<220> FEATURE:
<223> OTHER INFORMATION: Synthetic Peptide

<400> SEQUENCE: 247

Glu Val Arg Leu Met Glu Ser Gly Gly Gly Val Val Gln Pro Gly Lys
1               5                   10                  15

Ser Leu Arg Leu Ser Cys Val Thr Ser Gly Phe Ile Phe Lys Lys Tyr
            20                  25                  30

Pro Met Tyr Trp Ile Arg Gln Ala Pro Gly Lys Gly Leu Glu Trp Val
        35                  40                  45

Ala Ala Ile Ser Ala Asp Ala Trp His Val Asp Tyr Pro Gly Ser Val
    50                  55                  60

Arg Gly Arg Phe Thr Val Ser Arg Asp Asn Ser Lys Asn Ser Leu Tyr
65                  70                  75                  80

Leu Asp Met Asn Ser Leu Thr Val Glu Asp Thr Ala Ile Tyr Phe Cys
                85                  90                  95

Ala Lys Asp Gly Glu Glu His Glu Val Pro Gln Leu His Ser Trp Ser
            100                 105                 110

Gly Arg Asn Leu Tyr His Tyr Thr Gly Val Asp Val Trp Gly Pro Gly
        115                 120                 125

Thr Thr Val Thr Val Ser Ser
    130                 135

<210> SEQ ID NO 248
<211> LENGTH: 112
<212> TYPE: PRT
<213> ORGANISM: Artificial Sequence
```

```
<220> FEATURE:
<223> OTHER INFORMATION: Synthetic Peptide

<400> SEQUENCE: 248

Asp Ile Val Met Thr Gln Thr Pro Val Ser Val Ser Val Thr Leu Gly
1               5                   10                  15

Gln Pro Ala Ser Met Ser Cys Lys Ser Ser Gln Ser Val Arg Gln Ser
            20                  25                  30

Asp Gly Lys Thr Phe Leu Tyr Trp Tyr Arg Gln Lys Ala Gly Gln Ser
        35                  40                  45

Pro Gln Leu Leu Ile Tyr Glu Ala Ser Lys Arg Phe Ser Gly Val Ser
    50                  55                  60

Asp Arg Phe Ser Gly Ser Gly Ser Gly Thr Asp Phe Thr Leu Lys Ile
65                  70                  75                  80

Ser Arg Val Gly Ala Glu Asp Val Gly Val Tyr Phe Cys Met Gln Thr
                85                  90                  95

Lys Asp Phe Pro Leu Thr Phe Gly Gly Gly Thr Lys Val Asp Leu Lys
            100                 105                 110

<210> SEQ ID NO 249
<211> LENGTH: 104
<212> TYPE: PRT
<213> ORGANISM: Homo sapiens

<400> SEQUENCE: 249

Glu Ile Val Leu Thr Gln Ser Pro Gly Thr Leu Ser Leu Ser Pro Gly
1               5                   10                  15

Glu Thr Ala Ile Ile Ser Cys Arg Thr Ser Gln Tyr Gly Ser Leu Ala
            20                  25                  30

Trp Tyr Gln Gln Arg Pro Gly Gln Ala Pro Arg Leu Val Ile Tyr Ser
        35                  40                  45

Gly Ser Thr Arg Ala Ala Gly Ile Pro Asp Arg Phe Ser Gly Ser Arg
    50                  55                  60

Trp Gly Pro Asp Tyr Asn Leu Thr Ile Ser Asn Leu Glu Ser Gly Asp
65                  70                  75                  80

Phe Gly Val Tyr Tyr Cys Gln Gln Tyr Glu Phe Phe Gly Gln Gly Thr
                85                  90                  95

Lys Val Gln Val Asp Ile Lys Arg
            100

<210> SEQ ID NO 250
<211> LENGTH: 49
<212> TYPE: PRT
<213> ORGANISM: Homo sapiens

<400> SEQUENCE: 250

Gln Val Gln Leu Val Gln Ser Gly Gly Gln Met Lys Lys Pro Gly Glu
1               5                   10                  15

Ser Met Arg Ile Ser Cys Arg Ala Ser Gly Tyr Glu Phe Ile Asp Cys
            20                  25                  30

Thr Leu Asn Trp Ile Arg Leu Ala Pro Gly Lys Arg Pro Glu Trp Met
        35                  40                  45

Gly

<210> SEQ ID NO 251
<211> LENGTH: 104
<212> TYPE: PRT
<213> ORGANISM: Homo sapiens
```

<400> SEQUENCE: 251

Glu Ile Val Leu Thr Gln Ser Pro Gly Thr Leu Ser Leu Ser Pro Gly
1               5                   10                  15

Glu Thr Ala Ile Ile Ser Cys Arg Thr Ser Gln Tyr Gly Ser Leu Ala
            20                  25                  30

Trp Tyr Gln Gln Arg Pro Gly Gln Ala Pro Arg Leu Val Ile Tyr Ser
        35                  40                  45

Gly Ser Thr Arg Ala Ala Gly Ile Pro Asp Arg Phe Ser Gly Ser Arg
    50                  55                  60

Trp Gly Pro Asp Tyr Asn Leu Thr Ile Arg Asn Leu Glu Ser Gly Asp
65                  70                  75                  80

Phe Gly Leu Tyr Tyr Cys Gln Gln Tyr Glu Phe Phe Gly Gln Gly Thr
                85                  90                  95

Lys Val Gln Val Asp Ile Lys Arg
            100

<210> SEQ ID NO 252
<211> LENGTH: 121
<212> TYPE: PRT
<213> ORGANISM: Homo sapiens

<400> SEQUENCE: 252

Gln Val Gln Leu Val Gln Ser Gly Gly Gln Met Lys Lys Pro Gly Glu
1               5                   10                  15

Ser Met Arg Ile Ser Cys Gln Ala Ser Gly Tyr Glu Phe Ile Asp Cys
            20                  25                  30

Thr Leu Asn Trp Val Arg Leu Ala Pro Gly Arg Arg Pro Glu Trp Met
        35                  40                  45

Gly Trp Leu Lys Pro Arg Gly Gly Ala Val Asn Tyr Ala Arg Pro Leu
    50                  55                  60

Gln Gly Arg Val Thr Met Thr Arg Asp Val Tyr Ser Asp Thr Ala Phe
65                  70                  75                  80

Leu Glu Leu Arg Ser Leu Thr Ala Asp Asp Thr Ala Val Tyr Tyr Cys
                85                  90                  95

Thr Arg Gly Lys Asn Cys Asp Tyr Asn Trp Asp Phe Glu His Trp Gly
            100                 105                 110

Arg Gly Thr Pro Val Thr Val Ser Ser
        115                 120

<210> SEQ ID NO 253
<211> LENGTH: 107
<212> TYPE: PRT
<213> ORGANISM: Homo sapiens

<400> SEQUENCE: 253

Glu Ile Val Leu Thr Gln Ser Pro Ala Thr Leu Ser Leu Ser Pro Gly
1               5                   10                  15

Glu Thr Ala Ile Ile Ser Cys Arg Thr Ser Gln Ser Gly Ser Leu Ala
            20                  25                  30

Trp Tyr Gln Gln Arg Pro Gly Gln Ala Pro Arg Leu Val Ile Tyr Ser
        35                  40                  45

Gly Ser Thr Arg Ala Ala Gly Ile Pro Asp Arg Phe Ser Gly Ser Arg
    50                  55                  60

Trp Gly Ala Asp Tyr Asn Leu Ser Ile Ser Asn Leu Glu Ser Gly Asp
65                  70                  75                  80

```
Phe Gly Val Tyr Tyr Cys Gln Gln Tyr Glu Phe Phe Gly Gln Gly Thr
                85                  90                  95

Lys Val Gln Val Asp Ile Lys Arg Thr Val Ala
            100                 105

<210> SEQ ID NO 254
<211> LENGTH: 125
<212> TYPE: PRT
<213> ORGANISM: Homo sapiens

<400> SEQUENCE: 254

Gln Val Arg Leu Ser Gln Ser Gly Gly Gln Met Lys Lys Pro Gly Glu
1               5                   10                  15

Ser Met Arg Leu Ser Cys Arg Ala Ser Gly Tyr Glu Phe Leu Asn Cys
            20                  25                  30

Pro Ile Asn Trp Ile Arg Leu Ala Pro Gly Arg Arg Pro Glu Trp Met
        35                  40                  45

Gly Trp Leu Lys Pro Arg Gly Gly Ala Val Asn Tyr Ala Arg Lys Phe
    50                  55                  60

Gln Gly Arg Val Thr Met Thr Arg Asp Val Tyr Ser Asp Thr Ala Phe
65                  70                  75                  80

Leu Glu Leu Arg Ser Leu Thr Ser Asp Asp Thr Ala Val Tyr Phe Cys
                85                  90                  95

Thr Arg Gly Lys Tyr Cys Thr Ala Arg Asp Tyr Tyr Asn Trp Asp Phe
            100                 105                 110

Glu His Trp Gly Arg Gly Ala Pro Val Thr Val Ser Ser
        115                 120                 125

<210> SEQ ID NO 255
<211> LENGTH: 103
<212> TYPE: PRT
<213> ORGANISM: Homo sapiens

<400> SEQUENCE: 255

Asp Ile Gln Met Thr Gln Ser Pro Ser Ser Leu Ser Ala Arg Val Gly
1               5                   10                  15

Asp Thr Val Thr Ile Thr Cys Gln Ala Asn Gly Tyr Leu Asn Trp Tyr
            20                  25                  30

Gln Gln Arg Arg Gly Lys Ala Pro Lys Leu Leu Ile Tyr Asp Gly Ser
        35                  40                  45

Lys Leu Glu Arg Gly Val Pro Ala Arg Phe Ser Gly Arg Arg Trp Gly
    50                  55                  60

Gln Glu Tyr Asn Leu Thr Ile Asn Asn Leu Gln Pro Glu Asp Val Ala
65                  70                  75                  80

Thr Tyr Phe Cys Gln Val Tyr Glu Phe Ile Val Pro Gly Thr Arg Leu
                85                  90                  95

Asp Leu Lys Arg Thr Val Ala
            100

<210> SEQ ID NO 256
<211> LENGTH: 123
<212> TYPE: PRT
<213> ORGANISM: Homo sapiens

<400> SEQUENCE: 256

Gln Val His Leu Ser Gln Ser Gly Ala Ala Val Thr Lys Pro Gly Ala
1               5                   10                  15

Ser Val Arg Val Ser Cys Glu Ala Ser Gly Tyr Lys Ile Ser Asp His
```

```
            20                  25                  30
Phe Ile His Trp Trp Arg Gln Ala Pro Gly Gln Gly Leu Gln Trp Val
                35                  40                  45
Gly Trp Ile Asn Pro Lys Thr Gly Gln Pro Asn Asn Pro Arg Gln Phe
            50                  55                  60
Gln Gly Arg Val Ser Leu Thr Arg Gln Ala Ser Trp Asp Phe Asp Thr
65                  70                  75                  80
Tyr Ser Phe Tyr Met Asp Leu Lys Ala Val Arg Ser Asp Asp Thr Ala
                85                  90                  95
Ile Tyr Phe Cys Ala Arg Gln Arg Ser Asp Phe Trp Asp Phe Asp Val
                100                 105                 110
Trp Gly Ser Gly Thr Gln Val Thr Val Ser Ser
                115                 120

<210> SEQ ID NO 257
<211> LENGTH: 103
<212> TYPE: PRT
<213> ORGANISM: Homo sapiens

<400> SEQUENCE: 257

Asp Ile Gln Met Thr Gln Ser Pro Ser Ser Leu Ser Ala Ser Val Gly
1               5                   10                  15
Asp Thr Val Thr Ile Thr Cys Gln Ala Asn Gly Tyr Leu Asn Trp Tyr
                20                  25                  30
Gln Gln Arg Arg Gly Lys Ala Pro Lys Leu Leu Ile Tyr Asp Gly Ser
                35                  40                  45
Lys Leu Glu Arg Gly Val Pro Ser Arg Phe Ser Gly Arg Trp Gly
            50                  55                  60
Gln Glu Tyr Asn Leu Thr Ile Asn Asn Leu Gln Pro Glu Asp Ile Ala
65                  70                  75                  80
Thr Tyr Phe Cys Gln Val Tyr Glu Phe Val Val Pro Gly Thr Arg Leu
                85                  90                  95
Asp Leu Lys Arg Thr Val Ala
            100

<210> SEQ ID NO 258
<211> LENGTH: 123
<212> TYPE: PRT
<213> ORGANISM: Homo sapiens

<400> SEQUENCE: 258

Gln Val Gln Leu Leu Gln Ser Gly Ala Ala Val Thr Lys Pro Gly Ala
1               5                   10                  15
Ser Val Arg Val Ser Cys Glu Ala Ser Gly Tyr Asn Ile Arg Asp Tyr
                20                  25                  30
Phe Ile His Trp Trp Arg Gln Ala Pro Gly Gln Gly Leu Gln Trp Val
                35                  40                  45
Gly Trp Ile Asn Pro Lys Thr Gly Gln Pro Asn Asn Pro Arg Gln Phe
            50                  55                  60
Gln Gly Arg Val Ser Leu Thr Arg His Ala Ser Trp Asp Phe Asp Thr
65                  70                  75                  80
Phe Ser Phe Tyr Met Asp Leu Lys Ala Leu Arg Ser Asp Asp Thr Ala
                85                  90                  95
Val Tyr Phe Cys Ala Arg Gln Arg Ser Asp Tyr Trp Asp Phe Asp Val
                100                 105                 110
Trp Gly Ser Gly Thr Gln Val Thr Val Ser Ser
```

-continued

<210> SEQ ID NO 259
<211> LENGTH: 103
<212> TYPE: PRT
<213> ORGANISM: Homo sapiens

<400> SEQUENCE: 259

```
Asp Ile Gln Met Thr Gln Ser Pro Ser Ser Leu Ser Ala Arg Val Gly
1               5                   10                  15

Asp Thr Val Thr Ile Thr Cys Gln Ala Asn Gly Tyr Leu Asn Trp Tyr
            20                  25                  30

Gln Gln Arg Arg Gly Lys Ala Pro Lys Leu Leu Ile Tyr Asp Gly Ser
        35                  40                  45

Lys Leu Glu Thr Gly Val Pro Ser Arg Phe Thr Gly Arg Arg Trp Gly
    50                  55                  60

Gln Glu Tyr Asn Leu Thr Ile Asn Asn Leu Gln Pro Glu Asp Ile Ala
65                  70                  75                  80

Thr Tyr Phe Cys Gln Val Tyr Glu Phe Ile Val Pro Gly Thr Arg Leu
                85                  90                  95

Asp Leu Lys Arg Thr Val Ala
            100
```

<210> SEQ ID NO 260
<211> LENGTH: 123
<212> TYPE: PRT
<213> ORGANISM: Homo sapiens

<400> SEQUENCE: 260

```
Gln Val Arg Leu Leu Gln Ser Gly Ala Ala Val Thr Lys Pro Gly Ala
1               5                   10                  15

Ser Val Arg Val Ser Cys Glu Ala Ser Gly Tyr Glu Ile Arg Asp Tyr
            20                  25                  30

Phe Ile His Trp Trp Arg Gln Ala Pro Gly Gln Gly Leu Gln Trp Val
        35                  40                  45

Gly Trp Ile Asn Pro Lys Thr Gly Gln Pro Asn Asn Pro Arg Gln Phe
    50                  55                  60

Gln Gly Arg Val Ser Leu Thr Arg Gln Ala Ser Trp Asp Phe Asp Ser
65                  70                  75                  80

Tyr Ser Phe Tyr Met Asp Leu Lys Ala Leu Arg Ser Asp Asp Thr Gly
                85                  90                  95

Val Tyr Phe Cys Ala Arg Gln Arg Ser Asp Tyr Trp Asp Phe Asp Val
                100                 105                 110

Trp Gly Ser Gly Thr Gln Val Thr Val Ser Ser
            115                 120
```

<210> SEQ ID NO 261
<211> LENGTH: 103
<212> TYPE: PRT
<213> ORGANISM: Homo sapiens

<400> SEQUENCE: 261

```
Asp Ile Gln Met Thr Gln Ser Pro Ser Ser Leu Ser Ala Ser Val Gly
1               5                   10                  15

Asp Thr Val Thr Ile Thr Cys Gln Ala Asn Gly Tyr Leu Asn Trp Tyr
            20                  25                  30

Gln Gln Arg Arg Gly Lys Ala Pro Lys Leu Leu Ile Tyr Asp Gly Ser
        35                  40                  45
```

```
Lys Leu Glu Arg Gly Val Pro Ser Arg Phe Ser Gly Arg Trp Gly
    50                  55                  60

Gln Glu Tyr Asn Leu Thr Ile Asn Asn Leu Gln Pro Glu Asp Ile Ala
65                  70                  75                  80

Thr Tyr Phe Cys Gln Val Tyr Glu Phe Ile Val Pro Gly Thr Arg Leu
                85                  90                  95

Asp Leu Lys Arg Thr Val Ala
            100

<210> SEQ ID NO 262
<211> LENGTH: 123
<212> TYPE: PRT
<213> ORGANISM: Homo sapiens

<400> SEQUENCE: 262

Gln Val Gln Leu Leu Gln Ser Gly Ala Ala Val Thr Lys Pro Gly Ala
1               5                   10                  15

Ser Val Arg Val Ser Cys Glu Ala Ser Gly Tyr Asn Ile Arg Asp Tyr
                20                  25                  30

Phe Ile His Trp Trp Arg Gln Ala Pro Gly Gln Gly Leu Gln Trp Val
            35                  40                  45

Gly Trp Ile Asn Pro Lys Thr Gly Gln Pro Asn Asn Pro Arg Leu Phe
    50                  55                  60

Gln Gly Arg Val Ser Leu Thr Arg His Ala Ser Trp Asp Phe Asp Thr
65                  70                  75                  80

Phe Ser Phe Tyr Met Asp Leu Lys Ala Val Arg Ser Asp Asp Thr Ala
                85                  90                  95

Val Tyr Phe Cys Ala Arg Gln Arg Ser Asp Tyr Trp Asp Phe Asp Val
            100                 105                 110

Trp Gly Ser Gly Thr Gln Val Thr Val Ser Ser
        115                 120

<210> SEQ ID NO 263
<211> LENGTH: 103
<212> TYPE: PRT
<213> ORGANISM: Homo sapiens

<400> SEQUENCE: 263

Asp Ile Gln Met Thr Gln Ser Pro Ser Ser Leu Ser Ala Ser Val Gly
1               5                   10                  15

Asp Thr Val Thr Ile Thr Cys Gln Ala Asn Gly Tyr Leu Asn Trp Tyr
                20                  25                  30

Gln Gln Arg Arg Gly Lys Ala Pro Lys Leu Leu Ile Tyr Asp Gly Ser
            35                  40                  45

Lys Leu Glu Arg Gly Val Pro Ser Arg Phe Ser Gly Arg Trp Gly
    50                  55                  60

Gln Glu Tyr Asn Leu Thr Ile Asn Asn Leu Gln Ala Glu Asp Ile Ala
65                  70                  75                  80

Thr Tyr Phe Cys Gln Val Tyr Glu Phe Ala Val Pro Gly Thr Arg Leu
                85                  90                  95

Asp Leu Lys Arg Thr Val Ala
            100

<210> SEQ ID NO 264
<211> LENGTH: 123
<212> TYPE: PRT
<213> ORGANISM: Homo sapiens
```

<400> SEQUENCE: 264

Gln Val Gln Leu Leu Gln Ser Gly Ala Ala Val Thr Lys Pro Gly Ala
1               5                   10                  15

Ser Val Arg Val Ser Cys Glu Ala Ser Gly Tyr Asn Ile Arg Asp Tyr
                20                  25                  30

Phe Ile His Trp Trp Arg Gln Ala Pro Gly Gln Gly Leu Gln Trp Val
            35                  40                  45

Gly Trp Ile Asn Pro Lys Thr Gly Gln Pro Asn Asn Pro Arg Gln Phe
        50                  55                  60

Gln Gly Arg Val Ser Leu Thr Arg His Ala Ser Trp Asp Phe Asp Thr
65                  70                  75                  80

Phe Ser Phe Tyr Met Asp Leu Lys Gly Leu Arg Ser Asp Asp Thr Ala
                85                  90                  95

Ile Tyr Phe Cys Ala Arg Gln Arg Ser Asp Tyr Trp Asp Phe Asp Val
            100                 105                 110

Trp Gly Ser Gly Thr Gln Val Thr Val Ser Ser
            115                 120

<210> SEQ ID NO 265
<211> LENGTH: 107
<212> TYPE: PRT
<213> ORGANISM: Homo sapiens

<400> SEQUENCE: 265

Asp Ile Gln Met Thr Gln Ser Pro Ser Ser Leu Ser Ala Ser Val Gly
1               5                   10                  15

Asp Arg Val Thr Ile Thr Cys Gln Ala Gly Gln Gly Ile Gly Ser Ser
                20                  25                  30

Leu Gln Trp Tyr Gln Gln Lys Pro Gly Lys Ala Pro Lys Leu Leu Val
            35                  40                  45

His Gly Ala Ser Asn Leu His Arg Gly Val Pro Ser Arg Phe Ser Gly
        50                  55                  60

Ser Gly Phe His Thr Thr Phe Ser Leu Thr Ile Ser Gly Leu Gln Arg
65                  70                  75                  80

Asp Asp Phe Ala Thr Tyr Phe Cys Ala Val Leu Glu Phe Phe Gly Pro
                85                  90                  95

Gly Thr Lys Val Glu Ile Lys Arg Thr Val Ala
            100                 105

<210> SEQ ID NO 266
<211> LENGTH: 122
<212> TYPE: PRT
<213> ORGANISM: Homo sapiens

<400> SEQUENCE: 266

Ser Gln His Leu Val Gln Ser Gly Thr Gln Val Lys Lys Pro Gly Ala
1               5                   10                  15

Ser Val Arg Ile Ser Cys Gln Ala Ser Gly Tyr Ser Phe Thr Asp Tyr
                20                  25                  30

Val Leu His Trp Trp Arg Gln Ala Pro Gly Gln Gly Leu Glu Trp Met
            35                  40                  45

Gly Trp Ile Lys Pro Val Tyr Gly Ala Arg Asn Tyr Ala Arg Arg Phe
        50                  55                  60

Gln Gly Arg Ile Asn Phe Asp Arg Asp Ile Tyr Arg Glu Ile Ala Phe
65                  70                  75                  80

```
Met Asp Leu Ser Gly Leu Arg Ser Asp Asp Thr Ala Leu Tyr Phe Cys
            85                  90                  95

Ala Arg Asp Gly Ser Gly Asp Asp Thr Ser Trp His Leu Asp Pro Trp
            100                 105                 110

Gly Gln Gly Thr Leu Val Ile Val Ser Ala
            115                 120

<210> SEQ ID NO 267
<211> LENGTH: 102
<212> TYPE: PRT
<213> ORGANISM: Homo sapiens

<400> SEQUENCE: 267

Glu Ile Val Leu Thr Gln Ser Pro Gly Thr Leu Ser Leu Ser Pro Gly
1               5                   10                  15

Glu Thr Ala Ser Leu Ser Cys Thr Ala Ala Ser Tyr Gly His Met Thr
            20                  25                  30

Trp Tyr Gln Lys Lys Pro Gly Gln Pro Pro Lys Leu Leu Ile Phe Ala
            35                  40                  45

Thr Ser Lys Arg Ala Ser Gly Ile Pro Asp Arg Phe Ser Gly Ser Gln
50                  55                  60

Phe Gly Lys Gln Tyr Thr Leu Thr Ile Thr Arg Met Glu Pro Glu Asp
65                  70                  75                  80

Phe Ala Arg Tyr Tyr Cys Gln Gln Leu Glu Phe Phe Gly Gln Gly Thr
                85                  90                  95

Arg Leu Glu Ile Arg Arg
            100

<210> SEQ ID NO 268
<211> LENGTH: 125
<212> TYPE: PRT
<213> ORGANISM: Homo sapiens

<400> SEQUENCE: 268

Gln Val Gln Leu Val Gln Ser Gly Ser Gly Val Lys Lys Pro Gly Ala
1               5                   10                  15

Ser Val Arg Val Ser Cys Trp Thr Ser Glu Asp Ile Phe Glu Arg Thr
            20                  25                  30

Glu Leu Ile His Trp Val Arg Gln Ala Pro Gly Gln Gly Leu Glu Trp
            35                  40                  45

Ile Gly Trp Val Lys Thr Val Thr Gly Ala Val Asn Phe Gly Ser Pro
50                  55                  60

Asp Phe Arg Gln Arg Val Ser Leu Thr Arg Asp Arg Asp Leu Phe Thr
65                  70                  75                  80

Ala His Met Asp Ile Arg Gly Leu Thr Gln Gly Asp Thr Ala Thr Tyr
                85                  90                  95

Phe Cys Ala Arg Gln Lys Phe Tyr Thr Gly Gly Gln Gly Trp Tyr Phe
            100                 105                 110

Asp Leu Trp Gly Arg Gly Thr Leu Val Val Ser Ser
            115                 120                 125

<210> SEQ ID NO 269
<211> LENGTH: 103
<212> TYPE: PRT
<213> ORGANISM: Homo sapiens

<400> SEQUENCE: 269

Asp Ile Gln Met Thr Gln Ser Pro Ser Ser Leu Ser Ala Ser Leu Gly
```

```
            1               5                  10                 15
Asp Arg Val Thr Ile Thr Cys Gln Ala Ser Arg Gly Ile Gly Lys Asp
                20                  25                  30

Leu Asn Trp Tyr Gln Gln Lys Pro Gly Lys Ala Pro Lys Leu Leu Val
        35                  40                  45

Ser Asp Ala Ser Ile Leu Glu Gly Gly Val Pro Ser Arg Phe Ser Gly
    50                  55                  60

Ser Gly Phe His Gln Asn Phe Ser Leu Thr Ile Ser Ser Leu Gln Pro
65                  70                  75                  80

Glu Asp Val Ala Thr Tyr Phe Cys Gln Gln Tyr Glu Thr Phe Gly Gln
                85                  90                  95

Gly Thr Lys Val Asp Ile Lys
                100
```

<210> SEQ ID NO 270
<211> LENGTH: 131
<212> TYPE: PRT
<213> ORGANISM: Homo sapiens

<400> SEQUENCE: 270

```
Gln Val Gln Leu Val Gln Ser Gly Ala Ala Val Arg Lys Pro Gly Ala
1               5                   10                  15

Ser Val Thr Val Ser Cys Lys Phe Ala Glu Asp Asp Tyr Ser Pro
                20                  25                  30

His Trp Val Asn Pro Ala Pro Glu His Tyr Ile His Phe Leu Arg Gln
        35                  40                  45

Ala Pro Gly Gln Gln Leu Glu Trp Leu Ala Trp Met Asn Pro Thr Asn
    50                  55                  60

Gly Ala Val Asn Tyr Ala Trp Gln Leu His Gly Arg Leu Thr Ala Thr
65                  70                  75                  80

Arg Asp Gly Ser Met Thr Thr Ala Phe Leu Glu Val Arg Ser Leu Arg
                85                  90                  95

Ser Asp Asp Thr Ala Val Tyr Tyr Cys Ala Arg Ala Gln Lys Arg Gly
                100                 105                 110

Arg Ser Glu Trp Ala Tyr Ala His Trp Gly Gln Gly Thr Pro Val Leu
        115                 120                 125

Val Ser Ser
    130
```

<210> SEQ ID NO 271
<211> LENGTH: 103
<212> TYPE: PRT
<213> ORGANISM: Homo sapiens

<400> SEQUENCE: 271

```
Asp Ile Gln Met Thr Gln Ser Pro Ser Ser Leu Ser Ala Ser Leu Gly
1               5                   10                  15

Asp Arg Val Thr Ile Thr Cys Gln Ala Ser Arg Gly Ile Gly Lys Asp
                20                  25                  30

Leu Asn Trp Tyr Gln Gln Lys Ala Gly Lys Ala Pro Lys Leu Leu Val
        35                  40                  45

Ser Asp Ala Ser Thr Leu Glu Gly Gly Val Pro Ser Arg Phe Ser Gly
    50                  55                  60

Ser Gly Phe His Gln Asn Phe Ser Leu Thr Ile Ser Ser Leu Gln Ala
65                  70                  75                  80

Glu Asp Val Ala Thr Tyr Phe Cys Gln Gln Tyr Glu Thr Phe Gly Gln
```

Gly Thr Lys Val Asp Ile Lys
            100

<210> SEQ ID NO 272
<211> LENGTH: 131
<212> TYPE: PRT
<213> ORGANISM: Homo sapiens

<400> SEQUENCE: 272

Gln Val Gln Leu Val Gln Ser Gly Ala Ala Val Arg Lys Pro Gly Ala
1               5                   10                  15

Ser Val Thr Val Ser Cys Lys Phe Ala Glu Asp Asp Tyr Ser Pro
            20                  25                  30

Tyr Trp Val Asn Pro Ala Pro Glu His Phe Ile His Phe Leu Arg Gln
            35                  40                  45

Ala Pro Gly Gln Gln Leu Glu Trp Leu Ala Trp Met Asn Pro Thr Asn
        50                  55                  60

Gly Ala Val Asn Tyr Ala Trp Tyr Leu Asn Gly Arg Val Thr Ala Thr
65                  70                  75                  80

Arg Asp Arg Ser Met Thr Thr Ala Phe Leu Glu Val Lys Ser Leu Arg
                85                  90                  95

Ser Asp Asp Thr Ala Val Tyr Tyr Cys Ala Arg Ala Gln Lys Arg Gly
            100                 105                 110

Arg Ser Glu Trp Ala Tyr Ala His Trp Gly Gln Gly Thr Pro Val Val
        115                 120                 125

Val Ser Ser
    130

<210> SEQ ID NO 273
<211> LENGTH: 103
<212> TYPE: PRT
<213> ORGANISM: Homo sapiens

<400> SEQUENCE: 273

Asp Ile Gln Met Thr Gln Ser Pro Ser Ser Leu Ser Ala Ser Leu Gly
1               5                   10                  15

Asp Arg Val Thr Ile Thr Cys Gln Ala Ser Arg Gly Ile Gly Lys Asp
            20                  25                  30

Leu Asn Trp Tyr Gln Gln Lys Pro Gly Arg Ala Pro Lys Leu Leu Val
            35                  40                  45

Ser Asp Ala Ser Ile Leu Glu Gly Gly Val Pro Thr Arg Phe Ser Gly
        50                  55                  60

Ser Gly Phe His Gln Asn Phe Ser Leu Thr Ile Ser Ser Leu Gln Ala
65                  70                  75                  80

Glu Asp Val Ala Thr Tyr Phe Cys Gln Gln Tyr Glu Thr Phe Gly Gln
                85                  90                  95

Gly Thr Lys Val Asp Ile Lys
            100

<210> SEQ ID NO 274
<211> LENGTH: 131
<212> TYPE: PRT
<213> ORGANISM: Homo sapiens

<400> SEQUENCE: 274

Gln Val Gln Leu Val Gln Ser Gly Ala Ala Val Arg Lys Pro Gly Ala
1               5                   10                  15

```
Ser Val Thr Val Ser Cys Lys Phe Ala Glu Asp Asp Phe Ser Pro
            20                  25                  30

His Trp Val Asn Pro Ala Pro Glu His Tyr Ile His Phe Leu Arg Gln
        35                  40                  45

Ala Pro Gly Gln Gln Leu Glu Trp Leu Ala Trp Met Lys Pro Thr Asn
    50                  55                  60

Gly Ala Val Asn Tyr Ala Trp Gln Leu Gln Gly Arg Val Thr Val Thr
65                  70                  75                  80

Arg Asp Arg Ser Gln Thr Thr Ala Phe Leu Glu Val Lys Asn Leu Arg
                85                  90                  95

Ser Asp Asp Thr Ala Val Tyr Tyr Cys Ala Arg Ala Gln Lys Arg Gly
            100                 105                 110

Arg Ser Glu Trp Ala Tyr Ala His Trp Gly Gln Gly Thr Pro Val Val
        115                 120                 125

Ile Ser Ala
    130

<210> SEQ ID NO 275
<211> LENGTH: 103
<212> TYPE: PRT
<213> ORGANISM: Homo sapiens

<400> SEQUENCE: 275

Asp Ile Gln Met Thr Gln Ser Pro Ser Ser Leu Ser Ala Ser Leu Gly
1               5                   10                  15

Asp Arg Val Thr Ile Thr Cys Gln Ala Ser Arg Gly Ile Gly Lys Asp
            20                  25                  30

Leu Asn Trp Tyr Gln Gln Lys Arg Gly Arg Ala Pro Arg Leu Leu Val
        35                  40                  45

Ser Asp Ala Ser Val Leu Glu Gly Gly Val Pro Ser Arg Phe Ser Gly
    50                  55                  60

Ser Gly Phe His Gln Asn Phe Ser Leu Thr Ile Ser Thr Leu Gln Pro
65                  70                  75                  80

Glu Asp Val Ala Thr Tyr Phe Cys Gln Gln Tyr Glu Thr Phe Gly Gln
                85                  90                  95

Gly Thr Lys Val Asp Ile Lys
            100

<210> SEQ ID NO 276
<211> LENGTH: 131
<212> TYPE: PRT
<213> ORGANISM: Homo sapiens

<400> SEQUENCE: 276

Gln Val Gln Leu Val Gln Ser Gly Ala Ala Val Arg Lys Pro Gly Ala
1               5                   10                  15

Ser Ile Ser Val Ser Cys Lys Phe Ala Asp Ala Asp Asp Tyr Ser Pro
            20                  25                  30

His Trp Met Asn Pro Ala Pro Glu His Tyr Ile His Phe Leu Arg Gln
        35                  40                  45

Ala Pro Gly Gln Gln Leu Glu Trp Leu Ala Trp Met Asn Pro Thr Asn
    50                  55                  60

Gly Ala Val Asn Tyr Ala Trp Tyr Leu Asn Gly Arg Val Thr Ala Thr
65                  70                  75                  80

Arg Asp Arg Ser Met Thr Thr Ala Phe Leu Glu Val Arg Ser Leu Arg
                85                  90                  95
```

```
Ser Asp Asp Thr Ala Val Tyr Tyr Cys Ala Arg Ala Gln Lys Arg Ala
            100                 105                 110

Arg Ser Glu Trp Ala Tyr Ala His Trp Gly Gln Gly Thr Pro Val Val
        115                 120                 125

Val Ser Ser
    130

<210> SEQ ID NO 277
<211> LENGTH: 103
<212> TYPE: PRT
<213> ORGANISM: Homo sapiens

<400> SEQUENCE: 277

Asp Ile Gln Met Thr Gln Ser Pro Ser Ser Leu Ser Ala Ser Leu Gly
1               5                   10                  15

Asp Arg Val Thr Ile Thr Cys Gln Ala Ser Arg Gly Ile Gly Lys Asp
            20                  25                  30

Leu Asn Trp Tyr Gln Gln Lys Ala Gly Lys Ala Pro Lys Leu Leu Val
        35                  40                  45

Ser Asp Ala Ser Ile Leu Glu Gly Gly Val Pro Ser Arg Phe Ser Gly
50                  55                  60

Ser Gly Phe His Gln Asn Phe Ser Leu Thr Ile Ser Ser Leu Gln Pro
65                  70                  75                  80

Glu Asp Val Ala Thr Tyr Phe Cys Gln Gln Tyr Glu Thr Phe Gly Gln
                85                  90                  95

Gly Thr Lys Val Asp Ile Lys
            100

<210> SEQ ID NO 278
<211> LENGTH: 131
<212> TYPE: PRT
<213> ORGANISM: Homo sapiens

<400> SEQUENCE: 278

Gln Val Gln Leu Val Gln Ser Gly Ala Ala Val Arg Lys Pro Gly Ala
1               5                   10                  15

Ser Val Thr Val Ser Cys Lys Phe Ala Glu Asp Asp Trp Ser Pro
            20                  25                  30

His Trp Val Asn Pro Ala Pro Glu His Tyr Ile His Phe Leu Arg Gln
        35                  40                  45

Ala Pro Gly Gln Gln Leu Glu Trp Leu Ala Trp Met Asn Pro Thr Asn
    50                  55                  60

Gly Ala Val Asn Tyr Ala Trp Gln Leu Asn Gly Arg Leu Thr Ala Thr
65                  70                  75                  80

Arg Asp Thr Ser Met Thr Thr Ala Phe Leu Glu Val Lys Ser Leu Arg
                85                  90                  95

Ser Asp Asp Thr Ala Val Tyr Tyr Cys Ala Arg Ala Gln Lys Arg Gly
            100                 105                 110

Arg Ser Glu Trp Ala Tyr Ala His Trp Gly Gln Gly Thr Pro Val Val
        115                 120                 125

Val Ser Ser
    130

<210> SEQ ID NO 279
<211> LENGTH: 103
<212> TYPE: PRT
<213> ORGANISM: Homo sapiens
```

<400> SEQUENCE: 279

Glu Ile Val Leu Thr Gln Ser Pro Gly Ile Leu Ser Leu Ser Pro Gly
1               5                   10                  15

Glu Thr Ala Thr Leu Phe Cys Lys Ala Ser Gln Gly Gly Asn Ala Met
            20                  25                  30

Thr Trp Tyr Gln Lys Arg Arg Gly Gln Val Pro Arg Leu Leu Ile Tyr
        35                  40                  45

Asp Thr Ser Arg Arg Ala Ser Gly Val Pro Asp Arg Phe Val Gly Ser
    50                  55                  60

Gly Ser Gly Thr Asp Phe Phe Leu Thr Ile Asn Lys Leu Asp Arg Glu
65                  70                  75                  80

Asp Phe Ala Val Tyr Tyr Cys Gln Gln Phe Glu Phe Phe Gly Leu Gly
                85                  90                  95

Ser Glu Leu Glu Val His Arg
            100

<210> SEQ ID NO 280
<211> LENGTH: 130
<212> TYPE: PRT
<213> ORGANISM: Homo sapiens

<400> SEQUENCE: 280

Gln Val Gln Leu Val Gln Ser Gly Ala Val Ile Lys Thr Pro Gly Ser
1               5                   10                  15

Ser Val Lys Ile Ser Cys Arg Ala Ser Gly Tyr Asn Phe Arg Asp Tyr
            20                  25                  30

Ser Ile His Trp Val Arg Leu Ile Pro Asp Lys Gly Phe Glu Trp Ile
        35                  40                  45

Gly Trp Ile Lys Pro Leu Trp Gly Ala Val Ser Tyr Ala Arg Gln Leu
    50                  55                  60

Gln Gly Arg Val Ser Met Thr Arg Gln Leu Ser Gln Asp Pro Asp Asp
65                  70                  75                  80

Pro Asp Trp Gly Val Ala Tyr Met Glu Phe Ser Gly Leu Thr Pro Ala
                85                  90                  95

Asp Thr Ala Glu Tyr Phe Cys Val Arg Arg Gly Ser Cys Asp Tyr Cys
            100                 105                 110

Gly Asp Phe Pro Trp Gln Tyr Trp Gly Gln Gly Thr Val Val Val Val
        115                 120                 125

Ser Ser
    130

<210> SEQ ID NO 281
<211> LENGTH: 104
<212> TYPE: PRT
<213> ORGANISM: Homo sapiens

<400> SEQUENCE: 281

Asp Ile Gln Met Thr Gln Ser Pro Ser Ser Leu Ser Ala Ser Val Gly
1               5                   10                  15

Asp Lys Val Thr Ile Thr Cys Gln Thr Ser Ala Gly Tyr Leu Asn Trp
            20                  25                  30

Tyr Gln Gln Arg Arg Gly Arg Ala Pro Lys Leu Leu Met Tyr Asp Gly
        35                  40                  45

Ser Arg Leu Val Thr Gly Val Pro Ser Arg Phe Ser Gly Arg Arg Trp
    50                  55                  60

```
Gly Thr Gln Tyr Asn Leu Thr Ile Gly Ser Leu Gln Pro Glu Asp Ile
 65                  70                  75                  80

Ala Thr Tyr Tyr Cys Gln Val Tyr Glu Phe Phe Gly Pro Gly Thr Arg
                 85                  90                  95

Leu Asp Leu Lys Ser Thr Val Ala
            100

<210> SEQ ID NO 282
<211> LENGTH: 119
<212> TYPE: PRT
<213> ORGANISM: Homo sapiens

<400> SEQUENCE: 282

Gln Val Gln Leu Val Gln Ser Gly Thr Ala Val Lys Arg Pro Gly Ala
 1               5                  10                  15

Ser Val Arg Val Ser Cys Gln Ala Ser Gly Tyr Thr Phe Thr Asp Tyr
                 20                  25                  30

Phe Ile Tyr Trp Trp Arg Gln Ala Pro Gly Gln Gly Leu Glu Trp Leu
             35                  40                  45

Gly Trp Ile Asn Pro Leu Thr Ser Gln Pro Ser Tyr Pro Ser Arg Phe
 50                  55                  60

Gln Gly Arg Leu Thr Leu Thr Arg Asp Thr Phe Asp Glu Met Leu Tyr
 65                  70                  75                  80

Met Asp Leu Arg Gly Leu Arg Ser Asp Asp Thr Gly Ile Tyr Phe Cys
                 85                  90                  95

Ala Arg Arg His Ser Asp Tyr Cys Asp Phe Asp Ile Trp Gly Ser Gly
            100                 105                 110

Thr Gln Ile Ile Val Ser Ser
            115

<210> SEQ ID NO 283
<211> LENGTH: 103
<212> TYPE: PRT
<213> ORGANISM: Homo sapiens

<400> SEQUENCE: 283

Asp Ile Gln Met Thr Gln Ser Pro Ser Ser Leu Ser Ala Arg Val Gly
 1               5                  10                  15

Asp Thr Val Thr Ile Thr Cys Gln Ala Asn Gly Tyr Leu Asn Trp Tyr
                 20                  25                  30

Gln Gln Arg Arg Gly Lys Ala Pro Lys Leu Leu Ile Tyr Asp Gly Ser
             35                  40                  45

Lys Leu Glu Arg Gly Val Pro Ser Arg Phe Ser Gly Arg Arg Trp Gly
 50                  55                  60

Gln Glu Tyr Asn Leu Thr Ile Asn Asn Leu Gln Pro Glu Asp Ile Ala
 65                  70                  75                  80

Thr Tyr Phe Cys Gln Val Tyr Glu Phe Ala Val Pro Gly Thr Arg Leu
                 85                  90                  95

Asp Leu Lys Arg Thr Val Ala
            100

<210> SEQ ID NO 284
<211> LENGTH: 123
<212> TYPE: PRT
<213> ORGANISM: Homo sapiens

<400> SEQUENCE: 284

Gln Val Gln Leu Leu Gln Ser Gly Ala Val Val Thr Lys Pro Gly Ala
```

```
                1               5                  10                 15
            Ser Val Arg Val Ser Cys Glu Ala Ser Gly Tyr Lys Ile Arg Asp Tyr
                            20                  25                 30

Phe Ile His Trp Trp Arg Gln Ala Pro Gly Gln Gly Leu Gln Trp Val
                            35                  40                 45

Gly Trp Ile Asn Pro Gln Thr Gly Gln Pro Asn Ile Pro Arg Pro Phe
                        50                  55                 60

Gln Gly Arg Val Thr Leu Thr Arg His Ala Ser Trp Asp Phe Asp Thr
            65                  70                  75                 80

Phe Ser Phe Tyr Met Asp Leu Lys Ala Leu Arg Ser Asp Asp Thr Ala
                                85                  90                 95

Ile Tyr Phe Cys Ala Arg Arg Arg Ser Asp Tyr Cys Asp Phe Asp Val
                            100                 105                110

Trp Gly Ser Gly Thr His Val Thr Val Ser Ser
                        115                 120
```

<210> SEQ ID NO 285
<211> LENGTH: 107
<212> TYPE: PRT
<213> ORGANISM: Homo sapiens

<400> SEQUENCE: 285

```
            Asp Ile Gln Met Thr Gln Ser Pro Ser Ser Leu Ser Ala Ser Ile Gly
            1               5                  10                 15

Asp Arg Val Asn Ile Thr Cys Gln Ala Ser Arg Asp Thr Gly Ser Ala
                            20                  25                 30

Leu Asn Trp Tyr Gln Gln Lys Val Gly Arg Pro Pro Arg Leu Leu Ile
                            35                  40                 45

Ser Ala Val Ser Asn Leu Gly Ala Gly Val Pro Ser Arg Phe Ser Gly
                        50                  55                 60

Arg Arg Ser Gly Thr Gln Ser Thr Leu Thr Ile Asn Thr Leu Gln Pro
            65                  70                  75                 80

Glu Asp Ile Ala Thr Tyr Phe Cys Gln His Tyr Glu Phe Phe Gly Pro
                                85                  90                 95

Gly Thr Lys Val Asp Ile Lys Arg Thr Val Ala
                        100                 105
```

<210> SEQ ID NO 286
<211> LENGTH: 125
<212> TYPE: PRT
<213> ORGANISM: Homo sapiens

<400> SEQUENCE: 286

```
            Glu Val Gln Leu Val Gln Ser Gly Ser Asp Val Arg Lys Pro Gly Ala
            1               5                  10                 15

Thr Val Thr Val Ser Cys Lys Ala Asp Glu Asp Glu Asp Asp Phe Thr
                            20                  25                 30

Ala Tyr Asn Tyr Phe Met His Trp Val Arg Gln Ala Pro Gly His Gly
                            35                  40                 45

Leu Glu Trp Ile Gly Trp Ile Asn Pro Arg Thr Gly Gln Pro Asn His
                        50                  55                 60

Ala Lys Gln Phe Gln Gly Arg Val Thr Leu Thr Arg Glu Arg Ser Thr
            65                  70                  75                 80

Ser Thr Val Phe Met Lys Leu Thr Asn Leu Arg Leu Asp Asp Thr Ala
                                85                  90                 95

Val Tyr Phe Cys Ala Arg Pro Leu Arg Gly Gly Asp Thr Trp His Tyr
```

```
              100                 105                 110
His Ser Trp Gly Arg Gly Thr Ser Leu Thr Val Ser Ser
        115                 120                 125

<210> SEQ ID NO 287
<211> LENGTH: 104
<212> TYPE: PRT
<213> ORGANISM: Homo sapiens

<400> SEQUENCE: 287

Asp Ile Gln Met Thr Gln Ser Pro Ser Ser Leu Ser Ala Ser Val Gly
1               5                   10                  15

Asp Lys Val Thr Ile Thr Cys Gln Thr Ser Ala Gly Tyr Leu Asn Trp
            20                  25                  30

Tyr Gln Gln Arg Arg Gly Arg Ala Pro Lys Leu Leu Met Tyr Asp Gly
        35                  40                  45

Ser Arg Leu Val Thr Gly Val Pro Ser Arg Phe Ser Gly Arg Arg Trp
    50                  55                  60

Gly Thr Gln Tyr Asn Leu Thr Ile Gly Ser Leu Gln Pro Glu Asp Val
65                  70                  75                  80

Ala Thr Tyr Tyr Cys Gln Val Tyr Glu Phe Phe Gly Pro Gly Thr Arg
                85                  90                  95

Leu Asp Leu Lys Arg Thr Val Ala
            100

<210> SEQ ID NO 288
<211> LENGTH: 119
<212> TYPE: PRT
<213> ORGANISM: Homo sapiens

<400> SEQUENCE: 288

Gln Val Gln Leu Val Gln Ser Gly Thr Ala Val Lys Arg Pro Gly Ala
1               5                   10                  15

Ser Val Arg Val Ser Cys Gln Ala Ser Gly Tyr Thr Phe Ile Asp His
            20                  25                  30

Phe Ile Tyr Trp Trp Arg Gln Ala Pro Gly Gln Gly Leu Glu Trp Leu
        35                  40                  45

Gly Trp Ile Asn Pro Leu Thr Ser Gln Pro Ser Tyr Pro Ser Arg Phe
    50                  55                  60

Gln Gly Arg Leu Thr Leu Thr Arg Asp Thr Phe Asp Glu Met Leu Tyr
65                  70                  75                  80

Met Asp Leu Arg Gly Leu Arg Ser Asp Asp Thr Gly Ile Tyr Phe Cys
                85                  90                  95

Ala Arg Arg His Ser Asp Tyr Cys Asp Phe Asp Ile Trp Gly Ser Gly
            100                 105                 110

Thr Gln Ile Ile Val Ser Ser
        115

<210> SEQ ID NO 289
<211> LENGTH: 122
<212> TYPE: PRT
<213> ORGANISM: Homo sapiens

<400> SEQUENCE: 289

Asp Ile Gln Met Thr Gln Ser Pro Ser Ser Leu Ser Ala Ser Val Gly
1               5                   10                  15

Asp Arg Val Thr Ile Asn Cys Gln Ala Gly Gln Gly Ile Gly Ser Ser
            20                  25                  30
```

```
Leu Asn Trp Tyr Gln Lys Lys Pro Gly Arg Ala Pro Lys Leu Leu Val
            35                  40                  45

His Gly Ala Ser Asn Leu Gln Arg Gly Val Pro Ser Arg Phe Ser Gly
 50                  55                  60

Ser Gly Phe His Thr Thr Phe Thr Leu Thr Ile Ser Ser Leu Gln Pro
 65                  70                  75                  80

Asp Asp Val Ala Thr Tyr Phe Cys Ala Val Phe Gln Trp Phe Gly Pro
                 85                  90                  95

Gly Thr Lys Val Asp Ile Lys Arg Thr Val Ala Ala Pro Ser Val Phe
            100                 105                 110

Ile Phe Pro Pro Ser Asp Glu Gln Leu Lys
            115                 120
```

<210> SEQ ID NO 290
<211> LENGTH: 127
<212> TYPE: PRT
<213> ORGANISM: Homo sapiens

<400> SEQUENCE: 290

```
Ser Gln His Leu Val Gln Ser Gly Thr Gln Val Lys Lys Pro Gly Ala
 1               5                  10                  15

Ser Val Arg Val Ser Cys Gln Ala Ser Gly Tyr Thr Phe Thr Asn Tyr
            20                  25                  30

Ile Leu His Trp Trp Arg Gln Ala Pro Gly Gln Gly Leu Glu Trp Met
            35                  40                  45

Gly Leu Ile Lys Pro Val Phe Gly Ala Val Asn Tyr Ala Arg Gln Phe
 50                  55                  60

Gln Gly Arg Ile Gln Leu Thr Arg Asp Ile Tyr Arg Glu Ile Ala Phe
 65                  70                  75                  80

Leu Asp Leu Ser Gly Leu Arg Ser Asp Thr Ala Val Tyr Tyr Cys
                 85                  90                  95

Ala Arg Asp Glu Ser Gly Asp Asp Leu Lys Trp His Leu His Pro Trp
            100                 105                 110

Gly Gln Gly Thr Gln Val Ile Val Ser Pro Ala Ser Thr Lys Gly
            115                 120                 125
```

<210> SEQ ID NO 291
<211> LENGTH: 101
<212> TYPE: PRT
<213> ORGANISM: Homo sapiens

<400> SEQUENCE: 291

```
Glu Ile Val Leu Thr Gln Ser Pro Gly Thr Leu Ser Leu Ser Pro Gly
 1               5                  10                  15

Glu Thr Ala Ser Leu Ser Cys Thr Ala Ala Ser Tyr Gly His Met Thr
            20                  25                  30

Trp Tyr Gln Lys Lys Pro Gly Gln Pro Pro Lys Leu Leu Ile Phe Ala
            35                  40                  45

Thr Ser Lys Arg Ala Ser Gly Ile Pro Asp Arg Phe Ser Gly Ser Gln
 50                  55                  60

Phe Gly Lys Gln Tyr Thr Leu Thr Ile Thr Arg Met Glu Pro Glu Asp
 65                  70                  75                  80

Phe Ala Gly Tyr Tyr Cys Gln Gln Val Glu Phe Phe Gly Gln Gly Thr
                 85                  90                  95

Arg Leu Glu Ile Arg
            100
```

<210> SEQ ID NO 292
<211> LENGTH: 125
<212> TYPE: PRT
<213> ORGANISM: Homo sapiens

<400> SEQUENCE: 292

Gln Val Gln Leu Val Gln Ser Gly Ser Gly Val Lys Lys Pro Gly Ala
1               5                   10                  15

Ser Val Arg Val Ser Cys Trp Thr Ser Glu Asp Ile Phe Glu Arg Thr
                20                  25                  30

Glu Leu Ile His Trp Val Arg Gln Ala Pro Gly Gln Gly Leu Glu Trp
            35                  40                  45

Ile Gly Trp Val Lys Thr Val Thr Gly Ala Val Asn Phe Gly Ser Pro
        50                  55                  60

Asn Phe Arg His Arg Val Ser Leu Thr Arg Asp Arg Asp Leu Phe Thr
65                  70                  75                  80

Ala His Met Asp Ile Arg Gly Leu Thr Gln Gly Asp Thr Ala Thr Tyr
                85                  90                  95

Phe Cys Ala Arg Gln Lys Phe Glu Arg Gly Gly Gln Gly Trp Tyr Phe
                100                 105                 110

Asp Leu Trp Gly Arg Gly Thr Leu Ile Val Val Ser Ser
            115                 120                 125

<210> SEQ ID NO 293
<211> LENGTH: 104
<212> TYPE: PRT
<213> ORGANISM: Homo sapiens

<400> SEQUENCE: 293

Glu Ile Val Leu Thr Gln Ser Pro Gly Thr Leu Ser Leu Ser Pro Gly
1               5                   10                  15

Glu Thr Ala Ile Ile Ser Cys Arg Thr Ser Gln Tyr Gly Ser Leu Ala
                20                  25                  30

Trp Tyr Gln Gln Arg Pro Gly Gln Ala Pro Arg Leu Val Ile Tyr Ser
            35                  40                  45

Gly Ser Thr Arg Ala Ala Gly Ile Pro Asp Arg Phe Ser Gly Ser Arg
        50                  55                  60

Trp Gly Pro Asp Tyr Asn Leu Thr Ile Ser Asn Leu Glu Ser Gly Asp
65                  70                  75                  80

Phe Gly Val Tyr Tyr Cys Gln Gln Tyr Glu Phe Phe Gly Gln Gly Thr
                85                  90                  95

Lys Val Gln Val Asp Ile Lys Arg
            100

<210> SEQ ID NO 294
<211> LENGTH: 130
<212> TYPE: PRT
<213> ORGANISM: Homo sapiens

<400> SEQUENCE: 294

Gln Val Gln Leu Val Gln Ser Gly Ala Val Ile Lys Thr Pro Gly Ser
1               5                   10                  15

Ser Val Lys Ile Ser Cys Arg Ala Ser Gly Tyr Asn Phe Arg Asp Tyr
                20                  25                  30

Ser Ile His Trp Val Arg Leu Ile Pro Asp Lys Gly Phe Glu Trp Ile
            35                  40                  45

Gly Trp Ile Lys Pro Leu Trp Gly Ala Val Ser Tyr Ala Arg Gln Leu
            50                  55                  60

Gln Gly Arg Val Ser Met Thr Arg Gln Leu Ser Gln Asp Pro Asp Asp
65                  70                  75                  80

Pro Asp Trp Gly Val Ala Tyr Met Glu Phe Ser Gly Leu Thr Pro Ala
                    85                  90                  95

Asp Thr Ala Glu Tyr Phe Cys Val Arg Arg Gly Ser Cys Asp Tyr Cys
                100                 105                 110

Gly Asp Phe Pro Trp Gln Tyr Trp Gly Gln Gly Thr Val Val Val Val
                115                 120                 125

Ser Ser
    130

<210> SEQ ID NO 295
<211> LENGTH: 103
<212> TYPE: PRT
<213> ORGANISM: Homo sapiens

<400> SEQUENCE: 295

Glu Ile Val Leu Thr Gln Ser Pro Gly Ile Leu Ser Leu Ser Pro Gly
1               5                   10                  15

Glu Thr Ala Thr Leu Phe Cys Lys Ala Ser Gln Gly Gly Asn Ala Met
                20                  25                  30

Thr Trp Tyr Gln Lys Arg Gly Gln Val Pro Arg Leu Leu Ile Tyr
                35                  40                  45

Asp Thr Ser Arg Arg Ala Ser Gly Val Pro Asp Arg Phe Val Gly Ser
            50                  55                  60

Gly Ser Gly Thr Asp Phe Phe Leu Thr Ile Asn Lys Leu Asp Arg Glu
65                  70                  75                  80

Asp Phe Ala Val Tyr Tyr Cys Gln Gln Phe Glu Phe Phe Gly Leu Gly
                85                  90                  95

Ser Glu Leu Glu Val His Arg
            100

<210> SEQ ID NO 296
<211> LENGTH: 49
<212> TYPE: PRT
<213> ORGANISM: Homo sapiens

<400> SEQUENCE: 296

Gln Val Gln Leu Val Gln Ser Gly Gly Gln Met Lys Lys Pro Gly Glu
1               5                   10                  15

Ser Met Arg Ile Ser Cys Arg Ala Ser Gly Tyr Glu Phe Ile Asp Cys
                20                  25                  30

Thr Leu Asn Trp Ile Arg Leu Ala Pro Gly Lys Arg Pro Glu Trp Met
                35                  40                  45

Gly

<210> SEQ ID NO 297
<211> LENGTH: 102
<212> TYPE: PRT
<213> ORGANISM: Homo sapiens

<400> SEQUENCE: 297

Glu Ile Val Leu Thr Gln Ser Pro Gly Thr Leu Ser Leu Ser Pro Gly
1               5                   10                  15

Glu Thr Ala Ser Leu Ser Cys Thr Ala Ala Ser Tyr Gly His Met Thr
                20                  25                  30

Trp Tyr Gln Lys Lys Pro Gly Gln Pro Pro Lys Leu Leu Ile Phe Ala
            35                  40                  45

Thr Ser Lys Arg Ala Ser Gly Ile Pro Asp Arg Phe Ser Gly Ser Gln
    50                  55                  60

Phe Gly Lys Gln Tyr Thr Leu Thr Ile Thr Arg Met Glu Pro Glu Asp
65                  70                  75                  80

Phe Ala Arg Tyr Tyr Cys Gln Gln Leu Glu Phe Phe Gly Gln Gly Thr
                85                  90                  95

Arg Leu Glu Ile Arg Arg
            100

<210> SEQ ID NO 298
<211> LENGTH: 128
<212> TYPE: PRT
<213> ORGANISM: Homo sapiens

<400> SEQUENCE: 298

Gln Val Gln Leu Val Gln Ser Gly Gly Val Lys Lys Pro Gly Thr
1               5                   10                  15

Ser Ala Ser Phe Ser Cys Arg Thr Ser Asp Asp Ile Tyr Asp Asn Glu
                20                  25                  30

Phe Phe Asp Ser Ala Phe Met His Trp Val Arg Leu Ile Pro Gly Gln
            35                  40                  45

Arg Pro Glu Trp Met Gly Trp Met Asn Pro Arg Ser Gly Ala Val Asn
    50                  55                  60

Tyr Ala Arg Gln Leu Gln Pro Arg Val Ser Met Tyr Arg Asp Arg Asp
65                  70                  75                  80

Leu Ser Thr Ala Tyr Met Glu Phe Lys Ser Leu Thr Ser Ala Asp Thr
                85                  90                  95

Gly Thr Tyr Phe Cys Ala Arg Lys Lys Arg Gly Asp Gly Phe Asn Leu
                100                 105                 110

Tyr Phe Asp Leu Trp Gly Arg Gly Ser Gln Val Ile Val Ser Ser Ala
            115                 120                 125

<210> SEQ ID NO 299
<211> LENGTH: 102
<212> TYPE: PRT
<213> ORGANISM: Homo sapiens

<400> SEQUENCE: 299

Glu Ile Val Leu Thr Gln Ser Pro Gly Thr Leu Ser Leu Ser Pro Gly
1               5                   10                  15

Glu Thr Ala Ser Leu Ser Cys Thr Ala Ala Ser Tyr Gly His Met Thr
                20                  25                  30

Trp Tyr Gln Lys Lys Pro Gly Gln Pro Pro Lys Leu Leu Ile Phe Ala
            35                  40                  45

Thr Ser Lys Arg Ala Ser Gly Ile Pro Asp Arg Phe Ser Gly Ser Gln
    50                  55                  60

Phe Gly Lys Gln Tyr Thr Leu Thr Ile Thr Arg Met Glu Pro Glu Asp
65                  70                  75                  80

Phe Ala Arg Tyr Tyr Cys Gln Gln Leu Glu Phe Phe Gly Gln Gly Thr
                85                  90                  95

Arg Leu Glu Ile Arg Arg
            100

<210> SEQ ID NO 300

```
<211> LENGTH: 126
<212> TYPE: PRT
<213> ORGANISM: Homo sapiens

<400> SEQUENCE: 300

Gln Val Gln Leu Val Gln Ser Gly Ser Ala Met Lys Lys Pro Gly Ala
1               5                   10                  15

Ser Val Arg Val Ser Cys Trp Thr Ser Glu Asp Ile Phe Asp Thr Thr
            20                  25                  30

Glu Leu Ile His Trp Val Arg Gln Ala Pro Gly Gln Gly Leu Glu Trp
        35                  40                  45

Ile Gly Trp Val Lys Ala Val Ser Gly Ala Val Asn Tyr Gly Ser Leu
    50                  55                  60

Asp Phe Arg His Arg Val Ser Leu Thr Arg Asp Arg Asp Leu Ser Thr
65                  70                  75                  80

Ala His Met Asp Ile Arg Gly Leu Thr Gln Asp Asp Thr Ala Thr Tyr
                85                  90                  95

Phe Cys Ala Arg Gln Lys Phe Ala Arg Gly Asp Gln Gly Trp Phe Phe
            100                 105                 110

Asp Leu Trp Gly Arg Gly Thr Leu Ile Val Val Ser Ser Ala
        115                 120                 125

<210> SEQ ID NO 301
<211> LENGTH: 124
<212> TYPE: PRT
<213> ORGANISM: Artificial Sequence
<220> FEATURE:
<223> OTHER INFORMATION: Synthetic Peptide

<400> SEQUENCE: 301

Leu Val Gln Ser Gly Ala Glu Val Lys Lys Pro Gly Ala Ser Val Lys
1               5                   10                  15

Val Ser Cys Gln Ala Ser Gly Tyr Arg Phe Ser Asn Phe Val Ile His
            20                  25                  30

Trp Val Arg Gln Ala Pro Gly Gln Arg Phe Glu Trp Met Gly Trp Ile
        35                  40                  45

Asn Pro Tyr Asn Gly Asn Lys Glu Phe Ser Ala Lys Phe Gln Asp Arg
    50                  55                  60

Val Thr Phe Thr Ala Asp Thr Ser Ala Asn Thr Ala Tyr Met Glu Leu
65                  70                  75                  80

Arg Ser Leu Arg Ser Ala Asp Thr Ala Val Tyr Tyr Cys Ala Arg Val
                85                  90                  95

Gly Pro Tyr Ser Trp Asp Asp Ser Pro Gln Asp Asn Tyr Tyr Met Asp
            100                 105                 110

Val Trp Gly Lys Gly Thr Thr Val Ile Val Ser Ser
        115                 120

<210> SEQ ID NO 302
<211> LENGTH: 107
<212> TYPE: PRT
<213> ORGANISM: Artificial Sequence
<220> FEATURE:
<223> OTHER INFORMATION: Synthetic Peptide

<400> SEQUENCE: 302

Val Leu Thr Gln Ser Pro Gly Thr Leu Ser Leu Ser Pro Gly Glu Arg
1               5                   10                  15

Ala Thr Phe Ser Cys Arg Ser Ser His Ser Ile Arg Ser Arg Arg Val
            20                  25                  30
```

Ala Trp Tyr Gln His Lys Pro Gly Gln Ala Pro Arg Leu Val Ile His
            35                  40                  45

Gly Val Ser Asn Arg Ala Ser Gly Ile Ser Asp Arg Phe Ser Gly Ser
    50                  55                  60

Gly Ser Gly Thr Asp Phe Thr Leu Thr Ile Thr Arg Val Glu Pro Glu
65                  70                  75                  80

Asp Phe Ala Leu Tyr Tyr Cys Gln Val Tyr Gly Ala Ser Ser Tyr Thr
                85                  90                  95

Phe Gly Gln Gly Thr Lys Leu Glu Arg Lys Arg
            100                 105

<210> SEQ ID NO 303
<211> LENGTH: 22
<212> TYPE: DNA
<213> ORGANISM: Artificial Sequence
<220> FEATURE:
<223> OTHER INFORMATION: Synthetic Peptide

<400> SEQUENCE: 303
aagagctcct ccagacagtg ag                                              22

<210> SEQ ID NO 304
<211> LENGTH: 33
<212> TYPE: DNA
<213> ORGANISM: Artificial Sequence
<220> FEATURE:
<223> OTHER INFORMATION: Synthetic Peptide

<400> SEQUENCE: 304
tagagccctg gaagcatcca ggaagtcagc cta                                   33

<210> SEQ ID NO 305
<211> LENGTH: 22
<212> TYPE: DNA
<213> ORGANISM: Artificial Sequence
<220> FEATURE:
<223> OTHER INFORMATION: Synthetic Peptide

<400> SEQUENCE: 305
aagagctcct ccagacagtg ag                                              22

<210> SEQ ID NO 306
<211> LENGTH: 21
<212> TYPE: DNA
<213> ORGANISM: Artificial Sequence
<220> FEATURE:
<223> OTHER INFORMATION: Synthetic Peptide

<400> SEQUENCE: 306
atgagttttc cagagcaacc c                                               21

<210> SEQ ID NO 307
<211> LENGTH: 22
<212> TYPE: DNA
<213> ORGANISM: Artificial Sequence
<220> FEATURE:
<223> OTHER INFORMATION: Synthetic Peptide

<400> SEQUENCE: 307
aagagctcct ccagacagtg ag                                              22

<210> SEQ ID NO 308
<211> LENGTH: 21

```
<212> TYPE: DNA
<213> ORGANISM: Artificial Sequence
<220> FEATURE:
<223> OTHER INFORMATION: Synthetic Peptide

<400> SEQUENCE: 308
caagcccttg tctaatcctc c                                              21

<210> SEQ ID NO 309
<211> LENGTH: 21
<212> TYPE: DNA
<213> ORGANISM: Artificial Sequence
<220> FEATURE:
<223> OTHER INFORMATION: Synthetic Peptide

<400> SEQUENCE: 309
gaaagagcag aagacagtgg c                                              21

<210> SEQ ID NO 310
<211> LENGTH: 20
<212> TYPE: DNA
<213> ORGANISM: Artificial Sequence
<220> FEATURE:
<223> OTHER INFORMATION: Synthetic Peptide

<400> SEQUENCE: 310
attgtctggc ctgtaccgtc                                                20

<210> SEQ ID NO 311
<211> LENGTH: 21
<212> TYPE: DNA
<213> ORGANISM: Artificial Sequence
<220> FEATURE:
<223> OTHER INFORMATION: Synthetic Peptide

<400> SEQUENCE: 311
gaaagagcag aagacagtgg c                                              21

<210> SEQ ID NO 312
<211> LENGTH: 21
<212> TYPE: DNA
<213> ORGANISM: Artificial Sequence
<220> FEATURE:
<223> OTHER INFORMATION: Synthetic Peptide

<400> SEQUENCE: 312
atggaaatag ctccacccat c                                              21

<210> SEQ ID NO 313
<211> LENGTH: 244
<212> TYPE: PRT
<213> ORGANISM: Artificial Sequence
<220> FEATURE:
<223> OTHER INFORMATION: Synthetic Peptide

<400> SEQUENCE: 313

Gln Val Gln Leu Gln Glu Ser Gly Pro Gly Leu Val Lys Pro Ser Glu
 1               5                  10                  15

Thr Leu Ser Val Thr Cys Ser Val Ser Gly Asp Ser Met Asn Asn Tyr
            20                  25                  30

Tyr Trp Thr Trp Ile Arg Gln Ser Pro Gly Lys Gly Leu Glu Trp Ile
        35                  40                  45

Gly Tyr Ile Ser Asp Arg Glu Ser Ala Thr Tyr Asn Pro Ser Leu Asn
    50                  55                  60
```

```
Ser Arg Val Val Ile Ser Arg Asp Thr Ser Lys Asn Gln Leu Ser Leu
 65                  70                  75                  80

Lys Leu Asn Ser Val Thr Pro Ala Asp Thr Ala Val Tyr Tyr Cys Ala
                 85                  90                  95

Thr Ala Arg Arg Gly Gln Arg Ile Tyr Gly Val Val Ser Phe Gly Glu
            100                 105                 110

Phe Phe Tyr Tyr Tyr Ser Met Asp Val Trp Gly Lys Gly Thr Thr Val
        115                 120                 125

Thr Val Ser Ser Ala Ser Thr Lys Gly Pro Ser Val Phe Pro Leu Ala
    130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Arg Val Glu Pro Lys Ser Cys Asp Lys Thr His His
225                 230                 235                 240

His His His His

<210> SEQ ID NO 314
<211> LENGTH: 214
<212> TYPE: PRT
<213> ORGANISM: Artificial Sequence
<220> FEATURE:
<223> OTHER INFORMATION: Synthetic Peptide

<400> SEQUENCE: 314

Ser Tyr Val Arg Pro Leu Ser Val Ala Leu Gly Glu Thr Ala Arg Ile
 1               5                  10                  15

Ser Cys Gly Arg Gln Ala Leu Gly Ser Arg Ala Val Gln Trp Tyr Gln
             20                  25                  30

His Arg Pro Gly Gln Ala Pro Ile Leu Leu Ile Tyr Asn Asn Gln Asp
         35                  40                  45

Arg Pro Ser Gly Ile Pro Glu Arg Phe Ser Gly Thr Pro Asp Ile Asn
     50                  55                  60

Phe Gly Thr Arg Ala Thr Leu Thr Ile Ser Gly Val Glu Ala Gly Asp
 65                  70                  75                  80

Glu Ala Asp Tyr Tyr Cys His Met Trp Asp Ser Arg Ser Gly Phe Ser
                 85                  90                  95

Trp Ser Phe Gly Gly Ala Thr Arg Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
```

```
                180                 185                 190
Tyr Ser Cys Gln Val Thr His Glu Gly Ser Thr Val Glu Lys Thr Val
            195                 200                 205

Ala Pro Thr Glu Cys Ser
        210

<210> SEQ ID NO 315
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 315

Asn Tyr Tyr Trp Thr Trp
1               5

<210> SEQ ID NO 316
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 316

Tyr Ile Ser Asp Arg Glu Ser Ala Thr Tyr Asn Pro Ser Leu Asn Ser
1               5                   10                  15

<210> SEQ ID NO 317
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 317

Ala Arg Arg Gly Gln Arg Ile Tyr Gly Val Val Ser Phe Gly Glu Phe
1               5                   10                  15

Phe Tyr Tyr Tyr Ser Met Asp Val
            20

<210> SEQ ID NO 318
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 318

Gly Arg Gln Ala Leu Gly Ser Arg Ala Val Gln
1               5                   10

<210> SEQ ID NO 319
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 319

Asn Asn Gln Asp Arg Pro Ser
1               5

<210> SEQ ID NO 320
<211> LENGTH: 12
```

```
<212> TYPE: PRT
<213> ORGANISM: Artificial Sequence
<220> FEATURE:
<223> OTHER INFORMATION: Synthetic Peptide

<400> SEQUENCE: 320

His Met Trp Asp Ser Arg Ser Gly Phe Ser Trp Ser
1               5                   10

<210> SEQ ID NO 321
<211> LENGTH: 132
<212> TYPE: PRT
<213> ORGANISM: Artificial Sequence
<220> FEATURE:
<223> OTHER INFORMATION: Synthetic Peptide

<400> SEQUENCE: 321

Gln Val Gln Leu Gln Glu Ser Gly Pro Gly Leu Val Lys Pro Ser Glu
1               5                   10                  15

Thr Leu Ser Val Thr Cys Ser Val Ser Gly Asp Ser Met Asn Asn Tyr
            20                  25                  30

Tyr Trp Thr Trp Ile Arg Gln Ser Pro Gly Lys Gly Leu Glu Trp Ile
        35                  40                  45

Gly Tyr Ile Ser Asp Arg Glu Ser Ala Thr Tyr Asn Pro Ser Leu Asn
    50                  55                  60

Ser Arg Val Val Ile Ser Arg Asp Thr Ser Lys Asn Gln Leu Ser Leu
65                  70                  75                  80

Lys Leu Asn Ser Val Thr Pro Ala Asp Thr Ala Val Tyr Tyr Cys Ala
                85                  90                  95

Thr Ala Arg Arg Gly Gln Arg Ile Tyr Gly Val Val Ser Phe Gly Glu
            100                 105                 110

Phe Phe Tyr Tyr Tyr Ser Met Asp Val Trp Gly Lys Gly Thr Thr Val
        115                 120                 125

Thr Val Ser Ser
    130

<210> SEQ ID NO 322
<211> LENGTH: 108
<212> TYPE: PRT
<213> ORGANISM: Artificial Sequence
<220> FEATURE:
<223> OTHER INFORMATION: Synthetic Peptide

<400> SEQUENCE: 322

Ser Tyr Val Arg Pro Leu Ser Val Ala Leu Gly Glu Thr Ala Arg Ile
1               5                   10                  15

Ser Cys Gly Arg Gln Ala Leu Gly Ser Arg Ala Val Gln Trp Tyr Gln
            20                  25                  30

His Arg Pro Gly Gln Ala Pro Ile Leu Leu Ile Tyr Asn Asn Gln Asp
        35                  40                  45

Arg Pro Ser Gly Ile Pro Glu Arg Phe Ser Gly Thr Pro Asp Ile Asn
    50                  55                  60

Phe Gly Thr Arg Ala Thr Leu Thr Ile Ser Gly Val Glu Ala Gly Asp
65                  70                  75                  80

Glu Ala Asp Tyr Tyr Cys His Met Trp Asp Ser Arg Ser Gly Phe Ser
                85                  90                  95

Trp Ser Phe Gly Gly Ala Thr Arg Leu Thr Val Leu
            100                 105
```

HUMAN IMMUNODEFICIENCY VIRUS THERAPIES UTILIZING N332-GLYCAN-DEPENDENT ANTIBODIES AND A RESERVOIR ACTIVATOR

STATEMENT AS TO FEDERALLY FUNDED RESEARCH

This invention was made with government support under AI078526, AI084794, AI095985, and AI096040 awarded by NIH. The government has certain rights in the invention.

BACKGROUND OF THE INVENTION

Acquired immunodeficiency syndrome (AIDS) is a chronic, potentially life-threatening condition caused by the human immunodeficiency virus (HIV). In 2010, there were approximately 1.8 million deaths attributed to ADS, and nearly 30 million people with AIDS have died worldwide since the epidemic began (Centers for Disease Control and Prevention. *HIV Surveillance Report*. Vol. 23, 2011).

Even though current therapies, such as antiretroviral therapies (ARTs), have reduced AIDS-related deaths in many developed nations, HIV infections continue to be a serious health issue. In 2011, the estimated number of diagnoses of HIV infection was 49,273 in the United States alone. Worldwide, about 34.2 million people are living with HIV, with about 2.5 million new cases of HIV infection having been diagnosed in 2011 (Centers for Disease Control and Prevention. *HIV Surveillance Report*. Vol. 23, 2011).

Thus, there remains an unmet need in the field for the development of novel HIV therapies for HIV, particularly therapies that are capable of curing an HIV-infected individual or blocking an HIV infection in a subject at risk of HIV transmission.

SUMMARY OF THE INVENTION

In a first aspect, the invention features a method of curing a subject (e.g., a human) infected with human immunodeficiency virus (HIV) (e.g., HIV Type 1 (HIV-1)), wherein the method includes administering to said subject one or more (e.g., 1, 2, 3, 4, or 5 or more) N332 glycan-dependent antibodies (e.g., PGT121), thereby curing said subject. The subject may be a human (e.g., an adult, child, neonate or fetus).

In a second aspect, the invention features a method of blocking an HIV (e.g., HIV-1) infection in a subject (e.g., a human) at risk of HIV transmission, wherein the subject is a fetus of an HIV-infected (e.g., HIV-1-infected) pregnant female and the method includes administering to the HIV-infected pregnant female one or more (e.g., 1, 2, 3, 4, or 5 or more) N332 glycan-dependent antibodies (e.g., PGT121), thereby blocking the HIV infection in the fetus. In one embodiment, the HIV-infected pregnant female is administered the one or more N332 glycan-dependent antibodies (e.g., PGT121) following manifestation of one or more symptoms (e.g., 1, 2, 3, or 4 or more symptoms) associated with pregnancy. In another embodiment, the HIV-infected pregnant female is administered one or more N332 glycan-dependent antibodies (e.g., PGT121) following a diagnosis of pregnancy. In another embodiment, the HIV-infected pregnant female is in the third trimester of pregnancy.

In a related third aspect, the invention features a method of blocking an HIV (e.g., HIV-1) infection in a subject (e.g., a human) at risk of HIV transmission, wherein the method includes administering to the subject one or more (e.g., 1, 2, 3, 4, or 5 or more) N332 glycan-dependent antibodies (e.g., PGT121), thereby blocking the HIV infection in the subject. In one embodiment, the subject is a newborn having an HIV-infected (e.g., HIV-1-infected) mother. The newborn, in some embodiments, is administered one or more N332 glycan-dependent antibodies (e.g., PGT121) peripartum and/or postpartum. The newborn, in some embodiments, is administered one or more N332 glycan-dependent antibodies (e.g., PGT121) prior to, during, and/or following breastfeeding from the HIV-infected mother. In another embodiment, the subject is at risk of HIV transmission following a needlestick injury. Administration of the one or more N332 glycan-dependent antibodies (e.g., PGT121), in some embodiments, occurs less than 3 days following the needlestick injury. Administration of the one or more N332 glycan-dependent antibodies (e.g., PGT121), in other embodiments, occurs between 3 to 14 days following the needlestick injury. In another embodiment, the subject is at risk of HIV transmission following a sexual exposure to an HIV-infected individual. Administration of the one or more N332 glycan-dependent antibodies (e.g., PGT121), in some embodiments, occurs less than 3 days following the sexual exposure. Administration of the one or more N332 glycan-dependent antibodies (e.g., PGT121), in other embodiments, occurs between 3 to 14 days following the sexual exposure.

In one embodiment of the method of the first, second, or third aspect of the invention, the method includes administering a single dose of the one or more N332-glycan dependent antibodies (e.g., PGT121). In some embodiments, HIV therapy is concluded following the administration of the single dose of the one or more N332 glycan-dependent antibodies (e.g., PGT121). The method, in other embodiments, may further include administering the one or more N332-glycan dependent antibodies (e.g., PGT121) in conjunction with one or more (e.g., 1, 2, 3, 4, or 5 or more) antiretroviral therapies (ARTs). The one or more ARTs, in some embodiments, are concurrently administered with the single dose of the one or more N332 glycan-dependent antibodies (e.g., PGT121). In other embodiments, the one or more ARTs are administered prior to and/or subsequent to the single dose of the one or more N332 glycan-dependent antibodies (e.g., PGT121). In some embodiments, HIV therapy is concluded following the administration of the one or more ARTs subsequent to the single dose of the one or more N332 glycan-dependent antibodies (e.g., PGT121). In other embodiments, the method may further include administering the N332-glycan dependent antibody (e.g., PGT121) in conjunction with a second antibody (or, optionally, additional antibodies, e.g., a second and a third antibody), wherein the second antibody is an HIV-specific (e.g., HIV-1-specific), broadly neutralizing antibody (bnAb) (e.g., 3BNC117). The second antibody, in some embodiments, may be a CD4 binding site (CD4bs)-specific antibody (e.g., 3BNC117 or VRC07-523) or a V2 glycan-dependent antibody (e.g., CAP256-VRC26). The method may include, in some embodiments, administering the N332-glycan dependent antibody (e.g., PGT121) in conjunction with one or more (e.g., 1, 2, 3, 4, or 5 or more) CD4bs-specific antibodies and/or one or more (e.g., 1, 2, 3, 4, or 5 or more) V2 glycan-dependent antibodies. In certain embodiments, (i) the second antibody is a CD4bs-specific antibody and the third antibody is a V2 glycan-dependent antibody; (ii) the second antibody is a V2 glycan-dependent antibody and the third antibody is a CD4bs-specific antibody; or (iii) the second antibody is a CD4bs-specific antibody and the third antibody is a CD4bs-specific antibody. In a particular embodiment, the N332 glycan-dependent antibody is PGT121, the second antibody is 3BNC117, and the third antibody is CAP256-VRC26. In an alternate embodiment, the N332 glycan-dependent antibody is PGT121, the second antibody is VRC07-523, and the third antibody is CAP256-VRC26. In a further embodiment, the N332 glycan-dependent antibody is PGT121, the second antibody is 3BNC117, and the third antibody is VRC07-523. The second antibody (or, optionally, additional antibodies, e.g., a second and a third antibody), in some embodiments, is concurrently administered with the one or more ARTs and/or the single dose of the one or more N332 glycan-dependent antibodies. In other embodiments, the second antibody (or, optionally, additional antibodies, e.g., a second and a third antibody), is administered prior to and/or subsequent to the one or more ARTs and/or the single dose of the one or more N332 glycan-dependent antibodies. In certain embodiments, the ART, the single dose of said N332 glycan-dependent antibody, the second antibody, and/or the third antibody are sequentially administered in any order. In some embodiments, HIV therapy is concluded following the administration of the second antibody (or, optionally, additional antibodies) subsequent to the single dose of the one or more N332 glycan-dependent antibodies.

In another embodiment of the method of the first, second, or third aspect of the invention, the method includes administering a first regimen including one or more doses (e.g., 1, 2, 3, 4, or 5 or more doses, in particular, at least one dose is administered) of the one or more (e.g., 1, 2, 3, 4, or 5 or more) N332 glycan-dependent antibodies and a second regimen including one or more doses (e.g., 1, 2, 3, 4, or 5 or more doses, in particular, at least one dose is administered) of the one or more (e.g., 1, 2, 3, 4, or 5 or more) N332 glycan-dependent antibodies, wherein the second regimen is administered at least about 2 months (e.g., at least about 3, 4, 5, 6, 7, 8, 9, 10, or 11 months, or 1, 2, 3, 4, 5, 6, 7, 8, 9, 10, 11, 12, 13, 14, 15, 16, 17, 18, 19, or 20 years) after the first regimen. In particular embodiments, the second regimen is administered at least about 6 months, at least about 1 year, or at least about 5 years after the first regimen (in particular, the second regimen is administered at least about 6 months after the first regimen). In some embodiments, HIV therapy is concluded following the administration of the second regimen of the N332 glycan-dependent antibody. The method, in other embodiments, may further include administering the N332-glycan dependent antibody in conjunction with one or more (e.g., 1, 2, 3, 4, or 5 or more) ARTs. The one or more ARTs, in some embodiments, are concurrently administered with the first regimen and/or the second regimen of the N332 glycan-dependent antibody. In other embodiments, the one or more ARTs are administered prior to and/or subsequent to the first regimen and/or the second regimen of the N332 glycan-dependent antibody. In some embodiments, HIV therapy is concluded following the administration of the one or more ARTs subsequent to the second regimen of the N332 glycan-dependent antibody. In other embodiments, the method may further include administering the N332-glycan dependent antibody in conjunction with a second antibody (or, optionally, additional antibodies, e.g., a second and a third antibody), in which the second antibody is an HIV-specific (e.g., HIV-1-specific), bnAb. The second antibody, in some embodiments, may be a CD4bs-specific antibody. The method may include, in some embodiments, administering the first regimen and/or the second regimen of the N332-glycan dependent antibody in conjunction with one or more (e.g., 1, 2, 3, 4, or 5 or more) CD4bs-specific antibodies. The method may include, in other embodiments, administering the first regimen and/or the second regimen of the N332-glycan dependent antibody in conjunction with one or more (e.g., 1, 2, 3, 4, or 5 or more) V2 glycan-dependent antibodies (e.g., V2 glycan-dependent mAbs; e.g., CAP256-VRC26). In certain embodiments, the method may include administering the first regimen and/or the second regimen of the N332-glycan dependent antibody in conjunction with one or more (e.g., 1, 2, 3, 4, or 5 or more) CD4bs-specific antibodies and one or more (e.g., 1, 2, 3, 4, or 5 or more) V2 glycan-dependent antibodies. The second antibody (or, optionally, additional antibodies, e.g., a second and a third antibody), in some embodiments, is concurrently administered with the one or more ARTs and/or the first regimen and/or the second regimen of the N332 glycan-dependent antibody. In other embodiments, the second antibody (or, optionally, additional antibodies, e.g., a second and a third antibody), is administered prior to and/or subsequent to the one or more ARTs and/or the first regimen and/or the second regimen of the N332 glycan-dependent antibody. In some embodiments, HIV therapy is concluded following the administration of the second antibody (or, optionally, additional antibodies) subsequent to the second regimen of the N332 glycan-dependent antibody.

In some embodiments, the method further includes administering at least a third antibody, in which the third antibody is an HIV-1-specific, broadly neutralizing antibody (bnAb). In certain embodiments, the second antibody is a CD4 binding site (CD4bs)-specific antibody and the third antibody is a V2 glycan-dependent antibody; (ii) the second antibody is a V2 glycan-dependent antibody and the third antibody is a CD4bs-specific antibody; or (iii) the second antibody is a CD4bs-specific antibody and the third antibody is a CD4bs-specific antibody. In a particular embodiment, the N332 glycan-dependent antibody is PGT121, the second antibody is 3BNC117, and the third antibody is CAP256-VRC26. In an alternate embodiment, the N332 glycan-dependent antibody is PGT121, the second antibody is VRC07-523, and the third antibody is CAP256-VRC26. In a further embodiment, the N332 glycan-dependent antibody is PGT121, the second antibody is 3BNC117, and the third antibody is VRC07-523. In certain embodiments, the third antibody is concurrently administered with the first regimen of the N332 glycan-dependent antibody, the second regimen of the N332 glycan-dependent antibody, and/or the second antibody. In alternate embodiments, the third antibody is administered prior to and/or subsequent to the first regimen of the N332 glycan-dependent antibody, the second regimen of the N332 glycan-dependent antibody, and/or the second antibody.

For any of the above aspects, the method may result in a reduction of proviral DNA level in tissue (e.g., is lymph node tissue, gastrointestinal tissue, e.g., gastrointestinal mucosal tissue, and/or peripheral blood) of the subject relative to an amount of proviral DNA level in tissue of the subject before the administration of the N332 glycan-dependent antibody. In some embodiments, the proviral DNA level in tissue is reduced to below about 1,000 DNA copies/$10^6$ cells, below about 100 DNA copies/$10^6$ cells, below about 10 DNA copies/$10^6$ cells, or below about 1 DNA copy/$10^6$ cells. In some embodiments, the proviral DNA in tissue is reduced to an undetectable level. In other embodiments, HIV (e.g., HIV-1) therapy is concluded following a determination that the proviral DNA level in tissue is reduced to an undetectable level.

For any of the above aspects, the subject may have a plasma viral load of less than 3,500 RNA copies/ml. In some embodiments, the subject has a plasma viral load of less than 2,000 RNA copies/ml, less than 400 RNA copies/ml, less than 50 RNA copies/ml, or less than 1 RNA copy/ml. In some embodiments, the subject has an undetectable plasma viral load (e.g., before administration of the one or more N332 glycan-dependent antibodies, or regimen(s) thereof). In other embodiments, administration of the one or more N332 glycan-dependent antibodies, or regimen(s) thereof, results in the subject having an undetectable plasma viral load. The subject, in some embodiments, may have an undetectable plasma viral load for at least 2 months (e.g., at least 6 months, at least 9 months, at least 1 year, at least 5 years, at least 10 years, at least 20 years) following the administration of the one or more N332 glycan-dependent antibodies, or regimen(s) thereof.

For any of the above aspects, the method may result in an increase in the level of HIV-specific (e.g., HIV-1-specific) cell-mediated immune response and/or humoral immune response in the subject relative to the level of HIV-specific cell-mediated immune response and/or humoral immune response in the subject before the administration of the one or more N332 glycan-dependent antibodies, or regimen(s) thereof.

For any of the above aspects, the administered one or more (e.g., 1, 2, 3, 4, or 5 or more) N332 glycan-dependent antibodies may be one or more (e.g., 1, 2, 3, 4, or 5 or more) PGT family antibodies selected from the group consisting of PGT121, PGT122, PGT123, PGT124, PGT125, PGT126, PGT127, PGT128, PGT130, PGT131, PGT132, PGT133, PGT134, PGT135, PGT136, PGT137, PGT138, PGT139, PGT141, PGT142, PGT143, PGT144, PGT145, PGT151, PGT152, PGT153, PGT154, PGT155, PGT156, PGT157, and PGT158; in particular the N332 glycan dependent antibody is PGT121. The one or more N332 glycan-dependent antibodies, in some embodiments, may include the following six complementarity determining regions (CDRs): a CDR-H1 comprising the amino acid sequence of DSYWS (SEQ ID NO: 1); a CDR-H2 comprising the amino acid sequence of YVHKSGDTNYSPSLKS (SEQ ID NO: 2); a CDR-H3 comprising the amino acid sequence of TLHGRRIYGIVAFNEWFTYFYMDV (SEQ ID NO: 3); a CDR-L1 comprising the amino acid sequence of GEKSLGSRAVQ (SEQ ID NO: 4); a CDR-L2 comprising the amino acid sequence of NNQDRPS (SEQ ID NO: 5); and a CDR-L3 comprising the amino acid sequence of HIWDSRVPTKWV (SEQ ID NO: 6). In other embodiments, the heavy chain variable domain sequence(s) of the one or more N332 glycan-dependent antibodies may include an amino acid sequence having at least 90% sequence identity (e.g., at least 91%, 92%, 93%, 94%, 95%, 96%, 97%, 98%, or 99% sequence identity) to, or the sequence of, QMQLQESGPGLVKPSETLSLTCSVSGASISDSYWSWIRRSPGKGLEWIGYVHKSGDTNYSPSLKSRVNL SLDTSKNQVSLSLVAATAADSGKYYCARTLHGRRIYGIVAFNEWFTYFYMDVWGNGTQVTVSS (SEQ ID NO: 7), and the light chain variable domain sequence(s) of the one or more N332 glycan-dependent antibodies may include an amino acid sequence having at least 90% sequence identity (e.g., at least 91%, 92%, 93%, 94%, 95%, 96%, 97%, 98%, or 99% sequence identity) to, or the sequence of, SDISVAPGETARISCGEKSLGSRAVQWYQHRAGQAPSLIIYNNQDRPSGIPERFSGSPDSPFGTTATLTIT SVEAGDEADYYCHIWDSRVPTKWVFGGGTTLTVL (SEQ ID NO: 8). In a particular embodiment, the method includes administering to the subject the N332 glycan-dependent antibody, PGT121. The PGT121 antibody may be administered alone or in conjunction with one or more (e.g., 1, 2, 3, 4, or 5 or more) PGT family antibodies selected from PGT122, PGT123, PGT124, PGT125, PGT126, PGT127, PGT128, PGT130, PGT131, PGT132, PGT133, PGT134, PGT135, PGT136, PGT137, PGT138, PGT139, PGT141, PGT142, PGT143, PGT144, PGT145, PGT151, PGT152, PGT153, PGT154, PGT155, PGT156, PGT157, and PGT158.

For any of the above aspects, the optionally administered one or more (e.g., 1, 2, 3, 4, or 5 or more) ARTs may be selected from efavirenz, emtricitabine, and tenofovir disoproxil fumarate (Atripla); emtricitabine, rilpivirine, and tenofovir disoproxil fumarate (Complera); elvitegravir, cobicistat, emtricitabine, and tenofovir disoproxil fumarate (Stribild); lamivudine and zidovudine (Combivir); emtricitabine, FTC (Emtriva); lamivudine, 3TC (Epivir); abacavir and lamivudine (Ebzicom); zalcitabine, dideoxycytidine, ddC (Hivid); zidovudine, azidothymidine, AZT, ZDV (Retrovir); abacavir, zidovudine, and lamivudine (Trizivir); tenofovir disoproxil fumarate and emtricitabine (Truvada); enteric coated didanosine, ddI EC (Videx EC); didanosine, dideoxyinosine, ddI (Videx); tenofovir disoproxil fumarate, TDF (Viread); stavudine, d4T (Zerit); abacavir sulfate, ABC (Ziagen); Rilpivirine (Edurant); Etravirine (Intelence); delavirdine, DLV (Rescriptor); efavirenz, EFV (Sustiva); nevirapine, NVP (Viramune or Viramune XR); amprenavir, APV (Agenerase); tipranavir, TPV (Aptivus); indinavir, IDV (Crixivan); saquinavir (Fortovase); saquinavir mesylate, SQV (Invirase); lopinavir and ritonavir, LPV/RTV (Kaletra); Fosamprenavir Calcium, FOS-APV (Lexiva); ritonavir, RTV (Norvir); Darunavir (Prezista); atazanavir sulfate, ATV (Reyataz); nelfinavir mesylate, NFV (Viracept); enfuvirtide, T-20 (Fuzeon); maraviroc (Selzentry); raltegravir, RAL (Isentress); and dolutegravir (Tivicay).

For any of the above aspects, the optionally administered one or more (e.g., 1, 2, 3, 4, or 5 or more) CD4bs-specific antibodies may be selected from 3BNC117, VRC07-523, b12, VRC01, VRC02, NIH-45-46, 3BNC60, 3BNC62, 3BNC95, 3BNC176, 12A12, VRC-PG04, VRC-CH30, VRC-CH31, VRC-CH32, VRC-CH33, VRC-CH34, VRC03, 3BNC55, 3BNC91, 3BNC104, 3BNC89, 12A21, VRC-PG04b, VRC03HC-VRC01LC, VRC01HC/VRC03LC, gVRC-H5(d74)/VRC-PG04LC, and gVRC0H12(D74)/VRC-PG04LC. In one particular embodiment, the CD4bs-specific antibody is 3BNC117. In an embodiment, the administered N332 glycan-dependent antibody is PGT121 and the optionally administered CD4bs-specific antibody is 3BNC117. In another embodiment, the administered N332 glycan-dependent antibody is PGT121 and the optionally administered CD4bs-specific antibody is VRC07-523.

For any of the above aspects, the optionally administered one or more (e.g., 1, 2, 3, 4, or 5 or more) V2 glycan-dependent antibodies may be CAP256-VRC26. In a specific embodiment, the administered N332 glycan-dependent antibody is PGT121 and the optionally administered V2 glycan-dependent antibody is CAP256-VRC26. In still other embodiments, the methods of the invention include the administration of cocktails of 2 anti-HIV mAbs (e.g., cocktails of an N332 glycan-dependent antibody (e.g., PGT121) and either a CD4bs-specific antibody (e.g., one or both of 3BNC117 and VRC07-523; in particular 3BNC117) or a V2 glycan-dependent antibody (e.g., CAP256-VRC26)) or cocktails of 3 anti-HIV mAbs (e.g., cocktails of an N332 glycan-dependent antibody (e.g., PGT121), a CD4bs-specific antibody (e.g., one or both of 3BNC117 and VRC07-523; in particular 3BNC117), and a V2 glycan-dependent antibody (e.g., CAP256-VRC26). The antibodies of the cocktail may be administered concurrently (e.g., in a single dosage form or in multiple dosage forms) or sequentially in any order.

For any of the above aspects, the method may further include administration of one or more (e.g., 1, 2, 3, 4, or 5 or more) immunomodulators. The one or more immunomodulators may, optionally, be selected from AS-101, Bropirimine, Acemannan, CL246,738, EL10, FP-21399, Gamma Interferon, Granulocyte Macrophage Colony Stimulating Factor, HIV Core Particle Immunostimulant, IL-2, Immune Globulin Intravenous, IMREG-1, IMREG-2, Imuthiol Diethyl Dithio Carbamate, Alpha-2 Interferon, Methionine-Enkephalin, MTP-PE Muramyl-Tripeptide, Granulocyte Colony Stimulating Factor, REMUNE™ (beta-propiolactone inactive HIV-1), CD4 (e.g., recombinant soluble CD4), rCD4-IgG hybrids, SK&F106528 Soluble T4, Thymopentin, Tumor Necrosis Factor, and Infliximab.

For any of the above aspects, the one or more (e.g., 1, 2, 3, 4, or 5 or more) N332 glycan-dependent antibodies may be administered intravenously, intramuscularly, intradermally, percutaneously, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subcutaneously, subconjunctivally, intravesicularly, mucosally, intrapericardially, intraumbilically, intraocularly, orally, topically, locally, by inhalation, by injection, by infusion, by continuous infusion, by localized perfusion bathing target cells directly, by catheter, by lavage, by gavage, in creams, or in lipid compositions. In some embodiments, the one or more N332 glycan-dependent antibodies are be administered to the subject at a concentration of about 0.01 mg/kg to about 20 mg/kg, e.g., about 0.1 mg/kg to about 10 mg/kg, e.g., about 1 mg/kg to about 10 mg/kg, e.g., about 10 mg/kg. In some embodiments, the one or more N332 glycan-dependent antibodies are administered as a composition (e.g., a pharmaceutical composition). In some embodiments, the composition (e.g., pharmaceutical composition) further comprises a pharmaceutically acceptable carrier.

Accordingly, in certain embodiments, PGT121 is administered intravenously, for example, in combination with 3BNC117, and optionally in combination with one or more ARTs (e.g., emtricitabine (FTC)) and/or one or more immunomodulators. In other embodiments, PGT121 is administered intravenously, for example, in combination with b12, and optionally in combination with one or more ARTs (e.g., emtricitabine (FTC)) and/or one or more immunomodulators. In other embodiments, PGT121 is administered intravenously, for example, in combination with 3BNC117 and b12, and optionally in combination with one or more ARTs (e.g., emtricitabine (FTC)) and/or one or more immunomodulators.

In preferred embodiments of all aspects of the invention, the subject is a mammal, preferably a primate, such as a human.

Definitions

As used herein, the term "about" refers to a value that is ±10% of the recited value.

The term "antibody" or "immunoglobulin (Ig)" is used in the broadest sense and includes monoclonal antibodies (e.g., full-length or intact monoclonal antibodies), polyclonal antibodies, chimeric antibodies, multivalent antibodies, multispecific antibodies (e.g., bispecific antibodies so long as they exhibit the desired biological activity), and antibody fragments (as described in greater detail herein). An antibody typically comprises both "light chains" and "heavy chains." The light chains of antibodies (immunoglobulins) from any vertebrate species can be assigned to one of two clearly distinct types, called kappa (K) and lambda (A), based on the amino acid sequences of their constant domains. Depending on the amino acid sequence of the constant domain of their heavy chains, immunoglobulins can be assigned to different classes. There are five major classes of immunoglobulins: IgA, IgD, IgE, IgG, and IgM, and several of these can be further divided into subclasses (isotypes), e.g., IgG1, IgG2, IgG3, IgG4, IgA1, and IgA2. The heavy chain constant domains that correspond to the different classes of immunoglobulins are called α, δ, ε, γ, and μ, respectively. The subunit structures and three-dimensional configurations of different classes of immunoglobulins are well known.

"Antibody fragments" or "fragments" comprise only a portion of an intact antibody. The portion preferably retains at least one, preferably most or all, of the functions normally associated with that portion when present in an intact antibody. Examples of antibody fragments include Fab, Fab', F(ab')$_2$, and Fv fragments (e.g., single-chain variable fragments (scFv)); diabodies; linear antibodies; single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as FcRn binding, antibody half life modulation, ADCC function, ADCVI function, and complement binding. In one embodiment, an antibody fragment is a monovalent antibody that has an in vivo half life substantially similar to an intact antibody. For example, such an antibody fragment may comprise on antigen binding arm linked to an Fc sequence capable of conferring in vivo stability to the fragment.

The term "antibody-dependent cellular cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII, and FcγRIII. FcR expression on hematopoietic cells is summarized in Table 3 on page 464 of Ravetch and Kinet (*Annu. Rev. Immunol.* 9:457-92, 1991), incorporated herein by reference. To assess ADCC activity of a molecule of interest, an in vitro ADCC assay, such as that described in U.S. Pat. No. 5,500,362 or 5,821,337 or Presta U.S. Pat. No. 6,737,056, incorporated herein by reference, may be performed.

"Cure" and "curing," as used herein, can refer to one or more of the following: (i) sterilizing cure, e.g., in which virus is killed to undetectable levels in a subject (e.g., a human), (ii) functional cure, in which viral load is undetectable in a subject (e.g., a human) without ART, and/or (iii)

reduction of viral reservoirs (e.g., partial reduction of viral reservoirs, in which the infection is not reduced to undetectable levels in the subject, for example, in which the subject shows undetectable plasma load but detectable proviral DNA) in a subject (e.g., a human). In an embodiment, "cure" means killing the virus to undetectable levels in a subject (e.g., a human), as determined by methods well known in the art.

By "antiretroviral therapy" or "ART" is meant any of the therapies used to manage progression of a retrovirus (e.g., HIV) infection in a subject (e.g., a human), including, for example, nucleoside reverse transcriptase inhibitors (NRTIs), non-nucleoside reverse transcriptase inhibitors (NNRTIs), protease inhibitors (PIs), fusion inhibitors, entry inhibitors, maturation inhibitors, cellular inhibitors, integrase strand transfer inhibitors, and multi-class combinations. Such drugs include lamivudine and zidovudine, emtricitabine (FTC), zidovudine (ZDV), azidothymidine (AZT), lamivudine (3TC), zalcitabine, dideoxycytidine (ddC), tenofovir disoproxil fumarate (TDF), didanosine (ddI), stavudine (d4T), abacavir sulfate (ABC), etravirine, delavirdine (DLV), efavirenz (EFV), nevirapine (NVP), amprenavir (APV), tipranavir (TPV), indinavir (IDV), saquinavir, saquinavir mesylate (SQV), lopinavir (LPV), ritonavir (RTV), fosamprenavir calcium (FOS-APV), ritonavir, RTV, darunavir, atazanavir sulfate (ATV), nelfinavir mesylate (NFV), enfuvirtide, T-20, maraviroc and raltegravir. ART drugs can also include antibodies, such as ibalizumab, that target HIV proteins or cellular proteins associated with disease progression. Also included are immune-based therapies, such as IL-2, IL-12, and alpha-epibromide. Each of these drugs can be administered alone or in combination with any other ART drug or any HIV-specific neutralizing antibody, such as a broadly neutralizing antibody, e.g., an N332 glycan-dependent antibody (e.g., PGT121).

By "reservoir activator" is meant an agent (e.g., a compound, complex, drug, protein, nucleic acid, or pharmaceutical composition) that has the effect of activating a viral reservoir (e.g., an HIV reservoir). Exemplary reservoir activators include histone deacytelase (HDAC) inhibitors (e.g., romidepsin, vorinostat, and panobinostat), immunologic activators (e.g., cytokines and TLR agonists), and dedicated small molecule drugs.

As used herein, by "blocking" a retroviral (e.g., human immunodeficiency virus (HIV) (e.g., HIV Type 1 or HIV Type 2)) infection in a subject (e.g., a human, including a human fetus, at risk of retroviral infection) is meant preventing retroviral establishment and propagation in the subject following exposure to HIV. Blocking an HIV infection may be, in some instances, a means of post-exposure prophylaxis (PEP).

By "broadly neutralizing antibody" or "bnAb," with respect to HIV (e.g., HIV-1), is meant an antibody that recognizes a specific antigen (e.g., gp120 of HIV) and inhibits the effect(s) of the antigen of at least 2, 3, 4, 5, 6, 7, 8, 9 or more different strains of HIV, the strains belonging to the same or different blades, in the host subject (e.g., human). As used herein, the antibody can be a single antibody or a plurality of antibodies.

By "CD4" or "cluster of differentiation 4" is meant an isolated, soluble, or cell surface-attached glycoprotein that is capable of binding and/or forming a complex with gp120. CD4 includes, for example, human CD4 protein (NCBI RefSeq No. NP_000607.1).

As used herein, by "CD4 binding site-specific antibody" or "CD4bs-specific antibody" is meant an antibody, or antibody fragment thereof, that specifically binds to gp120 of HIV (e.g., HIV Type 1 or HIV Type 2) at an epitope that overlaps partially or completely with that recognized by CD4, and/or that competes with CD4 for binding to gp120 of HIV. Examples of CD4bs-specific antibodies include 3BNC117 (Scheid et al., Nature. 458: 636-640, 2009), b12 (Roben et al., J Virol. 68: 4821-4828, 1994), and the other antibodies disclosed at Table 1 of U.S. Pub. No. 2012/0288502, which is incorporated herein by reference in its entirety.

As used herein, the term "clade" refers to related human immunodeficiency viruses (HIVs) classified according to their degree of genetic similarity. There are currently three groups of HIV-1 isolates: M, N and O. Group M (major strains) consists of at least ten clades, A through J. Group O (outer strains) may consist of a similar number of clades. Group N is a new HIV-1 isolate that has not been categorized in either group M or O. In certain exemplary embodiments, methods of the invention as described herein can be used to cure a subject (e.g., a human) infected with HIV (e.g., HIV-1) or to block HIV (e.g., HIV-1) infection in subject (e.g., a human) at risk of HIV transmission. The HIV may be of two, three, four, five, six, seven, eight, nine, ten, or more clades and/or two or more groups of HIV.

As used herein, the term "complementarity determining regions" or "CDRs" refers to the amino acid residues of an antibody variable domain the presence of which are necessary for antigen binding. Each variable domain typically has three CDR regions identified as CDR-1, CDR-2 and CDR-3. Each complementarity determining region may comprise amino acid residues from a "complementarity determining region" as defined by Kabat (i.e., about residues 24-34 (CDR-L1), 50-56 (CDR-L2) and 89-97 (CDR-L3) in the light chain variable domain and 31-35 (CDR-H1), 50-65 (CDR-H2) and 95-102 (CDR-H3) in the heavy chain variable domain; Kabat et al. Sequences of Proteins of Immunological Interest, 5th Ed. Public Health Service, National Institutes of Health, Bethesda, Md. (1991)) and/or those residues from a "hypervariable loop" (i.e., about residues 26-32 (CDR-L1), 50-52 (CDR-L2) and 91-96 (CDR-L3) in the light chain variable domain and 26-32 (CDR-H1), 53-55 (CDR-H2) and 96-101 (CDR-H3) in the heavy chain variable domain; Chothia and Lesk, J. Mol. Biol. 196:901-917 (1987)). In some instances, a complementarity determining region can include amino acids from both a CDR region defined according to Kabat and a hypervariable loop.

Throughout this specification and claims, the word "comprise," or variations such as "comprises" or "comprising," will be understood to imply the inclusion of a stated integer or group of integers but not the exclusion of any other integer or group of integers.

As used herein, by "curing" a subject (e.g., a human) infected with a retrovirus (e.g., human immunodeficiency virus (HIV) (e.g., HIV Type 1 or HIV Type 2)) is meant obtaining and maintaining virologic control in the absence of an antiretroviral therapy (ART) for a period of at least two months (e.g., 2 months, 2.5 months, 3 months, 4 months, 5 months, 6 months, 1 year, 1.5 years, 2 years, 3 years, 4 years, or 5 or more years).

As used herein, the term "envelope glycoprotein" refers, but is not limited to, the glycoprotein that is expressed on the surface of the envelope of HIV virions and the surface of the plasma membrane of HIV infected cells. The env gene encodes gp160, which is proteolytically cleaved into the gp120 and gp41 Envelope (Env) proteins. Gp120 binds to the CD4 receptor on a target cell that has such a receptor, such as, e.g., a T-helper cell. Gp41 is non-covalently bound to gp120, and provides the second step by which HIV enters the cell. It is originally buried within the viral envelope, but when gp120 binds to a CD4 receptor, gp120 changes its conformation causing gp41 to become exposed, where it can assist in fusion with the host cell.

The terms "human immunodeficiency virus" or "HIV," as used herein, refer generally to a retrovirus that is the causative agent for acquired immunodeficiency syndrome (AIDS), variants thereof (e.g., simian acquired immunodeficiency syndrome, SAIDS), and diseases, conditions, or opportunistic infections associated with AIDS or its variants, and includes HIV-Type 1 (HIV-1) and HIV-Type 2 (HIV-2) of any clade or strain therein, related retroviruses (e.g., simian immunodeficiency virus (SIV)), and variants thereof (e.g., engineered retroviruses, e.g., chimeric HIV viruses, e.g., simian-human immunodeficiency viruses (SHIVs)). Previous names for HIV include human T-lymphotropic virus-Ill (HTLV-III), lymphadenopathy-associated virus (LAV), and AIDS-associated retrovirus (ARV).

By "immunomodulator" is meant an agent, such as a protein or peptide, which is capable of increasing, inducing, or extending an immune response (e.g., a cell-mediated immune response and/or a humoral immune response) when administered to a subject (e.g., a human, e.g., a human infected with HIV or at risk of an HIV infection or transmission). Examples of immunomodulators include those disclosed at Table 1 of WO 01/38332, which is incorporated herein by reference in its entirety. An immunomodulator may be administered in conjunction with (e.g., prior to, concurrently with, or subsequent to, or within the context of a treatment regimen that includes the administration of an N332 glycan-dependent antibody (e.g., PGT121).

As used herein, by "N332 glycan-dependent antibody" is meant an antibody, or antibody fragment thereof, that requires the presence of the N332 glycan of gp120 of HIV (e.g., HIV Type 1 or HIV Type 2) for specific recognition of HIV, and specifically includes PGT family antibodies.

By "needlestick injury" is meant any wound of any size caused by a needle that intentionally or accidentally punctures the skin.

The term "plasma viral load," as used herein, means the amount of HIV in the circulating blood of a mammal, such as a human. The amount of HIV in the blood of a mammal can be determined by measuring the quantity of HIV RNA copies in the blood using methods known to those of ordinary skill in the art.

As used herein, by "PGT family antibody" is meant an antibody, or antibody fragment thereof, including PGT121, and PGT121 derivatives and clonal relatives thereof (e.g., antibody 10-1074), such as those disclosed in WO 2012/030904; WO 2013/055908; Walker et al. *Nature*. 477: 466-470, 2011; Mouquet et al. *Proc. Natl. Acad. Sci.* 109(47): E3268-E3277, 2012; Julien et al., *PLoS Pathog.* 9: e1003342, 2013; and Kong et al., *Nat. Struc. Mol. Biol.* 20: 796-803, 2013, which are incorporated herein by reference in their entirety.

By "pharmaceutical composition" is meant a composition containing a compound described herein (e.g., an N332 glycan-dependent antibody, e.g., PGT121) that can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein.

A "pharmaceutically acceptable carrier" is meant a carrier which is physiologically acceptable to a mammal (e.g., a human) while retaining the therapeutic properties of the compound (e.g., an N332 glycan-dependent antibody, e.g., PGT121) with which it is administered. One exemplary pharmaceutically acceptable carrier is physiological saline. Other physiologically acceptable carriers and their formulations are known to one skilled in the art and described, for example, in *Remington's Pharmaceutical Sciences* (18$^{th}$ edition, A. Gennaro, 1990, Mack Publishing Company, Easton, Pa.), incorporated herein by reference.

By "proviral DNA" is meant viral (e.g., retroviral, e.g., HIV, e.g., HIV-1) genomic DNA that is integrated into the DNA of a host cell, such as a tissue cell (e.g., a lymph node, gastrointestinal, or peripheral blood tissue cell).

As used herein, the term "reduce" with respect to proviral DNA level in tissue of a subject refers to a decrease of proviral DNA level by 5%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more in a subject administered an N332 glycan-dependent antibody (e.g., PGT121) compared to that of a control subject (e.g., a subject not administered an N332 glycan-dependent antibody (e.g., PGT121) or a subject administered a placebo). Administration of the N332 glycan-dependent antibody (e.g., PGT121) may, for example, result in a decrease in proviral DNA level in tissue to below about 1,000 DNA copies/$10^6$ cells (e.g., below about 100 DNA copies/$10^6$ cells, e.g., below about 10 DNA copies/$10^6$ cells, e.g., below about 1 DNA copy/$10^6$ cells).

The term "retrovirus," as used herein, refers to a virus belonging to the viral family Retroviridae, which includes viruses that possess an RNA genome, and that replicate via a DNA intermediate.

By "sequence identity" or "sequence similarity" is meant that the identity or similarity between two or more amino acid sequences, or two or more nucleotide sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene*, 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894)

and on the Internet, for use in connection with the sequence analysis programs blastp, blastn, blastx, tblastn and tblastx. These software programs match similar sequences by assigning degrees of homology to various substitutions, deletions, and other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. Additional information can be found at the NCBI web site.

BLASTN is used to compare nucleic acid sequences, while BLASTP is used to compare amino acid sequences. To compare two nucleic acid sequences, the options can be set as follows: –i is set to a file containing the first nucleic acid sequence to be compared (such as C:\seq1.txt); –j is set to a file containing the second nucleic acid sequence to be compared (such as C:\seq2.txt); –p is set to blastn; –o is set to any desired file name (such as C:\output.txt); –q is set to –1; –r is set to 2; and all other options are left at their default setting. For example, the following command can be used to generate an output file containing a comparison between two sequences: C:\BI2seq –c:\seq1.txt –j c:\seq2.txt –p blastn –o c:\output.txt –q –1 –r 2.

To compare two amino acid sequences, the options of BI2seq can be set as follows: –i is set to a file containing the first amino acid sequence to be compared (such as C:\seq1.txt); –j is set to a file containing the second amino acid sequence to be compared (such as C:\seq2.txt); –p is set to blastp; –o is set to any desired file name (such as C:\output.txt); and all other options are left at their default setting. For example, the following command can be used to generate an output file containing a comparison between two amino acid sequences: C:\BI2seq –i c:\seq1.txt –j c:\seq2.txt –p blastp –o c:\output.txt. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical amino acid or nucleotide residue is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For polypeptides, the length of comparison sequences will generally be at least 5, 6, 7, 8, 9, 10, 11, 12, 13, 14, 15, 16, 17, 18, 19, 20, 25, 50, 75, 90, 100, 110, 120, 130, 140, or 150 or more contiguous amino acids.

By "specifically binds" is meant the preferential association of an antibody, or fragment thereof, to a target molecule (e.g., a viral protein, e.g., gp120, e.g., the N332 glycan of gp120) in a sample (e.g., a biological sample) or in vivo or ex vivo. It is recognized that a certain degree of non-specific interaction may occur between an antibody and a non-target molecule. Nevertheless, specific binding may be distinguished as mediated through specific recognition of the target molecule. Specific binding results in a stronger association between the antibody, or fragment thereof, and, e.g., an antigen (e.g., gp120, e.g., the N332 glycan of gp120) than between the antibody and, e.g., a non-target molecule (e.g., non-viral polypeptide). In one example, the antibody may specifically bind to the N332 glycan of envelope glycoprotein gp120 of HIV. In another example, the antibody may specifically bind to the CD4 binding site (CD4bs) of envelope glycoprotein gp120 of HIV. The antibody (e.g., PGT121) may have, e.g., at least 2-fold greater affinity (e.g., 2, 3, 4, 5, 6, 7, 8, 9, 10, $10^2$-, $10^3$-, $10^4$-, $10^5$-, $10^6$-, $10^7$-, $10^8$-, $10^9$-, or $10^{10}$-fold greater affinity) to the gp120 protein than to other viral or non-viral polypeptides (e.g., PGT121 has at least 2-fold greater affinity to gp120 than a comparable IgG antibody).

A "subject" is a mammal, such as a human. Mammals also include, but are not limited to, primates (e.g., monkeys, e.g., rhesus monkeys) farm animals (e.g., cows), sport animals (e.g., horses), pets (e.g., cats and dogs), mice, rats, rabbits, and guinea pigs.

As used herein, and as well understood in the art, "treatment" is an approach for obtaining beneficial or desired results, such as clinical results. Beneficial or desired results can include, but are not limited to, cure or eradication of disease, disorder, or condition (e.g., HIV infection); alleviation or amelioration of one or more symptoms or conditions (e.g., HIV infection); diminishment of extent of disease, disorder, or condition (e.g., HIV infection); stabilization (i.e., not worsening) of a state of disease, disorder, or condition (e.g., HIV infection); prevention of spread or transmission of disease, disorder, or condition (e.g., HIV infection); delay or slowing the progress of the disease, disorder, or condition (e.g., HIV infection); amelioration or palliation of the disease, disorder, or condition (e.g., HIV infection); and remission (whether partial or total), whether detectable or undetectable.

As used herein, "variable domain" of an antibody, or fragment thereof, refers to the portions of the light and heavy chains of antibody molecules that include amino acid sequences of complementarity determining regions (CDRs; i.e., CDR-1, CDR-2, and CDR-3, e.g., CDR-H1, CDR-H2, CDR-H3, CDR-L1, CDR-L2, and CDR-L3), and framework regions (FRs). VH refers to the variable domain of the heavy chain. VL refers to the variable domain of the light chain. The amino acid residues assigned to CDRs are defined according to Kabat (*Sequences of Proteins of Immunological Interest*, 5th Ed. Public Health Service, National Institutes of Health, Bethesda, Md. (1991)). Amino acid numbering of antibodies or antigen binding fragments is also according to that of Kabat.

As used herein, the term "virologic control" is meant a condition characterized by undetectable proviral DNA level in tissue (e.g., lymph node tissue, gastrointestinal tissue, and/or peripheral blood), such as below about 1,000 DNA copies/$10^6$ cells (e.g., below about 100 DNA copies/$10^6$ cells, e.g., below about 10 DNA copies/$10^6$ cells, e.g., below about 1 DNA copy/$10^6$ cells), and/or undetectable plasma viral load, such as less than 3,500 RNA copies/ml (e.g., less than 2,000 RNA copies/ml, e.g., less than 400 RNA copies/ml, e.g., less than 50 RNA copies/ml, e.g., less than 1 RNA copy/ml).

The term "virus," as used herein, is defined as an infectious agent that is unable to grow or reproduce outside a host cell and that infects mammals (e.g., humans) or birds.

Other features and advantages of the invention will be apparent from the following Detailed Description and the claims.

DETAILED DESCRIPTION OF THE INVENTION

Figures 1A, 1B, 1C, 1D:
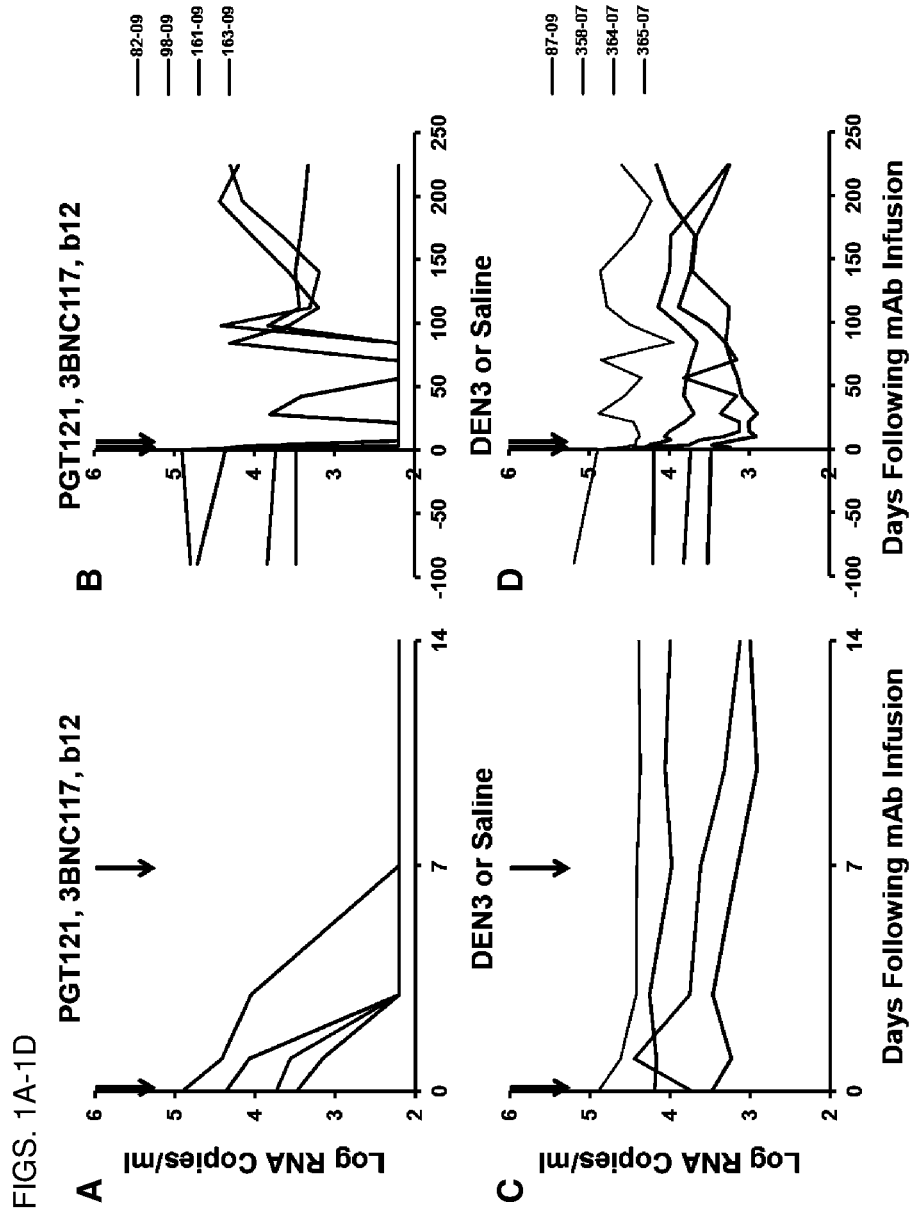
FIG. 1A is a graph showing the therapeutic efficacy of the triple PGT121/3BNC117/b12 antibody cocktail, as assessed by plasma viral RNA (copies/ml) levels in rhesus monkeys (monkeys 82-09, 98-09, 161-09, and 163-09) chronically infected with SHIV-SF162P3 following infusions of PGT121, 3BCN117, and b12 on day 0 and day 7 (arrows) for 14 days.
FIG. 1B is a graph showing the therapeutic efficacy of the triple PGT121/3BNC117/b12 antibody cocktail, as assessed by plasma viral RNA (copies/ml) levels in rhesus monkeys (monkeys 82-09, 98-09, 161-09, and 163-09) chronically infected with SHIV-SF162P3 following infusions of PGT121, 3BCN117, and b12 on day 0 and day 7 (arrows) for 224 days.
FIG. 1C is a graph showing plasma viral RNA (copies/ml) in rhesus monkeys chronically infected with SHIV-SF162P3 following infusions with the control antibody DEN3 (monkey 87-09) or saline (monkeys 358-07, 364-07, and 365-07) on day 0 and day 7 (arrows) for 14 days.
FIG. 1D is a graph showing plasma viral RNA (copies/ml) in rhesus monkeys chronically infected with SHIV-SF162P3 following infusions with the control antibody DEN3 (monkey 87-09) or saline (monkeys 358-07, 364-07, and 365-07) on day 0 and day 7 (arrows) for 224 days.

The present invention is based, at least in part, on the discovery that N332 glycan-dependent antibodies (e.g., PGT121), alone or in combination with other HIV-specific antibodies (e.g., as an antibody therapy cocktail), has a profound and unexpected therapeutic effect on achieving virologic control in rhesus monkeys chronically infected with the highly pathogenic virus SHIV-SF162P3. Prior to this study, HIV-specific antibodies have only been shown to suppress viremia in humanized mice, but not primates with intact immune systems. Here, we show that administration of a single infusion of N332 glycan-dependent antibody (e.g., PGT121) can result in markedly reduced proviral DNA levels in tissues; improved functionality of host Gag-specific T lymphocyte responses; and long-term virologic control in the absence of any further antibody infusions (i.e., antibody therapy). Taken together, these data strongly suggest antibody therapies using an N332 glycan-dependent antibody for HIV. In particular, the present invention features methods of curing subjects (e.g., humans) infected with HIV (e.g., HIV Type 1 (HIV-1)) and methods of blocking HIV infection in subjects at risk of HIV transmission by administration of an N332 glycan-dependent antibody (e.g., PGT121), alone, in combination with other HIV-specific antibodies, and/or in combination with antiretroviral therapies (ARTs).

I. Antibodies for Use in the Methods of the Invention

N332 Glycan-dependent Antibodies

The present invention features methods of curing subjects (e.g., humans) infected with HIV (e.g., HIV Type 1 (HIV-1)) and methods of blocking HIV (e.g., HIV Type 1 (HIV-1)) infection in subjects (e.g., humans) at risk of HIV transmission by administration of an N332 glycan-dependent antibody (e.g., PGT121), alone, in combination with other HIV-specific antibodies (e.g., other broadly neutralizing antibodies (bnAbs)), and/or in combination with antiretroviral therapies, which are described herein below.

An N332 glycan-dependent antibody for use in any of the methods of the present invention (e.g., curing a subject, e.g., a human, infected with HIV, e.g., HIV-1, or blocking an HIV (e.g., HIV-1) infection in a subject, e.g., a human, at risk of HIV transmission) can include the following six complementarity determining regions (CDRs): CDR-H1 including DSYWS (SEQ ID NO: 1); CDR-H2 including YVHKSGDTNYSPSLKS (SEQ ID NO: 2); CDR-H3 including TLHGRRIYGIVAFNEWFTYFYMDV (SEQ ID NO: 3); CDR-L1 including GEKSLGSRAVQ (SEQ ID NO: 4); CDR-L2 including NNQDRPS (SEQ ID NO: 5); and CDR-L3 including HIWDSRVPTKWV (SEQ ID NO: 6). In some instances, the N332 glycan-dependent antibody may have a heavy chain variable domain including an amino acid sequence having at least 90% sequence identity (e.g., at least 91%, 92%, 93%, 94%, 95%, 96%, 97%, 98%, or 99% sequence identity) to, or the sequence of, SEQ ID NO: 7 and/or a light chain variable domain including an amino acid sequence having at least 90% sequence identity (e.g., at least 91%, 92%, 93%, 94%, 95%, 96%, 97%, 98%, or 99% sequence identity) to, or the sequence of, SEQ ID NO: 8. In a particular instance, the N332 glycan-dependent antibody can be PGT121, or a derivative or clonal relative thereof.

An N332 glycan-dependent antibody for use in any of the methods of the present invention (e.g., curing a subject, e.g., a human, infected with HIV, e.g., HIV-1, or blocking an HIV (e.g., HIV-1) infection in a subject, e.g., a human, at risk of HIV transmission) can include the following six complementarity determining regions (CDRs): CDR-H1 including DNYWS (SEQ ID NO: 9); CDR-H2 including YVHDSGDTNYNPSLKS (SEQ ID NO: 10); CDR-H3 including TKHGRRIYGVVAFKEWFTYFYMDV (SEQ ID NO: 11); CDR-L1 including GEESLGSRSVI (SEQ ID NO: 12);

CDR-L2 including NNNDRPS (SEQ ID NO: 13); and CDR-L3 including HIWDSRRPTNWV (SEQ ID NO: 14). In some instances, the N332 glycan-dependent antibody may have a heavy chain variable domain including an amino acid sequence having at least 90% sequence identity (e.g., at least 91%, 92%, 93%, 94%, 95%, 96%, 97%, 98%, or 99% sequence identity) to, or the sequence of, SEQ ID NO: 15 and/or a light chain variable domain including an amino acid sequence having at least 90% sequence identity (e.g., at least 91%, 92%, 93%, 94%, 95%, 96%, 97%, 98%, or 99% sequence identity) to, or the sequence of, SEQ ID NO: 16. In a particular instance, the N332 glycan-dependent antibody can be PGT122, or a derivative or clonal relative thereof.

An N332 glycan-dependent antibody for use in any of the methods of the present invention (e.g., curing a subject, e.g., a human, infected with HIV, e.g., HIV-1, or blocking an HIV (e.g., HIV-1) infection in a subject, e.g., a human, at risk of HIV transmission) can include the following six complementarity determining regions (CDRs): CDR-H1 including DAYWS (SEQ ID NO: 17); CDR-H2 including YVHHS-GDTNYNPSLKR (SEQ ID NO: 18); CDR-H3 including ALHGKRIYGIVALGELFTYFYMDV (SEQ ID NO: 19); CDR-L1 including GKESIGSRAVQ (SEQ ID NO: 20); CDR-L2 including NNQDRPA (SEQ ID NO: 21); and CDR-L3 including HIYDARGGTNWV (SEQ ID NO: 22). In some instances, the N332 glycan-dependent antibody may have a heavy chain variable domain including an amino acid sequence having at least 90% sequence identity (e.g., at least 91%, 92%, 93%, 94%, 95%, 96%, 97%, 98%, or 99% sequence identity) to, or the sequence of, SEQ ID NO: 23 and/or a light chain variable domain including an amino acid sequence having at least 90% sequence identity (e.g., at least 91%, 92%, 93%, 94%, 95%, 96%, 97%, 98%, or 99% sequence identity) to, or the sequence of, SEQ ID NO: 24. In a particular instance, the N332 glycan-dependent antibody can be PGT123, or a derivative or clonal relative thereof.

An N332 glycan-dependent antibody for use in any of the methods of the present invention (e.g., curing a subject, e.g., a human, infected with HIV, e.g., HIV-1, or blocking an HIV (e.g., HIV-1) infection in a subject, e.g., a human, at risk of HIV transmission) can include the following six complementarity determining regions (CDRs): CDR-H1 including ACTYFWG (SEQ ID NO: 25); CDR-H2 including SLSH-CQSFWGSGWTFHNPSLKS (SEQ ID NO: 26); CDR-H3 including FDGEVLVYNHWPKPAWVDL (SEQ ID NO: 27); CDR-L1 including NGTATNFVS (SEQ ID NO: 28); CDR-L2 including GVDKRPP (SEQ ID NO: 29); and CDR-L3 including GSLVGNWDVI (SEQ ID NO: 30). In some instances, the N332 glycan-dependent antibody may have a heavy chain variable domain including an amino acid sequence having at least 90% sequence identity (e.g., at least 91%, 92%, 93%, 94%, 95%, 96%, 97%, 98%, or 99% sequence identity) to, or the sequence of, SEQ ID NO: 31 and/or a light chain variable domain including an amino acid sequence having at least 90% sequence identity (e.g., at least 91%, 92%, 93%, 94%, 95%, 96%, 97%, 98%, or 99% sequence identity) to, or the sequence of, SEQ ID NO: 32. In a particular instance, the N332 glycan-dependent antibody can be PGT125, or a derivative or clonal relative thereof.

An N332 glycan-dependent antibody for use in any of the methods of the present invention (e.g., curing a subject, e.g., a human, infected with HIV, e.g., HIV-1, or blocking an HIV (e.g., HIV-1) infection in a subject, e.g., a human, at risk of HIV transmission) can include the following six complementarity determining regions (CDRs): CDR-H1 including ACDYFWG (SEQ ID NO: 33); CDR-H2 including GLSHCAGYYNTGWTYHNPSLKS (SEQ ID NO: 34); CDR-H3 including FDGEVLVYHDWPKPAWVDL (SEQ ID NO: 35); CDR-L1 including TGTSNRFVS (SEQ ID NO: 36); CDR-L2 including GVNKRPS (SEQ ID NO: 37); and CDR-L3 including SSLVGNWDVI (SEQ ID NO: 38). In some instances, the N332 glycan-dependent antibody may have a heavy chain variable domain including an amino acid sequence having at least 90% sequence identity (e.g., at least 91%, 92%, 93%, 94%, 95%, 96%, 97%, 98%, or 99% sequence identity) to, or the sequence of, SEQ ID NO: 39 and/or a light chain variable domain including an amino acid sequence having at least 90% sequence identity (e.g., at least 91%, 92%, 93%, 94%, 95%, 96%, 97%, 98%, or 99% sequence identity) to, or the sequence of, SEQ ID NO: 40. In a particular instance, the N332 glycan-dependent antibody can be PGT126, or a derivative or clonal relative thereof.

An N332 glycan-dependent antibody for use in any of the methods of the present invention (e.g., curing a subject, e.g., a human, infected with HIV, e.g., HIV-1, or blocking an HIV (e.g., HIV-1) infection in a subject, e.g., a human, at risk of HIV transmission) can include the following six complementarity determining regions (CDRs): CDR-H1 including RCNYFWG (SEQ ID NO: 41); CDR-H2 including SLSH-CRSYYNTDWTYHNPSLKS (SEQ ID NO: 42); CDR-H3 including FGGEVLVYRDWPKPAWVDL (SEQ ID NO: 43); CDR-L1 including TGTSNNFVS (SEQ ID NO: 44); CDR-L2 including EVNKRPS (SEQ ID NO: 45); and CDR-L3 including SSLVGNWDVI (SEQ ID NO: 46). In some instances, the N332 glycan-dependent antibody may have a heavy chain variable domain including an amino acid sequence having at least 90% sequence identity (e.g., at least 91%, 92%, 93%, 94%, 95%, 96%, 97%, 98%, or 99% sequence identity) to, or the sequence of, SEQ ID NO: 47 and/or a light chain variable domain including an amino acid sequence having at least 90% sequence identity (e.g., at least 91%, 92%, 93%, 94%, 95%, 96%, 97%, 98%, or 99% sequence identity) to, or the sequence of, SEQ ID NO: 48. In a particular instance, the N332 glycan-dependent antibody can be PGT127, or a derivative or clonal relative thereof.

An N332 glycan-dependent antibody for use in any of the methods of the present invention (e.g., curing a subject, e.g., a human, infected with HIV, e.g., HIV-1, or blocking an HIV (e.g., HIV-1) infection in a subject, e.g., a human, at risk of HIV transmission) can include the following six complementarity determining regions (CDRs): CDR-H1 including ACNSFWG (SEQ ID NO: 49); CDR-H2 including SLSHCASYWNRGWTYHNPSLKS (SEQ ID NO: 50); CDR-H3 including FGGEVLRYTDWPKPAWVDL (SEQ ID NO: 51); CDR-L1 including TGTSNNFVS (SEQ ID NO: 52); CDR-L2 including DVNKRPS (SEQ ID NO: 53); and CDR-L3 including GSLVGNWDVI (SEQ ID NO: 54). In some instances, the N332 glycan-dependent antibody may have a heavy chain variable domain including an amino acid sequence having at least 90% sequence identity (e.g., at least 91%, 92%, 93%, 94%, 95%, 96%, 97%, 98%, or 99% sequence identity) to, or the sequence of, SEQ ID NO: 55 and/or a light chain variable domain including an amino acid sequence having at least 90% sequence identity (e.g., at least 91%, 92%, 93%, 94%, 95%, 96%, 97%, 98%, or 99% sequence identity) to, or the sequence of, SEQ ID NO: 56. In a particular instance, the N332 glycan-dependent antibody can be PGT128, or a derivative or clonal relative thereof.

An N332 glycan-dependent antibody for use in any of the methods of the present invention (e.g., curing a subject, e.g., a human, infected with HIV, e.g., HIV-1, or blocking an HIV (e.g., HIV-1) infection in a subject, e.g., a human, at risk of HIV transmission) can include the following six complementarity determining regions (CDRs): CDR-H1 including TGHYYWG (SEQ ID NO: 57); CDR-H2 including HIHYTTAVLHNPSLKS (SEQ ID NO: 58); CDR-H3 including SGGDILYYYEWQKPHWFSP (SEQ ID NO: 59); CDR-L1 including NGTSSDIGGWNFVS (SEQ ID NO: 60); CDR-L2 including EVNKRPS (SEQ ID NO: 61); and CDR-L3 including SSLFGRWDVV (SEQ ID NO: 62). In some instances, the N332 glycan-dependent antibody may have a heavy chain variable domain including an amino acid sequence having at least 90% sequence identity (e.g., at least 91%, 92%, 93%, 94%, 95%, 96%, 97%, 98%, or 99% sequence identity) to, or the sequence of, SEQ ID NO: 63 and/or a light chain variable domain including an amino acid sequence having at least 90% sequence identity (e.g., at least 91%, 92%, 93%, 94%, 95%, 96%, 97%, 98%, or 99% sequence identity) to, or the sequence of, SEQ ID NO: 64. In a particular instance, the N332 glycan-dependent antibody can be PGT130, or a derivative or clonal relative thereof.

An N332 glycan-dependent antibody for use in any of the methods of the present invention (e.g., curing a subject, e.g., a human, infected with HIV, e.g., HIV-1, or blocking an HIV (e.g., HIV-1) infection in a subject, e.g., a human, at risk of HIV transmission) can include the following six complementarity determining regions (CDRs): CDR-H1 including TGHHYWG (SEQ ID NO: 65); CDR-H2 including HIHYNTAVLHNPALKS (SEQ ID NO: 66); CDR-H3 including SGGDILYYIEWQKPHWFYP (SEQ ID NO: 67); CDR-L1 including SGTGSDIGSWNFVS (SEQ ID NO: 68); CDR-L2 including EVNRRRS (SEQ ID NO: 69); and CDR-L3 including SSLSGRWDIV (SEQ ID NO: 70). In some instances, the N332 glycan-dependent antibody may have a heavy chain variable domain including an amino acid sequence having at least 90% sequence identity (e.g., at least 91%, 92%, 93%, 94%, 95%, 96%, 97%, 98%, or 99% sequence identity) to, or the sequence of, SEQ ID NO: 71 and/or a light chain variable domain including an amino acid sequence having at least 90% sequence identity (e.g., at least 91%, 92%, 93%, 94%, 95%, 96%, 97%, 98%, or 99% sequence identity) to, or the sequence of, SEQ ID NO: 72. In a particular instance, the N332 glycan-dependent antibody can be PGT131, or a derivative or clonal relative thereof.

An N332 glycan-dependent antibody for use in any of the methods of the present invention (e.g., curing a subject, e.g., a human, infected with HIV, e.g., HIV-1, or blocking an HIV (e.g., HIV-1) infection in a subject, e.g., a human, at risk of HIV transmission) can include the following six complementarity determining regions (CDRs): CDR-H1 including GGEWGDKDYHWG (SEQ ID NO: 73); CDR-H2 including SIHWRGTTHYKESLRR (SEQ ID NO: 74); CDR-H3 including HRHHDVFMLVPIAGWFDV (SEQ ID NO: 75); CDR-L1 including RASQNINKNLA (SEQ ID NO: 76); CDR-L2 including ETYSKIA (SEQ ID NO: 77); and CDR-L3 including QQYEEWPRT (SEQ ID NO: 78). In some instances, the N332 glycan-dependent antibody may have a heavy chain variable domain including an amino acid sequence having at least 90% sequence identity (e.g., at least 91%, 92%, 93%, 94%, 95%, 96%, 97%, 98%, or 99% sequence identity) to, or the sequence of, SEQ ID NO: 79 and/or a light chain variable domain including an amino acid sequence having at least 90% sequence identity (e.g., at least 91%, 92%, 93%, 94%, 95%, 96%, 97%, 98%, or 99% sequence identity) to, or the sequence of, SEQ ID NO: 80. In a particular instance, the N332 glycan-dependent antibody can be PGT135, or a derivative or clonal relative thereof.

An N332 glycan-dependent antibody for use in any of the methods of the present invention (e.g., curing a subject, e.g., a human, infected with HIV, e.g., HIV-1, or blocking an HIV (e.g., HIV-1) infection in a subject, e.g., a human, at risk of HIV transmission) can include the following six complementarity determining regions (CDRs): CDR-H1 including GTDWGENDFHYG (SEQ ID NO: 81); CDR-H2 including SIHWRGRTTHYKTSFRS (SEQ ID NO: 82); CDR-H3 including HKYHDIFRVVPVAGWFDP (SEQ ID NO: 83); CDR-L1 including RASQNVKNNLA (SEQ ID NO: 84); CDR-L2 including DASSRAG (SEQ ID NO: 85); and CDR-L3 including QQYEEWPRT (SEQ ID NO: 86). In some instances, the N332 glycan-dependent antibody may have a heavy chain variable domain including an amino acid sequence having at least 90% sequence identity (e.g., at least 91%, 92%, 93%, 94%, 95%, 96%, 97%, 98%, or 99% sequence identity) to, or the sequence of, SEQ ID NO: 87 and/or a light chain variable domain including an amino acid sequence having at least 90% sequence identity (e.g., at least 91%, 92%, 93%, 94%, 95%, 96%, 97%, 98%, or 99% sequence identity) to, or the sequence of, SEQ ID NO: 88. In a particular instance, the N332 glycan-dependent antibody can be PGT136, or a derivative or clonal relative thereof.

An N332 glycan-dependent antibody for use in any of the methods of the present invention (e.g., curing a subject, e.g., a human, infected with HIV, e.g., HIV-1, or blocking an HIV (e.g., HIV-1) infection in a subject, e.g., a human, at risk of HIV transmission) can include the following six complementarity determining regions (CDRs): CDR-H1 including KYDVH (SEQ ID NO: 89); CDR-H2 including WMSHEGDKTESAQRFKG (SEQ ID NO: 90); CDR-H3 including GSKHRLRDYVLYDDYGLINY QEWNDYLEFLDV (SEQ ID NO: 91); CDR-L1 including SSTQSLRHSNGANYLA (SEQ ID NO: 92); CDR-L2 including LGSQRAS (SEQ ID NO: 93); and CDR-L3 including MQGLNRPWT (SEQ ID NO: 94). In some instances, the N332 glycan-dependent antibody may have a heavy chain variable domain including an amino acid sequence having at least 90% sequence identity (e.g., at least 91%, 92%, 93%, 94%, 95%, 96%, 97%, 98%, or 99% sequence identity) to, or the sequence of, SEQ ID NO: 95 and/or a light chain variable domain including an amino acid sequence having at least 90% sequence identity (e.g., at least 91%, 92%, 93%, 94%, 95%, 96%, 97%, 98%, or 99% sequence identity) to, or the sequence of, SEQ ID NO: 96. In a particular instance, the N332 glycan-dependent antibody can be PGT141, or a derivative or clonal relative thereof.

An N332 glycan-dependent antibody for use in any of the methods of the present invention (e.g., curing a subject, e.g., a human, infected with HIV, e.g., HIV-1, or blocking an HIV (e.g., HIV-1) infection in a subject, e.g., a human, at risk of HIV transmission) can include the following six complementarity determining regions (CDRs): CDR-H1 including GGEWGDSYHWG (SEQ ID NO: 97); CDR-H2 including SIHWRGTTHYNAPFRG (SEQ ID NO: 98); CDR-H3 including HKYHDIVMVVPIAGWFDP (SEQ ID NO: 99); CDR-L1 including RASQSVKNNLA (SEQ ID NO: 100); CDR-L2 including DTSSRAS (SEQ ID NO: 101); and CDR-L3 including QQYEEWPRT (SEQ ID NO: 102). In some instances, the N332 glycan-dependent antibody may have a heavy chain variable domain including an amino acid sequence having at least 90% sequence identity (e.g., at least 91%, 92%, 93%, 94%, 95%, 96%, 97%, 98%, or 99% sequence identity) to, or the sequence of, SEQ ID NO: 103 and/or a light chain variable domain including an amino acid sequence having at least 90% sequence identity (e.g., at least 91%, 92%, 93%, 94%, 95%, 96%, 97%, 98%, or 99% sequence identity) to, or the sequence of, SEQ ID NO: 104. In a particular instance, the N332 glycan-dependent antibody can be PGT137, or a derivative or clonal relative thereof.

An N332 glycan-dependent antibody for use in any of the methods of the present invention (e.g., curing a subject, e.g., a human, infected with HIV, e.g., HIV-1, or blocking an HIV (e.g., HIV-1) infection in a subject, e.g., a human, at risk of HIV transmission) can include the following six complementarity determining regions (CDRs): CDR-H1 including KYDVH (SEQ ID NO: 105); CDR-H2 including WISHERDKTESAQRFKG (SEQ ID NO: 106); CDR-H3 including GSKHRLRDYVLYDDYGLINYQEWNDYLEFLDV (SEQ ID NO: 107); CDR-L1 including SSTQSLRHSNGANYLA (SEQ ID NO: 108); CDR-L2 including LGSQRAS (SEQ ID NO: 109); and CDR-L3 including MQGLNRPWT (SEQ ID NO: 110). In some instances, the N332 glycan-dependent antibody may have a heavy chain variable domain including an amino acid sequence having at least 90% sequence identity (e.g., at least 91%, 92%, 93%, 94%, 95%, 96%, 97%, 98%, or 99% sequence identity) to, or the sequence of, SEQ ID NO: 111 and/or a light chain variable domain including an amino acid sequence having at least 90% sequence identity (e.g., at least 91%, 92%, 93%, 94%, 95%, 96%, 97%, 98%, or 99% sequence identity) to, or the sequence of, SEQ ID NO: 112. In a particular instance, the N332 glycan-dependent antibody can be PGT142, or a derivative or clonal relative thereof.

An N332 glycan-dependent antibody for use in any of the methods of the present invention (e.g., curing a subject, e.g., a human, infected with HIV, e.g., HIV-1, or blocking an HIV (e.g., HIV-1) infection in a subject, e.g., a human, at risk of HIV transmission) can include the following six complementarity determining regions (CDRs): CDR-H1 including KYDVH (SEQ ID NO: 113); CDR-H2 including WMSHEGDKTESAQRFKG (SEQ ID NO: 114); CDR-H3 including GSKHRLRDYVLYDDYGLINYQEWNDYLEFLDV (SEQ ID NO: 115); CDR-L1 including TSTQSLRHSNGANYLA (SEQ ID NO: 116); CDR-L2 including LGSQRAS (SEQ ID NO: 117); and CDR-L3 including MQGLNRPWT (SEQ ID NO: 118). In some instances, the N332 glycan-dependent antibody may have a heavy chain variable domain including an amino acid sequence having at least 90% sequence identity (e.g., at least 91%, 92%, 93%, 94%, 95%, 96%, 97%, 98%, or 99% sequence identity) to, or the sequence of, SEQ ID NO: 119 and/or a light chain variable domain including an amino acid sequence having at least 90% sequence identity (e.g., at least 91%, 92%, 93%, 94%, 95%, 96%, 97%, 98%, or 99% sequence identity) to, or the sequence of, SEQ ID NO: 120. In a particular instance, the N332 glycan-dependent antibody can be PGT143, or a derivative or clonal relative thereof.

An N332 glycan-dependent antibody for use in any of the methods of the present invention (e.g., curing a subject, e.g., a human, infected with HIV, e.g., HIV-1, or blocking an HIV (e.g., HIV-1) infection in a subject, e.g., a human, at risk of HIV transmission) can include the following six complementarity determining regions (CDRs): CDR-H1 including KYDVH (SEQ ID NO: 121); CDR-H2 including WMSHEGDKTESAQRFKG (SEQ ID NO: 122); CDR-H3 including GSKHRLRDYVLYDDYGLINQQEWNDYLEFLDV (SEQ ID NO: 123); CDR-L1 including TSTQSLRHSNGANYLA (SEQ ID NO: 124); CDR-L2 including LGSQRAS (SEQ ID NO: 125); and CDR-L3 including MQGLNRPWT (SEQ ID NO: 126). In some instances, the N332 glycan-dependent antibody may have a heavy chain variable domain including an amino acid sequence having at least 90% sequence identity (e.g., at least 91%, 92%, 93%, 94%, 95%, 96%, 97%, 98%, or 99% sequence identity) to, or the sequence of, SEQ ID NO: 127 and/or a light chain variable domain including an amino acid sequence having at least 90% sequence identity (e.g., at least 91%, 92%, 93%, 94%, 95%, 96%, 97%, 98%, or 99% sequence identity) to, or the sequence of, SEQ ID NO: 128. In a particular instance, the N332 glycan-dependent antibody can be PGT144, or a derivative or clonal relative thereof.

An N332 glycan-dependent antibody for use in any of the methods of the present invention (e.g., curing a subject, e.g., a human, infected with HIV, e.g., HIV-1, or blocking an HIV (e.g., HIV-1) infection in a subject, e.g., a human, at risk of HIV transmission) can include the following six complementarity determining regions (CDRs): CDR-H1 including NHDVH (SEQ ID NO: 129); CDR-H2 including WMSHEGDKTGLAQKFQG (SEQ ID NO: 130); CDR-H3 including GSKHRLRDYFLYNEYGPNYEEWGDYLATLDV (SEQ ID NO: 131); CDR-L1 including KCSHSLQHSTGANYLA (SEQ ID NO: 132); CDR-L2 including LATHRAS (SEQ ID NO: 133); and CDR-L3 including MQGLHSPWT (SEQ ID NO: 134). In some instances, the N332 glycan-dependent antibody may have a heavy chain variable domain including an amino acid sequence having at least 90% sequence identity (e.g., at least 91%, 92%, 93%, 94%, 95%, 96%, 97%, 98%, or 99% sequence identity) to, or the sequence of, SEQ ID NO: 135 and/or a light chain variable domain including an amino acid sequence having at least 90% sequence identity (e.g., at least 91%, 92%, 93%, 94%, 95%, 96%, 97%, 98%, or 99% sequence identity) to, or the sequence of, SEQ ID NO: 136. In a particular instance, the N332 glycan-dependent antibody can be PGT145, or a derivative or clonal relative thereof.

An N332 glycan-dependent antibody for use in any of the methods of the present invention (e.g., curing a subject, e.g., a human, infected with HIV, e.g., HIV-1, or blocking an HIV (e.g., HIV-1) infection in a subject, e.g., a human, at risk of HIV transmission) can include the following six complementarity determining regions (CDRs): CDR-H1 including NYYWT (SEQ ID NO: 137); CDR-H2 including YISDRETTTYNPSLNS (SEQ ID NO: 138); CDR-H3 including ARRGQRIYGVVSFGEFFYYYYMDV (SEQ ID NO: 139); CDR-L1 including GRQALGSRAVQ (SEQ ID NO: 140); CDR-L2 including NNQDRPS (SEQ ID NO: 141); and CDR-L3 including HMWDSRSGFSWS (SEQ ID NO: 142). In some instances, the N332 glycan-dependent antibody may have a heavy chain variable domain including an amino acid sequence having at least 90% sequence identity (e.g., at least 91%, 92%, 93%, 94%, 95%, 96%, 97%, 98%, or 99% sequence identity) to, or the sequence of, SEQ ID NO: 143 and/or a light chain variable domain including an amino acid sequence having at least 90% sequence identity (e.g., at least 91%, 92%, 93%, 94%, 95%, 96%, 97%, 98%, or 99% sequence identity) to, or the sequence of, SEQ ID NO: 144. In a particular instance, the N332 glycan-dependent antibody can be PGT124, or a derivative or clonal relative thereof.

An N332 glycan-dependent antibody for use in any of the methods of the present invention (e.g., curing a subject, e.g., a human, infected with HIV, e.g., HIV-1, or blocking an HIV (e.g., HIV-1) infection in a subject, e.g., a human, at risk of HIV transmission) can include the following six complementarity determining regions (CDRs): CDR-H1 including GRFWS (SEQ ID NO: 145); CDR-H2 including YFSDT-DRSEYNPSLRS (SEQ ID NO: 146); CDR-H3 including AQQGKRIYGI VSFGEFFYYYYMDA (SEQ ID NO: 147); CDR-L1 including GERSRGSRAVQ (SEQ ID NO: 148); CDR-L2 including NNQDRPA (SEQ ID NO: 149); and CDR-L3 including HYWDSRSPISWI (SEQ ID NO: 150). In some instances, the N332 glycan-dependent antibody may have a heavy chain variable domain including an amino acid sequence having at least 90% sequence identity (e.g., at least 91%, 92%, 93%, 94%, 95%, 96%, 97%, 98%, or 99% sequence identity) to, or the sequence of, SEQ ID NO: 151 and/or a light chain variable domain including an amino acid sequence having at least 90% sequence identity (e.g., at least 91%, 92%, 93%, 94%, 95%, 96%, 97%, 98%, or 99% sequence identity) to, or the sequence of, SEQ ID NO: 152. In a particular instance, the N332 glycan-dependent antibody can be PGT133, or a derivative or clonal relative thereof.

An N332 glycan-dependent antibody for use in any of the methods of the present invention (e.g., curing a subject, e.g., a human, infected with HIV, e.g., HIV-1, or blocking an HIV (e.g., HIV-1) infection in a subject, e.g., a human, at risk of HIV transmission) can include the following six complementarity determining regions (CDRs): CDR-H1 including GRFWS (SEQ ID NO: 153); CDR-H2 including YFSDT-DRSEYNPSLRS (SEQ ID NO: 154); CDR-H3 including AQQGKRIYGI VSFGELFYYYYMDA (SEQ ID NO: 155); CDR-L1 including GERSRGSRAVQ (SEQ ID NO: 156); CDR-L2 including NNQDRPA (SEQ ID NO: 157); and CDR-L3 including HYWDSRSPISWI (SEQ ID NO: 158). In some instances, the N332 glycan-dependent antibody may have a heavy chain variable domain including an amino acid sequence having at least 90% sequence identity (e.g., at least 91%, 92%, 93%, 94%, 95%, 96%, 97%, 98%, or 99% sequence identity) to, or the sequence of, SEQ ID NO: 159 and/or a light chain variable domain including an amino acid sequence having at least 90% sequence identity (e.g., at least 91%, 92%, 93%, 94%, 95%, 96%, 97%, 98%, or 99% sequence identity) to, or the sequence of, SEQ ID NO: 160. In a particular instance, the N332 glycan-dependent antibody can be PGT134, or a derivative or clonal relative thereof.

An N332 glycan-dependent antibody for use in any of the methods of the present invention (e.g., curing a subject, e.g., a human, infected with HIV, e.g., HIV-1, or blocking an HIV (e.g., HIV-1) infection in a subject, e.g., a human, at risk of HIV transmission) can include the following six complementarity determining regions (CDRs): CDR-H1 including TGHHYWG (SEQ ID NO: 161); CDR-H2 including HIHYNTAVLHNPALKS (SEQ ID NO: 162); CDR-H3 including SGGDILYYNEWQKPHWFYP (SEQ ID NO: 163); CDR-L1 including SGTASDIGSWNFVS (SEQ ID NO: 164); CDR-L2 including EVNRRRS (SEQ ID NO: 165); and CDR-L3 including SSLSGRWDIV (SEQ ID NO: 166). In some instances, the N332 glycan-dependent antibody may have a heavy chain variable domain including an amino acid sequence having at least 90% sequence identity (e.g., at least 91%, 92%, 93%, 94%, 95%, 96%, 97%, 98%, or 99% sequence identity) to, or the sequence of, SEQ ID NO: 167 and/or a light chain variable domain including an amino acid sequence having at least 90% sequence identity (e.g., at least 91%, 92%, 93%, 94%, 95%, 96%, 97%, 98%, or 99% sequence identity) to, or the sequence of, SEQ ID NO: 168. In a particular instance, the N332 glycan-dependent antibody can be PGT132, or a derivative or clonal relative thereof.

An N332 glycan-dependent antibody for use in any of the methods of the present invention (e.g., curing a subject, e.g., a human, infected with HIV, e.g., HIV-1, or blocking an HIV (e.g., HIV-1) infection in a subject, e.g., a human, at risk of HIV transmission) can include the following six complementarity determining regions (CDRs): CDR-H1 including ACDYFWG (SEQ ID NO: 169); CDR-H2 including SLSHCAGYYNSGWTYHNPSLKS (SEQ ID NO: 170); CDR-H3 including FGGDVLVYHDWPKPAWVDL (SEQ ID NO: 171); CDR-L1 including TGNINNFVS (SEQ ID NO: 172); CDR-L2 including GVNKRPS (SEQ ID NO: 173); and CDR-L3 including GSLAGNWDVV (SEQ ID NO: 174). In some instances, the N332 glycan-dependent antibody may have a heavy chain variable domain including an amino acid sequence having at least 90% sequence identity (e.g., at least 91%, 92%, 93%, 94%, 95%, 96%, 97%, 98%, or 99% sequence identity) to, or the sequence of, SEQ ID NO: 175 and/or a light chain variable domain including an amino acid sequence having at least 90% sequence identity (e.g., at least 91%, 92%, 93%, 94%, 95%, 96%, 97%, 98%, or 99% sequence identity) to, or the sequence of, SEQ ID NO: 176. In a particular instance, the N332 glycan-dependent antibody can be PGT138, or a derivative or clonal relative thereof.

An N332 glycan-dependent antibody for use in any of the methods of the present invention (e.g., curing a subject, e.g., a human, infected with HIV, e.g., HIV-1, or blocking an HIV (e.g., HIV-1) infection in a subject, e.g., a human, at risk of HIV transmission) can include the following six complementarity determining regions (CDRs): CDR-H1 including GCDYFWG (SEQ ID NO: 177); CDR-H2 including GLSHCAGYYNTGWTYHNPSLKS (SEQ ID NO: 178); CDR-H3 including FDGEVLVYNDWPKPAWVDL (SEQ ID NO: 179); CDR-L1 including TGTSNNFVS (SEQ ID NO: 180); CDR-L2 including GVNKRPS (SEQ ID NO: 181); and CDR-L3 including GSLVGNWDVI (SEQ ID NO: 182). In some instances, the N332 glycan-dependent antibody may have a heavy chain variable domain including an amino acid sequence having at least 90% sequence identity (e.g., at least 91%, 92%, 93%, 94%, 95%, 96%, 97%, 98%, or 99% sequence identity) to, or the sequence of, SEQ ID NO: 183 and/or a light chain variable domain including an amino acid sequence having at least 90% sequence identity (e.g., at least 91%, 92%, 93%, 94%, 95%, 96%, 97%, 98%, or 99% sequence identity) to, or the sequence of, SEQ ID NO: 184. In a particular instance, the N332 glycan-dependent antibody can be PGT139, or a derivative or clonal relative thereof.

An N332 glycan-dependent antibody for use in any of the methods of the present invention (e.g., curing a subject, e.g., a human, infected with HIV, e.g., HIV-1, or blocking an HIV (e.g., HIV-1) infection in a subject, e.g., a human, at risk of HIV transmission) can include the following six complementarity determining regions (CDRs): CDR-H1 including KYPMY (SEQ ID NO: 185); CDR-H2 including AIS-GDAWHVVYSNSVQ (SEQ ID NO: 186); CDR-H3 including MFQESGPPRLDRWSGRNYYYYSGMDV (SEQ ID NO: 187); CDR-L1 including KSSESLRQSNGKTSLY (SEQ ID NO: 188); CDR-L2 including EVSNRFS (SEQ ID NO: 189); and CDR-L3 including MQSKDFPLT (SEQ ID NO: 190). In some instances, the N332 glycan-dependent antibody may have a heavy chain variable domain including an amino acid sequence having at least 90% sequence identity (e.g., at least 91%, 92%, 93%, 94%, 95%, 96%, 97%, 98%, or 99% sequence identity) to, or the sequence of, SEQ ID NO: 191 and/or a light chain variable domain including an amino acid sequence having at least 90% sequence identity (e.g., at least 91%, 92%, 93%, 94%, 95%, 96%, 97%, 98%, or 99% sequence identity) to, or the sequence of, SEQ ID NO: 192. In a particular instance, the N332 glycan-dependent antibody can be PGT151, or a derivative or clonal relative thereof.

An N332 glycan-dependent antibody for use in any of the methods of the present invention (e.g., curing a subject, e.g., a human, infected with HIV, e.g., HIV-1, or blocking an HIV (e.g., HIV-1) infection in a subject, e.g., a human, at risk of HIV transmission) can include the following six complementarity determining regions (CDRs): CDR-H1 including KYPMY (SEQ ID NO: 193); CDR-H2 including AISADAWHVVYSGSVQG (SEQ ID NO: 194); CDR-H3 including MFQESGPPRFDSWSGRNYYYYSGMDV (SEQ ID NO: 195); CDR-L1 including KSSQSLRQSNG-KTSLY (SEQ ID NO: 196); CDR-L2 including EVSNRFS (SEQ ID NO: 197); and CDR-L3 including MQSKDFPLT (SEQ ID NO: 198). In some instances, the N332 glycan-dependent antibody may have a heavy chain variable domain including an amino acid sequence having at least 90% sequence identity (e.g., at least 91%, 92%, 93%, 94%, 95%, 96%, 97%, 98%, or 99% sequence identity) to, or the sequence of, SEQ ID NO: 199 and/or a light chain variable domain including an amino acid sequence having at least 90% sequence identity (e.g., at least 91%, 92%, 93%, 94%, 95%, 96%, 97%, 98%, or 99% sequence identity) to, or the sequence of, SEQ ID NO: 200. In a particular instance, the N332 glycan-dependent antibody can be PGT152, or a derivative or clonal relative thereof.

An N332 glycan-dependent antibody for use in any of the methods of the present invention (e.g., curing a subject, e.g., a human, infected with HIV, e.g., HIV-1, or blocking an HIV (e.g., HIV-1) infection in a subject, e.g., a human, at risk of HIV transmission) can include the following six complementarity determining regions (CDRs): CDR-H1 including KRHMH (SEQ ID NO: 201); CDR-H2 including VISS-DAIHVDYASSVRG (SEQ ID NO: 202); CDR-H3 including DRDGYGPPQIQTWSGRYLHLYSGIDA (SEQ ID NO: 203); CDR-L1 including KSSQSLRQSNGKTYLY (SEQ ID NO: 204); CDR-L2 including EVSIRFS (SEQ ID NO: 205); and CDR-L3 including MQSKDFPLT (SEQ ID NO: 206). In some instances, the N332 glycan-dependent antibody may have a heavy chain variable domain including an amino acid sequence having at least 90% sequence identity (e.g., at least 91%, 92%, 93%, 94%, 95%, 96%, 97%, 98%, or 99% sequence identity) to, or the sequence of, SEQ ID NO: 207 and/or a light chain variable domain including an amino acid sequence having at least 90% sequence identity (e.g., at least 91%, 92%, 93%, 94%, 95%, 96%, 97%, 98%, or 99% sequence identity) to, or the sequence of, SEQ ID NO: 208. In a particular instance, the N332 glycan-dependent antibody can be PGT153, or a derivative or clonal relative thereof.

An N332 glycan-dependent antibody for use in any of the methods of the present invention (e.g., curing a subject, e.g., a human, infected with HIV, e.g., HIV-1, or blocking an HIV (e.g., HIV-1) infection in a subject, e.g., a human, at risk of HIV transmission) can include the following six complementarity determining regions (CDRs): CDR-H1 including KYPMY (SEQ ID NO: 209); CDR-H2 including AISADAWHVDYAASVKD (SEQ ID NO: 210); CDR-H3 including NIEEFSVPQFDSWSGRSYYHYFGMDV (SEQ ID NO: 211); CDR-L1 including SSSESLGRGDGRTYLH (SEQ ID NO: 212); CDR-L2 including EVSTRFS (SEQ ID NO: 213); and CDR-L3 including MQSRDFPIT (SEQ ID NO: 214). In some instances, the N332 glycan-dependent antibody may have a heavy chain variable domain including an amino acid sequence having at least 90% sequence identity (e.g., at least 91%, 92%, 93%, 94%, 95%, 96%, 97%, 98%, or 99% sequence identity) to, or the sequence of, SEQ ID NO: 215 and/or a light chain variable domain including an amino acid sequence having at least 90% sequence identity (e.g., at least 91%, 92%, 93%, 94%, 95%, 96%, 97%, 98%, or 99% sequence identity) to, or the sequence of, SEQ ID NO: 216. In a particular instance, the N332 glycan-dependent antibody can be PGT154, or a derivative or clonal relative thereof.

An N332 glycan-dependent antibody for use in any of the methods of the present invention (e.g., curing a subject, e.g., a human, infected with HIV, e.g., HIV-1, or blocking an HIV (e.g., HIV-1) infection in a subject, e.g., a human, at risk of HIV transmission) can include the following six complementarity determining regions (CDRs): CDR-H1 including EYPMY (SEQ ID NO: 217); CDR-H2 including AISADAWHVDYAGSVRG (SEQ ID NO: 218); CDR-H3 including DGEEHKVPQLHSWSGRNLYHYTGFDV (SEQ ID NO: 219); CDR-L1 including KSSQSVRQSDGKTFLY (SEQ ID NO: 220); CDR-L2 including EGSSRFS (SEQ ID NO: 221); and CDR-L3 including LQTKDFPLT (SEQ ID NO: 222). In some instances, the N332 glycan-dependent antibody may have a heavy chain variable domain including an amino acid sequence having at least 90% sequence identity (e.g., at least 91%, 92%, 93%, 94%, 95%, 96%, 97%, 98%, or 99% sequence identity) to, or the sequence of, SEQ ID NO: 223 and/or a light chain variable domain including an amino acid sequence having at least 90% sequence identity (e.g., at least 91%, 92%, 93%, 94%, 95%, 96%, 97%, 98%, or 99% sequence identity) to, or the sequence of, SEQ ID NO: 224. In a particular instance, the N332 glycan-dependent antibody can be PGT155, or a derivative or clonal relative thereof.

An N332 glycan-dependent antibody for use in any of the methods of the present invention (e.g., curing a subject, e.g., a human, infected with HIV, e.g., HIV-1, or blocking an HIV (e.g., HIV-1) infection in a subject, e.g., a human, at risk of HIV transmission) can include the following six complementarity determining regions (CDRs): CDR-H1 including QYPMY (SEQ ID NO: 225); CDR-H2 including AISADAWHVDYPGSVRG (SEQ ID NO: 226); CDR-H3 including DGEEHKVPQLHSWSGRNLYHYTGFDV (SEQ ID NO: 227); CDR-L1 including KSSQTVRQSDGKTFLY (SEQ ID NO: 228); CDR-L2 including EGSNRFS (SEQ ID NO: 229); and CDR-L3 including LQTKDFPLT (SEQ ID NO: 230). In some instances, the N332 glycan-dependent antibody may have a heavy chain variable domain including an amino acid sequence having at least 90% sequence identity (e.g., at least 91%, 92%, 93%, 94%, 95%, 96%, 97%, 98%, or 99% sequence identity) to, or the sequence of, SEQ ID NO: 231 and/or a light chain variable domain including an amino acid sequence having at least 90% sequence identity (e.g., at least 91%, 92%, 93%, 94%, 95%, 96%, 97%, 98%, or 99% sequence identity) to, or the sequence of, SEQ ID NO: 232. In a particular instance, the N332 glycan-dependent antibody can be PGT156, or a derivative or clonal relative thereof.

An N332 glycan-dependent antibody for use in any of the methods of the present invention (e.g., curing a subject, e.g., a human, infected with HIV, e.g., HIV-1, or blocking an HIV (e.g., HIV-1) infection in a subject, e.g., a human, at risk of HIV transmission) can include the following six complementarity determining regions (CDRs): CDR-H1 including QYPMY (SEQ ID NO: 233); CDR-H2 including AISADAWHVDYAGSVRG (SEQ ID NO: 234); CDR-H3 including DGEEHEVPQLHSWSGRNLYHYTGVDI (SEQ ID NO: 235); CDR-L1 including KSSQSLRQSDGKTFLY (SEQ ID NO: 236); CDR-L2 including EASNRFS (SEQ ID NO: 237); and CDR-L3 including MQTKDFPLT (SEQ ID NO: 238). In some instances, the N332 glycan-dependent antibody may have a heavy chain variable domain including an amino acid sequence having at least 90% sequence identity (e.g., at least 91%, 92%, 93%, 94%, 95%, 96%, 97%, 98%, or 99% sequence identity) to, or the sequence of, SEQ ID NO: 239 and/or a light chain variable domain including an amino acid sequence having at least 90% sequence identity (e.g., at least 91%, 92%, 93%, 94%, 95%, 96%, 97%, 98%, or 99% sequence identity) to, or the sequence of, SEQ ID NO: 240. In a particular instance, the N332 glycan-dependent antibody can be PGT157, or a derivative or clonal relative thereof.

An N332 glycan-dependent antibody for use in any of the methods of the present invention (e.g., curing a subject, e.g., a human, infected with HIV, e.g., HIV-1, or blocking an HIV (e.g., HIV-1) infection in a subject, e.g., a human, at risk of HIV transmission) can include the following six complementarity determining regions (CDRs): CDR-H1 including KYPMY (SEQ ID NO: 241); CDR-H2 including AISADAWHVDYPGSVRG (SEQ ID NO: 242); CDR-H3 including DGEEHEVPQLHSWSGRNLYHYTGVDV (SEQ ID NO: 243); CDR-L1 including KSSQSVRQSDG-KTFLY (SEQ ID NO: 244); CDR-L2 including EASKRFS (SEQ ID NO: 245); and CDR-L3 including MQTKDFPLT (SEQ ID NO: 246). In some instances, the N332 glycan-dependent antibody may have a heavy chain variable domain including an amino acid sequence having at least 90% sequence identity (e.g., at least 91%, 92%, 93%, 94%, 95%, 96%, 97%, 98%, or 99% sequence identity) to, or the sequence of, SEQ ID NO: 247 and/or a light chain variable domain including an amino acid sequence having at least 90% sequence identity (e.g., at least 91%, 92%, 93%, 94%, 95%, 96%, 97%, 98%, or 99% sequence identity) to, or the sequence of, SEQ ID NO: 248. In a particular instance, the N332 glycan-dependent antibody can be PGT158, or a derivative or clonal relative thereof.

In some instances, an N332 glycan-dependent antibody for use in any of the methods of the present invention (e.g., curing a subject, e.g., a human, infected with HIV, e.g., HIV-1, or blocking an HIV (e.g., HIV-1) infection in a subject, e.g., a human, at risk of HIV transmission) can be a derivative or clonal relative of a PGT family antibody, such as, without limitation, any of the PGT antibodies disclosed above. For example, the N332 glycan-dependent antibody can include the following six complementarity determining regions (CDRs): CDR-H1 including the sequence of SEQ ID NO: 315; CDR-H2 including the sequence of SEQ ID NO: 316; CDR-H3 including the sequence of SEQ ID NO: 317; CDR-L1 including the sequence of SEQ ID NO: 318; CDR-L2 including the sequence of SEQ ID NO: 319; and CDR-L3 including the sequence of SEQ ID NO: 320. An example of one such antibody may have a heavy chain including an amino acid sequence having at least 90% sequence identity (e.g., at least 91%, 92%, 93%, 94%, 95%, 96%, 97%, 98%, or 99% sequence identity) to, or the sequence of, SEQ ID NO: 313 and/or a light chain including an amino acid sequence having at least 90% sequence identity (e.g., at least 91%, 92%, 93%, 94%, 95%, 96%, 97%, 98%, or 99% sequence identity) to, or the sequence of, SEQ ID NO: 314. In some instances, the N332 glycan-dependent antibody may have a heavy chain variable domain including an amino acid sequence having at least 90% sequence identity (e.g., at least 91%, 92%, 93%, 94%, 95%, 96%, 97%, 98%, or 99% sequence identity) to, or the sequence of, SEQ ID NO: 321 and/or a light chain variable domain including an amino acid sequence having at least 90% sequence identity (e.g., at least 91%, 92%, 93%, 94%, 95%, 96%, 97%, 98%, or 99% sequence identity) to, or the sequence of, SEQ ID NO: 322. In a particular instance, the N332 glycan-dependent antibody can be 10-1074, a clonal relative of PGT121.

Broadly Neutralizing Antibodies (bnAbs)—CD4 Binding Site-Specific Antibodies

In other instances, a method of the invention (e.g., curing a subject, e.g., a human, infected with HIV, e.g., HIV-1, or blocking an HIV (e.g., HIV-1) infection in a subject, e.g., a human, at risk of HIV transmission) may further include administering a second antibody, such as an HIV (e.g., HIV-1)-specific broadly neutralizing antibody (bnAb). A bnAb may, for example, be a CD4 binding site (CD4bs)-specific antibody.

A CD4bs-specific antibody for use in the methods of the invention may, for example, have a light chain including an amino acid sequence having at least 90% sequence identity (e.g., at least 91%, 92%, 93%, 94%, 95%, 96%, 97%, 98%, or 99% sequence identity) to, or the sequence of, SEQ ID NO: 257 and/or a heavy chain including an amino acid sequence having at least 90% sequence identity (e.g., at least 91%, 92%, 93%, 94%, 95%, 96%, 97%, 98%, or 99% sequence identity) to, or the sequence of, SEQ ID NO: 258. In a particular instance, the CD4bs-specific antibody can be 3BNC117.

In other instances, the CD4bs-specific antibody may have a heavy chain variable domain including an amino acid sequence having at least 90% sequence identity (e.g., at least 91%, 92%, 93%, 94%, 95%, 96%, 97%, 98%, or 99% sequence identity) to, or the sequence of, SEQ ID NO: 301 and/or a light chain variable domain including an amino acid sequence having at least 90% sequence identity (e.g., at least 91%, 92%, 93%, 94%, 95%, 96%, 97%, 98%, or 99% sequence identity) to, or the sequence of, SEQ ID NO: 302. In a particular instance, the CD4bs-specific antibody can be b12.

In other instances, the CD4bs-specific antibody may, for example, have a light chain including an amino acid sequence having at least 90% sequence identity (e.g., at least 91%, 92%, 93%, 94%, 95%, 96%, 97%, 98%, or 99% sequence identity) to, or the sequence of, SEQ ID NO: 249 and/or a heavy chain including an amino acid sequence having at least 90% sequence identity (e.g., at least 91%, 92%, 93%, 94%, 95%, 96%, 97%, 98%, or 99% sequence identity) to, or the sequence of, SEQ ID NO: 250. In a particular instance, the CD4bs-specific antibody can be VRC01.

In other instances, the CD4bs-specific antibody may, for example, have a light chain including an amino acid sequence having at least 90% sequence identity (e.g., at least 91%, 92%, 93%, 94%, 95%, 96%, 97%, 98%, or 99% sequence identity) to, or the sequence of, SEQ ID NO: 251 and/or a heavy chain including an amino acid sequence having at least 90% sequence identity (e.g., at least 91%, 92%, 93%, 94%, 95%, 96%, 97%, 98%, or 99% sequence identity) to, or the sequence of, SEQ ID NO: 252. In a particular instance, the CD4bs-specific antibody can be VRC02.

In other instances, the CD4bs-specific antibody may, for example, have a light chain including an amino acid sequence having at least 90% sequence identity (e.g., at least 91%, 92%, 93%, 94%, 95%, 96%, 97%, 98%, or 99% sequence identity) to, or the sequence of, SEQ ID NO: 253 and/or a heavy chain including an amino acid sequence having at least 90% sequence identity (e.g., at least 91%, 92%, 93%, 94%, 95%, 96%, 97%, 98%, or 99% sequence identity) to, or the sequence of, SEQ ID NO: 254. In a particular instance, the CD4bs-specific antibody can be NIH-45-46.

In other instances, the CD4bs-specific antibody may, for example, have a light chain including an amino acid sequence having at least 90% sequence identity (e.g., at least 91%, 92%, 93%, 94%, 95%, 96%, 97%, 98%, or 99% sequence identity) to, or the sequence of, SEQ ID NO: 255 and/or a heavy chain including an amino acid sequence having at least 90% sequence identity (e.g., at least 91%, 92%, 93%, 94%, 95%, 96%, 97%, 98%, or 99% sequence identity) to, or the sequence of, SEQ ID NO: 256. In a particular instance, the CD4bs-specific antibody can be 3BNC60.

In other instances, the CD4bs-specific antibody may, for example, have a light chain including an amino acid sequence having at least 90% sequence identity (e.g., at least 91%, 92%, 93%, 94%, 95%, 96%, 97%, 98%, or 99% sequence identity) to, or the sequence of, SEQ ID NO: 259 and/or a heavy chain including an amino acid sequence having at least 90% sequence identity (e.g., at least 91%, 92%, 93%, 94%, 95%, 96%, 97%, 98%, or 99% sequence identity) to, or the sequence of, SEQ ID NO: 260. In a particular instance, the CD4bs-specific antibody can be 3BNC62.

In other instances, the CD4bs-specific antibody may, for example, have a light chain including an amino acid sequence having at least 90% sequence identity (e.g., at least 91%, 92%, 93%, 94%, 95%, 96%, 97%, 98%, or 99% sequence identity) to, or the sequence of, SEQ ID NO: 261 and/or a heavy chain including an amino acid sequence having at least 90% sequence identity (e.g., at least 91%, 92%, 93%, 94%, 95%, 96%, 97%, 98%, or 99% sequence identity) to, or the sequence of, SEQ ID NO: 262. In a particular instance, the CD4bs-specific antibody can be 3BNC95.

In other instances, the CD4bs-specific antibody may, for example, have a light chain including an amino acid sequence having at least 90% sequence identity (e.g., at least 91%, 92%, 93%, 94%, 95%, 96%, 97%, 98%, or 99% sequence identity) to, or the sequence of, SEQ ID NO: 263 and/or a heavy chain including an amino acid sequence having at least 90% sequence identity (e.g., at least 91%, 92%, 93%, 94%, 95%, 96%, 97%, 98%, or 99% sequence identity) to, or the sequence of, SEQ ID NO: 264. In a particular instance, the CD4bs-specific antibody can be 3BNC176.

In other instances, the CD4bs-specific antibody may, for example, have a light chain including an amino acid sequence having at least 90% sequence identity (e.g., at least 91%, 92%, 93%, 94%, 95%, 96%, 97%, 98%, or 99% sequence identity) to, or the sequence of, SEQ ID NO: 265 and/or a heavy chain including an amino acid sequence having at least 90% sequence identity (e.g., at least 91%, 92%, 93%, 94%, 95%, 96%, 97%, 98%, or 99% sequence identity) to, or the sequence of, SEQ ID NO: 266. In a particular instance, the CD4bs-specific antibody can be 12A12.

In other instances, the CD4bs-specific antibody may, for example, have a light chain including an amino acid sequence having at least 90% sequence identity (e.g., at least 91%, 92%, 93%, 94%, 95%, 96%, 97%, 98%, or 99% sequence identity) to, or the sequence of, SEQ ID NO: 267 and/or a heavy chain including an amino acid sequence having at least 90% sequence identity (e.g., at least 91%, 92%, 93%, 94%, 95%, 96%, 97%, 98%, or 99% sequence identity) to, or the sequence of, SEQ ID NO: 268. In a particular instance, the CD4bs-specific antibody can be VRC-PG04.

In other instances, the CD4bs-specific antibody may, for example, have a light chain including an amino acid sequence having at least 90% sequence identity (e.g., at least 91%, 92%, 93%, 94%, 95%, 96%, 97%, 98%, or 99% sequence identity) to, or the sequence of, SEQ ID NO: 269 and/or a heavy chain including an amino acid sequence having at least 90% sequence identity (e.g., at least 91%, 92%, 93%, 94%, 95%, 96%, 97%, 98%, or 99% sequence identity) to, or the sequence of, SEQ ID NO: 270. In a particular instance, the CD4bs-specific antibody can be VRC-CH30.

In other instances, the CD4bs-specific antibody may, for example, have a light chain including an amino acid sequence having at least 90% sequence identity (e.g., at least 91%, 92%, 93%, 94%, 95%, 96%, 97%, 98%, or 99% sequence identity) to, or the sequence of, SEQ ID NO: 271 and/or a heavy chain including an amino acid sequence having at least 90% sequence identity (e.g., at least 91%, 92%, 93%, 94%, 95%, 96%, 97%, 98%, or 99% sequence identity) to, or the sequence of, SEQ ID NO: 272. In a particular instance, the CD4bs-specific antibody can be VRC-CH31.

In other instances, the CD4bs-specific antibody may, for example, have a light chain including an amino acid sequence having at least 90% sequence identity (e.g., at least 91%, 92%, 93%, 94%, 95%, 96%, 97%, 98%, or 99% sequence identity) to, or the sequence of, SEQ ID NO: 273 and/or a heavy chain including an amino acid sequence having at least 90% sequence identity (e.g., at least 91%, 92%, 93%, 94%, 95%, 96%, 97%, 98%, or 99% sequence identity) to, or the sequence of, SEQ ID NO: 274. In a particular instance, the CD4bs-specific antibody can be VRC-CH32.

In other instances, the CD4bs-specific antibody may, for example, have a light chain including an amino acid sequence having at least 90% sequence identity (e.g., at least 91%, 92%, 93%, 94%, 95%, 96%, 97%, 98%, or 99% sequence identity) to, or the sequence of, SEQ ID NO: 275 and/or a heavy chain including an amino acid sequence having at least 90% sequence identity (e.g., at least 91%, 92%, 93%, 94%, 95%, 96%, 97%, 98%, or 99% sequence identity) to, or the sequence of, SEQ ID NO: 276. In a particular instance, the CD4bs-specific antibody can be VRC-CH33.

In other instances, the CD4bs-specific antibody may, for example, have a light chain including an amino acid sequence having at least 90% sequence identity (e.g., at least 91%, 92%, 93%, 94%, 95%, 96%, 97%, 98%, or 99% sequence identity) to, or the sequence of, SEQ ID NO: 277 and/or a heavy chain including an amino acid sequence having at least 90% sequence identity (e.g., at least 91%, 92%, 93%, 94%, 95%, 96%, 97%, 98%, or 99% sequence identity) to, or the sequence of, SEQ ID NO: 278. In a particular instance, the CD4bs-specific antibody can be VRC-CH34.

In other instances, the CD4bs-specific antibody may, for example, have a light chain including an amino acid sequence having at least 90% sequence identity (e.g., at least 91%, 92%, 93%, 94%, 95%, 96%, 97%, 98%, or 99% sequence identity) to, or the sequence of, SEQ ID NO: 279 and/or a heavy chain including an amino acid sequence having at least 90% sequence identity (e.g., at least 91%, 92%, 93%, 94%, 95%, 96%, 97%, 98%, or 99% sequence identity) to, or the sequence of, SEQ ID NO: 280. In a particular instance, the CD4bs-specific antibody can be VRC03.

In other instances, the CD4bs-specific antibody may, for example, have a light chain including an amino acid sequence having at least 90% sequence identity (e.g., at least 91%, 92%, 93%, 94%, 95%, 96%, 97%, 98%, or 99% sequence identity) to, or the sequence of, SEQ ID NO: 281 and/or a heavy chain including an amino acid sequence having at least 90% sequence identity (e.g., at least 91%, 92%, 93%, 94%, 95%, 96%, 97%, 98%, or 99% sequence identity) to, or the sequence of, SEQ ID NO: 282. In a particular instance, the CD4bs-specific antibody can be 3BNC55.

In other instances, the CD4bs-specific antibody may, for example, have a light chain including an amino acid sequence having at least 90% sequence identity (e.g., at least 91%, 92%, 93%, 94%, 95%, 96%, 97%, 98%, or 99% sequence identity) to, or the sequence of, SEQ ID NO: 283 and/or a heavy chain including an amino acid sequence having at least 90% sequence identity (e.g., at least 91%, 92%, 93%, 94%, 95%, 96%, 97%, 98%, or 99% sequence identity) to, or the sequence of, SEQ ID NO: 284. In a particular instance, the CD4bs-specific antibody can be 3BNC91.

In other instances, the CD4bs-specific antibody may, for example, have a light chain including an amino acid sequence having at least 90% sequence identity (e.g., at least 91%, 92%, 93%, 94%, 95%, 96%, 97%, 98%, or 99% sequence identity) to, or the sequence of, SEQ ID NO: 285 and/or a heavy chain including an amino acid sequence having at least 90% sequence identity (e.g., at least 91%, 92%, 93%, 94%, 95%, 96%, 97%, 98%, or 99% sequence identity) to, or the sequence of, SEQ ID NO: 286. In a particular instance, the CD4bs-specific antibody can be 3BNC104.

In other instances, the CD4bs-specific antibody may, for example, have a light chain including an amino acid sequence having at least 90% sequence identity (e.g., at least 91%, 92%, 93%, 94%, 95%, 96%, 97%, 98%, or 99% sequence identity) to, or the sequence of, SEQ ID NO: 287 and/or a heavy chain including an amino acid sequence having at least 90% sequence identity (e.g., at least 91%, 92%, 93%, 94%, 95%, 96%, 97%, 98%, or 99% sequence identity) to, or the sequence of, SEQ ID NO: 288. In a particular instance, the CD4bs-specific antibody can be 3BNC89.

In other instances, the CD4bs-specific antibody may, for example, have a light chain including an amino acid sequence having at least 90% sequence identity (e.g., at least 91%, 92%, 93%, 94%, 95%, 96%, 97%, 98%, or 99% sequence identity) to, or the sequence of, SEQ ID NO: 289 and/or a heavy chain including an amino acid sequence having at least 90% sequence identity (e.g., at least 91%, 92%, 93%, 94%, 95%, 96%, 97%, 98%, or 99% sequence identity) to, or the sequence of, SEQ ID NO: 290. In a particular instance, the CD4bs-specific antibody can be 12A21.

In other instances, the CD4bs-specific antibody may, for example, have a light chain including an amino acid sequence having at least 90% sequence identity (e.g., at least 91%, 92%, 93%, 94%, 95%, 96%, 97%, 98%, or 99% sequence identity) to, or the sequence of, SEQ ID NO: 291 and/or a heavy chain including an amino acid sequence having at least 90% sequence identity (e.g., at least 91%, 92%, 93%, 94%, 95%, 96%, 97%, 98%, or 99% sequence identity) to, or the sequence of, SEQ ID NO: 292. In a particular instance, the CD4bs-specific antibody can be VRC-PG04b.

In other instances, the CD4bs-specific antibody may, for example, have a light chain including an amino acid sequence having at least 90% sequence identity (e.g., at least 91%, 92%, 93%, 94%, 95%, 96%, 97%, 98%, or 99% sequence identity) to, or the sequence of, SEQ ID NO: 293 and/or a heavy chain including an amino acid sequence having at least 90% sequence identity (e.g., at least 91%, 92%, 93%, 94%, 95%, 96%, 97%, 98%, or 99% sequence identity) to, or the sequence of, SEQ ID NO: 294. In a particular instance, the CD4bs-specific antibody can be VRC03HC-VRC01LC.

In other instances, the CD4bs-specific antibody may, for example, have a light chain including an amino acid sequence having at least 90% sequence identity (e.g., at least 91%, 92%, 93%, 94%, 95%, 96%, 97%, 98%, or 99% sequence identity) to, or the sequence of, SEQ ID NO: 295 and/or a heavy chain including an amino acid sequence having at least 90% sequence identity (e.g., at least 91%, 92%, 93%, 94%, 95%, 96%, 97%, 98%, or 99% sequence identity) to, or the sequence of, SEQ ID NO: 296. In a particular instance, the CD4bs-specific antibody can be VRC01HC/VRC03LC.

In other instances, the CD4bs-specific antibody may, for example, have a light chain including an amino acid sequence having at least 90% sequence identity (e.g., at least 91%, 92%, 93%, 94%, 95%, 96%, 97%, 98%, or 99% sequence identity) to, or the sequence of, SEQ ID NO: 297 and/or a heavy chain including an amino acid sequence having at least 90% sequence identity (e.g., at least 91%, 92%, 93%, 94%, 95%, 96%, 97%, 98%, or 99% sequence identity) to, or the sequence of, SEQ ID NO: 298. In a particular instance, the CD4bs-specific antibody can be gVRC-H5(d74)VRC-PG04LC.

In other instances, the CD4bs-specific antibody may, for example, have a light chain including an amino acid sequence having at least 90% sequence identity (e.g., at least 91%, 92%, 93%, 94%, 95%, 96%, 97%, 98%, or 99% sequence identity) to, or the sequence of, SEQ ID NO: 299 and/or a heavy chain including an amino acid sequence having at least 90% sequence identity (e.g., at least 91%, 92%, 93%, 94%, 95%, 96%, 97%, 98%, or 99% sequence identity) to, or the sequence of, SEQ ID NO: 300. In a particular instance, the CD4bs-specific antibody can be gVRC0H12(D74)/VRC-PG04LC.

One or more of the above CD4bs-specific antibodies may be administered according to the methods of the invention, in addition to an N332 glycan-dependent antibody (e.g., PGT121), either alone, prior to, and/or subsequent to administration of the N332 glycan-dependent antibody to the subject (e.g., human).

II. Antiretroviral Therapies (ARTs) for Use in the Methods of the Invention

In other instances, a method of the invention (e.g., curing a subject, e.g., a human, infected with HIV, e.g., HIV-1, or blocking an HIV (e.g., HIV-1) infection in a subject, e.g., a human, at risk of HIV transmission) may further include administering one or more (e.g., 2, 3, 4, 5, 6, 7, 8, 9, 10, or more) antiretroviral therapy (ARTs), such as, without limitation, any one or more ARTs set forth in Table 1 below.

TABLE 1

Antiretroviral Therapies

| Generic Name (Brand Name) | Class |
| --- | --- |
| efavirenz, emtricitabine and tenofovir disoproxil fumarate (Atripla) | Multi-class |
| emtricitabine, rilpivirine, and tenofovir disoproxil fumarate (Complera) | Multi-class |
| elvitegravir, cobicistat, emtricitabine, tenofovir disoproxil fumarate (Stribild) | Multi-class |
| lamivudine and zidovudine (Combivir) | NRTI |
| emtricitabine, FTC (Emtriva) | NRTI |
| lamivudine, 3TC (Epivir) | NRTI |
| abacavir and lamivudine (Ebzicom) | NRTI |
| zalcitabine, dideoxycytidine, ddC (Hivid) | NRTI |
| zidovudine, azidothymidine, AZT, ZDV (Retrovir) | NRTI |
| abacavir, zidovudine, and lamivudine (Trizivir) | NRTI |
| tenofovir disoproxil fumarate and emtricitabine (Truvada) | NRTI |
| enteric coated didanosine, ddI EC (Videx EC) | NRTI |
| didanosine, dideoxyinosine, ddI (Videx) | NRTI |
| tenofovir disoproxil fumarate, TDF (Viread) | NRTI |
| stavudine, d4T (Zerit) | NRTI |
| abacavir sulfate, ABC (Ziagen) | NRTI |
| Rilpivirine (Edurant) | NNRTI |
| Etravirine (Intelence) | NNRTI |
| delavirdine, DLV (Rescriptor) | NNRTI |
| efavirenz, EFV (Sustiva) | NNRTI |
| nevirapine, NVP (Viramune) | NNRTI |
| nevirapine, NVP (Viramune XR) | NNRTI |
| amprenavir, APV (Agenerase) | PI |
| tipranavir, TPV (Aptivus) | PI |
| indinavir, IDV (Crixivan) | PI |
| saquinavir (Fortovase) | PI |
| saquinavir mesylate, SQV (Invirase) | PI |
| lopinavir and ritonavir, LPV/RTV (Kaletra) | PI |
| Fosamprenavir Calcium, FOS-APV (Lexiva) | PI |
| ritonavir, RTV (Norvir) | PI |
| Darunavir (Prezista) | PI |
| atazanavir sulfate, ATV (Reyataz) | PI |
| nelfinavir mesylate, NFV (Viracept) | PI |
| enfuvirtide, T-20 (Fuzeon) | Fusion Inhibitor |
| maraviroc (Selzentry) | Entry Inhibitor - CCR5 co-receptor antagonist |
| raltegravir (Isentress) | HIV integrase strand transfer inhibitors |
| dolutegravir (Tivicay) | HIV integrase strand transfer inhibitors |

One or more of the above ARTs may be administered according to the methods of the invention, in addition to an N332 glycan-dependent antibody (e.g., PGT121) and, optionally, a CD4bs-specific antibody (e.g., 3BNC117 or VRC07-523) and/or a V2 glycan-dependent antibody (e.g., CAP256-VRC26), either alone, prior to, and/or subsequent to administration of the N332 glycan-dependent antibody to the subject (e.g., human).

III. Immunomodulators for Use in the Methods of the Invention

In other instances, a method of the invention (e.g., curing a subject, e.g., a human, infected with HIV, e.g., HIV-1, or blocking an HIV (e.g., HIV-1) infection in a subject, e.g., a human, at risk of HIV transmission) may further include administering one or more (e.g., 2, 3, 4, 5, 6, 7, 8, 9, 10, or more) immunomodulators, such as, without limitation, any one or more immunomodulators set forth in Table 2 below.

TABLE 2

Exemplary Immunomodulators for HIV Therapy
Drug Name

AS-101
Bropirimine
Acemannan
CL246,738
EL10
FP-21399
Gamma Interferon
Granulocyte Macrophage Colony Stimulating Factor
HIV Core Particle Immunostimulant
Interleukin-2 (IL-2)
Immune Globulin Intravenous (human)
IMREG-1
IMREG-2
Imuthiol Diethyl Dithio Carbamate
Alpha-2 Interferon
Methionine-Enkephalin
MTP-PE Muramyl-Tripeptide
Granulocyte Colony Stimulating Factor
REMUNE ™
rCD4-IgG hybrids
Recombinant Soluble Human CD4
SK&F106528 Soluble T4
Thymopentin
Tumor Necrosis Factor
Infliximab One or more of the above immunomodulators may be administered according to the methods of the invention, in addition to an N332 glycan-dependent antibody (e.g., PGT121) and, optionally, one or more (e.g., 1, 2, 3, 4, or 5 or more) bnAbs (e.g., a CD4bs-specific antibody, e.g., 3BNC117 or VRC07-523; and/or with a V2 glycan-dependent antibody, e.g., CAP256-VRC26) and/or one or more (e.g., 1, 2, 3, 4, or 5 or more) ARTs, either alone, prior to, concurrently with, and/or subsequent to administration of the N332 glycan-dependent antibody to the subject (e.g., human).

IV. Therapeutic Methods of the Invention

The invention relates to methods of antibody therapy for HIV. In particular, the invention features methods of curing a subject (e.g., a human) infected with HIV (e.g., HIV-1), wherein the methods include administering to the subject an N332 glycan-dependent antibody (e.g., one or more of the N332 glycan-dependent antibodies described hereinabove), thereby curing the subject. These methods are supported by the unprecedented and unexpected findings that a single administration of an N332 glycan-dependent antibody (e.g., PGT121) alone, in an antibody cocktail (e.g., with, e.g., a CD4bs-specific antibody, e.g., 3BNC117 or VRC07-523; and/or with a V2 glycan-dependent antibody, e.g., CAP256-VRC26), or as part of a therapeutic regimen including a second or more antibodies and/or one or more ARTs, in rhesus monkeys chronically infected with the highly pathogenic virus SHIV-SF162P3 can result, in some instances, in long-term virologic control (e.g., undetectable proviral DNA level in tissue (e.g., lymph node tissue, gastrointestinal tissue, and/or peripheral blood), such as below about 1,000 DNA copies/$10^6$ cells (e.g., below about 100 DNA copies/$10^6$ cells, e.g., below about 10 DNA copies/$10^6$ cells, e.g., below about 1 DNA copy/$10^6$ cells), and/or undetectable plasma viral load, such as less than 3,500 RNA copies/ml (e.g., less than 2,000 RNA copies/ml, e.g., less than 400 RNA copies/ml, e.g., less than 50 RNA copies/ml, e.g., less than 1 RNA copy/ml).

The invention also features methods of blocking an HIV (e.g., HIV-1) infection in a subject (e.g., a human) at risk of HIV transmission. For example, in one aspect, the subject may be a fetus of an HIV-infected pregnant female and the method includes administering to the HIV-infected pregnant female an N332 glycan-dependent antibody (e.g., one or more of the N332 glycan-dependent antibodies described hereinabove), thereby blocking the HIV infection in the fetus. In other instances, the subject is a newborn having an HIV-infected mother, a subject at risk of HIV transmission following a needlestick injury, or a subject at risk of HIV transmission following a sexual exposure to an HIV-infected individual. These methods are also supported by the unprecedented and unexpected findings that a single administration of an N332 glycan-dependent antibody (e.g., PGT121) alone, in an antibody cocktail (e.g., with, e.g., a CD4bs-specific antibody, e.g., 3BNC117 or VRC07-523; and/or with a V2 glycan-dependent antibody, e.g., CAP256-VRC26), or as part of a therapeutic regimen including a second or more antibodies and/or one or more ARTs, in rhesus monkeys chronically infected with the highly pathogenic virus SHIV-SF162P3 can result in the unexpectedly rapid and potent reduction in proviral DNA level in tissue and/or plasma viral load and, in some instances, in long-term virologic control.

In instances when the subject is a fetus of an HIV-infected pregnant female, the HIV-infected pregnant female can be administered the N332 glycan-dependent antibody (e.g., PGT121) following manifestation of one or more symptoms associated with pregnancy (e.g., a missed period, tender or swollen breasts, nausea with or without vomiting, increased urination, fatigue, and/or uncharacteristic food aversions or cravings), following a diagnosis of pregnancy, and/or in the third trimester of pregnancy, in order to block an HIV infection in the fetus.

In instances when the subject is a newborn having an HIV-infected mother, the newborn can be administered the N332 glycan-dependent antibody (e.g., PGT121) peripartum and/or postpartum, for example, prior to, during, and/or following breastfeeding from the HIV-infected mother, in order to block an HIV infection in the newborn.

In instances when the subject is at risk of HIV transmission following a needlestick injury, the subject can be administered the N332 glycan-dependent antibody (e.g., PGT121) less than 3 days following the needlestick injury, for example, 1, 2, 3, 4, 5, 6, 7, 8, 9, 10, 15, 20, 30, 35, 40, 45, 50, 55, or 60 minutes, 2, 4, 6, 10, 15, or 24 hours, 1.5, 2, or 2.5 days following the needlestick injury, in order to block an HIV infection in the subject. Alternatively, or additionally, the subject can be administered the N332 glycan-dependent antibody (e.g., PGT121) between 3 to 14 days following the needlestick injury, for example, 3, 4, 5, 6, 7, 8, 9, 10, 11, 12, 13, or 14 days following the needlestick injury, in order to block an HIV infection in the subject.

In instances when the subject is at risk of HIV transmission following a sexual exposure to an HIV-infected individual, the subject can be administered the N332 glycan-dependent antibody (e.g., PGT121) less than 3 days following the sexual exposure, for example, 1, 2, 3, 4, 5, 6, 7, 8, 9, 10, 15, 20, 30, 35, 40, 45, 50, 55, or 60 minutes, 2, 4, 6, 10, 15, or 24 hours, 1.5, 2, or 2.5 days following the sexual exposure, in order to block an HIV infection in the subject. Alternatively, or additionally, the subject can be administered the N332 glycan-dependent antibody (e.g., PGT121) between 3 to 14 days following the sexual exposure, for example, 3, 4, 5, 6, 7, 8, 9, 10, 11, 12, 13, or 14 days following the sexual exposure, in order to block an HIV infection in the subject.

In any of the methods of antibody therapy described above, the subject can have an undetectable plasma viral load, such as less than 3,500 RNA copies/ml (e.g., less than 2,000 RNA copies/ml, e.g., less than 400 RNA copies/ml, e.g., less than 50 RNA copies/ml, e.g., less than 1 RNA copy/ml), prior to commencement of antibody therapy. In such instances, the subject may already be on ART. However, ART alone, in contrast to N332 glycan-dependent antibody therapy, is unable to reduce tissue reservoirs of the virus. Accordingly, the methods of the invention feature administration of an N332 glycan-dependent antibody (e.g., PGT121), alone or in combination with ART and/or a second antibody (e.g., a CD4 binding site (CD4bs)-specific antibody, e.g., 3BNC117 or VRC07-523; and/or a V2 glycan-dependent antibody, e.g., CAP256-VRC26), as described in detail below, to cure a subject (e.g., a human) infected with HIV (e.g., HIV-1) or block an HIV infection in a subject at risk of HIV transmission, based, at least in part, on the unprecedented finding that N332 glycan-dependent antibody therapy is capable of rapidly reducing proviral DNA levels in tissue as well as plasma viral loads following treatment. Preferably, the subject either maintains or achieves an undetectable plasma viral load for at least about 2 months (e.g., at least about 3, 4, 5, 6, 7, 8, 9, 10, or 11 months, or 1, 2, 3, 4, 5, 6, 7, 8, 9, 10, 11, 12, 13, 14, 15, 16, 17, 18, 19, or 20 years) following administration of the N332 glycan-dependent antibody (e.g., PGT121).

In any of the methods described above, further administration of an immunomodulator (e.g., an agent, such as a protein or peptide, which is capable of increasing, inducing, or extending an immune response, e.g., a cell-mediated immune response and/or a humoral immune response, when administered to a subject, e.g., a human, e.g., a human infected with HIV or at risk of an HIV infection or transmission) is contemplated. For example, one or more immunomodulators (e.g., 1, 2, 3, 4, or 5 or more immunomodulators) can be administered in conjunction with, e.g., prior to, concurrently with, subsequent to, or within the context of a treatment regimen that includes administration of, an N332 glycan-dependent antibody (e.g., PGT121).

As described below in more detail, in any of the methods described above, the HIV therapy (e.g., HIV-1 therapy) may be concluded following administration of at least one dose (e.g., 1, 2, 3, 4, or more doses) of the N332 glycan-dependent antibody (e.g., PGT121), alone or in combination with a second antibody (e.g., a bnAb, e.g., a CD4bs-specific antibody, e.g., 3BNC117 or VRC07-523; and/or a V2 glycan-dependent antibody, e.g., CAP256-VRC26) or, optionally, more antibodies (e.g., a second and a third antibody), one or more (e.g., 1, 2, 3, 4, or 5 or more) ARTs, and/or one or more (e.g., 1, 2, 3, 4, or 5 or more) immunomodulators, following a duration of time post-therapy (e.g., at least two months or longer). In particular embodiments, the HIV-1 therapy is concluded following the administration of the third antibody subsequent to the second regimen of said N332 glycan-dependent antibody. The subject (e.g., a human infected with HIV or at risk of HIV transmission) can be monitored post-therapy to confirm that they exhibit and/or maintain virologic control in the absence of any intervening therapies, which, optionally, can be determined based upon measurements made from a biological sample of the subject (e.g., a measurement of proviral DNA level in a tissue and/or plasma viral load). If the subject exhibits and/or maintains virologic control during this post-therapy period, the subject may be taken off one or more, or all, HIV therapies indefinitely or until such time as the subject begins to exhibit loss of virologic control.

V. Methods of Administration and Dosage

For any of the methods of the invention describe above, the one or more (e.g., 1, 2, 3, 4, or 5 or more) N332 glycan-dependent antibody will be formulated, dosed, and administered in a fashion consistent with good medical practice. Antibody therapy according to the invention may be performed alone or in conjunction with another therapy, and may be provided at home, the doctor's office, a clinic, a hospital's outpatient department, or a hospital. Antibody therapy optionally begins at a hospital so that the doctor can observe the therapy's effects closely and make any adjustments that are needed, or it may begin on an outpatient basis.

The dosage administered depends on the subject to be treated (e.g., the age, body weight, capacity of the immune system, and general health of the subject being treated), the form of administration (e.g., as a solid or liquid), the manner of administration (e.g., by injection, inhalation, dry powder propellant), and the cells targeted (e.g., mucosal cells, epithelial cells, such as blood vessel epithelial cells, nasal epithelial cells, or pulmonary epithelial cells). Additionally, pharmacogenomic (the effect of genotype on the pharmacokinetic, pharmacodynamic, or efficacy profile of a therapeutic) information about a particular subject may affect the dosage used. Antibody therapy of the invention is preferably administered in an amount that provides a sufficient level of the antibody (e.g., N332 glycan-dependent antibody) to yield a therapeutic effect in the subject without undue adverse physiological effects caused by treatment.

The N332 glycan-dependent antibody can be administered to a subject (e.g., a human infected with HIV and/or at risk of HIV transmission) intramuscularly, intravenously, intradermally, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subcutaneously, subconjunctival, intravesicularly, mucosally, intrapericardially, intraumbilically, intraocularally, orally, topically, locally, by inhalation, by injection, by infusion, by continuous infusion, by localized perfusion bathing target cells directly, by catheter, by lavage, in cremes, or in lipid compositions, in accord with known methods. For example, the N332 glycan-dependent antibody can be administered by infusion, such as by continuous infusion, mucosally or subcutaneously. Alternatively, it is envisioned that the N332 glycan-dependent antibody may be delivered by gene therapy.

For any of the methods described above, a single dose of the N332 glycan-dependent antibody can be administered to the subject. The single dose may be of a single N332 glycan-dependent antibody (e.g., PGT121) or of more than one antibody (i.e., an antibody cocktail including an N332 glycan-dependent antibody, such as PGT121). In some instances, HIV therapy (e.g., HIV-1 therapy) may be concluded following the administration of the single dose of the N332 glycan-dependent antibody. In some instances, the single dose may be administered along with one or more (e.g., 1, 2, 3, 4, or 5 or more) ARTs, such as one or more of the ARTs listed in Table 1 above, wherein the ART is administered concurrently, prior to, and/or subsequent to the single dose of the N332 glycan-dependent antibody. Accordingly, HIV therapy can, in some instances, be concluded following the administration of the ART subsequent to the single dose of the N332 glycan-dependent antibody. Alternatively, or additionally, the single dose may be administered along with a second antibody (and, optionally, more, e.g., a second and a third antibody), wherein the second antibody is an HIV (e.g., HIV-1)-specific, broadly neutralizing antibody (bnAb), such as any one of the CD4 binding site (CD4bs)-specific antibodies described above (e.g., 3BNC117 or VRC07-523) and/or any one of the V2 glycan-dependent antibodies described above (e.g., CAP256-VRC26). Accordingly, HIV therapy can, in some instances, be concluded following the administration of the second antibody (e.g., 3BNC117, VRC07-523, or CAP256-VRC26) subsequent to the single dose of the N332 glycan-dependent antibody.

In other instances, the method can include administering a first regimen including one or more doses (e.g., 1, 2, 3, 4, 5, 6, or more doses) of the N332 glycan-dependent antibody (e.g., PGT121) and a second regimen including one or more doses (e.g., 1, 2, 3, 4, 5, 6, or more doses) of the N332 glycan-dependent antibody, wherein the second regimen is administered at least about 2 months (e.g., at least about 3, 4, 5, 6, 7, 8, 9, 10, or 11 months, or 1, 2, 3, 4, 5, 6, 7, 8, 9, 10, 11, 12, 13, 14, 15, 16, 17, 18, 19, or 20 years) after the first regimen. The duration of time between the first and second regimens is preferably a longer duration of time than necessary for viral rebound to occur in a subject (e.g., a human) infected with HIV (e.g., HIV-1) under current standard of care (e.g., ART), which is approximately two months. Thus, the second regimen of N332 glycan-dependent antibody can be considered a maintenance dose, and in some instances, HIV therapy may be concluded following the administration of the second regimen of the N332 glycan-dependent antibody. In some instances, the method can further include administering one or more (e.g., 1, 2, 3, 4, or 5 or more) ART, such as one or more of the ARTs listed in Table 1 above, wherein the ART is administered concurrently, prior to, and/or subsequent to the first regimen and/or the second regimen of the N332 glycan-dependent antibody. Accordingly, HIV therapy can, in some instances, be concluded following the administration of the ART subsequent to the second regimen of the N332 glycan-dependent antibody. Alternatively, or additionally, the first and second regimens may be administered along with a second antibody (and, optionally, more, e.g., a second and a third antibody), wherein the second antibody is an HIV (e.g., HIV-1)-specific, broadly neutralizing antibody (bnAb), such as any one of the CD4 binding site (CD4bs)-specific antibodies described above (e.g., 3BNC117 or VRC07-523) and/or any one of the V2 glycan-dependent antibodies described above (e.g., CAP256-VRC26). Accordingly, HIV therapy can, in some instances, be concluded following the administration of the second antibody (e.g., 3BNC117, VRC07-523, or CAP256-VRC26) subsequent to second regimen of the N332 glycan-dependent antibody.

For any of the methods described above, a single dose of the N332 glycan-dependent antibody can be administered to the subject at a concentration of about 0.01 mg/kg to about 20 mg/kg, e.g., about 0.1 mg/kg to about 10 mg/kg, e.g., about 1 mg/kg to about 10 mg/kg, e.g., about 10 mg/kg.

In some of the methods of the invention, HIV (e.g., HIV-1) therapy is concluded following a determination that the proviral DNA level in tissue of the subject (as assessed, e.g., by biopsy) is reduced to an undetectable level. The method can result in a reduction of proviral DNA level in tissue of the subject relative to an amount of proviral DNA level in tissue of the subject before the administration of the N332 glycan-dependent antibody (e.g., PGT121). For example, the proviral DNA level in tissue (e.g., lymph node tissue, gastrointestinal tissue, and/or peripheral blood) may be reduced to an undetectable level, such as below about 1,000 DNA copies/$10^6$ cells (e.g., below about 100 DNA copies/$10^6$ cells, e.g., below about 10 DNA copies/$10^6$ cells, e.g., below about 1 DNA copy/10$^6$ cells). Thus, a definitive end to HIV therapy can be determined based upon measurements made from a biological sample of the subject and/or time post-administration of the N332 glycan-dependent antibody (e.g., PGT121).

According to any one of the methods of the invention described herein, the N332 glycan-dependent antibody (e.g., PGT121) can be administered as a pharmaceutical composition. The pharmaceutical composition may be formulated to release the N332 glycan-dependent antibody immediately upon administration (e.g., targeted delivery) or at any predetermined time period after administration using controlled or extended release formulations. Administration of the pharmaceutical composition in controlled or extended release formulations is useful where the composition, either alone or in combination, has (i) a narrow therapeutic index (e.g., the difference between the plasma concentration leading to harmful side effects or toxic reactions and the plasma concentration leading to a therapeutic effect is small; generally, the therapeutic index, TI, is defined as the ratio of median lethal dose (LD$_{50}$) to median effective dose (ED$_{50}$)); (ii) a narrow absorption window at the site of release (e.g., the gastro-intestinal tract); or (iii) a short biological half-life, so that frequent dosing during a day is required in order to sustain a therapeutic level.

Many strategies can be pursued to obtain controlled or extended release in which the rate of release outweighs the rate of metabolism of the pharmaceutical composition. For example, controlled release can be obtained by the appropriate selection of formulation parameters and ingredients, including, e.g., appropriate controlled release compositions and coatings. Suitable formulations are known to those of skill in the art. Examples include single or multiple unit tablet or capsule compositions, oil solutions, suspensions, emulsions, microcapsules, microspheres, nanoparticles, patches, and liposomes.

The pharmaceutical compositions may be sterilized by conventional sterilization techniques, or may be sterile filtered. The resulting aqueous solutions may be packaged for use as is or lyophilized. The lyophilized preparation may be administered in powder form or combined with a sterile aqueous carrier prior to administration. The pH of the preparations typically will be between 3 and 11, more preferably between 5 and 9 or between 6 and 8, and most preferably between 7 and 8, such as 7 to 7.5. The resulting pharmaceutical compositions in solid form may, for example, be packaged in multiple single-dose units, each containing a fixed amount of the N332 glycan-dependent antibody (e.g., PGT121), and, if desired, one or more immunomodulatory agents, additional antibodies (e.g., bnAbs, e.g., CD4bs-specific antibodies, e.g., 3BNC117 or VRC07-523; and/or with a V2 glycan-dependent antibody, e.g., CAP256-VRC26), and/or ARTs, such as in a sealed package of tablets or capsules, or in a suitable dry powder inhaler (DPI) capable of administering one or more doses.

The pharmaceutical compositions, including an N332 glycan-dependent antibody (e.g., PGT121), can be prepared using standard methods known in the art by mixing the active ingredient (i.e., the N332 glycan-dependent antibody) having the desired degree of purity with, optionally, pharmaceutically acceptable carriers, excipients, or stabilizers (Remington's Pharmaceutical Sciences (20$^{th}$ edition), ed. A. Gennaro, 2000, Lippincott, Williams & Wilkins, Philadelphia, Pa.). Acceptable carriers, include saline, or buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagines, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™, or PEG.

Optionally, but preferably, the formulation contains a pharmaceutically acceptable salt, preferably sodium chloride, and preferably at about physiological concentrations. Optionally, the formulations of the invention can contain a pharmaceutically acceptable preservative. In some embodiments the preservative concentration ranges from 0.1 to 2.0%, typically v/v. Suitable preservatives include those known in the pharmaceutical arts. Benzyl alcohol, phenol, m-cresol, methylparaben, and propylparaben are preferred preservatives. Optionally, the formulations of the invention can include a pharmaceutically acceptable surfactant at a concentration of 0.005 to 0.02%.

EXAMPLES

The present invention is illustrated by the following examples, which are in no way intended to be limiting of the invention.

Example 1

Materials and Methods

Animals and Monoclonal Antibodies

34 Indian-origin, outbred, young adult, male and female, specific pathogen-free (SPF) rhesus monkeys (*Macaca mulatta*) that did not express the class I alleles Mamu-A*01, Mamu-B*08, and Mamu-B*17 associated with spontaneous virologic control (Yant et al., *J Virol.* 80: 5074-5077, 2006; Mothe et al., *J Virol.* 77: 2736-2740, 2003; Loffredo et al., *J Virol.* 81: 8827-8832, 2007) were housed at New England Primate Research Center, Bioqual, or Alphagenesis. Groups were balanced for susceptible and resistant TRIM5a alleles (Lim et al., *PLoS Pathog.* 6: e1000738, 2010; Letvin et al., *Sci Transl Med.* 3: 81ra36, 2011). Animals infected by the intrarectal route with our rhesus-derived SHIV-SF162P3 challenge stock for 9 months prior to antibody administration were utilized for the studies. PGT121, b12, and DEN3 antibodies were generated as previously described and were expressed in Chinese hamster ovary (CHO-K1) cells and purified by Protein A affinity chromatography. 3BNC117 was manufactured by Celldex Therapeutics in CHO cells and purified by chromatography and sterile filtration. All the antibody preparations were endotoxin free. Cocktails of antibodies or single antibodies were administered to monkeys once or twice by the intravenous route at a dose of 10 mg/kg for each antibody. Monkeys were bled up to three times per week for viral loads. All animal studies were approved by the appropriate Institutional Animal Care and Use Committee (IACUC).

Cellular Immune Assays

SIV Gag-specific cellular immune responses were assessed by multiparameter intracellular cytokine staining (ICS) assays essentially as described (Okoye et al., *The Journal of experimental medicine.* 204: 2171-2185, 2007; Hansen et al., *Nature* 473: 523-527, 2011; Pitcher et al., *J Immunol.* 168: 29-43, 2002; Liu et al., *J Virol.* 82: 4844-4852, 2008). 12-color ICS assays were performed with the Aqua green-fluorescent reactive dye (Invitrogen, L23101)

and predetermined titers of antibodies (Becton-Dickinson) against CD3 (SP34; Alexa Fluor 700), CD4 (OKT4; BV711, Biolegend), CD8 (SK1; allophycocyanin-cyanine 7 [APC-Cy7]), CD28 (L293; BV610), CD95 (DX2; allophycocyanin [APC]), CD69 (TP1.55.3; phycoerythrin-Texas red [energy-coupled dye; ECD]; Beckman Coulter), gamma interferon (IFN-γ) (B27; phycoerythrin-cyanine 7 [PE-Cy7]), Ki67 (B56; fluorescein isothiocyanate [FITC]), CCR5 (3A9; phycoerythrin [PE]), CCR7(3D12; Pacific Blue), and PD-1 (EH21.1; peridinin chlorophyll-A-cyanine 5.5 [PerCP-Cy5.5]). IFN-γ backgrounds were consistently <0.01% in PBMC and LNMC and <0.05% in colorectal biopsy specimens.

Neutralizing Antibody Assays

HIV-1-specific neutralizing antibody responses against primary infectious stocks of SHIV-SF162P3 and SHIV-SF162P4 were assessed by TZM-bl luciferase-based neutralization assays (Montefiori et al., Current Protocols in Immunology., 2004). PGT121 titers determined by X2088_c9 and ZM247v1(Rev-) pseudovirus neutralization; 3BNC117 titers were determined by 6041.v3.c23 and Q461.ez pseudovirus neutralization; and b12 titers were determined by Du422.1.N332A pseudovirus neutralization and B2.1 ELISA.

Pro Viral DNA Assay

Lymph node and gastrointestinal mucosal biopsies were processed as single cell suspensions essentially as previously described (Li et al., J Virol 85: 11007-11015, 2011). Tissue-specific proviral DNA was quantitated as previously reported (Whitney et al., J Virol. 83: 10840-10843, 2009). Total cellular DNA was isolated from $5 \times 10^6$ cells using a QIAamp DNA Blood Mini kit (Qiagen). The absolute quantification of viral DNA in each sample was determined by qPCR using primers specific to a conserved region SIVmac239. All samples were directly compared to a linear virus standard and the simultaneous amplification of a fragment of human GAPDH gene. The sensitivity of linear standards was compared against the 3D8 cell line as a reference standard as described (Whitney et al., J Virol. 83: 10840-10843, 2009). All PCR assays were performed with 100 and 200 ng of sample DNA.

Virus Sequencing

Virus sequencing of breakthrough virus was performed essentially as described (Klein et al., Nature. 492: 118-122, 2012). Plasma samples of 1 ml were centrifuged for 30 min at 20,000×g and the lowest fraction was subjected to RNA purification (QiaAmp MinElute Virus Spin kit; Qiagen). Random hexamers (Roche) or SHIV-SF162P3-specific (5'-AAGAGCTCCTCCAGACAGTGAG-3' (SEQ ID NO: 303) or 5'-TAGAGCCCTGGAAGCATCCAGGAAGTCAGC-CTA-3' (SEQ ID NO: 304)) primers were used for cDNA synthesis with SuperScript™ III Reverse Transcriptase (Invitrogen). SHIV envelope sequences were amplified by a double-nested PCR approach using the Expand High Fidelity PCR System (Roche). First round primers for gp120 were 5'-AAGAGCTCCTCCAGACAGTGAG-3' (SEQ ID NO: 305) and 5'-ATGAGTTTTCCAGAGCAACCC-3' (SEQ ID NO: 306) and for gp160 were 5'-AAGAGCTCCTCCA-GACAGTGAG-3' (SEQ ID NO: 307) and 5'-CAAGCCCT-TGTCTAATCCTCC-3' (SEQ ID NO: 308). Second round primers for gp120 were 5'-GAAAGAGCAGAAGACA-GTGGC-3' (SEQ ID NO: 309) and 5'-ATTGTCTGGCCT-GTACCGTC-3' (SEQ ID NO: 310) and for gp160 were 5'-GAAAGAGCAGAAGACAGTGGC-3' (SEQ ID NO: 311) and 5'-ATGGAAATAGCTCCACCCATC-3' (SEQ ID NO: 312). Following second round PCR, all products were spiked with 0.5 μl Taq polymerase and incubated for 15 min at 72° C. Amplicons were excised from a gel and purified following cloning into the pCR™4-TOPO vector (Invitrogen) and expansion in One Shot® TOP10 cells at 30° C. Single colonies were sequenced using M13F/M13R primers as well as primers annealing to the envelope sequence. A consensus sequence of each clone was derived using Geneious Pro software (Biomatters), and sequence analysis was performed using Geneious Pro and antibody database software (West et al. PNAS. 110: 10598-10603, 2013).

Mathematical Modeling

Based on the work of Perelson and coworkers on the effects of antiretroviral therapy (Perelson et al. Science. 271: 1582-1586, 1996; DeBoer et al. PLoS Comput. Biol. 6: e1000906, 2010), we developed an in silico two-compartment model of viral dynamics in response to antibody therapy and ART (see Example 5 below). Ordinary differential equations (ODEs) describing the time evolution of the concentrations (see Example 5 below) of virus (V), infected cells (I) and healthy target cells (T) in two physiological compartments—blood (B) and tissue (T)—were simulated in Matlab using the standard solver ode45. Exponential decay rates in Table 4 (below) were estimated using standard ordinary least squares regression on $\log_{10}$ (viral load) measurements vs. time (days).

Statistical Analyses

Analyses of virologic and immunologic data were performed by two-tailed nonparametric Mann-Whitney tests. Correlations were evaluated by Spearman rank-correlation tests. P values less than 0.05 were considered significant. Statistical analyses were performed using GraphPad Prism.

Example 2

Therapeutic Efficacy of a Cocktail of HIV-Specific Antibodies, Including PGT121

A series of broad and potent HIV-1 Env-specific antibodies have recently been isolated and target the CD4 binding site (CD4bs) (Scheid et al., Nature. 458: 636-640, 2009; Wu et al., Science. 329: 856-861, 2010; Zhou et al., Science. 329: 811-817, 2010; Scheid et al., Science. 333: 1633-1637, 2011; Diskin et al., Science. 334: 1289-1293, 2011), the V1/V2 loops (Walker et al., Science. 326: 285-289, 2009; McLellan et al., Nature. 480: 336-343, 2011), the V3/V4 loops and N332 glycans (Walker et al., Nature. 477: 466-470, 2011; Julien et al., PLoS Pathog. 9: e1003342, 2013; Mouquet et al., Proc Natl Acad Sci USA. 109: E3268-3277, 2012; Kong et al., Nature structural & molecular biology. 20: 796-803, 2013), and the membrane proximal external region (MPER) (Huang et al., Nature. 491: 406-412, 2012). The therapeutic efficacy of these antibodies in chronically simian-human immunodeficiency virus (SHIV)-infected rhesus monkeys, however, remains to be determined. Previous studies in humanized mice and humans using the previous generation of HIV-1 Env-specific antibodies have suggested that the therapeutic potential of antibodies is severely limited by the rapid emergence of viral escape mutations in the context of a diverse virus swarm (Poignard et al., Immunity. 10: 431-438, 1999; Trkola et al., Nat Med. 11: 615-622, 2005; Mehandru et al., J Virol. 81: 11016-11031, 2007). However, cocktails of 3 or 5 of the newer more potent antibodies targeting multiple epitopes have been shown to suppress HIV-1 replication in humanized mice until antibody levels decline to sub-therapeutic levels (Klein et al., Nature. 492: 118-122, 2012; Diskin et al., J Exp Med. 210: 1235-1249, 2013).

To evaluate the therapeutic potential of broad and potent HIV-1-specific antibodies in nonhuman primates, we infused cocktails of antibodies, as well as single antibodies, in chronically SHIV-infected rhesus monkeys. We focused on the N332 glycan-dependent antibody PGT121 (Walker et al., Nature. 477: 466-470, 2011) and the CD4bs-specific antibodies 3BNC117 (Scheid et al., Nature. 458: 636-640, 2009) and b12 (Roben et al., J Virol. 68: 4821-4828, 1994). In the first study, we infected 8 Indian origin adult rhesus monkeys (Macaca mulatta) that did not express the class I alleles Mamu-A*01, Mamu-B*08, and Mamu-B*17 associated with spontaneous virologic control (Yant et al., J. Virol. 80: 5074-5077, 2006; Mothe et al., J. Virol. 77: 2736-2740, 2003; Loffredo et al., J. Virol. 81: 8827-8832, 2007) by the intrarectal route with the pathogenic virus SHIV-SF162P3 and followed these animals for 9 months prior to the antibody infusions. These animals exhibited chronic setpoint viral loads of 3.4-4.9 log RNA copies/ml. We performed two antibody infusions by the intravenous route on day 0 and day 7 with 10 mg/kg of each of PGT121, 3BNC117, and b12 (N=4); or with 30 mg/kg of the isotype matched control antibody DEN3 (N=1) or saline (N=3).

Figures 1E, 1F, 1G:
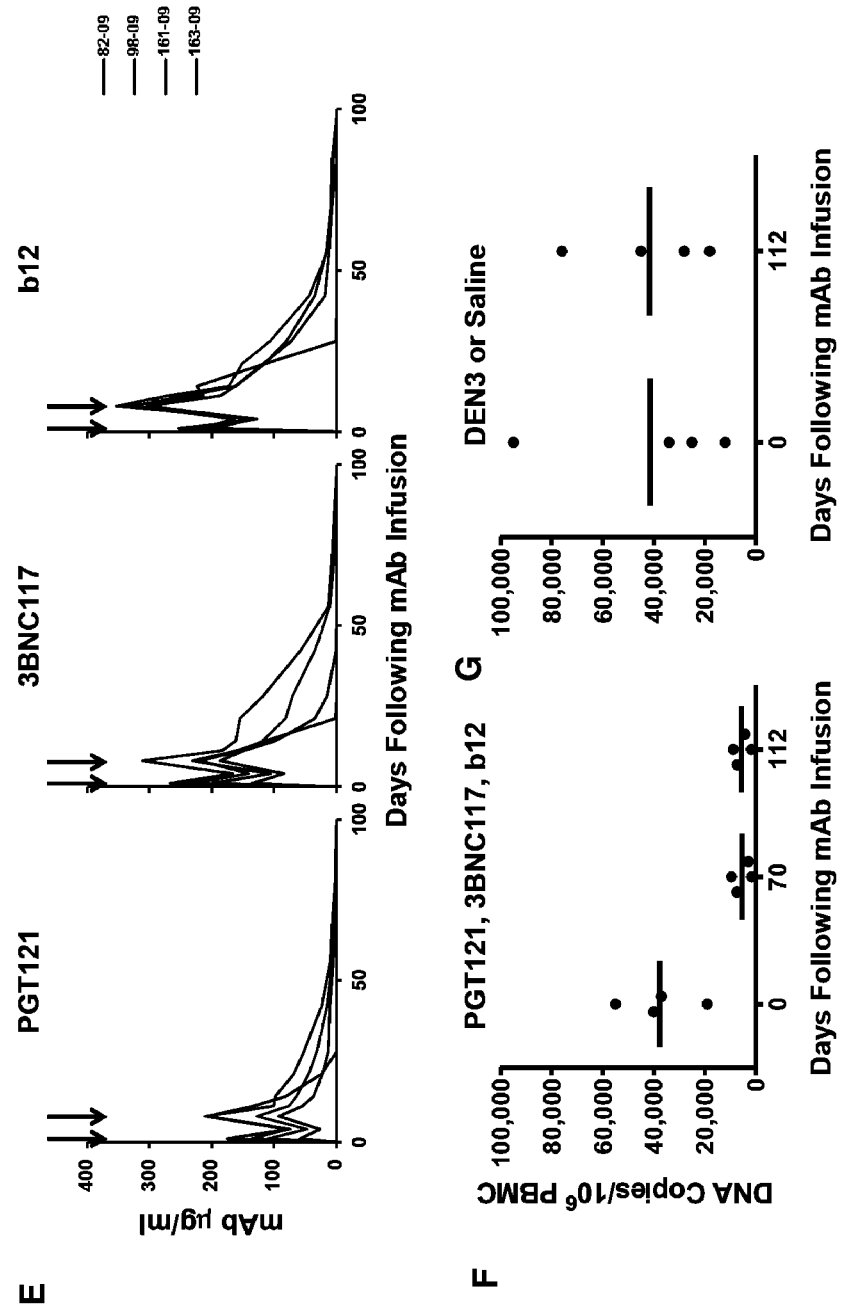
FIG. 1E is a panel of graphs showing the PGT121 (left), 3BNC117 (center), and b12 (right) titers in the monkeys that received the therapeutic triple PGT121/3BNC117/b12 antibody cocktail (monkeys 82-09, 98-09, 161-09, and 163-09). Arrows indicate infusion days.
FIG. 1F is a graph showing the therapeutic efficacy of the triple PGT121/3BNC117/b12 antibody cocktail, as assessed by proviral DNA (copies/$10^6$) levels in PBMC in the monkeys that received the therapeutic triple PGT121/3BNC117/b12 antibody cocktail (monkeys 82-09, 98-09, 161-09, and 163-09) at the indicated days following antibody cocktail infusion.
FIG. 1G is a graph showing proviral DNA (copies/$10^6$) levels in PBMC in the monkeys that received control antibody DEN (monkey 87-09) or saline (monkeys 358-07, 364-07, and 365-07) at the indicated days following antibody cocktail infusion.

Following the initial antibody infusion, we observed rapid and precipitous declines of plasma viral loads to undetectable levels by day 7 in 4 of 4 monkeys (FIG. 1A). Virologic control persisted for 84 to 98 days in animals 82-09, 98-09, and 161-09 (FIG. 1B). Monkey 82-09 exhibited transient viremia on day 28, which correlated with the decline of serum antibody titers to undetectable levels <1 µg/ml(FIG. 1E), but this animal then spontaneously re-controlled viral replication until day 98. Rebound viremia in animals 98-09 and 161-09 also correlated with the decline of serum antibody titers to undetectable levels (FIG. 1E). Following viral rebound, no N332 or other signature viral resistance mutations were detected. Monkey 163-09, which had the lowest baseline viral load of 3.4 log RNA copies/ml prior to the antibody infusion, exhibited long-term virologic control for over 200 days despite the absence of detectable serum antibody titers after day 70 (FIGS. 1B and 1E). Proviral DNA in PBMC also declined by a mean of 10-fold in the monkeys that received the antibodies (FIG. 1F). Virologic control was not observed in the monkeys that received DEN3 or saline (FIGS. 1C, 1D, and 1G).

Figures 1H, 1I, 1J, 1K:
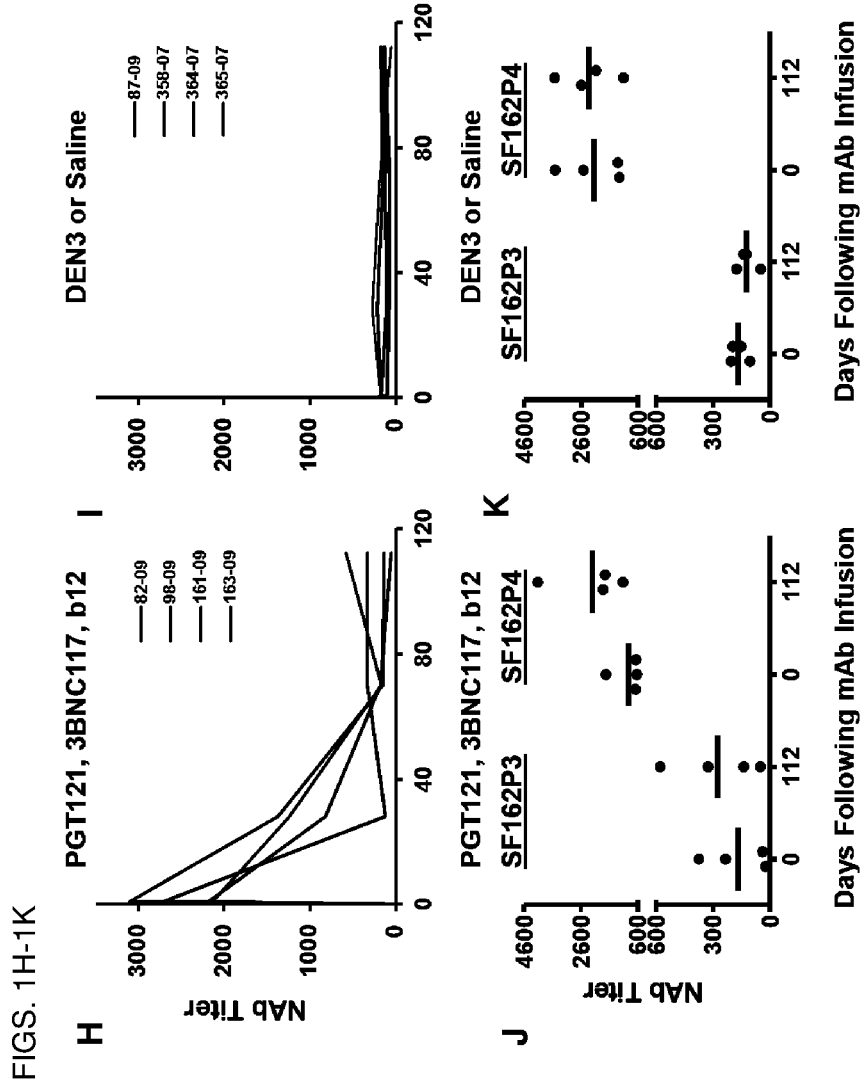
FIG. 1H is a graph showing the decline of SHIV-SF162P3 neutralizing antibody (NAb) titers following a dramatic increase shortly after administration of the triple PGT121/3BNC117/b12 antibody cocktail in monkeys 82-09, 98-09, 161-09, and 163-09.
FIG. 1I is a graph showing the SHIV-SF162P3 neutralizing antibody (NAb) titers after administration of antibody DEN3 (monkey 87-09) or saline (monkeys 358-07, 364-07, and 365-07) controls.
FIG. 1J is a graph showing the relative level of NAb titers to SHIV-SF162P3 and SHIV-SF162P4 at days 0 and 112 in monkeys that received the therapeutic triple PGT121/3BNC117/b12 antibody cocktail (monkeys 82-09, 98-09, 161-09, and 163-09).
FIG. 1K is a graph showing the relative level of NAb titers to SHIV-SF162P3 and SHIV-SF162P4 at days 0 and 112 in monkeys that received antibody DEN3 (monkey 87-09) or saline (monkeys 358-07, 364-07, and 365-07) control.
Figures 1L, 1M, 1N, 1O:
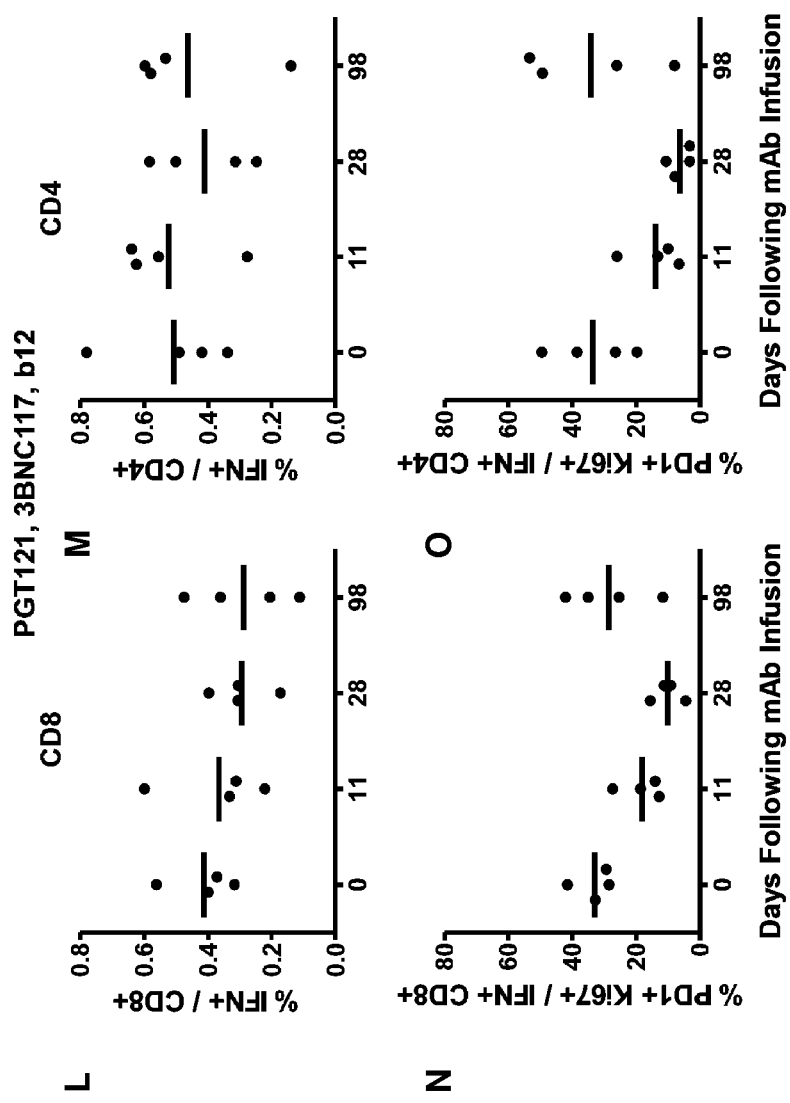
FIG. 1L is a graph showing the magnitude of Gag-specific CD8+ T lymphocyte response at 0, 11, 28, and 98 days following antibody infusion in monkeys that received the therapeutic triple PGT121/3BNC117/b12 antibody cocktail (monkeys 82-09, 98-09, 161-09, and 163-09).
FIG. 1M is a graph showing the magnitude of Gag-specific CD4+ T lymphocyte response at 0, 11, 28, and 98 days following antibody infusion in monkeys that received the therapeutic triple PGT121/3BNC117/b12 antibody cocktail (monkeys 82-09, 98-09, 161-09, and 163-09).
FIG. 1N is a graph showing the level of functionally exhausted and chronically activated virus-specific CD8+ T lymphocytes (as measured by the percentage of CD8+ T lymphocytes that expressed PD-1 and Ki67) at 0, 11, 28, and 98 days following antibody infusion in monkeys that received the therapeutic triple PGT121/3BNC117/b12 antibody cocktail (monkeys 82-09, 98-09, 161-09, and 163-09).
FIG. 1O is a graph showing the level of functionally exhausted and chronically activated virus-specific CD4+ T lymphocytes (as measured by the percentage of CD4+ T lymphocytes that expressed PD-1 and Ki67) at 0, 11, 28, and 98 days following antibody infusion in monkeys that received the therapeutic triple PGT121/3BNC117/b12 antibody cocktail (monkeys 82-09, 98-09, 161-09, and 163-09).
Figures 1P, 1Q, 1R, 1S:
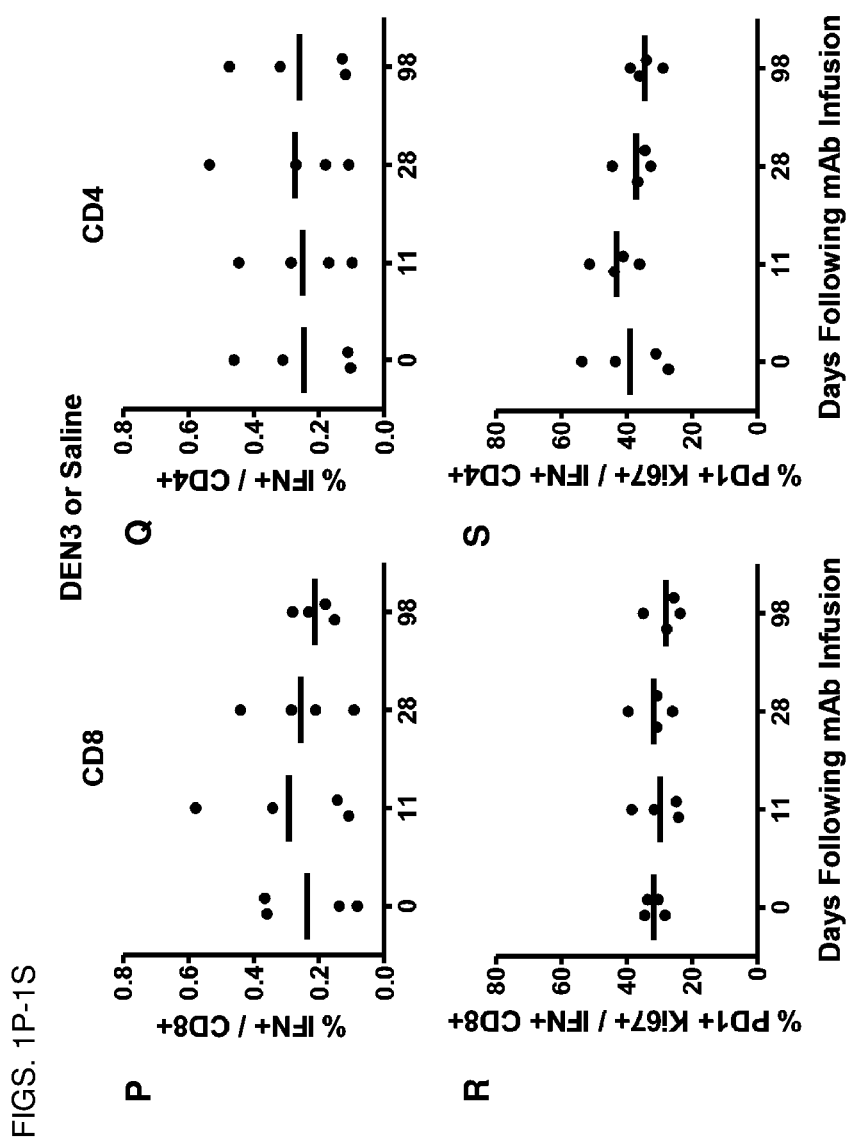
FIG. 1P is a graph showing the magnitude of Gag-specific CD8+ T lymphocyte response at 0, 11, 28, and 98 days following administration of antibody DEN3 (monkey 87-09) or saline (monkeys 358-07, 364-07, and 365-07) control.
FIG. 1Q is a graph showing the magnitude of Gag-specific CD4+ T lymphocyte response at 0, 11, 28, and 98 days following administration of antibody DEN3 (monkey 87-09) or saline (monkeys 358-07, 364-07, and 365-07) control.
FIG. 1R is a graph showing the level of functionally exhausted and chronically activated virus-specific CD8+ T lymphocytes (as measured by the percentage of CD8+ T lymphocytes that expressed PD-1 and Ki67) at 0, 11, 28, and 98 days following administration of antibody DEN3 (monkey 87-09) or saline (monkeys 358-07, 364-07, and 365-07) control.
FIG. 1S is a graph showing the level of functionally exhausted and chronically activated virus-specific CD4+ T lymphocytes (as measured by the percentage of CD4+ T lymphocytes that expressed PD-1 and Ki67) at 0, 11, 28, and 98 days following administration of antibody DEN3 (monkey 87-09) or saline (monkeys 358-07, 364-07, and 365-07) control.

As expected, serum neutralizing antibody (NAb) ID50 titers to the SHIV-SF162P3 challenge virus increased dramatically following the antibody administration and then declined over time (FIGS. 1H and 1I). Following clearance of the antibodies, however, NAb titers to SHIV-SF162P3 as well as to the related neutralization-sensitive virus SHIV-SF162P4 remained slightly higher than baseline titers (FIGS. 1J and 1K). The magnitude of Gag-specific CD8+ and CD4+ T lymphocyte responses was not detectably modulated following antibody administration (FIGS. 1L, 1M, 1P, and 1O). However, by day 28, we observed significant 3- and 5-fold reductions, respectively, in the percentage of Gag-specific CD8+ and CD4+ T lymphocytes that expressed PD-1 and Ki67 (FIGS. 1N, 1O, 1R, and 1S) (P=0.02 for both CD8+ and CD4+ T lymphocytes, Mann-Whitney tests), reflecting a reduction in functionally exhausted and chronically activated virus-specific T lymphocytes. These markers of cellular immune dysfunction increased by day 98 largely back to baseline levels in the three animals that exhibited viral rebound. Taken together, these data suggest that antibody administration not only exerted direct antiviral effects but also modulated host immune responses, presumably by reducing the detrimental effects of chronic viral replication.

Example 3

Therapeutic Efficacy of a Single Infusion of Cocktails of HIV-specific Antibodies, Including PGT121

Figures 2A, 2B, 2C, 2D:
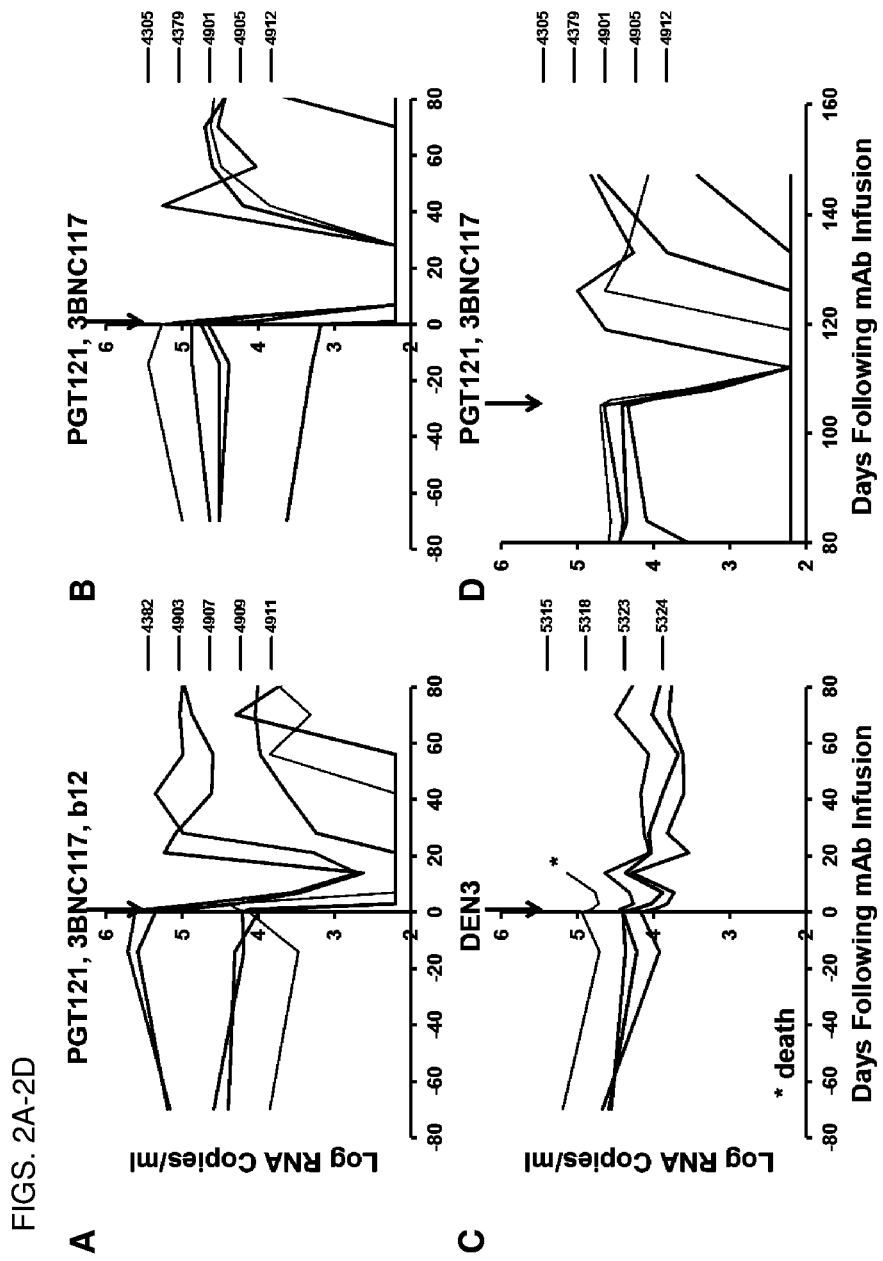
FIG. 2A is a graph showing the level of plasma viral RNA (log RNA copies/ml) in rhesus monkeys chronically infected with SHIV-SF162P3 following a single infusion (arrow) of PGT121, 3BCN117, and b12 (monkeys 4383, 4903, 4907, 4909, and 4911).
FIG. 2B is a graph showing the level of plasma viral RNA (log RNA copies/ml) in rhesus monkeys chronically infected with SHIV-SF162P3 following a single infusion (arrow) of PGT121 and 3BNC117 (monkeys 4305, 4379, 4901, 4905, and 4912).
FIG. 2C is a graph showing the level of plasma viral RNA (log RNA copies/ml) in rhesus monkeys chronically infected with SHIV-SF162P3 following a single infusion (arrow) of control antibody DEN3 (monkeys 5315, 5318, 5323, and 5324).
FIG. 2D is a graph showing the level of plasma viral RNA (log RNA copies/ml) in monkeys that received PGT121 and 3BNC117 following a second infusion (arrow) on day 105.
Figures 2E, 2F, 2G:
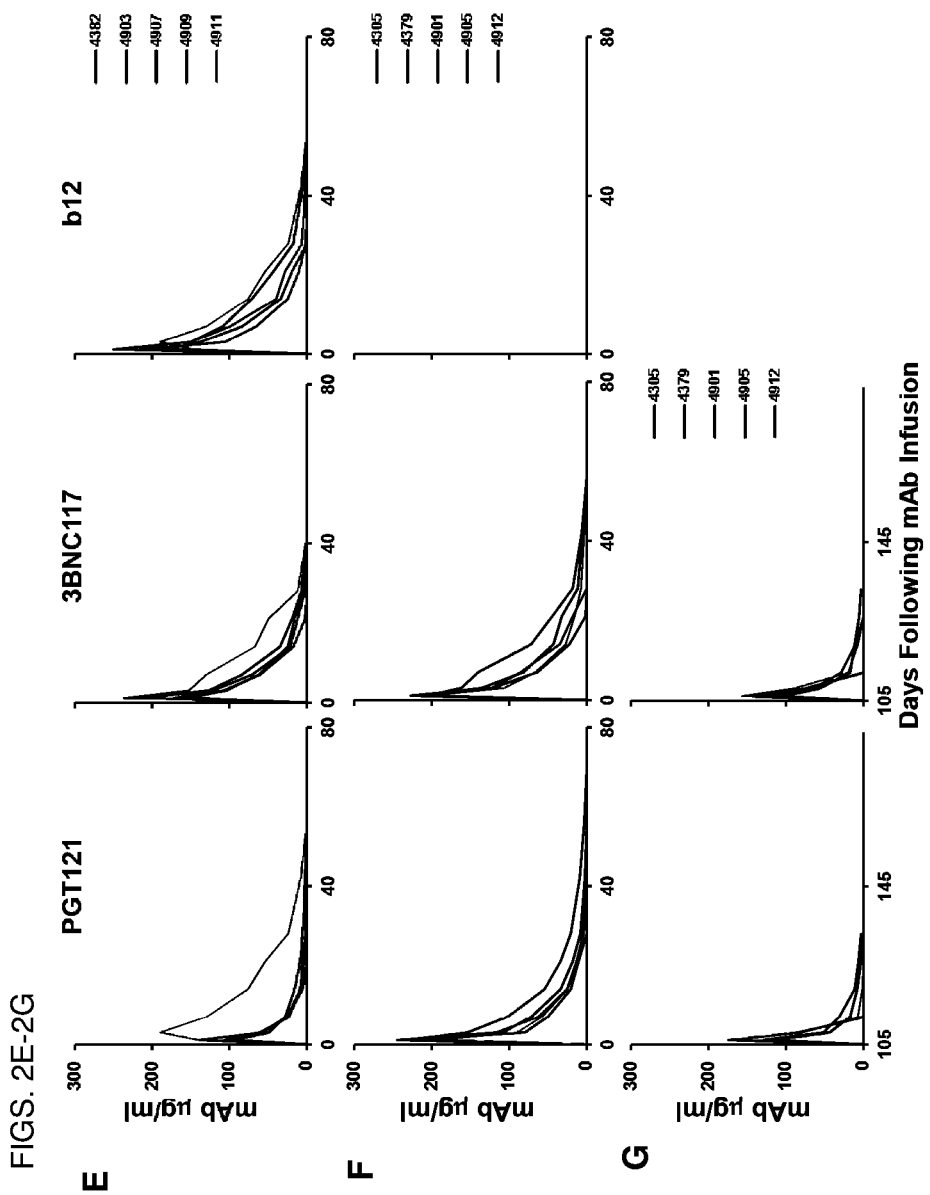
FIG. 2E is a panel of graphs showing PGT121 (left), 3BNC117 (center), and b12 (right) titers in the monkeys that received a single infusion of PGT121, 3BCN117, and b12 (monkeys 4383, 4903, 4907, 4909, and 4911).
FIG. 2F is a panel of graphs showing PGT121 (left), 3BNC117 (center), and b12 (right) titers in the monkeys that received a single infusion of PGT121 and 3BNC117 (monkeys 4305, 4379, 4901, 4905, and 4912).
FIG. 2G is a panel of graphs showing PGT121 (left) and 3BNC117 (center) titers in the monkeys that received a second infusion of PGT121 and 3BNC117 at day 105 (monkeys 4305, 4379, 4901, 4905, and 4912).

We next investigated the therapeutic efficacy of a single infusion of the cocktail of three antibodies as well as a combination of only two antibodies. 14 rhesus monkeys infected with SHIV-SF162P3 for 9 months prior to the antibody infusion with chronic setpoint viral loads of 3.2-5.6 log RNA copies/ml received a single infusion on day 0 with 10 mg/kg of each of the antibodies PGT121, 3BNC117, and b12 (N=5); PGT121 and 3BNC117 (N=5); or the isotype matched control antibody DEN3 (N=4). We observed rapid virologic control to undetectable levels by day 7 in 3 of 5 animals that received the cocktail of three antibodies and in 5 of 5 animals that received only PGT121 and 3BNC117 (FIGS. 2A-2C). The 2 animals that failed to achieve complete virologic suppression had the highest baseline plasma viral loads of 5.4 and 5.6 log RNA copies/ml before the antibody infusion and exhibited 2.8 and 2.9 log declines, respectively, in plasma viremia prior to rapid viral rebound on day 21 (monkeys 4907, 4909; FIG. 2A). No N332 or other signature viral resistance mutations were detected in the breakthrough viruses. The animals that suppressed viral loads to undetectable levels exhibited up to a 3.1 log decline of plasma viral RNA copies/ml by day 7 (monkey 4912; FIG. 2B). Viral rebound occurred in the majority of animals between day 28 and day 84 (FIGS. 2A and 2B) and was associated with declines of serum antibody titers to undetectable levels (FIGS. 2E and 2F). The animal with the lowest baseline viral load of 3.2 log RNA copies/ml exhibited long-term virologic control for over 100 days (monkey 4905; FIG. 2B).

Figures 2H, 2I:
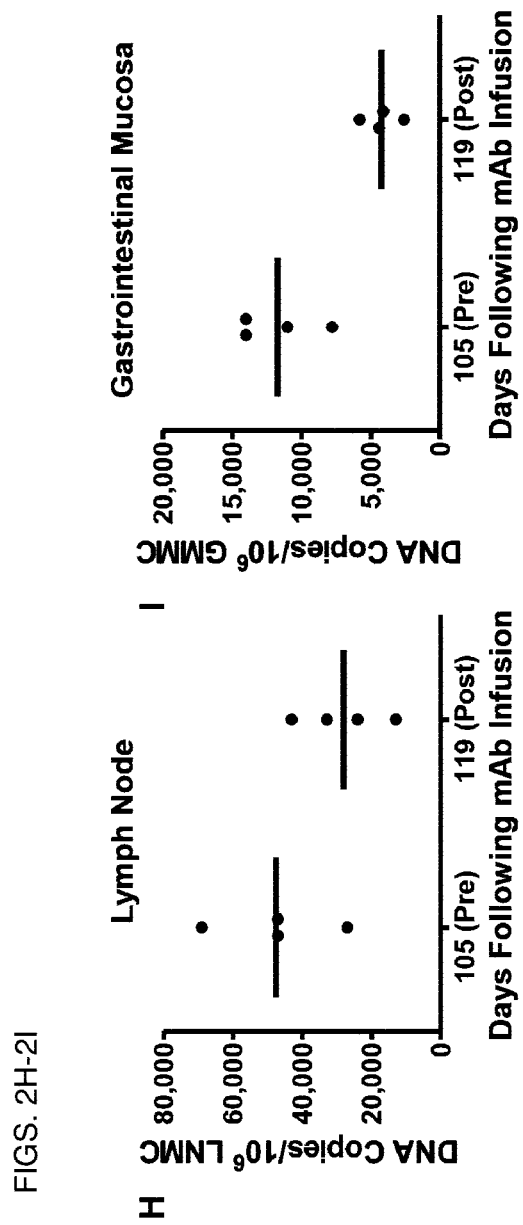
FIG. 2H is a graph showing the level of proviral DNA (copies/$10^6$ cells) in lymph node tissue before (day 105) and 14 days after (day 119) the second antibody infusion with PGT121 and 3BCN117 in the four animals with detectable viremia (monkeys 4305, 4379, 4901, and 4912).
FIG. 2I is a graph showing the level of proviral DNA (copies/$10^6$ cells) in gastrointestinal mucosal tissue before (day 105) and 14 days after (day 119) the second antibody infusion with PGT121 and 3BCN117 in the four animals with detectable viremia (monkeys 4305, 4379, 4901, and 4912).

To confirm whether viral rebound was associated with the development of viral resistance to the antibodies, we performed a second infusion of antibodies on day 105 in the monkeys that received PGT121 and 3BNC117. Viral re-suppression was observed in 4 of 4 animals following the second antibody infusion, indicating that the antibodies controlled viremia without selection for resistance (FIG. 2D). However, virologic control appeared less durable and serum antibody titers were lower following the second antibody infusion (FIGS. 2D and 2G) as compared with the first antibody infusion (FIGS. 2B and 2F), presumably as a result of low titers of monkey anti-human antibody responses that developed following the first antibody administration. Nevertheless, we assessed the impact of the second antibody infusion on proviral DNA in various tissue compartments (Whitney et al., J Virol. 83: 10840-10843, 2009) and observed a 2-fold decline in lymph nodes (P=0.1; FIG. 2H) and a 3-fold decline in gastrointestinal mucosa (P=0.02; FIG. 2I) 14 days following antibody administration. These data show that the potent antibodies not only suppressed viremia but also reduced proviral DNA in tissues without the generation of viral resistance.

Example 4

Therapeutic Efficacy of a Single Infusion of PGT121

Figures 3A, 3B, 3C:
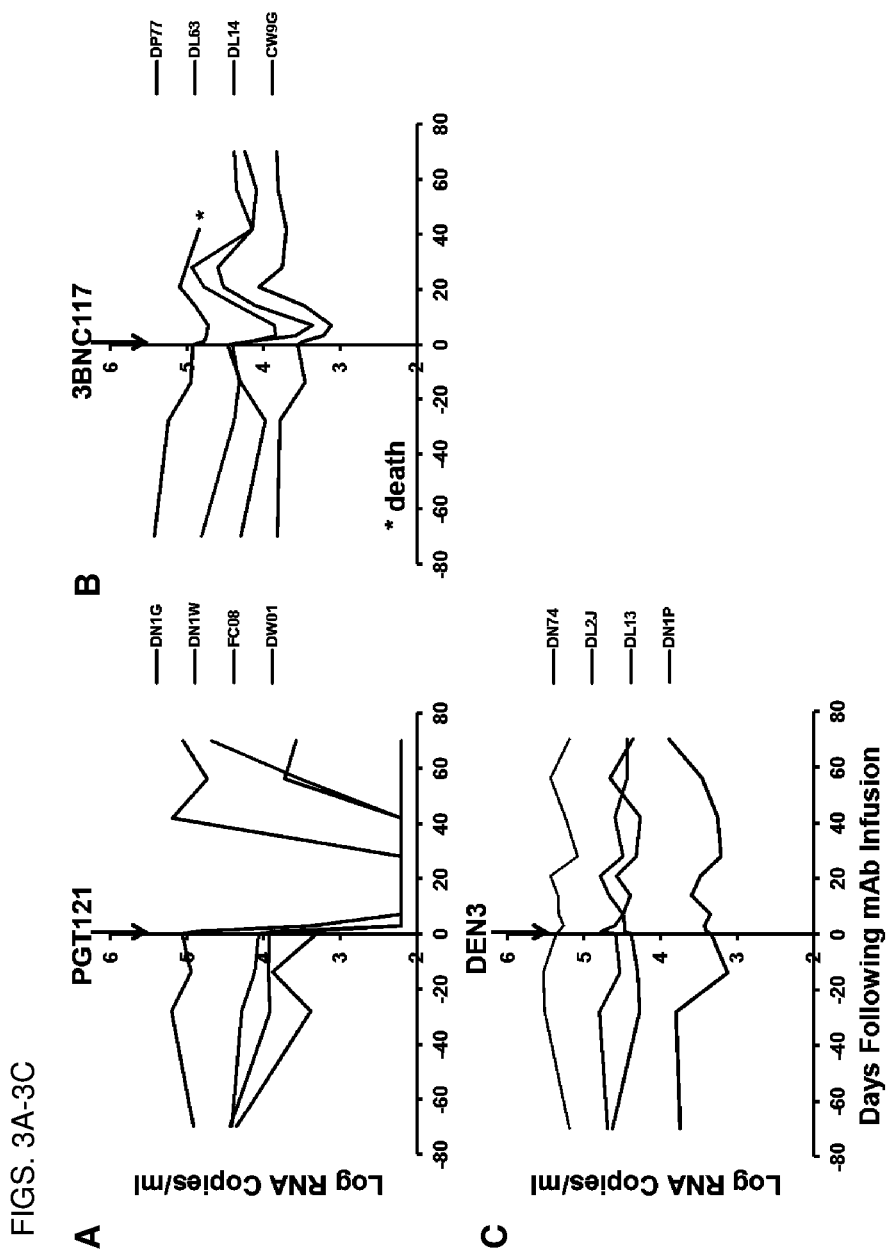
FIG. 3A is a graph showing the therapeutic efficacy of antibody PGT121 alone, as assessed by plasma viral RNA level (log RNA copies/ml) in rhesus monkeys chronically infected with SHIV-SF162P3 following a single infusion (arrow) of PGT121 (monkeys DN1G, DN1W, FC08, and DW01).
FIG. 3B is a graph showing the therapeutic efficacy of antibody 3BNC117 alone, as assessed by plasma viral RNA level (log RNA copies/ml) in rhesus monkeys chronically infected with SHIV-SF162P3 following a single infusion (arrow) of 3BNC117 (monkeys DP77, DL63, DL14, and CW9G).
FIG. 3C is a graph showing the plasma viral RNA level (log RNA copies/ml) in rhesus monkeys chronically infected with SHIV-SF162P3 following a single infusion (arrow) of antibody DEN3 (monkeys DN74, DL2J, DL13, and DN1P).
Figures 3D, 3E, 3F:
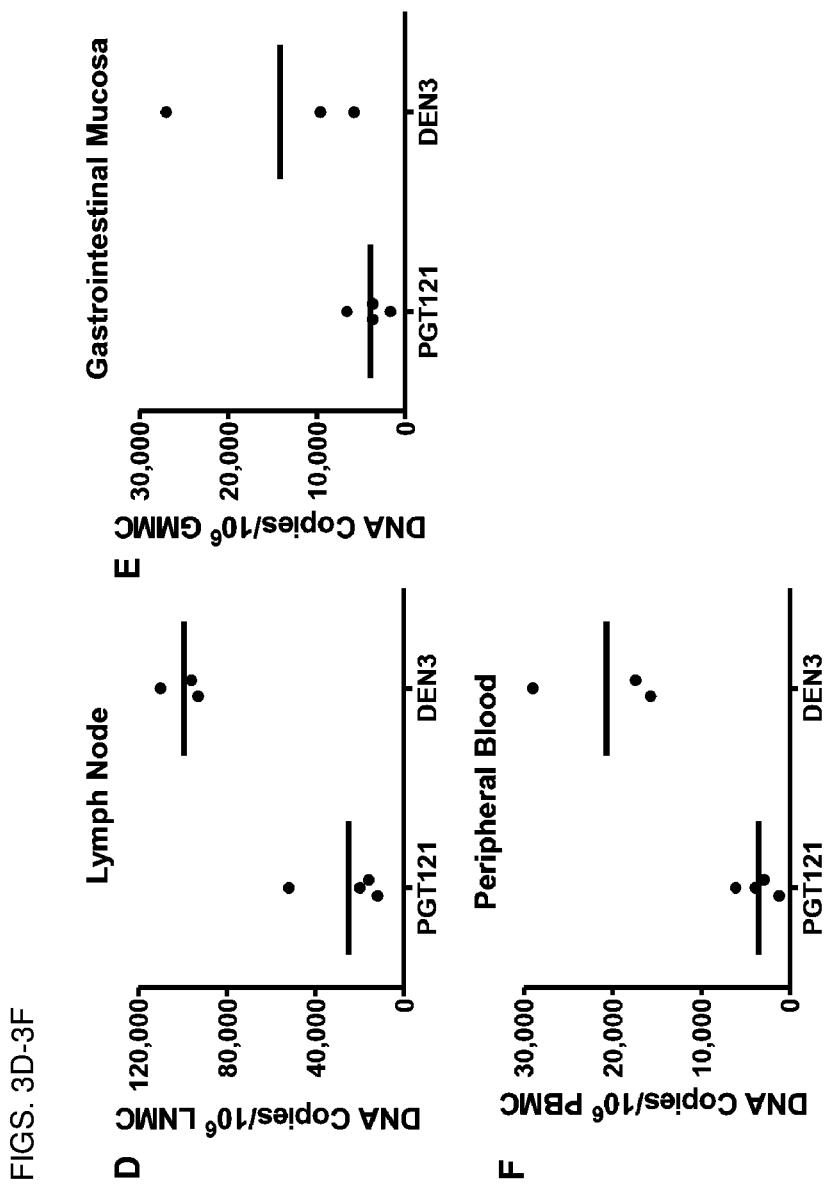
FIG. 3D is a graph showing the level of proviral DNA (copies/$10^6$ cells) in lymph node tissue 14 days following the antibody infusion in the animals that received PGT121 and DEN3 (one of the DEN3 animals failed).
FIG. 3E is a graph showing the level of proviral DNA (copies/$10^6$ cells) in gastrointestinal mucosal tissue 14 days following the antibody infusion in the animals that received PGT121 and DEN3 (one of the DEN3 animals failed).
FIG. 3F is a graph showing the level of proviral DNA (copies/$10^6$ cells) in peripheral blood tissue 14 days following the antibody infusion in the animals that received PGT121 and DEN3 (one of the DEN3 animals failed).
Figures 3G, 3H, 3I, 3J:
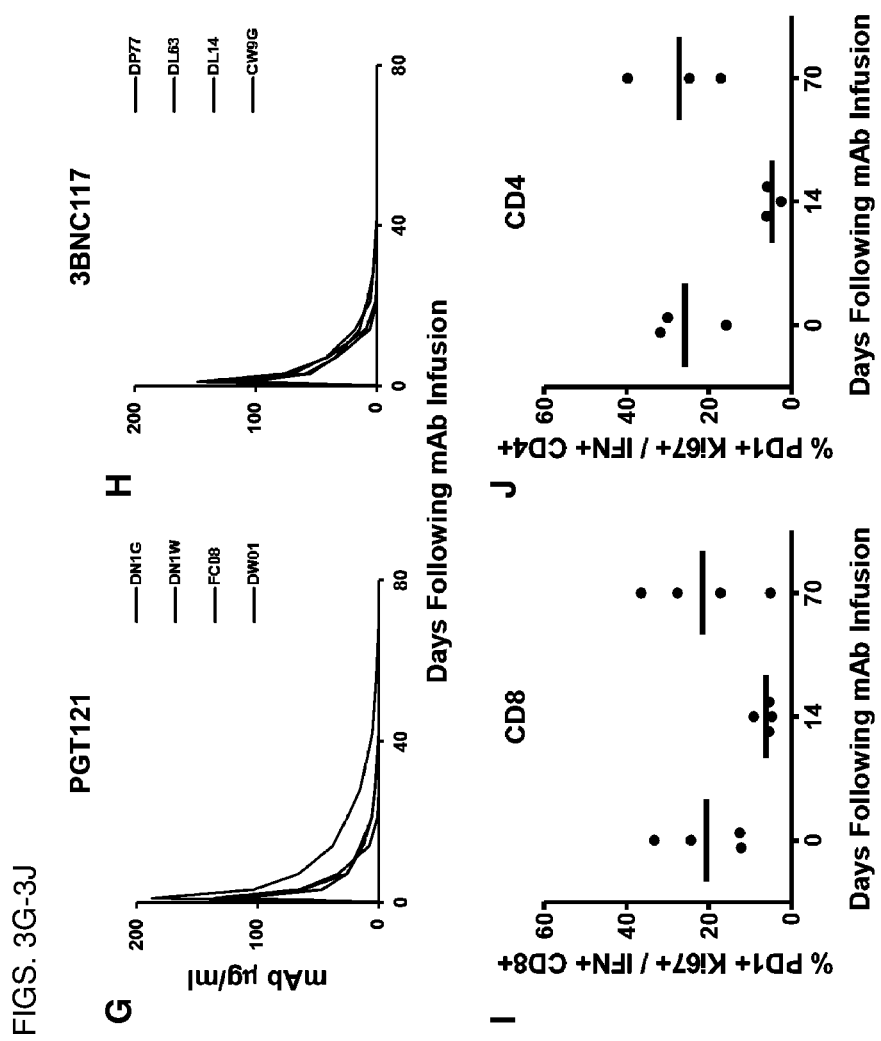
FIG. 3G is a graph showing PGT121 titers in rhesus monkeys chronically infected with SHIV-SF162P3 following a single infusion (arrow) of PGT121 (monkeys DN1G, DN1W, FC08, and DW01).
FIG. 3H is a graph showing 3BNC117 titers in rhesus monkeys chronically infected with SHIV-SF162P3 following a single infusion (arrow) of 3BNC117 (monkeys DP77, DL63, DL14, and CW9G).
FIG. 3I is a graph showing PD-1+Ki67+ expression on Gag-specific CD8+ T lymphocytes in the monkeys that received a single infusion of PGT121 only (monkeys DN1G, DN1W, FC08, and DW01).
FIG. 3J is a graph showing PD-1+Ki67+ expression on Gag-specific CD4+ T lymphocytes in the monkeys that received a single infusion of PGT121 only (monkeys DN1G, DN1W, FC08, and DW01).

It is generally believed that a combination of antibodies directed against multiple epitopes will be required for virologic control (Klein et al., Nature. 492: 118-122, 2012; Poignard et al., Immunity. 10: 431-438, 1999; Trkola et al., Nat Med. 11: 615-622, 2005; Diskin et al., *J Exp Med.* 210: 1235-1249, 2013). However, the current extraordinarily potent and broad antibodies have not previously been evaluated in nonhuman primates with intact immune systems. Although the cloned SHIV-SF162P3 pseudovirus is highly sensitive to 3BNC117, we observed that our particular SHIV-SF162P3 challenge stock was largely resistant to 3BNC117, which raised the possibility that the observed therapeutic efficacy in the previous experiment (FIG. 2B) may have been due to PGT121 alone. We therefore performed a single infusion of 10 mg/kg PGT121 alone (N=4), 3BNC117 alone (N=4), or the control antibody DEN3 (N=4) in 12 rhesus monkeys infected with SHIV-SF162P3 for 9 months prior to the antibody infusion with chronic setpoint viral loads of 3.3-5.4 log RNA copies/ml. PGT121 alone resulted in rapid virologic control to undetectable levels by day 7 in 4 of 4 animals, followed by viral rebound by day 42 to day 56 in 3 animals that again correlated with declines in serum PGT121 titers to undetectable levels (FIGS. 3A, 3C, and 3G). One animal exhibited long-term virologic control (monkey DN1G; FIG. 3A). PGT121 alone also reduced proviral DNA by 4-fold in lymph nodes (P=0.05; FIG. 3D), 4-fold in gastrointestinal mucosa (P=0.1; FIG. 3E), and 6-fold in peripheral blood (P=0.05; FIG. 3F) as compared with the DEN3 control on day 14. Moreover, PGT121 alone resulted in 3- and 5-fold reductions, respectively, in the percentage of functionally exhausted PD-1+ Ki67+Gag-specific CD8+ and CD4+ T lymphocytes (FIGS. 3I and 3J). In contrast, 3BNC117 alone, to which our SHIV-SF162P3 stock was relatively resistant, resulted in only a transient 0.2-1.1 log reduction of plasma viral loads (FIGS. 3B and 3H).

Example 5

In Silico Kinetic Modeling

To gain mechanistic insight into these kinetics of decline of plasma viremia, we developed an in silico model for the time-evolution of free virus, target cells, and productively infected cells in plasma and tissues. Following the work of Perelson and co-workers on the effect of antiretroviral therapy (ART) (Perelson et al., *Science.* 271: 1582-1586, 1996; Kirschner et al., *JAIDS.* 18: 95-109, 1998; Perelson et al., *Math Biosci.* 114: 81-125, 1993; Ho et al., *Nature.* 373: 123-126, 1995), we modeled viral dynamics in SHIV-infected macaques. We employed mean-field rate equations governing the time-evolution of the concentration of free virions, productively infected cells, target cells and the action of antibodies in two physiological compartments, blood and tissue (Equations (1)-(8)).

$$\frac{dT_B}{dt} = s + rT_B\left(1 - \frac{T_B}{T_0}\right) - kV_BT_B - \delta T_B - R_BT_B + R_TT_T \quad (1)$$

$$\frac{dI_B}{dt} = kV_BT_B - \lambda I_B \quad (2)$$

$$\frac{dV_B}{dt} = N\lambda I_B - kV_BT_B - r_BV_B + r_TV_T - b_BV_B \quad (3)$$

$$\frac{dT_T}{dt} = rT_T\left(1 - \frac{T_T}{T_0}\right) - kV_TT_T - \delta T_T + R_BT_B - R_TT_T \quad (4)$$

$$\frac{dI_T}{dt} = kV_TT_T - \lambda I_T \quad (5)$$

$$\frac{dV_T}{dt} = N\lambda I_T - kV_TT_T + r_BV_B - r_TV_T - (c + b_T)V_B \quad (6)$$

$$\frac{db_B}{dt} = -\alpha b_B + \eta(b_T - b_B) \quad (7)$$

$$\frac{db_T}{dt} = -\alpha b_T + \eta(b_B - b_T) \quad (8)$$

The variables and parameters used in our model are set forth below in Tables 3 and 4, respectively.

TABLE 3

List of variables (all concentrations are per mm$^{-3}$ of blood volume)

| Variable | Description |
|---|---|
| T$_B$ | Concentration of target cells in blood |
| T$_T$ | Concentration of target cells in tissue |
| I$_B$ | Concentration of infected cells in blood |
| I$_T$ | Concentration of infected cells in tissue |
| V$_B$ | Concentration of free virus in blood |
| V$_T$ | Concentration of free virus in tissue |
| b$_B$ | antibody activity in blood |
| b$_T$ | antibody activity in tissue |

TABLE 4

List of parameters and their values

| Parameters | Description | Value | Source/Notes |
|---|---|---|---|
| s | Rate of new target cell supply to the blood | 100 mm$^{-3}$ day$^{-1}$ | Studies relying on PBMC measurements have estimated minimal rates of new CD4+ T cell production to be 10 mm$^{-3}$ day$^{-1}$ (Hellerstein et al., *Nat Med.* 5: 83-89, 1999). Previous computational studies focusing on blood kinetics have employed values of s in the range 10-100 mm$^{-3}$ day$^{-1}$ (Perelson et al., *Math Biosci.* 114: 81-125, 1993; Althaus et al., *PLoS Comput Biol.* 4: e1000103, 2008). We explored values of s in the range 10-200 mm$^{-3}$ day$^{-1}$ |
| T$_0$ | Saturation T-cell concentration at which proliferation stops | 2.5 × 10$^4$ mm$^{-3}$ | This was tuned to yield an equilibrium blood target cell concentration of 800-1100 mm$^{-3}$. |
| r | Homeostatic proliferation rate of target cells | 0.03 day$^{-1}$ | Perelson et al., *Math Biosci.* 114: 81-125, 1993. |

TABLE 4-continued

List of parameters and their values

| Parameters | Description | Value | Source/Notes |
|---|---|---|---|
| k | Specific rate of infection | $2.4 \times 10^{-5}$ mm$^3$ day$^{-1}$ | Perelson et al., *Math Biosci.* 114: 81-125, 1993. |
| $\delta$ | Target cell death rate | 0.02 day$^{-1}$ | Perelson et al., *Math Biosci.* 114: 81-125, 1993. |
| $\lambda$ | Infected cell death rate | 0.24 day$^{-1}$ | Perelson et al., *Math Biosci.* 114: 81-125, 1993. |
| N | Viral burst frequency | $2 \times 10^4$ | De Boer et al., *PLoS Comput Biol.* 6: e1000906, 2010. |
| $r_B$ | Viral efflux rate from blood | 23 day$^{-1}$ | Studies (reviewed in De Boer et al., *PLoS Comput Biol.* 6: e1000906, 2010) suggest that the viral efflux rates from blood to tissue $r_B$ are very different between humans and monkeys (23 day$^{-1}$ vs 288 day$^{-1}$). Variations of $r_B$ in the range 10-500 day$^{-1}$ did not affect our results qualitatively as long as the viral influx rate $r_T$ was at least ten-fold lower than the efflux rate. This ensured that the viral load in the tissue (particularly lymphoid tissue) is much larger than that in the blood, a feature consistent with experimental facts (Kirschner et al., *JAIDS.* 24: 352-362, 2000). |
| $r_T$ | Viral efflux rate from tissue | 2.3 day$^{-1}$ | See $r_B$ notes above. |
| $R_B$ | Target cell efflux rate from blood | 33 day$^{-1}$ | We assumed that the CD4+ T cells have an average half-life within blood of 30 minutes. This results in an efflux rate $R_B$ = 33 day$^{-1}$ from blood to tissue. To achieve a steady state where >90% of the T cell concentration was confined to tissue, we chose a T cell influx rate from tissue to blood equal to 2 day$^{-1}$. These values are very close to those used in Kirschner et al., *JAIDS.* 24: 352-362, 2000. The qualitative results were insensitive to values of in $R_B$ as long as $R_B > 10$ day$^{-1}$ and $R_B > R_T$. |
| $R_T$ | Target cell efflux rate from tissue | 2 day$^{-1}$ | See $R_B$ notes above. |
| c | Baseline clearance rate of free virus | 40 day$^{-1}$ | It is assumed, following De Boer et al. (*PLoS Comput Biol.* 6: e1000906, 2010), that virus is predominantly cleared in the tissue, and that "clearance" in blood is predominantly efflux into the tissue. Estimates of clearance rates vary widely across studies (reviewed in De Boer et al. *PLoS Comput Biol.* 6: e1000906, 2010). Our results were qualitatively consistent in the range c = 20-250 day$^{-1}$. However, increasing c lowered the viral steady state and it was necessary to tune s, $T_0$ or N to achieve $\log_{10}(V_B) = 4.4$-$4.8$ at steady state. |
| $\alpha$ | First order decay rate for antibody activity | $0.07^{-1}$ | Our data, at FIGS. 2E-2G. |
| $\eta$ | Mass transfer coefficient for antibodies | ln(2) day$^{-1}$ | It was assumed that Abs have a half-life (t½) of 1 day in either compartment, leading to a mass transfer coefficient $\eta$ = ln(2) day$^{-1}$. |

Simulating Antibody Therapy

Antibody-mediated Enhancement of Clearance and ADCC

To simulate antibody-mediated viral suppression, we first obtained "healthy subjects" by evolving Eqs. 1 and 4 with $V_T=V_B=0$ until steady state was established. We then "infected" these healthy subjects at t=0 with trace amounts of virus in blood ($V_B(0)=10^{-3}$), and evolved the system for t=275 days (≈9 months); by this time most of these subjects were chronically infected, with a steady state viral load. At t=275 days, antibodies were "injected" intravenously such that their initial activity was $b_B=B_0$. Since $B_0$ determines the strength of antibody-mediated clearance, we estimated its value from experimental data (see below).

Antibody-mediated clearance of free viruses involves neutralization of the viral-spike by antibody binding and formation of immune complexes that are ingested by phagocytic cells. In our simple treatment, we assumed that the clearance rate by antibody is directly proportional to its titer, which was found to decay exponentially at a median rate of $\alpha$=0.07 day$^{-1}$ (estimated from FIGS. 2E-2G). We also assumed that antibodies could diffuse between blood and tissue with a transfer coefficient $\eta$=ln(2) day$^{-1}$, as in Eqs. 7 and 8.

Figures 4A, 4B:
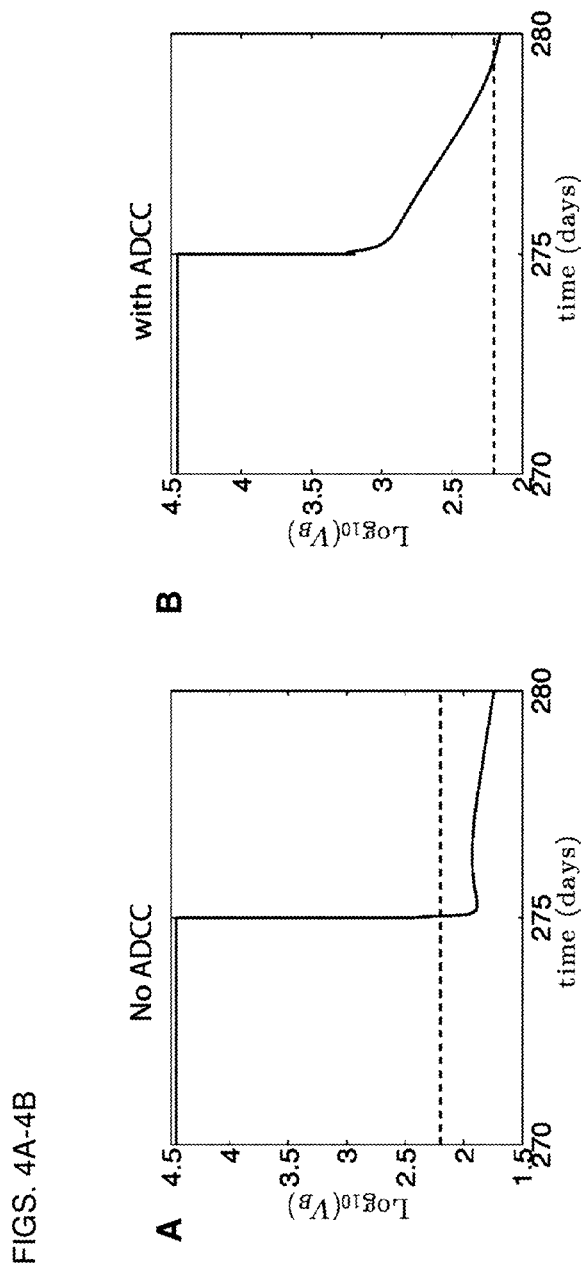
FIG. 4A is a graph showing the qualitative shape of viral decline in blood following antibody injection at t=275 days if ADCC is absent (E=50). The dashed line shows the lower limit of viral detection ($\log_{10}(V_B)$=2.2).
FIG. 4B is a graph showing the qualitative shape of viral decline in blood following antibody injection at t=275 days if ADCC is present (E=6, A'=3A). The dashed line shows the lower limit of viral detection ($\log_{10}(V_B)$=2.2).

To quantify the strength of antibody-mediated clearance, we defined $E=(b_T(t=275)+b_B(t=275))/2c$ as the "average enhancement parameter," where $(b_T(t=275)+b_B(t=275))=B_0$, as introduced previously. We asked what was the minimum value of E necessary to bring down log-viral load below the undetectable threshold (2.2) starting from a set point of 4.4 (FIG. 4A). For a baseline clearance rate $c=40$ day$^{-1}$, we found that $E>40$ ($B_0>3000$) was necessary, namely that antibodies had to enhance baseline clearance rates by 40-fold or greater, on average, in these macaques.

Our results, however, also indicated that if this were the case, the decline in viral load would occur over a very short time scale (FIG. 4A, plot for E=50). Because clearance is a first-order process in our model the time scale over which the viral load is suppressed is an inverse function of the strength of antibody-mediated clearance. This may be avoided by dividing the process of antibody-mediated clearance into two subprocesses occurring at different relative time scales: (1) antibodies bind to free viruses to form non-infectious immune complexes (fast), and (2) immune complexes are subsequently ingested by circulating phagocytic cells (slow compared to the former but faster than infected cell death, which governs ART response, investigated below). The first process sequesters free viruses, effectively lowering the rate of infection of target cells. Only the second process, however, results in a decline of the viral load, which would now occur more slowly as compared to first-order clearance. It was difficult to test these scenarios from experimental data in the present study because of the lack of time resolution in viral RNA measurements.

In addition to forming immune complexes, antibodies can also bind to viral antigens on the surface of infected cells and this can cause an effector cell (NK cells, macrophages) to lyse the antibody-bound cell through antibody-dependent cellular cytotoxity (ADCC). We explored the qualitative effect of ADCC on the kinetics of viral decline. This was implemented in the simplest possible manner within our model by allowing the infected cell death rate $\lambda$ to increase in the presence of antibodies (Eqs. 2, 3, 5, and 6). For the same subject described in FIG. 4A, we found that a three-fold increase in the death rate of infected cells together with a six-fold enhancement of viral-clearance led to a biphasic viral decline wherein a graded decay mediated by ADCC followed an initial sharp decline mediated by antibody-mediated clearance. Thus moderate levels of ADCC required lower enhancements of viral clearance and viral decline occurred over a 5-day period (FIG. 4B), rather than in a few hours following antibody injection (FIG. 4A).

Taken together, these results indicate that a combination of rate processes that involve different time scales can cooperate to account for the kinetics of viral decline. Also, considering the large uncertainty in the estimates of baseline clearance rates of HIV/SIV/SHIV and variations therein from one tissue to another (De Boer et al., *PLoS Comput Biol.* 6: e1000906, 2010), one ought to treat our "fitted estimates" of clearance enhancement with caution. Our results suggest antibody-mediated neutralization of viruses into immune complexes that are eventually cleared by phagocytic cells enhances the baseline clearance rate by 10-fold order of magnitude estimate, and its value depends on the contribution of ADCC. The availability of viral load measurements at higher temporal resolution in future studies can aid in more precisely quantifying the relative contributions of antibody-mediated clearance and ADCC to viral decline.

Antibodies Need to Directly Act in the Tissue to Impact Immunologic Parameters

Figures 5A, 5B, 5C, 5D:
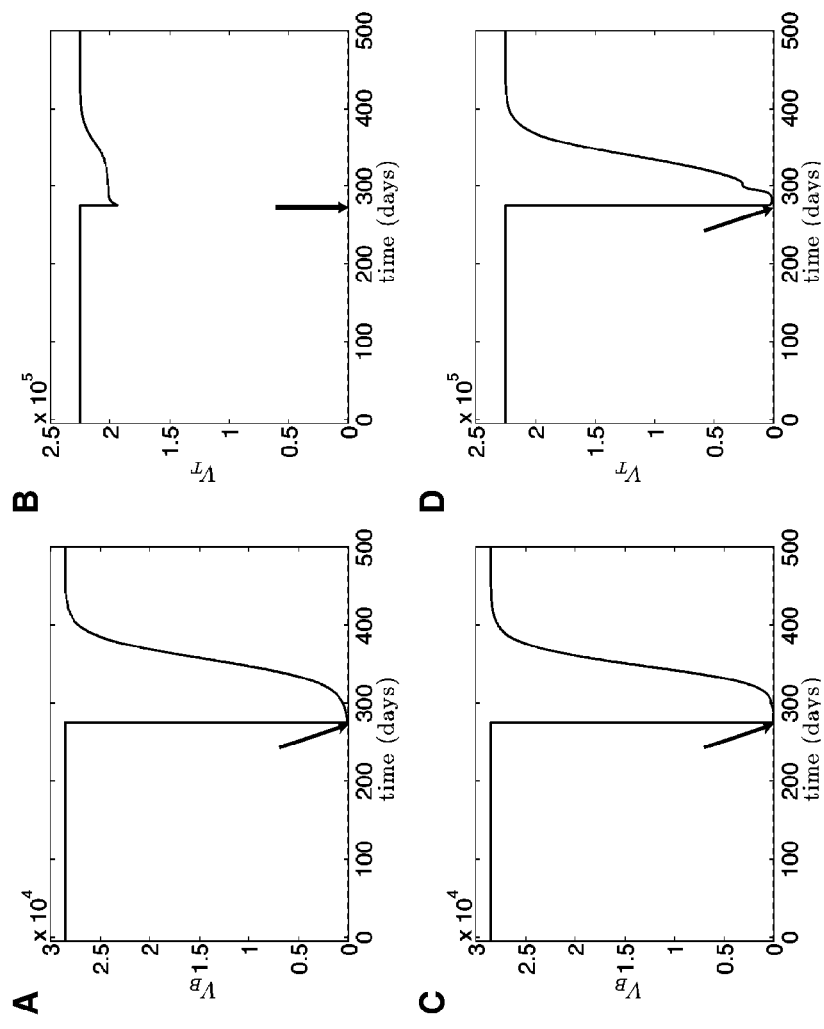
FIG. 5A is a graph showing the viral load ($mm^{-3}$ blood volume) in blood ($V_B$) when antibodies are active only in blood. The arrow indicates commencement of antibody therapy (t=275). Because a single dose of antibody is injected, the viral load rebounds once antibody titers decline. The dashed line at bottom of the graph in all panels shows the lower limit of viral detection ($\log_{10}(V_B)$=2.2).
FIG. 5B is a graph showing the viral load ($mm^{-3}$ blood volume) in tissue ($V_T$) when antibodies are active only in blood. The arrow indicates commencement of antibody therapy (t=275). Because a single dose of antibody is injected, the viral load rebounds once antibody titers decline. The dashed line at bottom of the graph in all panels shows the lower limit of viral detection ($\log_{10}(V_B)$=2.2).
FIG. 5C is a graph showing the viral load ($mm^{-3}$ blood volume) in blood ($V_B$) when antibodies are active in both blood and tissue. The arrow indicates commencement of antibody therapy (t=275). Because a single dose of antibody is injected, the viral load rebounds once antibody titers decline. The dashed line at bottom of the graph in all panels shows the lower limit of viral detection ($\log_{10}(V_B)$=2.2).
FIG. 5D is a graph showing the viral load ($mm^{-3}$ blood volume) in tissue ($V_T$) when antibodies are active in both blood and tissue. The arrow indicates commencement of antibody therapy (t=275). Because a single dose of antibody is injected, the viral load rebounds once antibody titers decline. The dashed line at bottom of the graph in all panels shows the lower limit of viral detection ($\log_{10}(V_B)$=2.2).
Figures 6A, 6B, 6C, 6D:
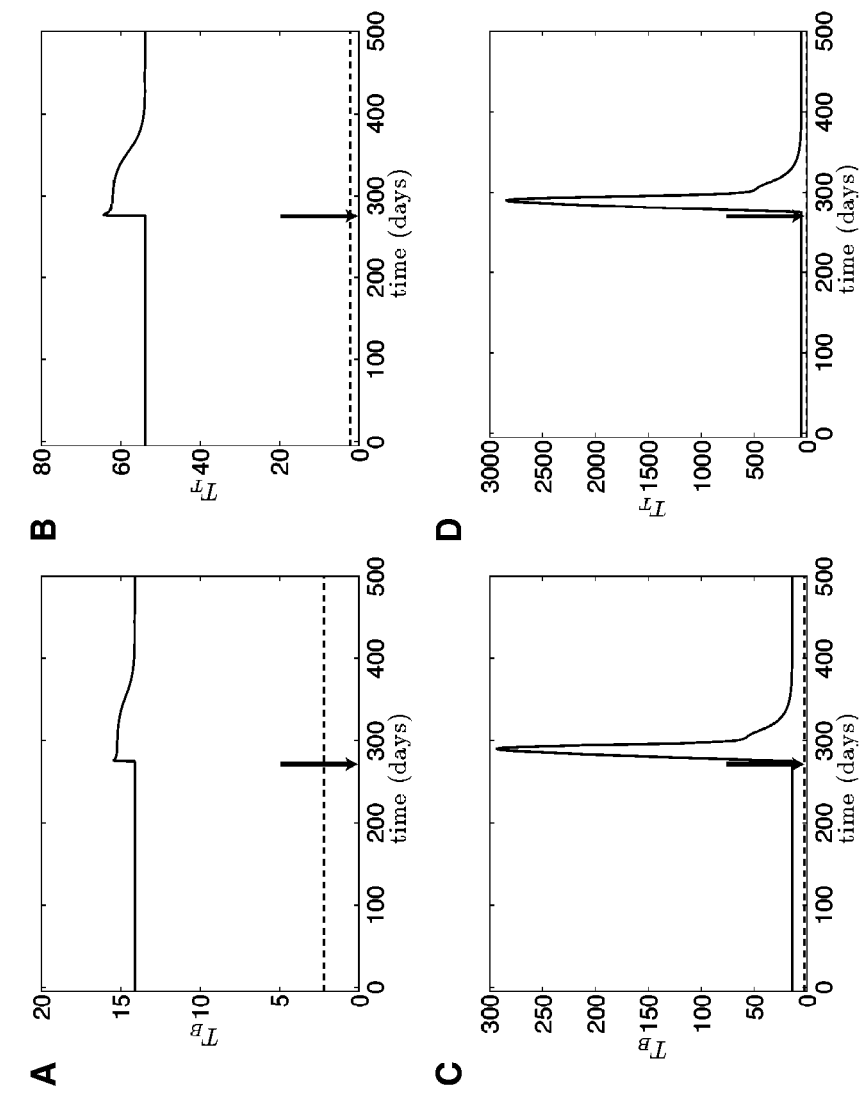
FIG. 6A is a graph showing target cell concentrations ($mm^{-3}$ blood volume) in blood ($T_B$) when antibodies are active only in blood. The arrow indicates commencement of antibody therapy (t=275). Because only a single dose of antibody is injected the concentration of healthy T cells retracts to its chronic steady state value once antibody titers decline.
FIG. 6B is a graph showing target cell concentrations ($mm^{-3}$ blood volume) in tissue ($T_T$) when antibodies are active only in blood. The arrow indicates commencement of antibody therapy (t=275). Because only a single dose of antibody is injected the concentration of healthy T cells retracts to its chronic steady state value once antibody titers decline.
FIG. 6C is a graph showing target cell concentrations ($mm^{-3}$ blood volume) in blood ($T_B$) when antibodies are active in both blood and tissue. The arrow indicates commencement of antibody therapy (t=275). Because only a single dose of antibody is injected the concentration of healthy T cells retracts to its chronic steady state value once antibody titers decline.
FIG. 6D is a graph showing target cell concentrations ($mm^{-3}$ blood volume) in tissue ($T_T$) when antibodies are active in both blood and tissue. The arrow indicates commencement of antibody therapy (t=275). Because only a single dose of antibody is injected the concentration of healthy T cells retracts to its chronic steady state value once antibody titers decline.

We next asked whether there are qualitative differences in the kinetics of different species (V, I, T; see Table 3) depending on whether antibodies acted only in the blood (setting $\eta=0$) or if they acted in both blood and tissue. Our simulations indicated that blood viral kinetics was indistinguishable in the two cases (FIGS. 5A and 5C). When antibodies were not active in tissues, however, the viral load therein was hardly impacted (FIG. 5B) in contrast to when antibodies were active (FIG. 5D). We found, however, that antibody action in the tissue was necessary for recovery of target cells in both blood and tissue (FIGS. 6A and 6B). When antibodies were active only in blood, despite decline in viral levels, the concentration of target cells did not recover (FIGS. 6C and 6D). Since target cells represent key immunologic components, our results indicate that antibodies need to act directly in tissue to improve immune pathology. In our experimental studies, this prediction is borne out by decline of proviral DNA in tissues and the concomitant increase in the proportion of CD4$^+$ T cells that are not high in markers of exhaustion and chronic activation like PD-1 and Ki67 (FIGS. 1N, 1O, 3I, and 3J).

The mechanistic reason for this is as follows. The virus in tissue accounts for >90% of the total viral load in the body (De Boer et al., *PLoS Comput Biol.* 6: e1000906, 2010) and a large proportion of infected cells reside in the tissue. Therefore, merely clearing "viral spillage" into blood does not impact viral load in the tissue despite the fact that viral load declines in blood. Since a great preponderance of target cells (representing CD4 T cells, DCs, etc.) reside in the tissue (Kirschner et al., *JAIDS*. 24: 352-362, 2000; Ho et al., *Nature*. 373: 123126, 1995), if antibodies have no impact therein, then infection of these cells continues unabated. In contrast, when antibodies substantially impact tissue viral load, the rate of infection of healthy target cells is also reduced. As a result the target cell count increases in tissue, which results in an efflux of these cells into blood. Our model therefore predicts that following therapy, increased concentrations of key immune cells targeted by the virus and decreased viral load in tissues, rather than decline in viral RNA levels in blood alone, are strongly correlated with antibody-mediated clearance of the viral reservoirs within tissue.

This qualitative observation remains true even with modest variations in parameters. One condition required is that numbers of immune cells and viral load must be greater in tissue than in blood, which is encoded by the fact that the efflux rates of these species from blood to tissue is much higher than the influx rates into blood from tissue. Although Eqs. 2 and 5 not consider migration of immune cells between the two compartments, adding this feature such that infected cells could diffuse between the compartments, while being in larger concentrations within the tissue, did not affect our results qualitatively. Since s represents the rate at which the healthy target cell pool (including CD4$^+$ cells, DCs) is replenished, we found that the extent of recovery following antibody therapy depended on its value. For example, when $s=10$ mm$^{-3}$/day, we found that target cell levels recovered to 4% of their equilibrium value in a healthy individual while antibodies were active, while when $s=100$ mm$^{-3}$ day$^{-1}$, the recovery was 35%.

Rebound Time

Figure 7:
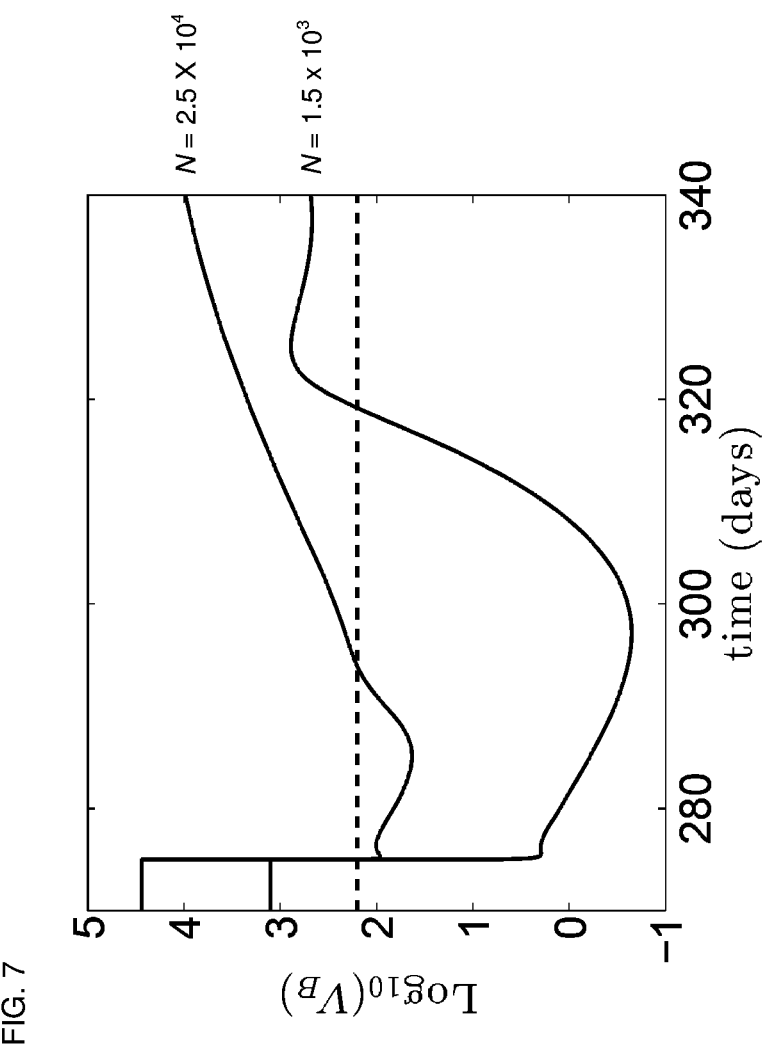
FIG. 7 is a graph showing the time to viral rebound is an inverse function of the value of initial viral setpoint. The lines correspond to subjects with N=2.5×$10^4$ and N=1.5×$10^3$, as indicated, leading to approximately 1.2 log difference in baseline viral load. The dashed line shows the lower limit of viral detection ($\log_{10}(V_B)$=2.2).

Our model also predicted that time to rebound should correlate inversely with the initial viral load (FIG. 7). This is because subjects with lower initial viral load are likely to exhibit superior intrinsic immune responses (higher $\Delta$, lower N) that can maintain viral control for extended periods of time after antibody titers have declined. Furthermore, lower initial viral loads can also result in a greater proportional reduction of the virus for the same antibody dosage. This prediction is strongly supported by the data summarized in Example 7 below.

Simulating Antiretroviral Therapy (ART)

We adapted the in silico model described by Eqs. 1-6 (with $b_T=bB=0$) to simulate viral dynamics in response to antiretroviral therapy (ART) in chronically infected rhesus macaques. As described above, healthy subjects were infected at t=0 with trace amounts of virus in blood ($V_B(0)=10^{-3}$) and equations were propagated until t=275 days when ART was initiated. Here we followed previous work in assuming that these drugs act with 100% efficacy and upon therapy initiation, new viral infections are completely blocked (k=0 for t>275). For certain inhibitors like ritanovir it is probably more accurate (Perelson et al., Science. 271: 1582-1586, 1996) to partition the viral species into tranches that are infectious ($V_I$) and non-infectious ($V_{NI}$) such that only virions produced after initiation of therapy are non-infectious. The already circulating infectious pool ($V_I$) rapidly decays once therapy is initiated, since it is no longer replenished by production. Introducing this feature did not, however, affect our kinetic results qualitatively, since a high physiological viral clearance rate (c=40 day$^{-1}$) and high production rate per infected cell (N$\lambda$=15000 day$^{-1}$) ensure rapid turnover of the viral population (as noted in Perelson et al., Science. 271: 1582-1586, 1996; Ho et al., Nature. 373: 123-126, 1995). Taking into account the presence of an infectious pool ($V_I$) merely slowed down by a small measure the initial viral decay during the first 4-5 hours following therapy.

Figures 8A, 8B, 8C, 8D:
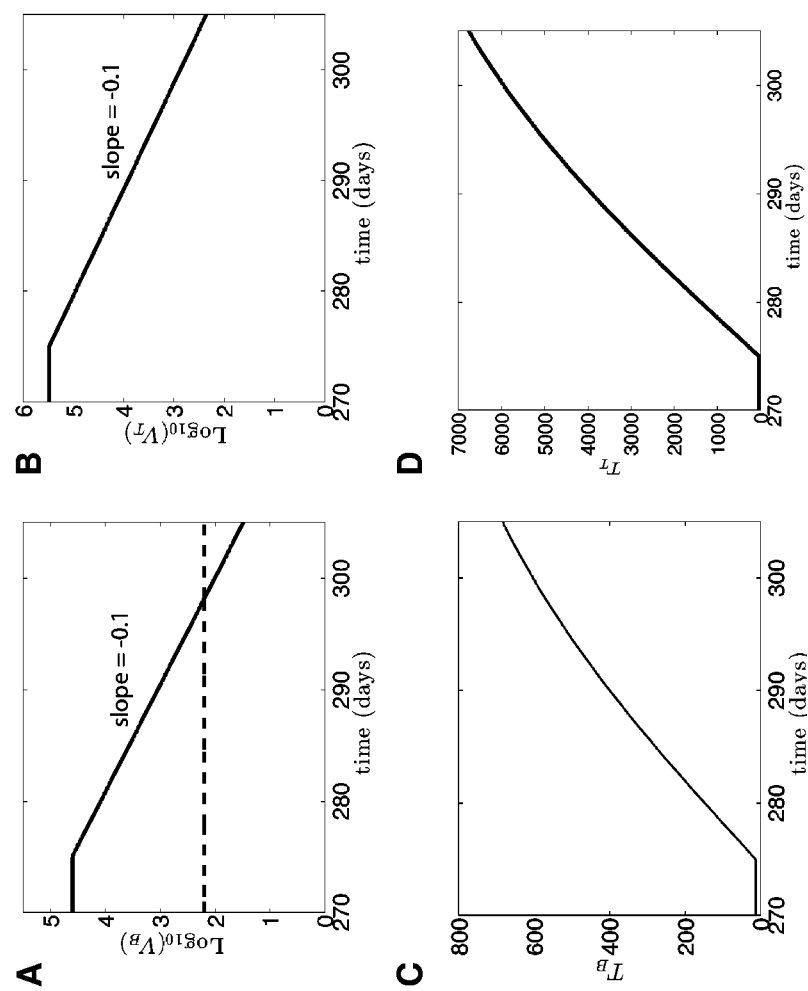
FIG. 8A is a graph showing the change in concentration ($mm^{-3}$ blood volume) of virus blood ($\log_{10}$ units) following initiation of ART on day 275. The dashed line in panel (A) shows the lower limit of viral detection ($\log_{10}(V_B)$=2.2).
FIG. 8B is a graph showing the change in concentration ($mm^{-3}$ blood volume) of virus in tissue ($\log_{10}$ units) following initiation of ART on day 275. The dashed line in panel (A) shows the lower limit of viral detection ($\log_{10}(V_B)$=2.2).
FIG. 8C is a graph showing the change in concentration ($mm^{-3}$ blood volume) of target cells in blood following initiation of ART on day 275. The dashed line in panel (A) shows the lower limit of viral detection ($\log_{10}(V_B)$=2.2).
FIG. 8D is a graph showing the change in concentration (mm$^{-3}$ blood volume) of target cells in tissue following initiation of ART on day 275. The dashed line in panel (A) shows the lower limit of viral detection ($\log_{10}(V_B)$=2.2).

Our simulations indicated that in response to ART the viral population in blood and tissue decayed exponentially with time for t>1 day in that $\log_{10}(V)/dt$ vs. time was a straight line (FIGS. 8A and 8B). One-compartment models, such as in Perelson et al. (Science. 271: 1582-1586, 1996), predict the slope of this line to be related to the death rate of infected cells, such that $d \log_{10}(V)/dt = -\lambda \log_{10}(e)$ where $e \approx 2.718$ is the base of the natural logarithm. This is because at long times, the decline in viral load is dominated by the slow loss of infected cells (and thereby, decrease in viral influx) rather than direct clearance of free virus, which dominates extremely short time scales (typically a few hours following ART initiation). While we did not pursue an exact analytical solution for our two-compartment system, similar physical arguments would apply and, one would expect viral decay to be governed by death rate of infected cells. Consistent with this expectation, we find that in our simulations, the slope of $\log_{10}(V_B)$ vs. time equals $\lambda \log_{10}(e) \approx 0.1$ logs/day (FIGS. 8A and 8B).

We compared viral kinetics in blood with experimental measurements of viral decline following antiretroviral therapy in SIV-infected monkeys. Fitting the log-viral decline using a single exponential suggested a median decay rate of 0.08 logs/day (N=6), suggesting that the death rate of infected cells in humans and macaques might be of similar magnitude. Recently, however, using ultra-sensitive and single-copy assays for measurements of blood virus, Andrade et al. (J Infect Dis. 208: 884-891, 2013) have found that viral decay following antiretroviral therapy in humans occurs in three distinct exponential phases, whose rates are respectively governed by the half-lives of short-lived productively infected cells, long-lived productively infected cells, and latently infected cells. It is plausible that this picture might apply to ART treatment in macaques too, but this remains to be tested using ultrasensitive assays and measurements of viral load at high temporal resolution. Our in silico model does not consider different kinds of infected cells, and, therefore, predicts monophasic decay of viral load.

Example 6

A Comparative Analysis of Viral Decline in Response to Different Therapies

Table 5 below compares antibody therapy in macaques with antiretroviral regimens in macaques and humans (Andrade et al., J Infect Dis. 208: 884-891, 2013) in terms of the resulting rates of viral decline following therapy initiation. The kinetics of decline of plasma viremia following infusion of PGT121 or PGT121-containing antibody cocktails was a median of 0.382 logs/day (IQR 0.338-0.540). In contrast, the initial kinetics of decline of plasma viremia following raltegravir (RAL)-containing combination antiretroviral therapy (ART) in HIV-1-infected humans was a median of 0.264 logs/day (IQR 0.253-0.284) (Andrade et al. J. Infect. Dis. A5248, 2013) and following combination ART in SIV-infected monkeys was a median of 0.229 logs/day (IQR 0.198-0.265). Although these reflect different models, the rapid control of virus following antibody administration in the present study is striking.

TABLE 5

Kinetics of decline of plasma viremia

| Therapy | r (logs/day) † Median (IQR) | Median t½ (days)# | Fold decrease viral load over 7-day period |
|---|---|---|---|
| ART in SIV infected macaques | 0.229 (0.198-0.265)* | 1.31 | 40 |
| EFV + 2 NRTI (humans) | 0.294 (0.273-0.334) | 1.02 | 112 |
| RAL + FTC/TDF (humans) | 0.264 (0.253-0.284) | 1.15 | 70 |
| antibody (macaques) | 0.382 (0.338-0.540) | 0.78 | 468 |

† In case of EFV (efavirenz) and RAL therapies, decline rates r correspond to the "first phase" of viral decline. Values reported in ref. (Andrade et al., J Infect Dis. 208: 884-891, 2013) have been converted to logs/day (base 10). Note that the specific rate of decline due to RAL is slower than that due to EFV. The rapid viral decline in RAL compared to EFV is due to a longer duration in the first phase and a slower transition into the second phase, where viral decline rates are lower.
The half-life, t½ = In(2)/r*In(10)
*Computed using viral load measurements at day 0 and day 12

Example 7

Summary of the Therapeutic Effect of PGT121 Alone or PGT121-containing Antibody Cocktails Antiretroviral drugs block virus replication and the generation of new infected cells, thereby reducing viremia, and the rate of virus decline is governed predominantly by the death of productively infected cells (FIG. 8). In contrast, antibodies bind free virus and form immune complexes that are ingested by phagocytic cells, and they can also bind to surface antigens on infected cells and potentially expedite their clearance through antibody-dependent cell-mediated cytotoxicity (ADCC) (Igarashi et al., Nat Med. 5: 211-216, 1999). The first process occurs on a much shorter time scale as compared to the lifetime of infected cells, and the second may enhance the death of infected cells. Comparing our simulations to our experimental data, we estimate that the antibodies afforded an order of 10-fold enhancement in the clearance rate of virus. If ADCC plays even a modest role, then a lower enhancement of the clearance rate is sufficient (FIG. 4). Our in silico model also indicates that antibodies need to act directly in tissues in order to reduce tissue viral loads and to impact immunologic parameters (FIGS. 5 and 6). This model together with our experimental data (FIGS. 2H, 2I, 3D, and 3E) suggest that the antibodies are in fact functional in tissues.

Figures 9A, 9B, 9C, 9D:
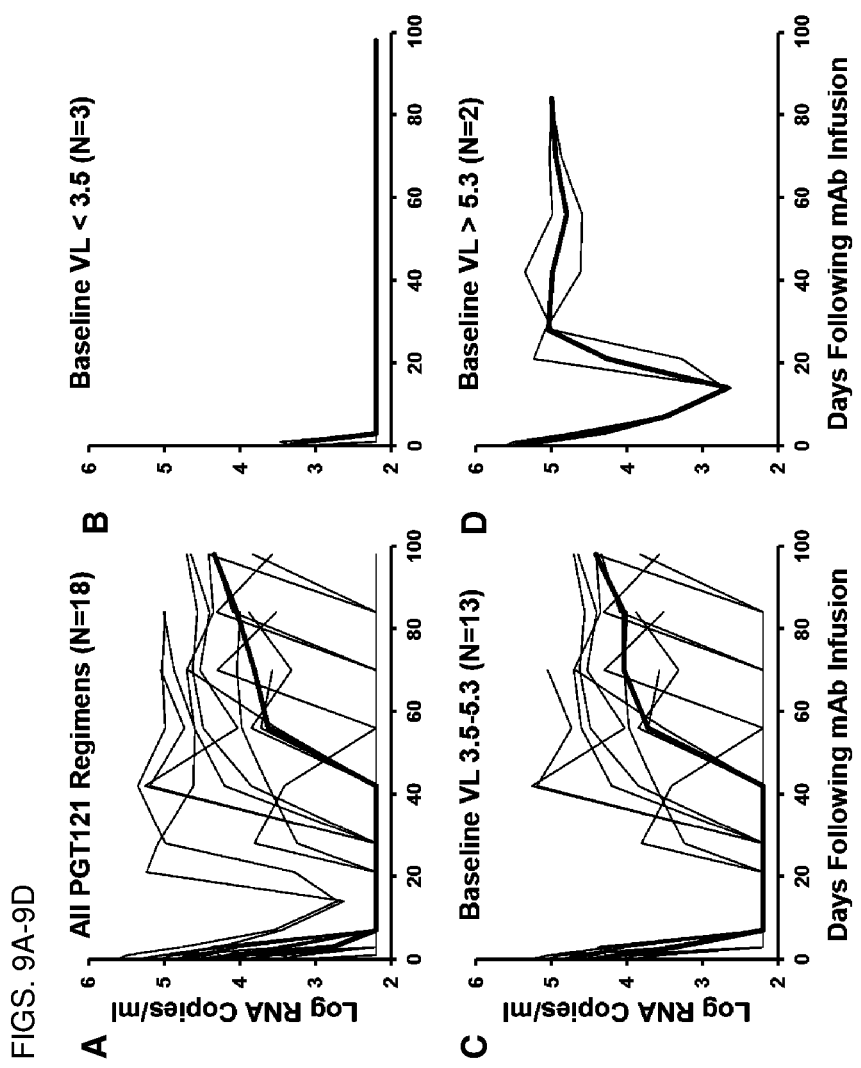
FIG. 9A is a graph showing the therapeutic effect of PGT121 alone or PGT121-containing antibody cocktails in the 18 rhesus monkeys chronically infected with SHIV-SF162P3. The bold line indicates median viral loads.
FIG. 9B is a graph showing PGT121 results in long-term virologic control with no evidence of viral rebound for over 100 days in three rhesus monkeys with low baseline viral loads of <3.5 log RNA copies/ml. The bold line indicates median viral loads.
FIG. 9C is a graph showing the therapeutic effect of PGT121 in 13 rhesus monkeys with baseline viral loads of 3.5-5.3 log RNA copies/ml. The bold line indicates median viral loads.
FIG. 9D is a graph showing the therapeutic effect of PGT121 in two rhesus monkeys with baseline viral loads of >5.3 log RNA copies/ml. The bold line indicates median viral loads.
Figures 9E, 9F:
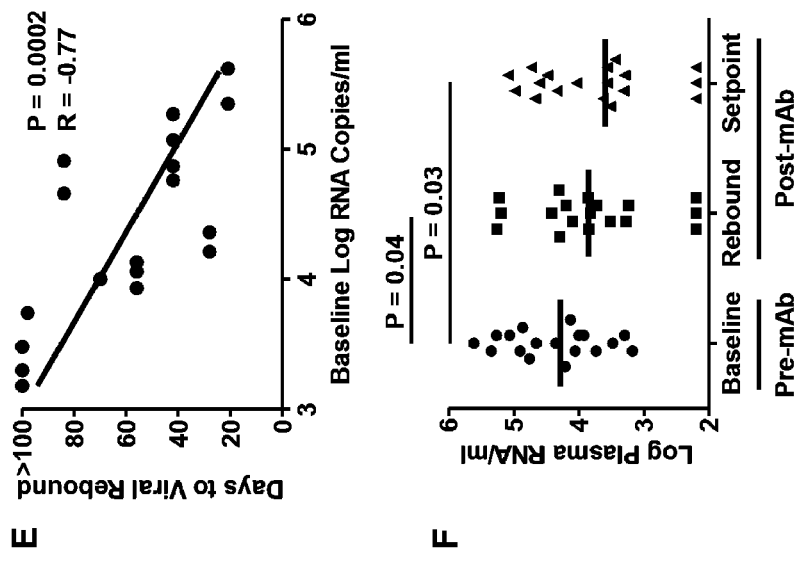
FIG. 9E is a graph showing the correlation of baseline viral loads with times to viral rebound for all 18 rhesus monkeys chronically infected with SHIV-SF162P3 and administered PGT121. P value reflects Spearman rank-correlation test.
FIG. 9F is a graph comparing setpoint viral loads before antibody administration and following viral rebound for all 18 rhesus monkeys chronically infected with SHIV-SF162P3 and administered PGT121. Horizontal bars indicate median viral loads. P values reflect Mann-Whitney tests.

Our studies demonstrate unprecedented therapeutic efficacy of PGT121 and PGT121-containing antibody cocktails in chronically SHIV-SF162P3 infected rhesus monkeys. The therapeutic efficacy in the 18 animals that received PGT121 alone or as part of a cocktail (FIG. 9A) was critically dependent on baseline viral loads before antibody administration. In the 17% of animals (3 of 18) with low baseline viral loads <3.5 log RNA copies/ml, long-term control of viral replication was observed for the duration of the follow-up period (FIG. 9B), with no evidence of viral rebound for over 100 days in monkeys 4905 and DN1G and for over 200 days in monkey 163-09, reflecting a substantial period of time after serum antibody titers had declined to undetectable levels. These observations are consistent with data from humanized mice (Klein et al., *Nature*. 492: 118-122, 2012; Diskin et al., *J Exp Med*. 210: 1235-1249, 2013) and suggest that PGT121 may have converted animals with low baseline viremia into an "elite controller" phenotype. It is important to emphasize that these animals still have detectable, albeit substantially reduced, proviral DNA in tissues (FIGS. 2H, 2I, 3D, and 3E), and thus virus has not been eradicated. In the 72% of animals (13 of 18) with intermediate baseline viral loads 3.5-5.3 log RNA copies/ml, plasma viremia was uniformly and rapidly reduced to undetectable levels within 7 days but then rebounded in a median of 56 days when serum antibody titers declined to undetectable levels <1 µg/ml (FIG. 9C). In the 11% animals (2 of 18) with high baseline viral loads >5.3 log RNA copies/ml, incomplete control of viral replication and rapid viral rebound occurred, suggesting a therapeutic ceiling in this model (FIG. 9D). Taken together, baseline viral loads strongly correlated with the time to viral rebound (P=0.0002, Spearman rank-correlation test; FIG. 9E), which was also predicted by our in silico model (FIG. 7).

We speculate that the therapeutic impact of these antibodies reflected not only direct antiviral activity but also indirect improvement of host antiviral immune responses. Following antibody infusion, we observed modest increases in host virus-specific NAb activity that persisted even after antibody titers declined to undetectable levels (FIG. 1J) as well as significant improvements in the quality of host Gag-specific CD8+ and CD4+ T lymphocyte responses (FIGS. 1N, 1O, 3I, and 3J). Consistent with the improved host immune responses, mean setpoint viral loads following viral rebound were 0.61 log lower than mean baseline setpoint viral loads before the antibody infusions (P=0.03, Mann-Whitney test; FIG. 9F), and 3 of 18 monkeys exhibited persistent virologic control to undetectable levels (FIG. 9B). Defining the precise immunologic mechanisms of the improved control of viral replication following antibody administration warrants further investigation.

Previous studies in humanized mice and humans showed that the earlier generation of neutralizing HIV-1-specific antibodies was unable to control viremia and that both single antibodies and antibody cocktails rapidly selected for escape variants with viral resistance mutations (Poignard et al., *Immunity*. 10: 431-438, 1999; Trkola et al., *Nat Med*. 11: 615-622, 2005; Mehandru et al., *J Virol*. 81: 11016-11031, 2007). More recent studies in humanized mice have shown that combinations of 3 or 5 of the new generation of more potent antibodies suppressed HIV-1 replication, whereas single antibodies rapidly selected for resistance (Klein et al., *Nature*. 492: 118-122, 2012; Diskin et al., *J Exp Med*. 210: 1235-1249, 2013). In contrast, we observed in the present study that a single infusion of PGT121 resulted in rapid kinetics of suppression of SHIV-SF162P3 viremia in rhesus monkeys as well as reductions in proviral DNA in lymph nodes and gastrointestinal mucosa. Virus only rebounded when PGT121 concentrations declined to undetectable levels, consistent with the mouse experiments (Klein et al., *Nature*. 492: 118-122, 2012; Diskin et al., *J Exp Med*. 210: 1235-1249, 2013). It is possible that intrinsic differences between HIV-1 replication in mice and SHIV replication in monkeys may account for these differences. Another key difference is the functional immune system in monkeys as compared with the humanized mice. It is possible that the profound suppression of virus without the development of resistance reflects in part host antibody effector activity and intrinsic antiviral cellular immune responses. Further studies are required to understand all the factors that contribute to antibody suppression of virus in rhesus monkeys. In summary, our data demonstrate unprecedented therapeutic efficacy of broad and potent HIV-1-specific antibodies in rhesus monkeys chronically infected with the pathogenic virus SHIV-SF162P3.

Example 8

Therapeutic Efficacy of PGT121 in ART-suppressed, SHIV-infected Rhesus Monkeys

We have demonstrated that PGT121 reduced proviral DNA in tissues in viremic monkeys. Here, we assessed if PGT121 can target the viral reservoir in antiretroviral therapy (ART)-suppressed animals. Clinical development programs can evaluate broadly neutralizing mAbs in combination with ART. A key question is whether reservoir cells express sufficient Env to be targeted by mAbs (e.g., homeostatic proliferation, low levels of virus production, or immune or pharmacologic activation). Thus, we evaluated the impact of PGT121 in ART-suppressed, SHIV-infected rhesus monkeys.

Nine rhesus monkeys were infected with SHIV-SF162P3 virus for 7 months, with baseline viral loads of 3.3-5.1 log RNA copies/mL. A daily suppressive ART regimen (including tenofovir, emtricitabine, and dolutegravir) was initiated in all animals and continued for 20 weeks. The monkeys were divided into two treatment groups: Group A (N=5), which received 20 weeks of ART and were additionally treated with PGT121 on weeks 0, 4, 8, and 12; and Group B (N=4), which received the 20 weeks of ART alone.

Figures 10A, 10B:
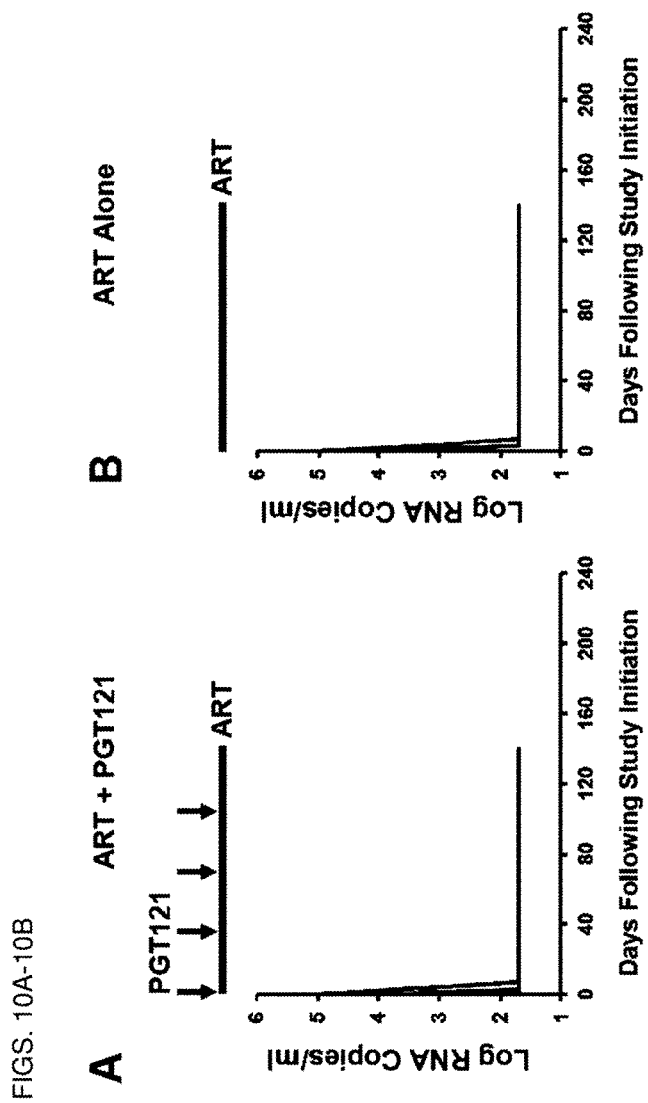
FIGS. 10A and 10B are graphs showing rapid and complete virologic suppression in rhesus monkeys, as assessed by plasma viral RNA (copies/ml) levels, following initiation of both (A) ART+PGT121 treatment and (B) ART1 treatment alone. ART was provided over twenty weeks in all animals, while animals also receiving PGT121 were treated with PGT121 on weeks 0, 4, 8, and 12 (arrows). Each line in the graph represents an individual animal.
Figures 11A, 11B:
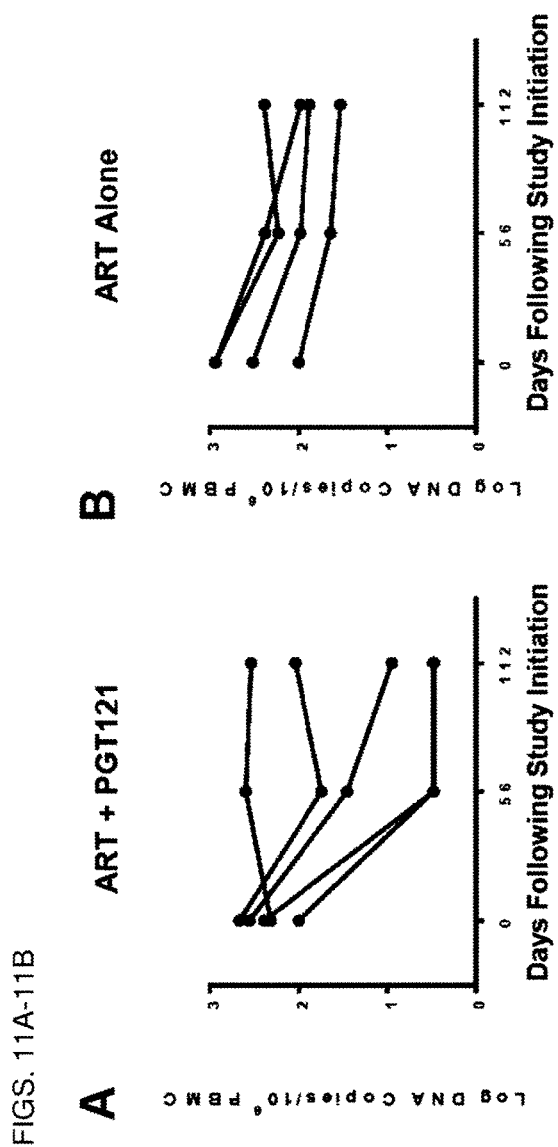
FIGS. 11A and 11B are graphs showing reduction in proviral DNA in peripheral blood mononuclear cells (PBMCs) in (A) ART+PGT121 treated rhesus monkeys and (B) rhesus monkeys treated with ART alone. Each monkey was evaluated for proviral DNA levels in PBMCs at days 0, 56, and 112 following initiation of the study.
Figures 12A, 12B:
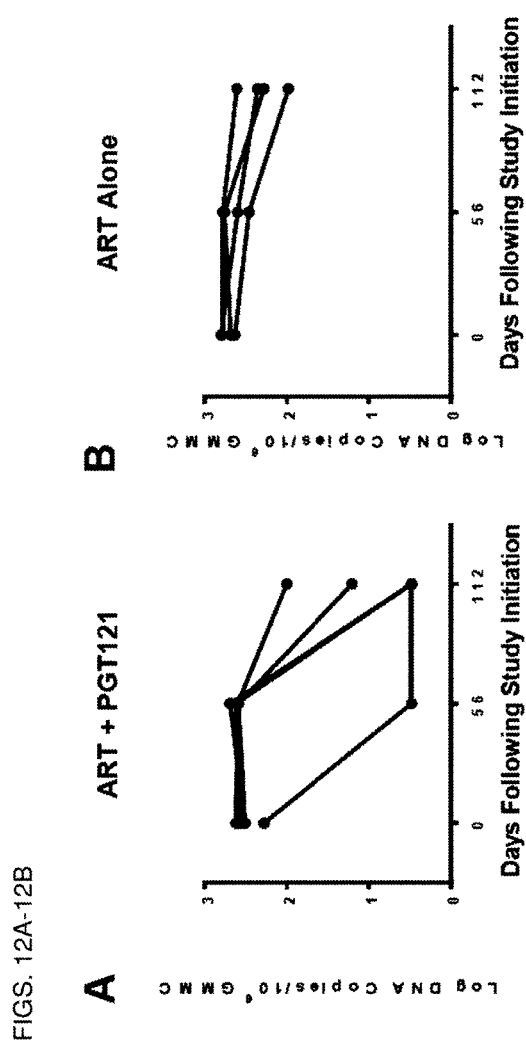
FIGS. 12A and 12B are graphs showing reduction in proviral DNA in gastrointestinal mucosa in (A) ART+PGT121-treated monkeys and (B) monkeys treated with ART alone. Each monkey was evaluated for gastrointestinal mucosa proviral DNA levels at days 0, 56, and 112 following initiation of the study.

As shown in FIGS. 10A and 10B, we observed rapid and complete virologic suppression in both Group A (ART+PGT121) and Group B (ART alone). Both treatment groups showed similarly strong reduction in log RNA copies per mL in all animals shortly after initiation of treatment. However, animals treated with both ART and PGT121 showed a greater reduction in proviral DNA in peripheral blood mononuclear cells (PBMCs), starting by day 56 and maintained through day 112, compared to animals treated with ART alone (FIGS. 11A and 11B). Similarly, animals treated with both ART and PGT121 showed a greater reduction in proviral DNA in gastrointestinal mucosa compared to ART-alone controls (FIGS. 12A and 12B), with some ART+PGT121 animals showing a strong decrease in gastrointestinal proviral DNA levels by day 56 (maintained through day 112), and others showing decrease by day 112.

Figures 13A, 13B:
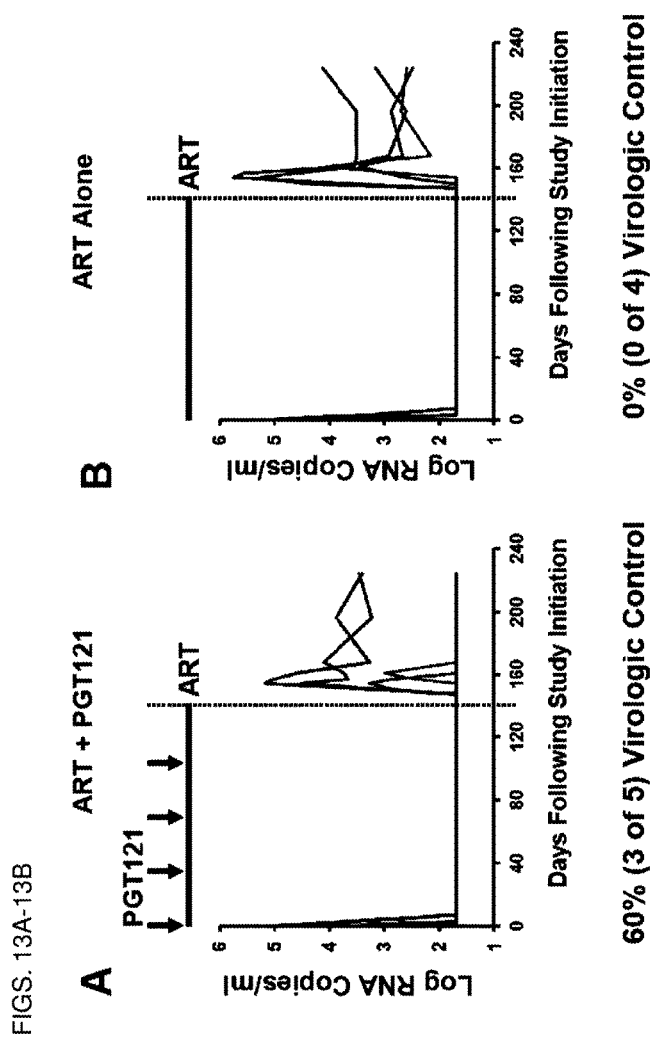
FIGS. 13A and 13B are graphs showing virologic control observed in (A) ART+PGT121 and (B) ART alone rhesus monkeys after discontinuation of ART, as assessed by plasma viral RNA (copies/ml) levels. Each line in the graph represents an individual animal.

For both treatment groups, ART was discontinued at week 20. Animals were monitored for virologic control after discontinuation of ART. Whereas 0% of Group B (ART alone) animals maintained virologic control, 60% of Group A (ART+PGT121) animals showed continued virologic control even after ART discontinuation (FIGS. 13A and 13B). Taken together, these results demonstrate that PGT121 treatment can successfully target the viral reservoir in ART-suppressed animals and reduce viral rebound following ART discontinuation.

PGT121, both alone and in combination with other mAbs, in humans can be administered as part of HIV-1 eradication strategies. PGT121 itself covers approximately 70% of clade C viruses. As such, cocktails of 2 or 3 mAbs will be useful for global coverage and advanced clinical development. PGT121 can, for example, be combined with either a CD4 binding site (CD4bs)-specific mAb or a V2 glycan-dependent mAb, or both, as described herein.

Example 9

Figures 14A, 14B, 14C, 14D:
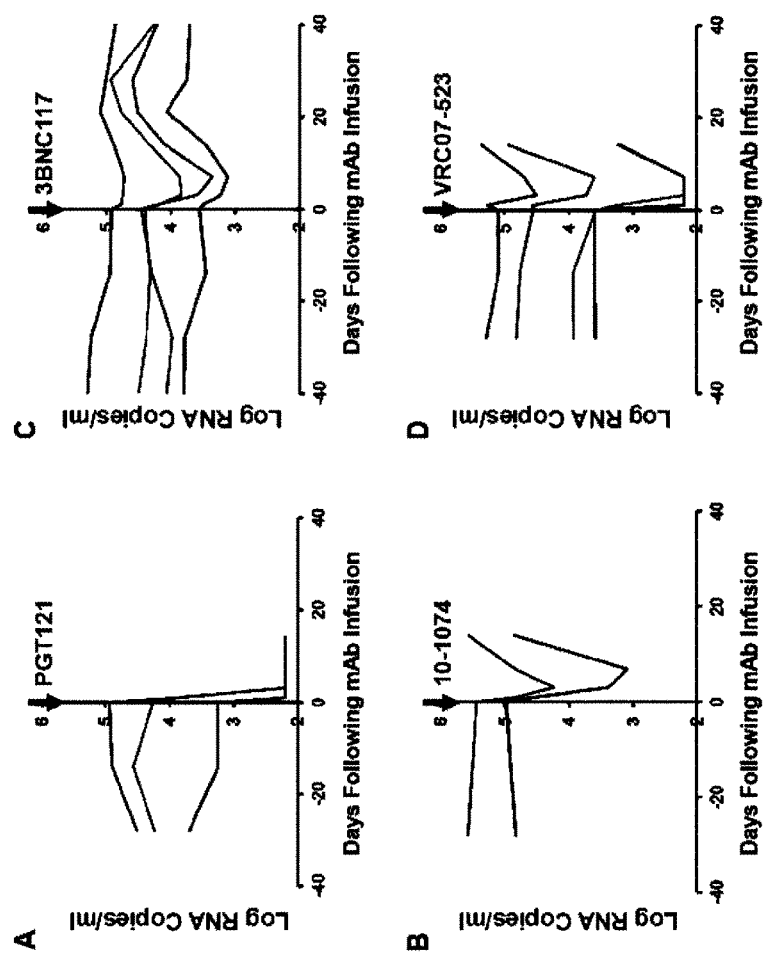
FIGS. 14A-14D are graphs showing therapeutic efficiency of four antibodies ((A) PGT121, (B) 10-1074, (C) 3BNC117, and (D) VRC07-523) on SHIV-SF162P3-infected rhesus monkeys, as assessed by plasma viral RNA (copies/ml) levels. Each line in the graph represents an individual animal.

Therapeutic Efficacy of PGT121, 10-1074, 3BNC117, and VRC07-523 Antibodies in SHIV-SF162P3-infected Rhesus Monkeys We assessed the therapeutic antiviral activity of PGT121 in vivo in comparison with a set of additional antibodies also known to show broad and potent in vitro neutralization. Rhesus monkeys infected with SHIV-SF162P3 virus were treated on "day 0" with an infusion of one of the following antibodies: PGT121 (n=3), 10-1074 (n=2), 3BNC117 (n=4), or VRC07-523 (n=4). Surprisingly, PGT121-treated monkeys showed extremely potent virologic suppression (FIG. 14A) compared to those treated with 10-1074, 3BNC117, or VRC07-523 (FIGS. 14B-14D, respectively), which would not have been predicted based on their similar in vitro activity. Indeed, the three monkeys treated with PGT121 displayed virtually undetectable levels of viral RNA within days of treatment, which was maintained for at least 15 days after treatment (FIG. 14A). These data indicate that PGT121 has unexpectedly potent antiviral activity in vivo compared to other antibodies, and may have strong potential as a therapy and/or cure for HIV.

Other Embodiments

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth.

All publications, patents, and patent applications are herein incorporated by reference in their entirety to the same extent as if each individual publication, patent or patent application was specifically and individually indicated to be incorporated by reference in its entirety.

The invention claimed is:

1. A method for inhibiting viral replication, reducing proviral DNA, or reducing viral load comprising administering to a subject infected with human immunodeficiency virus type 1 (HIV-1) a first regimen comprising one or more doses of an N332 glycan-dependent antibody and a reservoir activator until a proviral DNA level in a tissue of the subject is below about 1,000 DNA copies/$10^6$ cells, and, at least two months after completion of the first regimen, administering a second regimen comprising one or more doses of the N332 glycan-dependent antibody with or without a reservoir activator, wherein said N332 glycan-dependent antibody is selected from the group consisting of:

(a) an antibody comprising:
  (i) a heavy chain complementarity determining region (CDR-H) CDR-H1 comprising the amino acid sequence of SEQ ID NO: 1, a CDR-H2 comprising the amino acid sequence of SEQ ID NO: 2, and a CDR-H3 comprising the amino acid sequence of SEQ ID NO: 3, and a light chain complementarity determining region (CDR-L) CDR-L1 comprising the amino acid sequence of SEQ ID NO: 4, a CDR-L2 comprising the amino acid sequence of SEQ ID NO: 5, and a CDR-L3 comprising the amino acid sequence of SEQ ID NO: 6; or
  (ii) a heavy chain variable domain having at least 95% sequence identity to the amino acid sequence of SEQ ID NO: 7, and a light chain variable domain having at least 97% sequence identity to the sequence of SEQ ID NO: 8;

(b) an antibody comprising
  a heavy chain complementarity determining region (CDR-H) CDR-H1 comprising the amino acid sequence of SEQ ID NO: 9, a CDR-H2 comprising the amino acid sequence of SEQ ID NO: 10, and a CDR-H3 comprising the amino acid sequence of SEQ ID NO: 11, and a light chain complementarity determining region (CDR-L) CDR-L1 comprising the amino acid sequence of SEQ ID NO: 12, a CDR-L2 comprising the amino acid sequence of SEQ ID NO: 13, and a CDR-L3 comprising the amino acid sequence of SEQ ID NO: 14;

(c) an antibody comprising
  a heavy chain complementarity determining region (CDR-H) CDR-H1 comprising the amino acid sequence of SEQ ID NO: 17, a CDR-H2 comprising the amino acid sequence of SEQ ID NO: 18, and a CDR-H3 comprising the amino acid sequence of SEQ ID NO: 19, and a light chain complementarity determining region (CDR-L) CDR-L1 comprising the amino acid sequence of SEQ ID NO: 20, a CDR-L2 comprising the amino acid sequence of SEQ ID NO: 21, and a CDR-L3 comprising the amino acid sequence of SEQ ID NO: 22;

(d) an antibody comprising
  a heavy chain complementarity determining region (CDR-H) CDR-H1 comprising the amino acid sequence of SEQ ID NO: 137, a CDR-H2 comprising the amino acid sequence of SEQ ID NO: 138, and a CDR-H3 comprising the amino acid sequence of SEQ ID NO: 139, and a light chain complementarity determining region (CDR-L) CDR-L1 comprising the amino acid sequence of SEQ ID NO: 140, a CDR-L2 comprising the amino acid sequence of SEQ ID NO: 142, and a CDR-L3 comprising the amino acid sequence of SEQ ID NO: 143;

(e) an antibody comprising
  a heavy chain complementarity determining region (CDR-H) CDR-H1 comprising the amino acid sequence of SEQ ID NO: 25, a CDR-H2 comprising the amino acid sequence of SEQ ID NO: 26, and a CDR-H3 comprising the amino acid sequence of SEQ ID NO: 27, and a light chain complementarity determining region (CDR-L) CDR-L1 comprising the amino acid sequence of SEQ ID NO: 28, a CDR-L2 comprising the amino acid sequence of SEQ ID NO: 29, and a CDR-L3 comprising the amino acid sequence of SEQ ID NO: 30;

(f) an antibody comprising
  a heavy chain complementarity determining region (CDR-H) CDR-H1 comprising the amino acid sequence of SEQ ID NO: 33, a CDR-H2 comprising the amino acid sequence of SEQ ID NO: 34, and a CDR-H3 comprising the amino acid sequence of SEQ ID NO: 35, and a light chain complementarity determining region (CDR-L) CDR-L1 comprising the amino acid sequence of SEQ ID NO: 36, a CDR-L2 comprising the amino acid sequence of SEQ ID NO: 37, and a CDR-L3 comprising the amino acid sequence of SEQ ID NO: 38;

(g) an antibody comprising
  a heavy chain complementarity determining region (CDR-H) CDR-H1 comprising the amino acid sequence of SEQ ID NO: 41, a CDR-H2 comprising the amino acid sequence of SEQ ID NO: 42, and a CDR-H3 comprising the amino acid sequence of SEQ ID NO: 43, and a light chain complementarity determining region (CDR-L) CDR-L1 comprising the amino acid sequence of SEQ ID NO: 44, a CDR-L2 comprising the amino acid sequence of SEQ ID NO: 45, and a CDR-L3 comprising the amino acid sequence of SEQ ID NO: 46;

(h) an antibody comprising
  a heavy chain complementarity determining region (CDR-H) CDR-H1 comprising the amino acid sequence of SEQ ID NO: 49, a CDR-H2 comprising the amino acid sequence of SEQ ID NO: 50, and a CDR-H3 comprising the amino acid sequence of SEQ ID NO: 51, and a light chain complementarity determining region (CDR-L) CDR-L1 comprising the amino acid sequence of SEQ ID NO: 52, a CDR-L2 comprising the amino acid sequence of SEQ ID NO: 53, and a CDR-L3 comprising the amino acid sequence of SEQ ID NO: 54;

(i) an antibody comprising
  a heavy chain complementarity determining region (CDR-H) CDR-H1 comprising the amino acid sequence of SEQ ID NO: 57, a CDR-H2 comprising the amino acid sequence of SEQ ID NO: 58, and a CDR-H3 comprising the amino acid sequence of SEQ ID NO: 59, and a light chain complementarity determining region (CDR-L) CDR-L1 comprising the amino acid sequence of SEQ ID NO: 60, a CDR-L2 comprising the amino acid sequence of SEQ ID NO: 61, and a CDR-L3 comprising the amino acid sequence of SEQ ID NO: 62;

(j) an antibody comprising
  a heavy chain complementarity determining region (CDR-H) CDR-H1 comprising the amino acid sequence of SEQ ID NO: 145, a CDR-H2 comprising the amino acid sequence of SEQ ID NO: 146, and a CDR-H3 comprising the amino acid sequence of SEQ ID NO: 147, and a light chain complementarity determining region (CDR-L) CDR-L1 comprising the amino acid sequence of SEQ ID NO: 148, a CDR-L2 comprising the amino acid sequence of SEQ ID NO: 149, and a CDR-L3 comprising the amino acid sequence of SEQ ID NO: 150;

(k) an antibody comprising
a heavy chain complementarity determining region (CDR-H) CDR-H1 comprising the amino acid sequence of SEQ ID NO: 153, a CDR-H2 comprising the amino acid sequence of SEQ ID NO: 154, and a CDR-H3 comprising the amino acid sequence of SEQ ID NO: 155, and a light chain complementarity determining region (CDR-L) CDR-L1 comprising the amino acid sequence of SEQ ID NO: 156, a CDR-L2 comprising the amino acid sequence of SEQ ID NO: 157, and a CDR-L3 comprising the amino acid sequence of SEQ ID NO: 158;

(l) an antibody comprising
a heavy chain complementarity determining region (CDR-H) CDR-H1 comprising the amino acid sequence of SEQ ID NO: 73, a CDR-H2 comprising the amino acid sequence of SEQ ID NO: 74, and a CDR-H3 comprising the amino acid sequence of SEQ ID NO: 75, and a light chain complementarity determining region (CDR-L) CDR-L1 comprising the amino acid sequence of SEQ ID NO: 76, a CDR-L2 comprising the amino acid sequence of SEQ ID NO: 77, and a CDR-L3 comprising the amino acid sequence of SEQ ID NO: 78;

(m) an antibody comprising
a heavy chain complementarity determining region (CDR-H) CDR-H1 comprising the amino acid sequence of SEQ ID NO: 81, a CDR-H2 comprising the amino acid sequence of SEQ ID NO: 82, and a CDR-H3 comprising the amino acid sequence of SEQ ID NO: 83, and a light chain complementarity determining region (CDR-L) CDR-L1 comprising the amino acid sequence of SEQ ID NO: 84, a CDR-L2 comprising the amino acid sequence of SEQ ID NO: 85, and a CDR-L3 comprising the amino acid sequence of SEQ ID NO: 86;

(n) an antibody comprising
a heavy chain complementarity determining region (CDR-H) CDR-H1 comprising the amino acid sequence of SEQ ID NO: 97, a CDR-H2 comprising the amino acid sequence of SEQ ID NO: 98, and a CDR-H3 comprising the amino acid sequence of SEQ ID NO: 99, and a light chain complementarity determining region (CDR-L) CDR-L1 comprising the amino acid sequence of SEQ ID NO: 100, a CDR-L2 comprising the amino acid sequence of SEQ ID NO: 101, and a CDR-L3 comprising the amino acid sequence of SEQ ID NO: 102;

(o) an antibody comprising
a heavy chain complementarity determining region (CDR-H) CDR-H1 comprising the amino acid sequence of SEQ ID NO: 169, a CDR-H2 comprising the amino acid sequence of SEQ ID NO: 170, and a CDR-H3 comprising the amino acid sequence of SEQ ID NO: 171, and a light chain complementarity determining region (CDR-L) CDR-L1 comprising the amino acid sequence of SEQ ID NO: 172, a CDR-L2 comprising the amino acid sequence of SEQ ID NO: 173, and a CDR-L3 comprising the amino acid sequence of SEQ ID NO: 174;

(p) an antibody comprising
a heavy chain complementarity determining region (CDR-H) CDR-H1 comprising the amino acid sequence of SEQ ID NO: 177, a CDR-H2 comprising the amino acid sequence of SEQ ID NO: 178, and a CDR-H3 comprising the amino acid sequence of SEQ ID NO: 179, and a light chain complementarity determining region (CDR-L) CDR-L1 comprising the amino acid sequence of SEQ ID NO: 180, a CDR-L2 comprising the amino acid sequence of SEQ ID NO: 181, and a CDR-L3 comprising the amino acid sequence of SEQ ID NO: 182; and (q) an antibody comprising
a heavy chain complementarity determining region (CDR-H) CDR-H1 comprising the amino acid sequence of SEQ ID NO: 315, a CDR-H2 comprising the amino acid sequence of SEQ ID NO: 316, and a CDR-H3 comprising the amino acid sequence of SEQ ID NO: 317, and a light chain complementarity determining region (CDR-L) CDR-L1 comprising the amino acid sequence of SEQ ID NO: 318, a CDR-L2 comprising the amino acid sequence of SEQ ID NO: 319, and a CDR-L3 comprising the amino acid sequence of SEQ ID NO: 320.

2. The method of claim 1, wherein said N332 glycan-dependent antibody is PGT121.

3. The method of claim 1, wherein said reservoir activator is a histone deacetylase (HDAC) inhibitor selected from romidepsin, vorinostat, and panobinostat.

4. The method of claim 1, wherein said method further comprises administering at least a second antibody and a third antibody; wherein:
(a) said N332 glycan-dependent antibody is PGT121, said second antibody is 3BNC117, and said third antibody is CAP256-VRC26,
(b) said N332 glycan-dependent antibody is PGT121, said second antibody is VRC07-523, and said third antibody is CAP256-VRC26, or
(c) said N332 glycan-dependent antibody is PGT121, said second antibody is 3BNC117, and said third antibody is VRC07-523.

5. The method of claim 1, wherein said N332 glycan-dependent antibody is 10-1074.

6. The method of claim 1, wherein said reservoir activator is an immunologic activator selected from a cytokine and a TLR agonist.

7. The method of claim 1, wherein said subject is a human.

8. The method of claim 1, wherein the N332 glycan-dependent antibody and the reservoir activator is administered to said subject in the first regimen until said proviral DNA level in the tissue is below about 100 DNA copies/$10^6$ cells.

9. The method of claim 1, wherein said tissue is lymph node tissue, gastrointestinal tissue, and/or peripheral blood.

10. The method of claim 1, wherein said subject has a plasma viral load of less than 3,500 RNA copies/ml.

11. The method of claim 10, wherein said subject has a plasma viral load of less than 2,000 RNA copies/ml.

12. The method of claim 1, wherein said subject has an undetectable plasma viral load for at least 2 months following administration of said N332 glycan-dependent antibody and said reservoir activator.

13. The method of claim 12, wherein said subject has an undetectable plasma viral load for at least 6 months following administration of said N332 glycan-dependent antibody and said reservoir activator.

14. The method of claim 1, wherein said N332 glycan-dependent antibody is administered intravenously, intramuscularly, intradermally, percutaneously, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subcutaneously, subconjunctivally, intravesicularlly, mucosally, intrapericardially, intraumbilically, intraocularly, orally, topically, locally, by inhalation, by injection, by infusion, by continuous infusion, by localized perfusion bathing target cells directly, by catheter, by lavage, by gavage, in cremes, or in lipid compositions.

15. The method of claim 1, wherein said N332 glycan-dependent antibody is administered at a concentration of about 0.01 mg/kg to about 20 mg/kg.

16. The method of claim 1, wherein said method comprises administering a single dose of said N332 glycan-dependent antibody.

17. The method of claim 1, wherein said second regimen is administered at least about 6 months after said first regimen.

18. The method of claim 1, further comprising administering one or more of an antiretroviral therapy (ART); an HIV1-specific, broadly neutralizing antibody (bnAb); a CD4 binding site (CD4bs)-specific antibody; a V2 glycan-dependent antibody; or an immunomodulator.

19. The method of claim 18, wherein the immunomodulator is AS-101, bropirimine, acemannan, CL246,738, EL10, FP-21399, gamma interferon, granulocyte macrophage colony stimulating factor, HIV core particle immunostimulant, IL-2, immune globulin intravenous, IMREG-1, IMREG-2, imuthiol diethyl dithio carbamate, alpha-2 interferon, methionine-enkephalin, MTP-PE muramyl-tripeptide, granulocyte colony stimulating factor, beta-propiolactone inactive HIV-1, CD4, a rCD4-IgG hybrid, SK&F 106528 Soluble T4, thymopentin, tumor necrosis factor, or infliximab.

20. The method of claim 18, wherein the ART is efavirenz, emtricitabine, and tenofovir disoproxil fumarate; emtricitabine, rilpivirine, and tenofovir disoproxil fumarate; elvitegravir, cobicistat, emtricitabine, and tenofovir disoproxil fumarate; lamivudine and zidovudine; emtricitabine (FTC); lamivudine (3TC); abacavir and lamivudine; zalcitabine, dideoxycytidine (ddC); zidovudine (ZDV) or azidothymidine (AZT); abacavir, zidovudine, and lamivudine; tenofovir disoproxil fumarate and emtricitabine; enteric coated didanosine (ddI EC); didanosine (ddI) or dideoxyinosine; tenofovir disoproxil fumarate (TDF); stavudine (d4T); abacavir sulfate (ABC); rilpivirine; etravirine; delavirdine (DLV); efavirenz (EFV); nevirapine (NVP); amprenavir (APV); tipranavir (TPV); indinavir (IDV); saquinavir; saquinavir mesylate (SQV); lopinavir and ritonavir (LPV/RTV); Fosamprenavir Calcium (FOS-APV); ritonavir (RTV); Darunavir; atazanavir sulfate (ATV); nelfinavir mesylate (NFV); enfuvirtide (T-20); maraviroc; raltegravir (RAL); or dolutegravir.

21. The method of claim 18, wherein said CD4bs-specific antibody is 3BNC117 or VRC07-523.

22. The method of claim 18, wherein said V2 glycan-dependent antibody is CAP256-VRC26.

23. The method of claim 18, wherein the antiretroviral therapy (ART) or the immunomodulator is administered prior to, concurrently with, or subsequent to administration of said N332 glycan-dependent antibody.

24. The method of claim 1, wherein said N332 glycan-dependent antibody is PGT121 and said reservoir activator is a TLR agonist.

25. The method of claim 1, wherein said reservoir activator is a TLR agonist.

26. The method of claim 1, wherein said reservoir activator is a cytokine.

27. The method of claim 1, wherein said N332 glycan-dependent antibody is PGT122, PGT123, PGT124, PGT125, PGT126, PGT127, PGT128, PGT130, PGT131, PGT132, PGT133, PGT134, PGT135, PGT136, PGT137, PGT138, PGT139, or 10-1074.

28. The method of claim 5, wherein said reservoir activator is a TLR agonist.

29. The method of claim 27, wherein said reservoir activator is a TLR agonist.

30. The method of claim 2, wherein said subject is a human.

31. The method of claim 5, wherein said subject is a human.

32. The method of claim 27, wherein said subject is a human.

33. The method of claim 1, wherein said reservoir activator is a histone deacetylase (HDAC) inhibitor.

34. The method of claim 1, wherein the antibody comprises
the CDR-H1, CDR-H2, and CDR-H3 comprising the amino acid sequence of SEQ ID NO: 1, SEQ ID NO: 2, and SEQ ID NO: 3, respectively, and the CDR-L1, CDR-L2, and CDR-L3 comprising the amino acid sequence of SEQ ID NO: 4, SEQ ID NO: 5, and SEQ ID NO: 6, respectively.

35. The method of claim 1, wherein
the heavy chain variable domain of the antibody has the amino acid sequence of SEQ ID NO: 15 and the light chain variable domain of the antibody has the amino acid sequence of SEQ ID NO: 16.

36. The method of claim 1, wherein
the heavy chain variable domain of the antibody has the amino acid sequence of SEQ ID NO: 23 and the light chain variable domain of the antibody has the amino acid sequence of SEQ ID NO: 24.

37. The method of claim 1, wherein
the heavy chain variable domain of the antibody has the amino acid sequence of SEQ ID NO: 143 and the light chain variable domain of the antibody has the amino acid sequence of SEQ ID NO: 144.

38. The method of claim 1, wherein
the heavy chain variable domain of the antibody has the amino acid sequence of SEQ ID NO: 31 and the light chain variable domain of the antibody has the amino acid sequence of SEQ ID NO: 32.

39. The method of claim 1, wherein
the heavy chain variable domain of the antibody has the amino acid sequence of SEQ ID NO: 39 and the light chain variable domain of the antibody has the amino acid sequence of SEQ ID NO: 40.

40. The method of claim 1, wherein
the heavy chain variable domain of the antibody has to the amino acid sequence of SEQ ID NO: 47 and the light chain variable domain of the antibody has the amino acid sequence of SEQ ID NO: 48.

41. The method of claim 1, wherein
the heavy chain variable domain of the antibody has the amino acid sequence of SEQ ID NO: 55 and the light chain variable domain of the antibody has the amino acid sequence of SEQ ID NO: 56.

42. The method of claim 1, wherein
the heavy chain variable domain of the antibody has to the amino acid sequence of SEQ ID NO: 63 and the light chain variable domain of the antibody has the amino acid sequence of SEQ ID NO: 64.

43. The method of claim 1, wherein the heavy chain variable domain of the antibody has the amino acid sequence of SEQ ID NO: 151 and the light chain variable domain of the antibody has the amino acid sequence of SEQ ID NO: 152.

44. The method of claim 1, wherein the heavy chain variable domain of the antibody has the amino acid sequence of SEQ ID NO: 159 and the light chain variable domain of the antibody has the amino acid sequence of SEQ ID NO: 160.

45. The method of claim 1, wherein the heavy chain variable domain of the antibody has the amino acid sequence of SEQ ID NO: 79 and the light chain variable domain of the antibody has the amino acid sequence of SEQ ID NO: 80.

46. The method of claim 1, wherein the heavy chain variable domain of the antibody has the amino acid sequence of SEQ ID NO: 87 and the light chain variable domain of the antibody has the amino acid sequence of SEQ ID NO: 88.

47. The method of claim 1, wherein the heavy chain variable domain of the antibody has the amino acid sequence of SEQ ID NO: 103 and the light chain variable domain of the antibody has the amino acid sequence of SEQ ID NO: 104.

48. The method of claim 1, wherein the heavy chain variable domain of the antibody has the amino acid sequence of SEQ ID NO: 175 and the light chain variable domain of the antibody has the amino acid sequence of SEQ ID NO: 176.

49. The method of claim 1, wherein the heavy chain variable domain of the antibody has the amino acid sequence of SEQ ID NO: 183 and the light chain variable domain of the antibody has the amino acid sequence of SEQ ID NO: 184.

50. The method of claim 1, wherein the heavy chain variable domain of the antibody has the amino acid sequence of SEQ ID NO: 321 and the light chain variable domain of the antibody has the amino acid sequence of SEQ ID NO: 322.

51. The method of claim 34, wherein said reservoir activator is a TLR agonist.

52. The method of claim 35, wherein said reservoir activator is a TLR agonist.

53. The method of claim 36, wherein said reservoir activator is a TLR agonist.

54. The method of claim 37, wherein said reservoir activator is a TLR agonist.

55. The method of claim 38, wherein said reservoir activator is a TLR agonist.

56. The method of claim 39, wherein said reservoir activator is a TLR agonist.

57. The method of claim 40, wherein said reservoir activator is a TLR agonist.

58. The method of claim 41, wherein said reservoir activator is a TLR agonist.

59. The method of claim 42, wherein said reservoir activator is a TLR agonist.

60. The method of claim 43, wherein said reservoir activator is a TLR agonist.

61. The method of claim 44, wherein said reservoir activator is a TLR agonist.

62. The method of claim 45, wherein said reservoir activator is a TLR agonist.

63. The method of claim 46, wherein said reservoir activator is a TLR agonist.

64. The method of claim 47, wherein said reservoir activator is a TLR agonist.

65. The method of claim 48, wherein said reservoir activator is a TLR agonist.

66. The method of claim 49, wherein said reservoir activator is a TLR agonist.

67. The method of claim 50, wherein said reservoir activator is a TLR agonist.

68. The method of claim 1, wherein the heavy chain variable domain of the antibody has at least 95% sequence identity to the amino acid sequence of SEQ ID NO: 7 and the light chain variable domain of the antibody has at least 97% sequence identity to the sequence of SEQ ID NO: 8.

69. The method of claim 68, wherein the CDR-H2 of the antibody comprises a serine to asparagine substitution at position 60 of SEQ ID NO: 7.

70. The method of claim 1, wherein the heavy chain variable domain of the antibody has the amino acid sequence of SEQ ID NO: 7 and the light chain variable domain of the antibody has the amino acid sequence of SEQ ID NO: 8.

71. The method of claim 1, wherein the heavy chain variable domain of the antibody has at least 95% sequence identity to the amino acid sequence of SEQ ID NO: 7 and the light chain variable domain of the antibody has the amino acid sequence of SEQ ID NO: 8.

72. The method of claim 1, wherein the heavy chain variable domain of the antibody has the amino acid sequence of SEQ ID NO: 7 and the light chain variable domain of the antibody has at least 97% sequence identity to the amino acid sequence of SEQ ID NO: 8.

73. The method of claim 1, further comprising measuring the proviral DNA level in the tissue of the subject during or after the first regimen.

\* \* \* \* \*

UNITED STATES PATENT AND TRADEMARK OFFICE
CERTIFICATE OF CORRECTION

PATENT NO. : 10,376,583 B2
APPLICATION NO. : 15/025961
DATED : August 13, 2019
INVENTOR(S) : Dan H. Barouch Page 1 of 1

It is certified that error appears in the above-identified patent and that said Letters Patent is hereby corrected as shown below:

In the Specification

Column 6, Line 15, replace "Ebzicom" with --EPZICOM®--.

Column 11, Line 19, replace "virus-I11" with --virus-III--.

Column 37, Table 1, Line 15, replace "Ebzicom" with --EPZICOM®--.

Column 54, Line 67, replace "higher Δ" with --higher λ--.

In the Claims

Column 229, Line 66, replace "SEQ ID NO: 142" with --SEQ ID NO: 141--.

Column 229, Line 67, replace "SEQ ID NO: 143" with --SEQ ID NO: 142--.

Signed and Sealed this
Twenty-sixth Day of May, 2020

Andrei Iancu
*Director of the United States Patent and Trademark Office*